(12) United States Patent
Chappell et al.

(10) Patent No.: US 8,084,489 B2
(45) Date of Patent: *Dec. 27, 2011

(54) GLUCAGON RECEPTOR ANTAGONISTS, PREPARATION AND THERAPEUTIC USES

(75) Inventors: Mark Donald Chappell, Noblesville, IN (US); Scott Eugene Conner, Indianapolis, IN (US); Allie Edward Tripp, Indianapolis, IN (US); Guoxin Zhu, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 1091 days.

This patent is subject to a terminal disclaimer.

(21) Appl. No.: 11/815,987

(22) PCT Filed: Feb. 9, 2006

(86) PCT No.: PCT/US2006/004461
§ 371 (c)(1),
(2), (4) Date: Aug. 10, 2007

(87) PCT Pub. No.: WO2006/086488
PCT Pub. Date: Aug. 17, 2006

(65) Prior Publication Data
US 2010/0137417 A1  Jun. 3, 2010

Related U.S. Application Data

(60) Provisional application No. 60/652,492, filed on Feb. 11, 2005.

(51) Int. Cl.
*A61K 31/381* (2006.01)
*C07D 333/22* (2006.01)
*C07D 409/12* (2006.01)
*A61P 3/10* (2006.01)

(52) U.S. Cl. ............. 514/444; 549/72; 549/59; 514/448
(58) Field of Classification Search .................. None
See application file for complete search history.

(56) References Cited

FOREIGN PATENT DOCUMENTS

| DK | WO 03/048109 | * | 6/2003 |
| WO | WO 03/048109 | | 6/2003 |
| WO | WO2004/002480 | | 1/2004 |
| WO | WO2005/118542 | | 12/2005 |
| WO | WO2005/123668 | | 12/2005 |

OTHER PUBLICATIONS

Olesen in Current Opinion in Drug Discovery and Development 4(4), 471-478 (2001).*
Kilbourn, M.R. in International Journal of Radiation Applications and Instrumentation. Part B. Nuclear Medicine and Biology, vol. 16, Issue 7, 1989, pp. 681-686.*
Kurukulasuriya et al: "Biaryl amide 1-16 glucagon receptor antagonists" Bioorganic & Medicinal Chemistry Letters, Oxford, GB, vol. 14, No. 9, 2004, pp. 2047-2050, XP002339903 ISSN: 0960-894X table 1.
Duffy, J.L.: "Discovery and investigation 1-16 of a novel class of thiophene-derived antagonists of the human glucagon receptor" Bioorganic & Medicinal Chemistry Letters, vol. 15, 2005, pp. 1401-1405, XP002392897 table 1.

* cited by examiner

*Primary Examiner* — Timothy Thomas
*Assistant Examiner* — Dennis Heyer
(74) *Attorney, Agent, or Firm* — Dan L. Wood

(57) ABSTRACT

The present invention discloses novel compounds of Formula (I) or pharmaceutically acceptable salts thereof which have glucagon receptor antagonist or inverse agonist activity, as well as methods of using these compounds and intermediates and methods for preparing such compounds. In another embodiment, the invention discloses pharmaceutical compositions comprising N compounds of Formula (I) as well as methods of using them to treat diabetic and other glucagon related metabolic disorders, and the like.

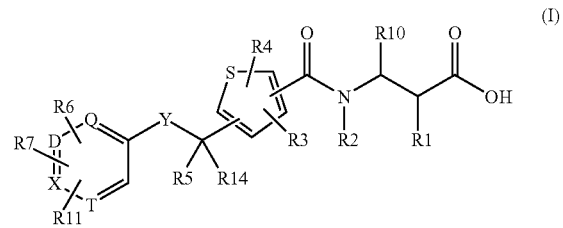

7 Claims, No Drawings

GLUCAGON RECEPTOR ANTAGONISTS, PREPARATION AND THERAPEUTIC USES

This is the national phase application, under 35 USC 371, for PCT/US2006/004461, filed Feb. 9, 2006, which claims the benefit, under 35 USC 119(e), of U.S. provisional application 60/652,492 filed Feb. 11, 2005.

This invention relates to compounds that are antagonists of the action of glucagon on the glucagon receptor, or inverse agonists of the glucagon receptor, and to pharmaceutical compositions thereof, and to the uses of these compounds and compositions in the treatment of the human or animal body. The invention also relates to intermediates and methods of making the glucagon antagonists, inverse agonists, and pharmaceutical compositions thereof. The present compounds show a high affinity and selective binding for the glucagon receptor, and as such are useful in the treatment of disorders responsive to the modulation of glucagon receptors, such as diabetic and other glucagon related metabolic disorders, and the like.

Glucagon is a key hormonal agent that, in cooperation with insulin, mediates homeostatic regulation of blood glucose. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Both glucagon and insulin are peptide hormones. Native glucagon is a 29 amino acid peptide and is produced in the alpha islet cells of the pancreas and insulin is produced in the beta islet cells. Glucagon exerts its action by binding to and activating its receptor, which is a member of the Glucagon-Secretin branch of the 7-transmembrane G-protein coupled receptor family. The receptor functions by activating the adenylyl cyclase second messenger system resulting in an increase in cAMP levels. The glucagon receptor, or naturally occurring variants of the receptor, may possess intrinsic constitutive activity, in vitro as well as in vivo (i.e. activity in the absence of an agonist). Compounds acting as inverse agonists can inhibit this activity.

Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that prevent or inhibit constituitive, or glucagon-induced, glucagon receptor mediated responses.

Several publications disclose peptides that are stated to act as glucagon antagonists. Probably, the most thoroughly characterized antagonist is DesHis[1][Glu[9]]-glucagon amide (Unson et al., Peptides 10, 1171 (1989); Post et al., Proc. Natl. Acad. Sci. USA 90, 1662 (1993)). Other antagonists are DesHis[1], Phe[6][Glu[9]]-glucagon amide (Azizh et al., Bioorganic & Medicinal Chem. Lett. 16, 1849 (1995)) and NLeu[9], Ala[11,16]-glucagon amide (Unson et al., J. Biol. Chem. 269 (17), 12548 (1994)). Peptide antagonists of peptide hormones are often potent, however they are generally known not to be orally available because of degradation by physiological enzymes, and poor distribution in vivo. Therefore, orally available non-peptide antagonists of peptide hormones are generally preferred.

A number of publications have appeared in recent years reporting non-peptide agents that act at the glucagon receptor. In spite of the number of treatments for diseases that involve glucagon, the current therapies suffer from one or more inadequacies, including poor or incomplete efficacy, unacceptable side effects, and contraindications for certain patient populations. Thus there remains a need for improved treatments using alternative or improved pharmaceutical agents that modulate glucagon receptor activity and treat the diseases that could benefit from glucagon receptor modulation. The present invention provides such a contribution to the art based on the finding that a novel class of compounds has a high affinity, selective, and potent inhibitory activity at the glucagon receptor. The present invention is distinct in the particular structures and their activities.

SUMMARY OF THE INVENTION

The present invention provides a compound structurally represented by Formula I:

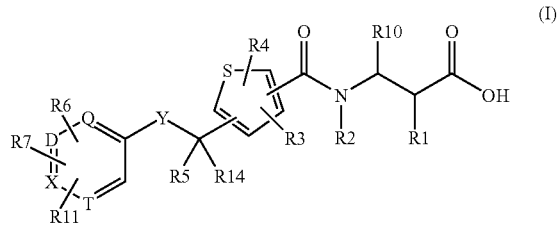

or a pharmaceutically acceptable salt thereof wherein:

Y is —O—, —S—, or —O—CH$_2$—;

Q, D, X and T independently represent carbon or nitrogen, provided that no more than two of Q, D, X and T are nitrogen;

R1 is -hydrogen, —OH, or -halogen;

R2 is -hydrogen, or —(C$_1$-C$_3$)alkyl;

R3 and R4 are independently at each occurrence -hydrogen, -halogen, —CN, —(C$_1$-C$_7$)alkoxy, —(C$_1$-C$_7$)alkyl, or —(C$_2$-C$_7$)alkenyl;

R5 and R14 are independently
-hydrogen, —(C$_1$-C$_{12}$)alkyl, —(C$_3$-C$_{12}$)cycloalkyl, —(C$_3$-C$_{12}$)cycloalkyl-(C$_1$-C$_{12}$)alkyl, -phenyl, -phenyl-phenyl-(C$_1$-C$_{12}$)alkyl, -phenyl-(C$_3$-C$_{12}$)cycloalkyl, -aryl, -aryl-(C$_1$-C$_{12}$)alkyl, -heteroaryl, -heteroaryl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, -aryl-(C$_2$-C$_{10}$)alkenyl, -heteroaryl-(C$_2$-C$_{10}$)alkenyl, —(C$_2$-C$_{12}$)alkynyl, —(C$_8$-C$_{12}$)cycloalkynyl, -aryl-(C$_2$-C$_{12}$)alkynyl, or -heteroaryl-(C$_2$-C$_{12}$)alkynyl,
wherein —(C$_1$-C$_{12}$)alkyl, —(C$_3$-C$_{12}$)cycloalkyl, -phenyl, -phenyl-phenyl-(C$_1$-C$_{12}$)alkyl, -phenyl-(C$_3$-C$_{12}$)cycloalkyl, -aryl, -aryl-(C$_1$-C$_{12}$)alkyl, -heteroaryl, -heteroaryl-(C$_1$-C$_{12}$)alkyl, -heterocycloalkyl, -heterocycloalkyl-(C$_1$-C$_{12}$)alkyl, —(C$_2$-C$_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_8$-$C_{12}$) cycloalkynyl, -aryl-($C_2$-$C_{12}$)alkynyl, or -heteroaryl-($C_2$-$C_{12}$)alkynyl are each optionally substituted with from one to three substituents each independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxy, —($C_3$-$C_7$)cycloalkyl, -aryloxy, -aryl, -aryl-($C_1$-$C_7$)alkyl, -heteroaryl,-heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

wherein optionally R5 and R14 may form a four, five, or six membered ring with the atom to which they are attached, and the ring so formed may optionally include one or two double bonds, and optionally may be substituted with up to four halogens.

R6 and R7 are independently
-hydrogen, -halogen, -hydroxy, —CN, —($C_1$-$C_7$)alkoxy, —($C_2$-$C_7$)alkenyl, —($C_1$-$C_7$)alkyl, -aryl, -heteroaryl, —($C_3$-$C_7$)cycloalkyl, or —($C_3$-$C_7$)heterocycloalkyl,
wherein —($C_2$-$C_7$)alkenyl, —($C_1$-$C_7$)alkyl, —($C_1$-$C_7$) alkoxy, -aryl, -heteroaryl, —($C_3$-$C_7$)cycloalkyl, —($C_3$-$C_7$)heterocycloalkyl, are each optionally substituted with from one to three substituents independently selected from the group consisting of -hydrogen, -hydroxy, -cyano, -nitro, -halo, -oxo, —($C_1$-$C_7$) alkyl, —($C_1$-$C_7$)alkyl-COOR12, —($C_1$-$C_7$)alkoxy, —($C_3$-$C_7$)cycloalkyl, -aryloxy, -aryl, -aryl-($C_1$-$C_7$) alkyl, -heteroaryl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and S(O)$_2$N(R12)$_2$;
provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;
and wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence
-hydrogen, -hydroxy, —CN, -nitro, -halo, —($C_1$-$C_7$)alkyl, —CF$_3$, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$) alkyl, -aryloxy, —C(O)R12, —COOR12, —OC(O) R12, —OS(O)$_2$R12, —N(R12)$_2$, —NR12C(O) R12, —NR12SO$_2$R12, —SR12, —S(O)R12, —S(O)$_2$R12, or —S(O)$_2$N(R12)$_2$;
wherein —($C_1$-$C_7$)alkyl, —($C_1$-$C_7$)alkoxy, —($C_3$-$C_7$) cycloalkyl, -aryl, -aryl-($C_1$-$C_7$)alkyl, -heteroaryl, -heteroaryl-($C_1$-$C_7$)alkyl, -aryloxy, are each optionally substituted with from one to three substituents independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-($C_1$-$C_7$)alkyl, -heteroaryl, -heterocycloalkyl, —C(O)R12, —COOR12, —OC(O)R12, —OS(O)$_2$R12, —N(R12)$_2$, —NR12C(O)R12, —C(O) NR12R12, —NR12SO$_2$R12, —SR12, —S(O)R12, —S(O)$_2$R12, and —S(O)$_2$N(R12)$_2$;

R10 is independently
-hydrogen, -halogen, —($C_1$-$C_{12}$)alkyl, -cycloalkyl, -aryl, -aryl-($C_1$-$C_7$)alkyl, -heteroaryl, -heteroaryl —($C_1$-$C_7$) alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_8$-$C_{12}$)cycloalkynyl, -aryl-($C_2$-$C_{12}$)alkynyl, or -heteroaryl-($C_2$-$C_{12}$)alkynyl,
wherein —($C_1$-$C_{12}$)alkyl, -cycloalkyl, -aryl, -aryl-($C_1$-$C_7$)alkyl, -heteroaryl, -heteroaryl —($C_1$-$C_7$)alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_8$-$C_{12}$)cycloalkynyl, -aryl-($C_2$-$C_{12}$)alkynyl, -heteroaryl-($C_2$-$C_{12}$)alkynyl, are each optionally substituted with from one to three substituents each independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-$C_1$-$C_7$ alkyl, -heteroaryl, -heterocycloalkyl, —C(O)R12, —COOR12, —OC(O) R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R11 is independently at each occurrence
-hydrogen;
or

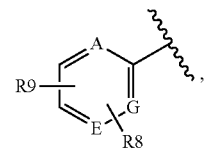

wherein the zig-zag mark represents the point of attachment to the R11 position in formula I,
wherein A, G, and E independently represent carbon or nitrogen, provided that no more than two of A, G, and E are nitrogen;
provided however that wherein A is nitrogen, then R8 or R9 are not attached to A, and provided that wherein G is nitrogen, then R8 or R9 are not attached to G, and provided that wherein E is nitrogen, then R8 or R9 are not attached to E;
or

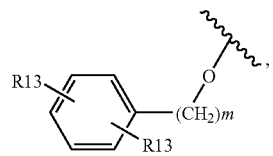

wherein the zig-zag mark represents the point of attachment to the R11 position in formula I, wherein m is an integer of 0, 1, 2, or 3, and when m is 0 then (CH$_2$)m is a bond,
provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

R12 is independently at each occurrence -hydrogen or —($C_1$-$C_7$)alkyl;

R13 is independently at each occurrence -hydrogen, -halogen, —($C_1$-$C_7$)alkyl, —$CF_3$, —$OCF_3$, or —($C_2$-$C_7$)alkenyl wherein —($C_1$-$C_7$)alkyl, —($C_2$-$C_7$)alkenyl are each optionally substituted once with substituents independently selected from the group consisting of —$CF_3$, —$OCF_3$.

DETAILED DESCRIPTION OF THE INVENTION

The present invention provides compounds and pharmaceutical compositions that are useful as glucagon receptor antagonists or inverse agonists. In another aspect the present invention provides compounds that are selective antagonists or inverse agonists of the glucagon receptor over the GLP-1 receptor. In yet another aspect, the present invention provides compounds, pharmaceutical compositions, and methods useful in the treatment of diabetic and other glucagon related metabolic disorders, and other disorders associated with glucagon receptor. In another aspect the present invention provides novel intermediates useful in preparation of the glucagon receptor antagonists of the invention.

In one embodiment, the present invention provides compounds of Formula I as described in detail herein. While all of the compounds of the present invention are useful, certain of the compounds are particularly interesting and are preferred. The following listing sets out several groups of preferred compounds. It will be understood that each of the listings may be combined with other listings to create additional groups of preferred embodiments as indicated herein.

In a preferred embodiment, the present invention provides a compound structurally represented by Formula Ia:

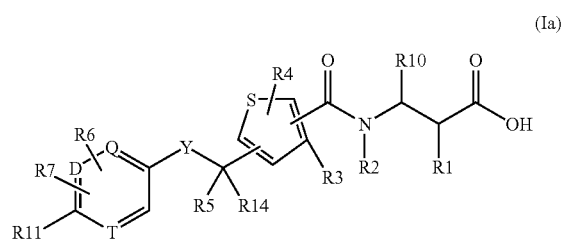

(Ia)

or a pharmaceutically acceptable salt thereof wherein:
Y is —O—, —S—, or —O—$CH_2$—;
Q, D, and T independently represent carbon or nitrogen, provided that no more than two of Q, D, and T are nitrogen;
R1 is -hydrogen, or —OH;
R2 is -hydrogen;
R3 and R4 are independently at each occurrence -hydrogen, or -halogen;
R5 and R14 are independently
-hydrogen, —($C_1$-$C_{12}$)alkyl, —($C_3$-$C_{12}$)cycloalkyl, —($C_3$-$C_{12}$)cycloalkyl-($C_1$-$C_{12}$)alkyl, —($C_2$-$C_{12}$)alkenyl, —($C_3$-$C_{12}$)cycloalkenyl, -heterocycloalkyl, -heterocycloalkyl-($C_1$-$C_{12}$)alkyl, —($C_2$-$C_{12}$)alkynyl, or —($C_8$-$C_{12}$)cycloalkynyl;
wherein —($C_1$-$C_{12}$)alkyl, —($C_3$-$C_{12}$)cycloalkyl, —($C_3$-$C_{12}$)cycloalkyl-($C_1$-$C_{12}$)alkyl, —($C_2$-$C_{12}$)alkenyl, —($C_3$-$C_{12}$)cycloalkenyl, -heterocycloalkyl, -heterocycloalkyl-($C_1$-$C_{12}$)alkyl, —($C_2$-$C_{12}$)alkynyl, or —($C_8$-$C_{12}$)cycloalkynyl are each optionally substituted with one to three halogens;

wherein optionally R5 and R14 may form a four, five, or six membered ring with the atom to which they are attached, and the ring so formed may optionally include one or two double bonds, and optionally may be substituted with up to three halogens.

R6 and R7 are independently
-hydrogen, -halogen, -hydroxy, —CN, —($C_1$-$C_7$)alkoxy, —($C_2$-$C_7$)alkenyl, —($C_1$-$C_7$)alkyl, —($C_3$-$C_7$)cycloalkyl, or —($C_3$-$C_7$)heterocycloalkyl,
wherein —($C_1$-$C_7$)alkoxy, —($C_2$-$C_7$)alkenyl, —($C_1$-$C_7$)alkyl, —($C_3$-$C_7$)cycloalkyl, or —($C_3$-$C_7$)heterocycloalkyl, are each optionally substituted with one to three halogens;
provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence
-hydrogen, -hydroxy, —CN, -nitro, -halo, —($C_1$-$C_7$)alkyl, —$CF_3$, —($C_1$-$C_7$)alkoxy, —($C_3$-$C_7$)cycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, or —S(O)$_2$N(R12$_2$;
wherein —($C_1$-$C_7$)alkyl, —($C_1$-$C_7$)alkoxy, —($C_3$-$C_7$)cycloalkyl, are each optionally substituted with from one to three halogens;

R10 is independently -hydrogen;
R11 is independently at each occurrence
-hydrogen;
or

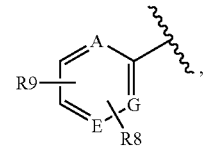

wherein the zig-zag mark represents the point of attachment to the R11 position in formula I;
wherein A, G, and E independently represent carbon or nitrogen, provided that no more than two of A, G, and E are nitrogen;
provided however that wherein A is nitrogen, then R8 or R9 are not attached to A, and provided that wherein G is nitrogen, then R8 or R9 are not attached to G, and provided that wherein E is nitrogen, then R8 or R9 are not attached to E; and
R12 is independently at each occurrence -hydrogen or —($C_1$-$C_7$)alkyl.

In another preferred embodiment, the present invention provides a compound structurally represented by Formula Ib:

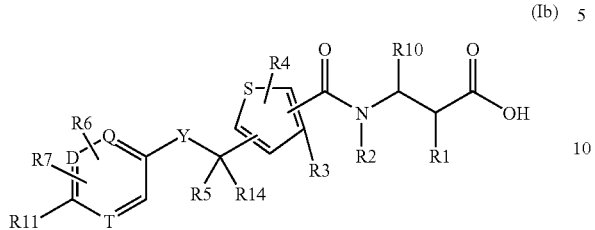
(Ib)

or a pharmaceutically acceptable salt thereof wherein:
Y is —O—, —S—, or —O—CH$_2$—;
Q, D, and T independently represent carbon or nitrogen, provided that no more than two of Q, D, and T are nitrogen;
R1 is -hydrogen, or —OH;
R2 is -hydrogen;
R3 and R4 are -hydrogen;
R5 and R14 are independently
-hydrogen, —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl;
wherein —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl are each optionally substituted with one to three halogens;
wherein optionally R5 and R14 may form a four, five, or six membered ring with the atom to which they are attached, and the ring so formed may optionally include one or two double bonds, and optionally may be substituted with up to three halogens.
R6 and R7 are independently
-hydrogen, -halogen, -hydroxy, —CN, —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl,
wherein —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl, are each optionally substituted with one to three halogens;
provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and wherein R6 and R7 may optionally form a six membered ring with the atoms to which they are attached, and the ring so formed may optionally contain up to two oxygens, and further the ring so formed may optionally be substituted with up to four halogens;
R8 and R9 are independently at each occurrence
-hydrogen, -hydroxy, —CN, -nitro, -halo, —(C$_1$-C$_7$)alkyl, —CF$_3$, —(C$_1$-C$_7$)alkoxy, —(C$_3$-C$_7$)cycloalkyl, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, or —S(O)$_2$N(R12)$_2$;
wherein —(C$_1$-C$_7$)alkyl, —(C$_1$-C$_7$)alkoxy, —(C$_3$-C$_7$)cycloalkyl, are each optionally substituted with from one to three halogens;

R10 is independently -hydrogen;
R11 is independently at each occurrence
-hydrogen;
or

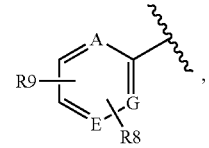

wherein the zig-zag mark represents the point of attachment to the R11 position in formula I;
wherein A, G, and E independently represent carbon or nitrogen, provided that no more than two of A, G, and E are nitrogen;
provided however that wherein A is nitrogen, then R8 or R9 are not attached to A, and provided that wherein G is nitrogen, then R8 or R9 are not attached to G, and provided that wherein E is nitrogen, then R8 or R9 are not attached to E; and
R12 is independently at each occurrence -hydrogen or —(C$_1$-C$_7$)alkyl.

In another preferred embodiment, the present invention provides a compound structurally represented by Formula Ic;

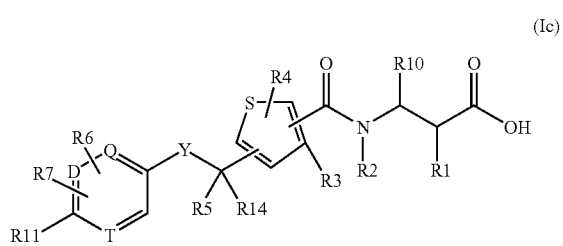
(Ic)

or a pharmaceutically acceptable salt thereof wherein:
Y is —O—, —S—, or —O—CH$_2$—;
Q, D, and T are carbon;
R1 is -hydrogen;
R2 is -hydrogen;
R3 and R4 are -hydrogen;
R5 is hydrogen;
R14 is
—(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl;
wherein —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl are each optionally substituted with one to three halogens;
R6 and R7 are independently
-hydrogen, -halogen, -hydroxy, —CN, —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl,
wherein —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl, are each optionally substituted with one to three halogens;

provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and wherein R6 and R7 may optionally form a six membered ring with the atoms to which they are attached, and the ring so formed may optionally contain up to two oxygens, and further the ring so formed may optionally be substituted with up to four halogens;

R8 and R9 are independently at each occurrence
-hydrogen, -hydroxy, —CN, -nitro, -halo, —($C_1$-$C_7$)alkyl, —$CF_3$, —($C_1$-$C_7$)alkoxy, —($C_3$-$C_7$)cycloalkyl, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, or —S(O)$_2$N(R12)$_2$;
wherein —($C_1$-$C_7$)alkyl, —($C_1$-$C_7$)alkoxy, —($C_3$-$C_7$)cycloalkyl, are each optionally substituted with from one to three halogens;

R10 is independently -hydrogen;
R11 is independently at each occurrence

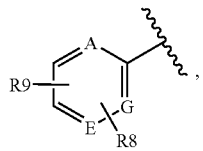

wherein the zig-zag mark represents the point of attachment to the R11 position in formula I;
wherein A, G, and E independently represent carbon or nitrogen, provided that no more than two of A, G, and E are nitrogen;
provided however that wherein A is nitrogen, then R8 or R9 are not attached to A, and provided that wherein G is nitrogen, then R8 or R9 are not attached to G, and provided that wherein E is nitrogen, then R8 or R9 are not attached to E; and
R12 is independently at each occurrence -hydrogen or —($C_1$-$C_7$)alkyl.

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably Y is —O—. Preferably Y is —S—. Preferably Y is —O—$CH_2$—. Preferably Q, D, X, and T independently represent carbon. Preferably X is carbon and R11 is attached to X. Preferably one of are nitrogen. Preferably T is nitrogen. Preferably two of Q, D, and T are nitrogen.

Preferably R1 is -hydrogen, or —OH. Preferably R1 is -hydrogen. Preferably R1 is —OH. Preferably R2 is -hydrogen. Preferably R3 and R4 are -hydrogen. Preferably R3 halogen and R4 is -hydrogen.

Preferably R5 is —($C_1$-$C_8$)alkyl(optionally substituted with 1 to 3 halogens). Preferably R5 is ethyl, propyl, isopropyl, butyl, tertbutyl, 3-methyl-butyl, pentyl, hexyl, heptyl, octyl, 3,3-dimethylbutyl, 2-methylpropyl, 4-methylpentyl, 2,2-dimethylpropyl, 3,3,3-trifluoropropyl, or 4,4,4-trifluorbutyl. Preferably R5 is isopropyl, butyl, tertbutyl, 3-methyl-butyl, pentyl, 3,3-dimethylbutyl, 2-methylpropyl, 4-methylpentyl, 2,2-dimethylpropyl, 3-trifluoropropyl, or 4,4,4-trifluorbutyl. Preferably R5 is isopropyl, 3-methyl-butyl, trifluoropropyl, or 4,4,4-trifluorbutyl.

Preferably R5 is —($C_3$-$C_7$)cycloalkyl. Preferably R5 is cyclopropyl, cyclobutyl, cyclopentyl, or cyclohexyl. Preferably R5 is cyclopropyl. Preferably R5 is cyclobutyl. Preferably R5 is cyclopentyl. Preferably R5 is cyclohexyl.

Preferably R5 is —($C_1$-$C_6$)alkyl-($C_3$-$C_7$)cycloalkyl. Preferably R5 is —($C_1$-$C_3$)alkyl-($C_3$-$C_6$)cycloalkyl. Preferably R5 is —($C_1$-$C_3$)alkyl-cyclopropyl. Preferably R5 is —($C_1$-$C_3$)alkyl-cyclobutyl. Preferably R5 is —($C_1$-$C_3$)alkyl-cyclopentyl. Preferably R5 is —($C_1$-$C_3$)alkyl-cyclohexyl.

Preferably R5 is —($C_3$-$C_7$)cycloalkyl-($C_1$-$C_6$)alkyl(optionally substituted with 1 to 3 halogens). Preferably R5 is -cyclopropyl-($C_1$-$C_6$)alkyl(optionally substituted with 1 to 3 halogens). Preferably R5 is -cyclobutyl-($C_1$-$C_6$)alkyl(optionally substituted with 1 to 3 halogens). Preferably R5 is -cyclopentyl-($C_1$-$C_6$)alkyl(optionally substituted with 1 to 3 halogens). Preferably R5 is -cyclohexyl-($C_1$-$C_6$)alkyl(optionally substituted with 1 to 3 halogens).

Preferably R6 is —H, -halogen, -hydroxy, hydroxymethyl, or —($C_1$-$C_6$)alkyl (optionally substituted with 1 to 3 halogens). Preferably R6 is —H, -halogen, or —($C_1$-$C_3$)alkyl (optionally substituted with 1 to 3 halogens). Preferably R6 is —H, -halogen, or —$CH_3$. Preferably R6 is —H. Preferably R6 is fluorine, chlorine, or bromine. Preferably R6 is —$CH_3$.

Preferably R7 is —H, -halogen, -hydroxy, hydroxymethyl, or —($C_1$-$C_6$)alkyl (optionally substituted with 1 to 3 halogens). Preferably R7 is —H, -halogen, or —($C_1$-$C_3$)alkyl (optionally substituted with 1 to 3 halogens). Preferably R7 is —H, -halogen, or —$CH_3$. Preferably R7 is —H. Preferably R7 is fluorine, chlorine, or bromine. Preferably R7 is —$CH_3$.

Preferably R6 and R7 are —H. Preferably R6 is halogen and R7 is —H. Preferably R6 is —H and R7 is —$CH_3$. Preferably R6 and R7 are —$CH_3$. Preferably R6 and R7 are —$CH_3$ and are attached to D and T respectively.

Preferably R11 is

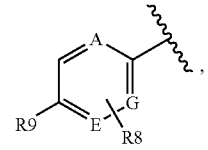

wherein the zig-zag mark represents the point of attachment to the R11 position in formula I; wherein A, G, and E are carbon.

Preferably R8 is -halogen, —($C_1$-$C_6$)alkyl(optionally substituted with 1 to 3 halogens), or —($C_1$-$C_6$)alkoxy. Preferably R8 is —H or -halogen. Preferably R8 is —H. Preferably R9 is —($C_1$-$C_6$)alkyl (optionally substituted with 1 to 3 halogens). Preferably R9 is methyl, ethyl, propyl, isopropyl, butyl, tertbutyl, trifluoromethyl, 3-methyl-butyl, pentyl, hexyl, 3,3-dimethylbutyl, 2-methylpropyl, 4-methylpentyl, 2,2-dimethylpropyl, 3-trifluoropropyl, or 4-trifluorbutyl. Preferably R9 is isopropyl, tertbutyl, or trifluoromethyl. Preferably R8 is —H, and R9 is isopropyl, tertbutyl, or trifluoromethyl.

Preferably R14 is —($C_1$-$C_8$)alkyl(optionally substituted with 1 to 3 halogens). Preferably R14 is ethyl, propyl, isopropyl, butyl, tertbutyl, 3-methyl-butyl, pentyl, hexyl, heptyl, octyl, 3,3-dimethylbutyl, 2-methylpropyl, 4-methylpentyl, 2,2-dimethylpropyl, 3,3,3-trifluoropropyl, or 4,4,4-trifluorbutyl. Preferably R14 is isopropyl, butyl, tertbutyl, 3-methylbutyl, pentyl, 3,3-dimethylbutyl, 2-methylpropyl, 4-methylpentyl, 2,2-dimethylpropyl, 3-trifluoropropyl, or 4,4,4-trifluorbutyl. Preferably R14 is isopropyl, 3-methyl-butyl, trifluoropropyl, or 4,4,4-trifluorbutyl.

Preferably R14 is —($C_3$-$C_7$)cycloalkyl. Preferably R14 is cyclopropyl, cyclobutyl, cyclopentyl, or cyclohexyl. Preferably R14 is cyclopropyl. Preferably R14 is cyclobutyl. Preferably R14 is cyclopentyl. Preferably R14 is cyclohexyl.

Preferably R14 is —($C_1$-$C_6$)alkyl-($C_3$-$C_7$)cycloalkyl. Preferably R14 is —($C_1$-$C_3$)alkyl-($C_3$-$C_6$)cycloalkyl. Preferably R14 is —($C_1$-$C_3$)alkyl-cyclopropyl. Preferably R14 is —($C_1$-$C_3$)alkyl-cyclobutyl. Preferably R14 is —($C_1$-$C_3$)alkyl-cyclopentyl. Preferably R14 is —($C_1$-$C_3$)alkyl-cyclohexyl.

Preferably R14 is —($C_3$-$C_7$)cycloalkyl-($C_1$-$C_6$)alkyl(optionally substituted with 1 to 3 halogens). Preferably R14 is -cyclopropyl-($C_1$-$C_6$)alkyl(optionally substituted with 1 to 3 halogens). Preferably R14 is -cyclobutyl-($C_1$-$C_6$)alkyl(optionally substituted with 1 to 3 halogens). Preferably R14 is -cyclopentyl-($C_1$-$C_6$)alkyl(optionally substituted with 1 to 3 halogens). Preferably R14 is -cyclohexyl-($C_1$-$C_6$)alkyl(optionally substituted with 1 to 3 halogens).

Embodiments of the invention include compounds represented by formulae X1 to X126 in Table 1, and pharmaceutically acceptable salts thereof.

TABLE 1

| Formula | Structure |
|---------|-----------|
| X1 | 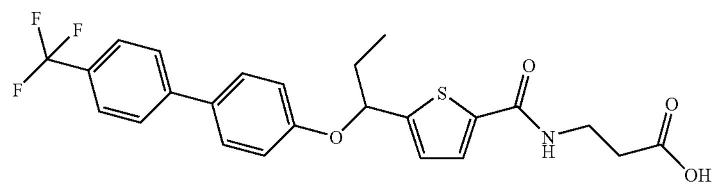 |
| X2 | 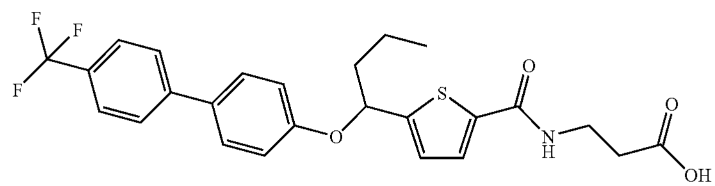 |
| X3 | 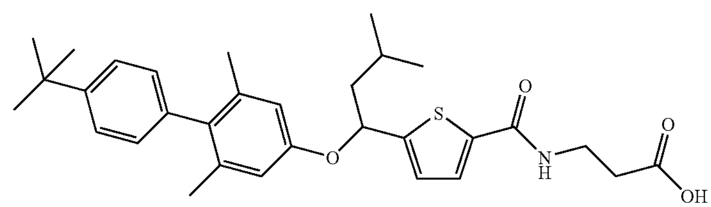 |
| X4 | 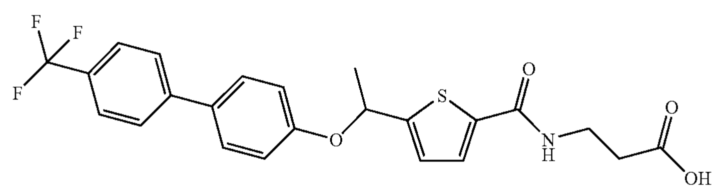 |
| X5 | 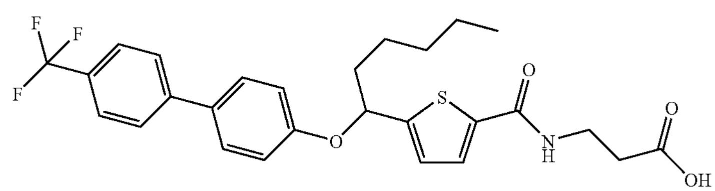 |
| X6 | 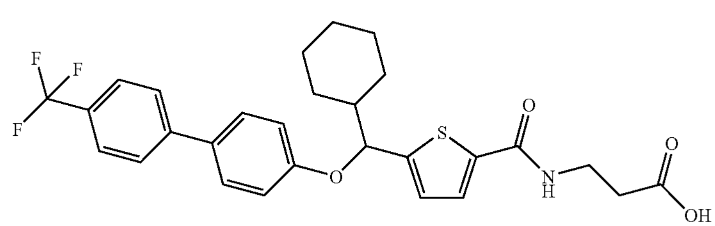 |

TABLE 1-continued

| Formula | Structure |
|---|---|
| X7 | 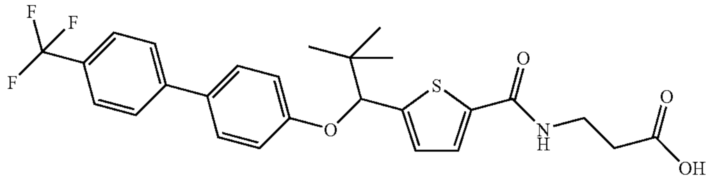 |
| X8 | 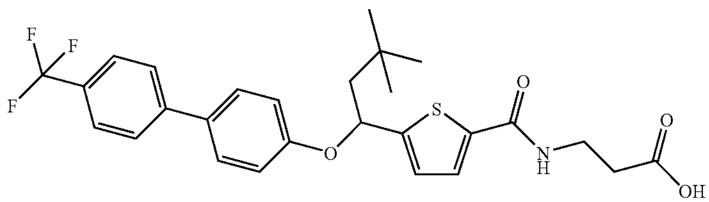 |
| X9 | 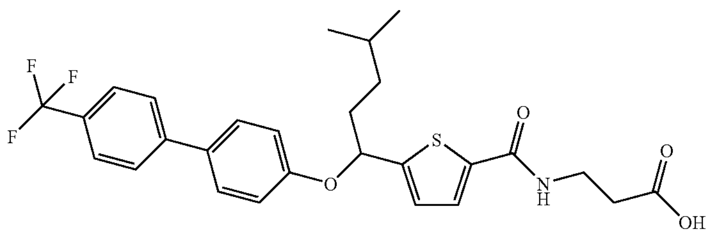 |
| X10 | 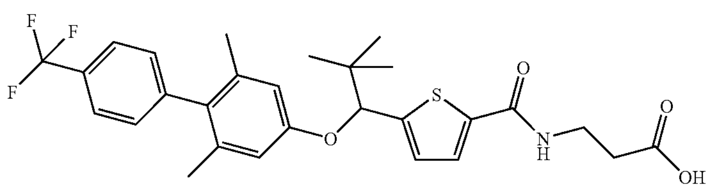 |
| X11 | 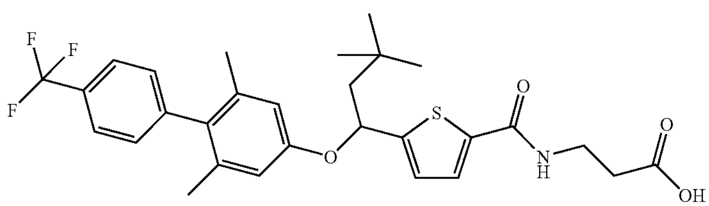 |
| X12 | 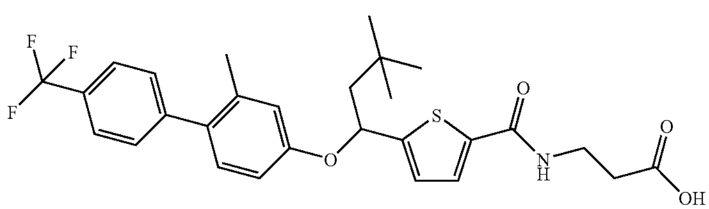 |
| X13 | 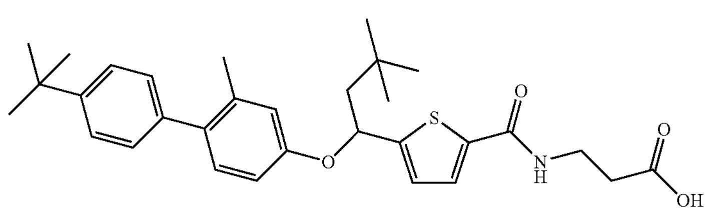 |

TABLE 1-continued
| Formula | Structure |
|---|---|
| X14 | 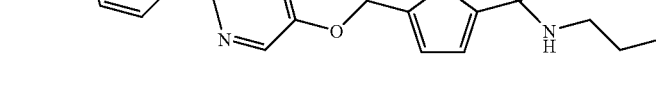 |
| X15 | 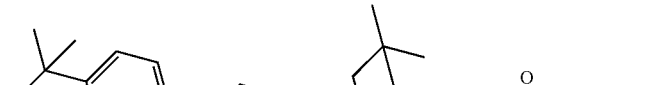 |
| X16 | 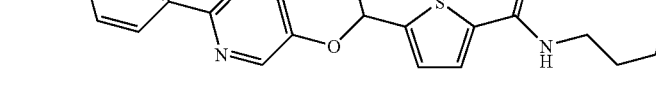 |
| X17 | 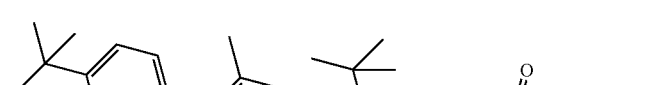 |
| X18 | 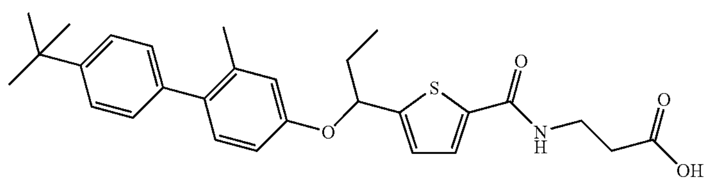 |
| X19 | 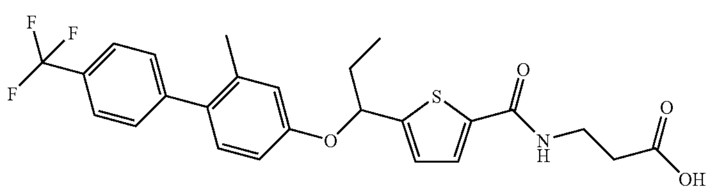 |
| X20 | 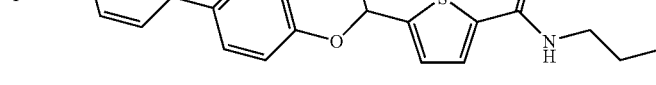 |
| X21 | 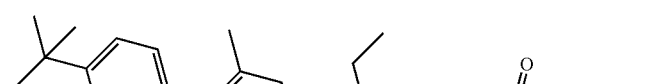 |

TABLE 1-continued

| Formula | Structure |
|---|---|
| X22 | 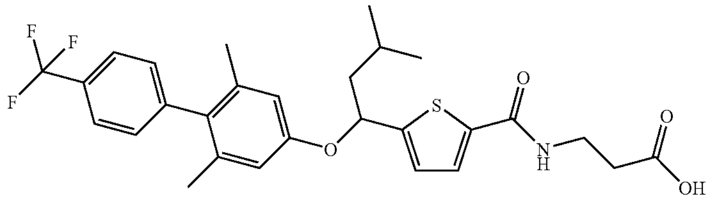 |
| X23 | 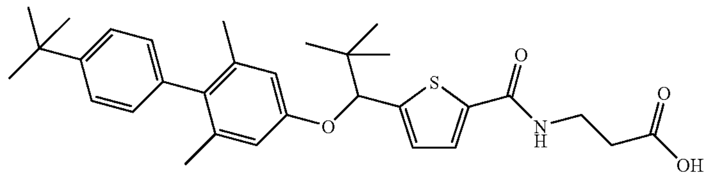 |
| X24 | 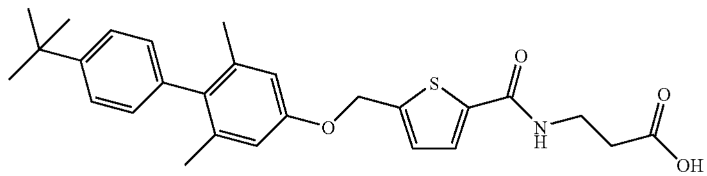 |
| X25 | 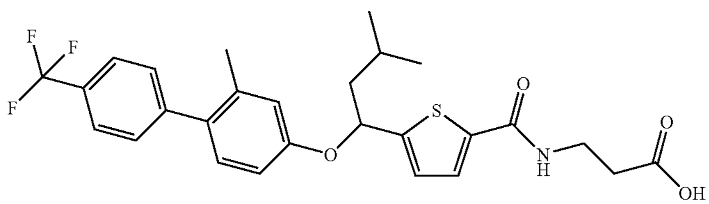 |
| X26 | 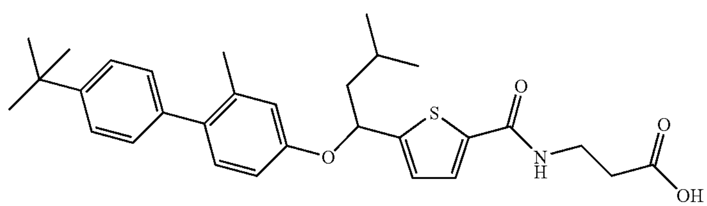 |
| X27 | 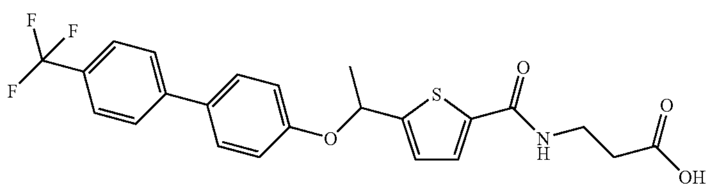 |
| X28 | 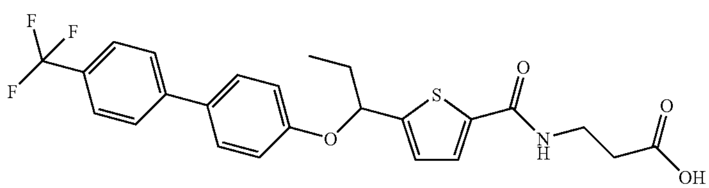 |
| X29 | 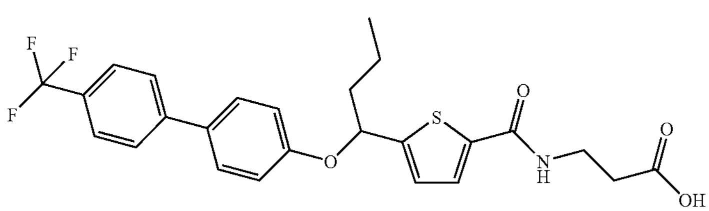 |

TABLE 1-continued
| Formula | Structure |
|---|---|
| X30 | 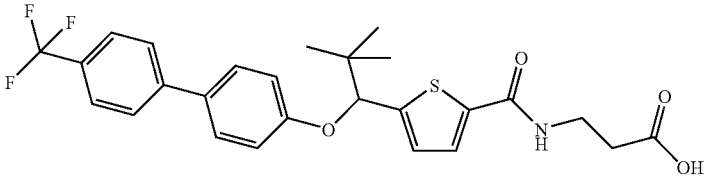 |
| X31 | 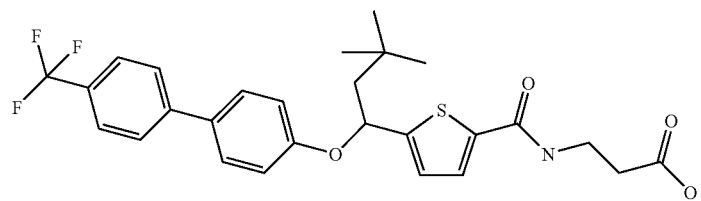 |
| X32 | 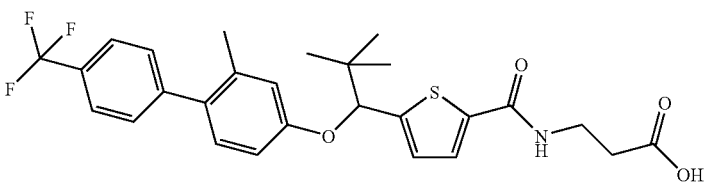 |
| X33 | 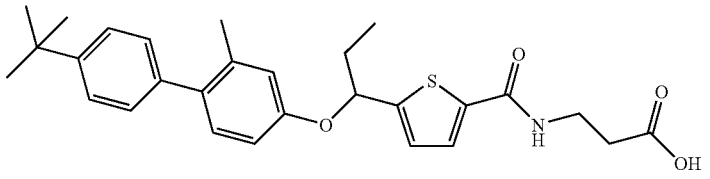 |
| X34 | 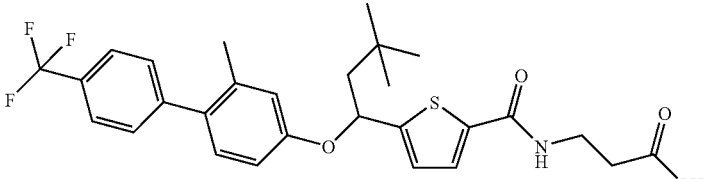 |
| X35 | 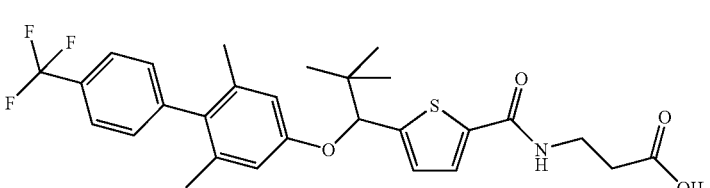 |
| X36 | 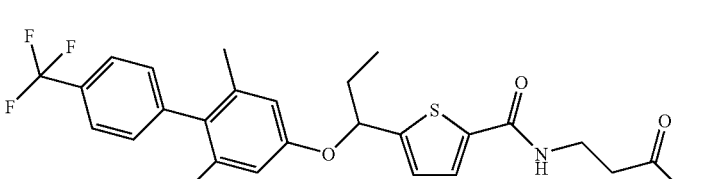 |
| X37 | 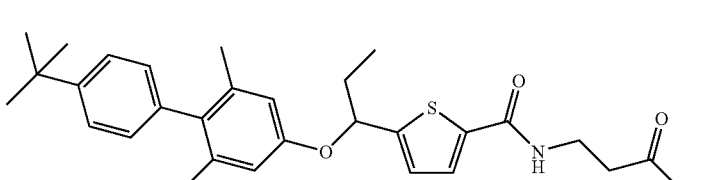 |

TABLE 1-continued

| Formula | Structure |
|---|---|
| X38 | 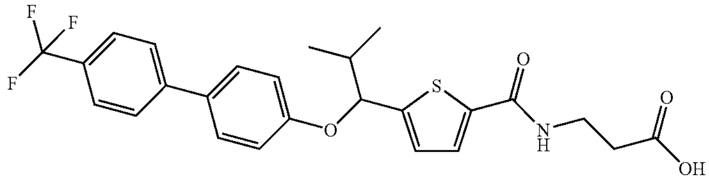 |
| X39 | 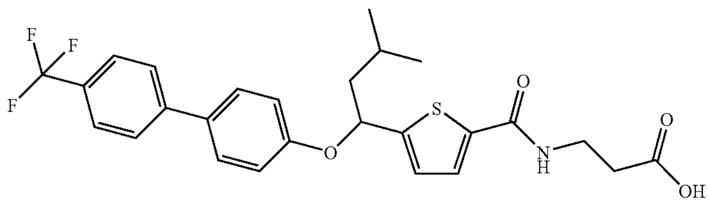 |
| X40 | 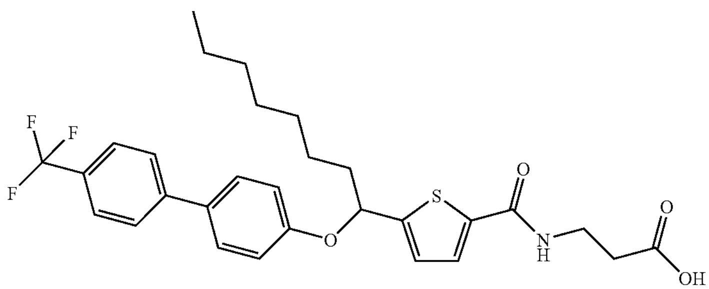 |
| X41 | 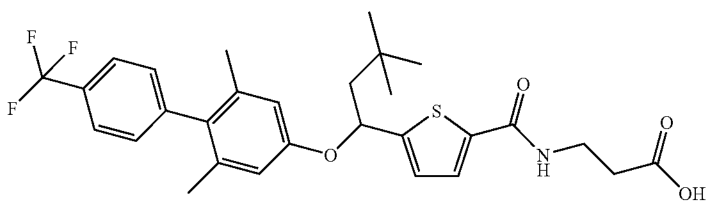 |
| X42 | 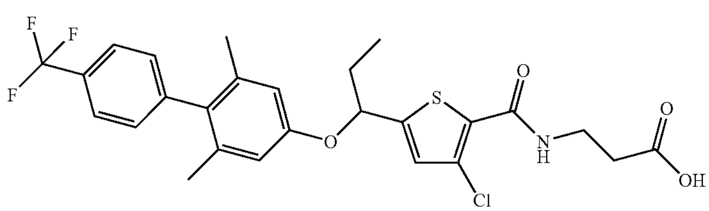 |
| X43 | 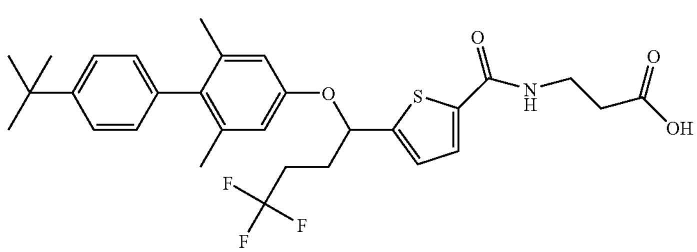 |
| X44 | 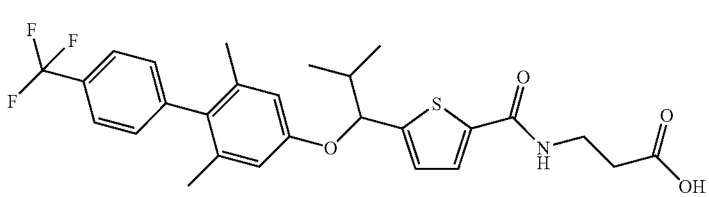 |

TABLE 1-continued

| Formula | Structure |
|---|---|
| X45 | 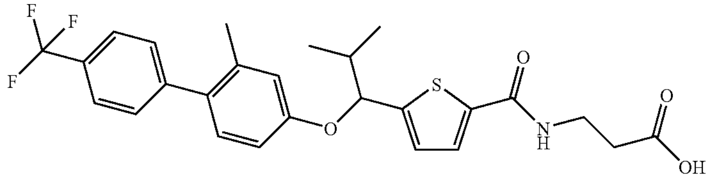 |
| X46 | 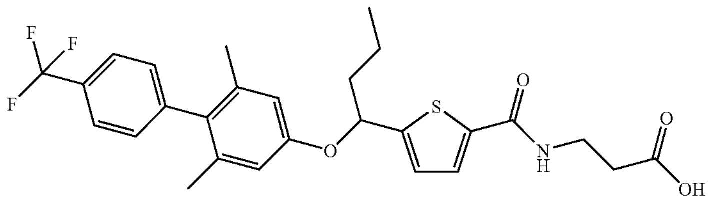 |
| X47 | 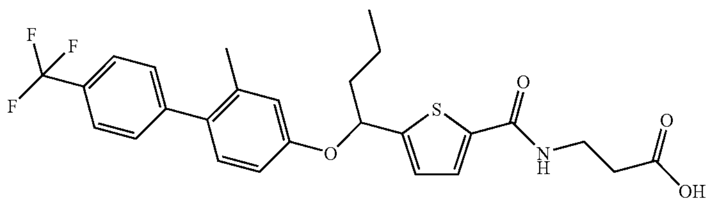 |
| X48 | 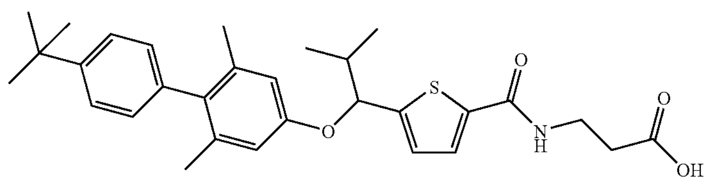 |
| X49 | 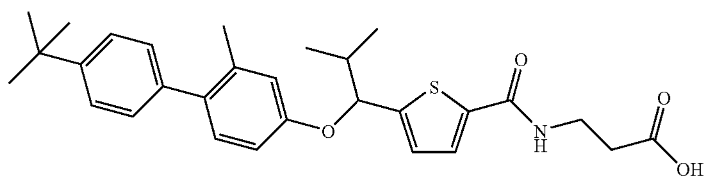 |
| X50 | 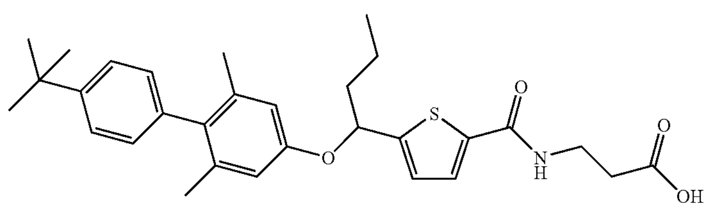 |
| X51 | 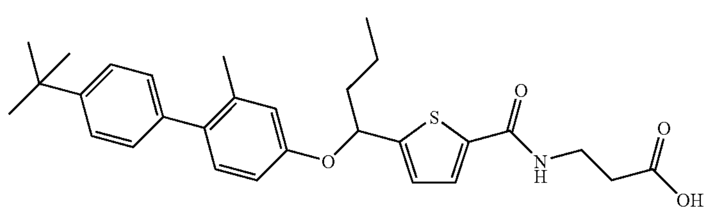 |
| X52 | 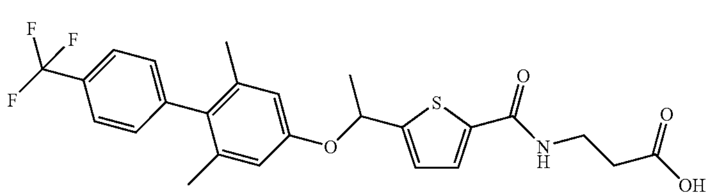 |

TABLE 1-continued

| Formula | Structure |
| --- | --- |
| X53 | 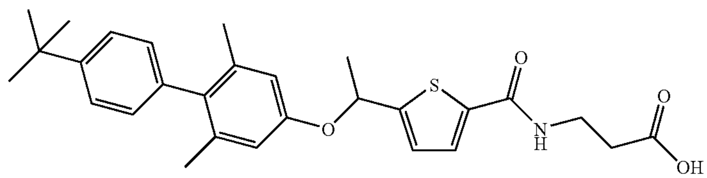 |
| X54 | 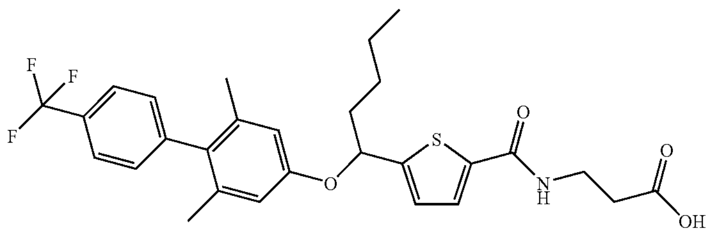 |
| X55 | 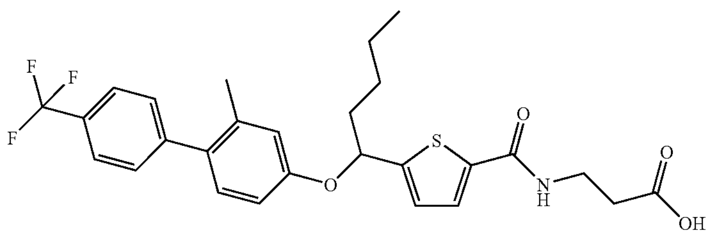 |
| X56 | 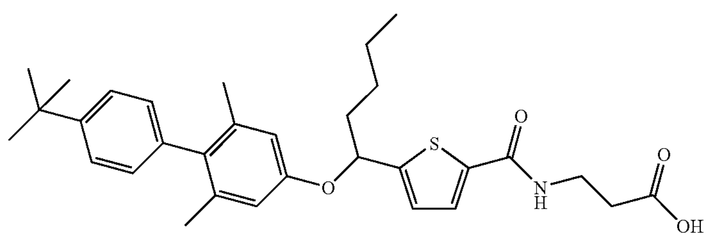 |
| X57 | 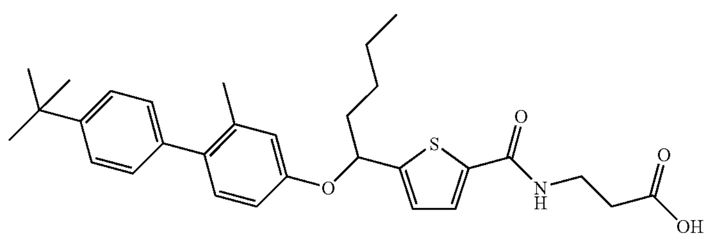 |
| X58 | 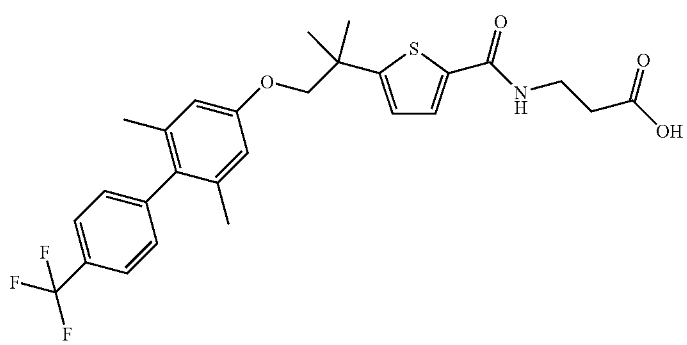 |

TABLE 1-continued

| Formula | Structure |
|---|---|
| X59 | 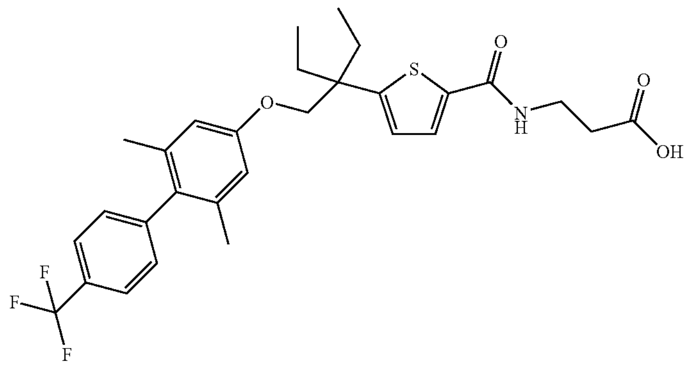 |
| X60 | 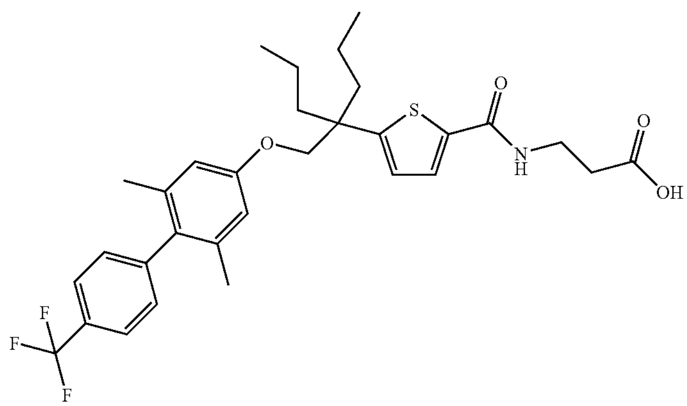 |
| X61 | 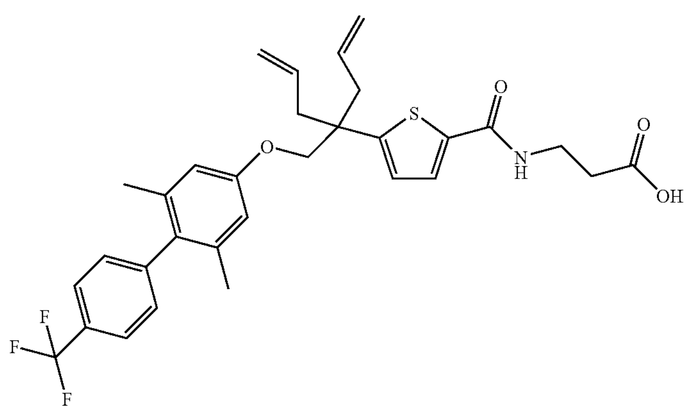 |
| X62 | 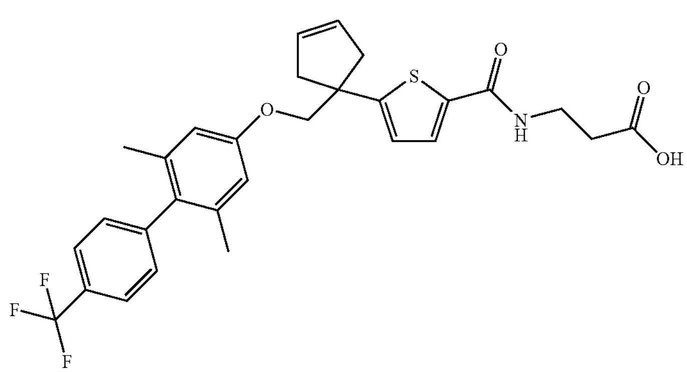 |

TABLE 1-continued
| Formula | Structure |
|---|---|
| X63 | 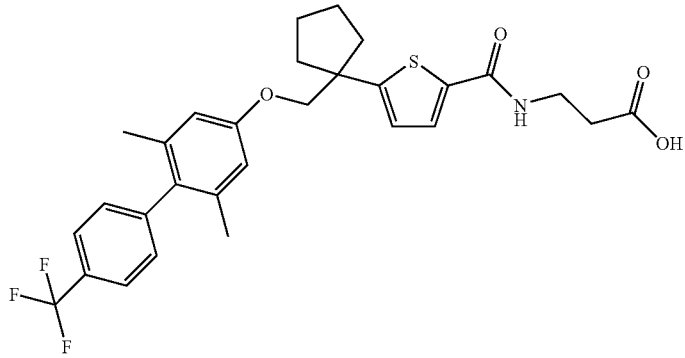 |
| X64 | 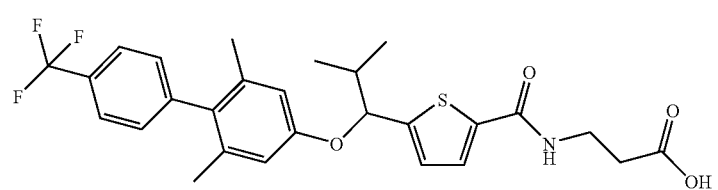 |
| X65 | 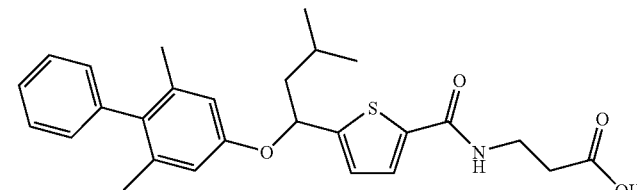 |
| X66 | 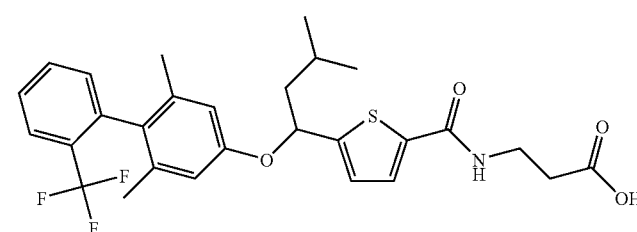 |
| X67 | 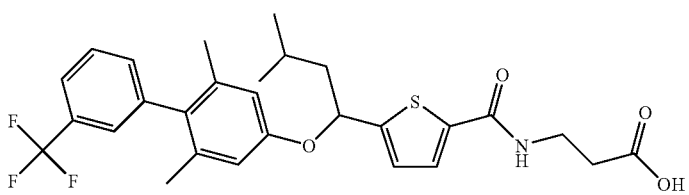 |
| X68 | 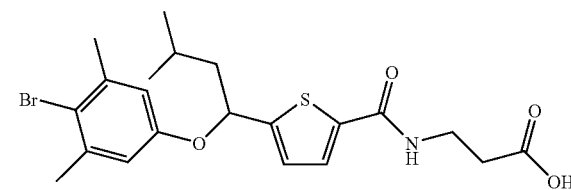 |
| X69 | 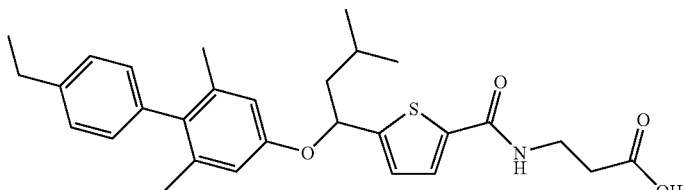 |

TABLE 1-continued

| Formula | Structure |
|---|---|
| X70 | 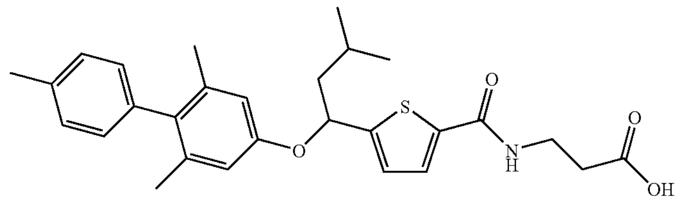 |
| X71 | 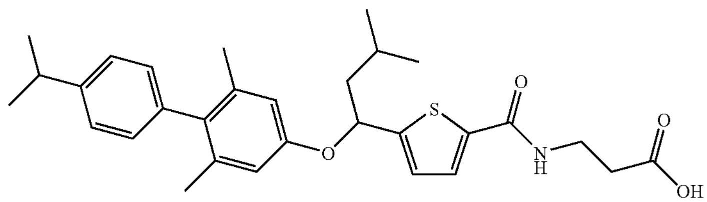 |
| X72 | 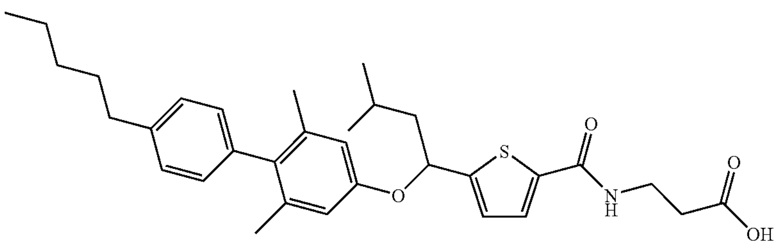 |
| X73 | 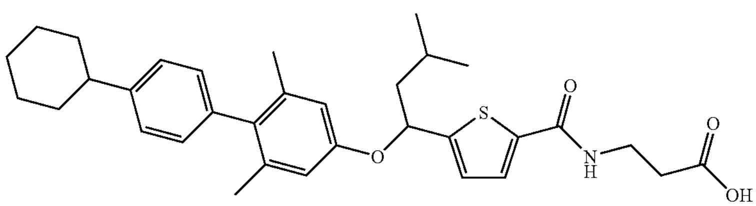 |
| X74 | 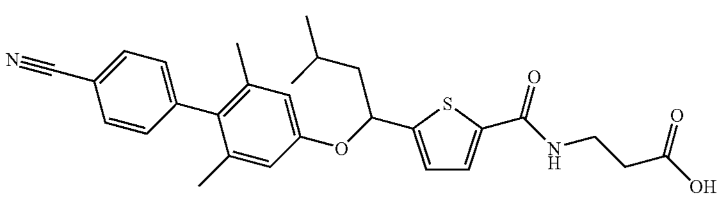 |
| X75 | 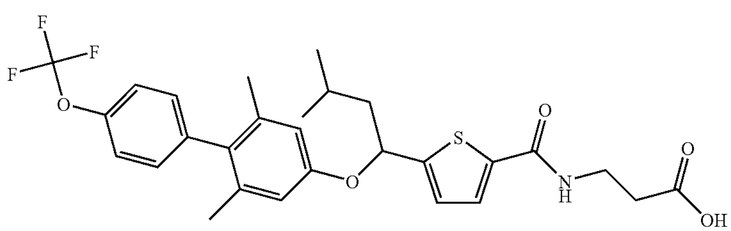 |
| X76 | 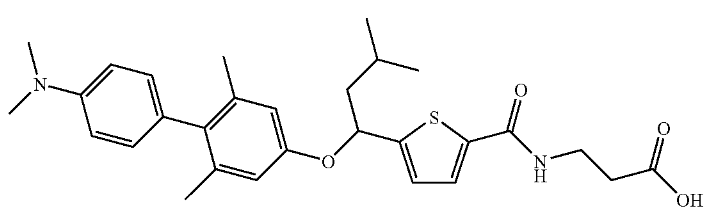 |

TABLE 1-continued
| Formula | Structure |
|---|---|
| X77 | 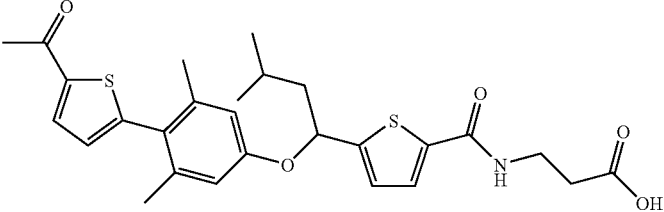 |
| X78 | 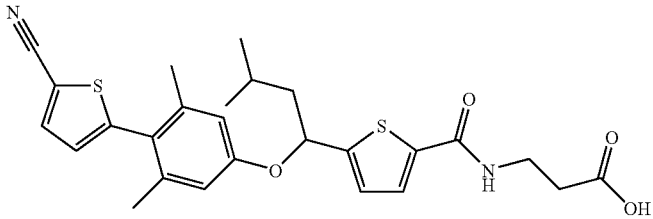 |
| X79 | 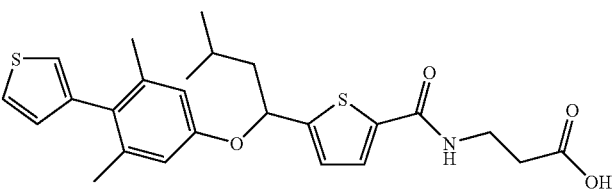 |
| X80 | 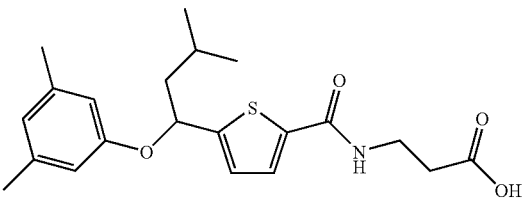 |
| X81 | 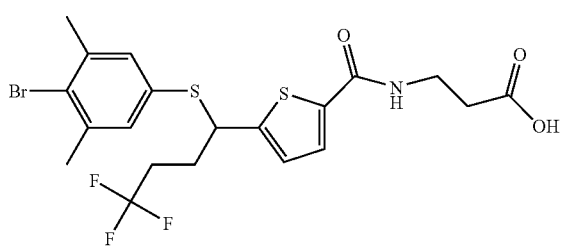 |
| X82 | 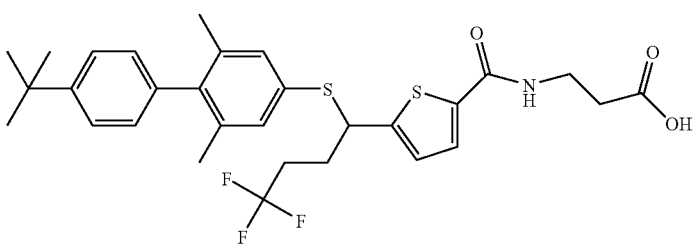 |
| X83 | 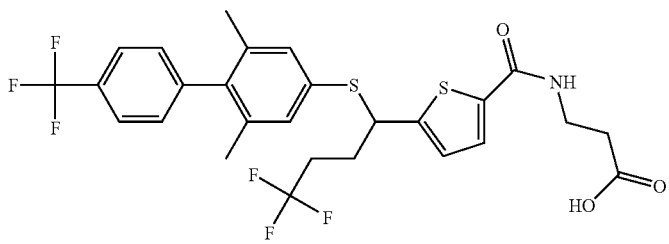 |

TABLE 1-continued

| Formula | Structure |
|---|---|
| X84 | 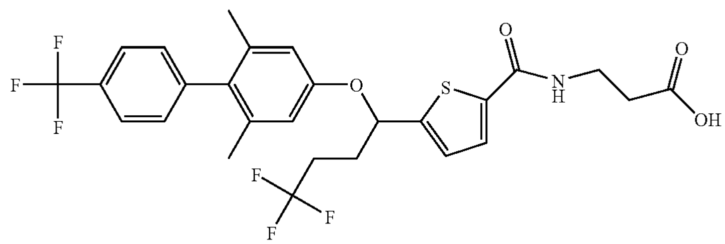 |
| X85 | 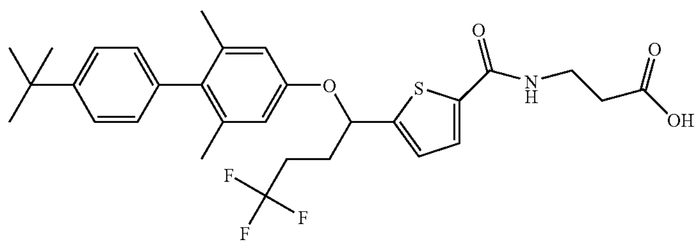 |
| X86 | 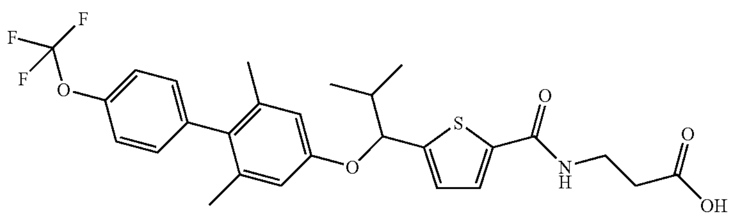 |
| X87 | 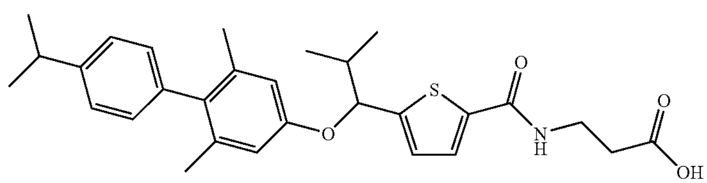 |
| X88 | 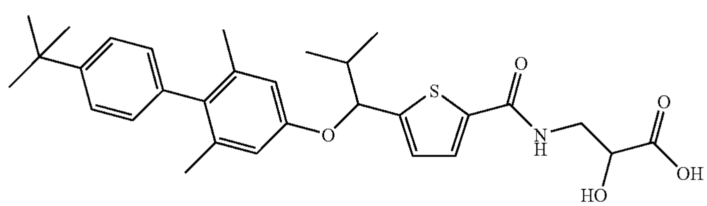 |
| X89 | 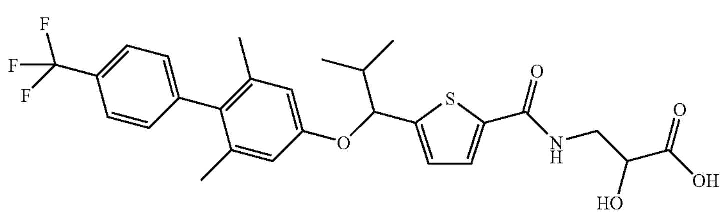 |
| X90 | 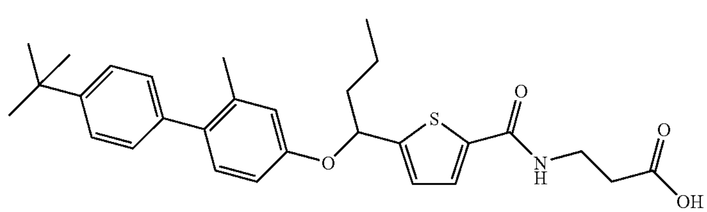 |

TABLE 1-continued

| Formula | Structure |
|---|---|
| X91 | 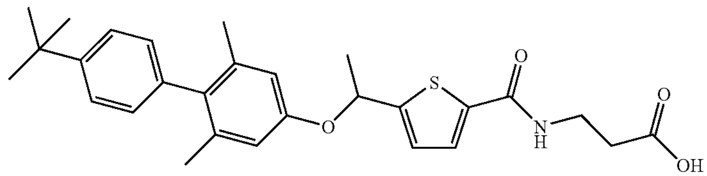 |
| X92 | 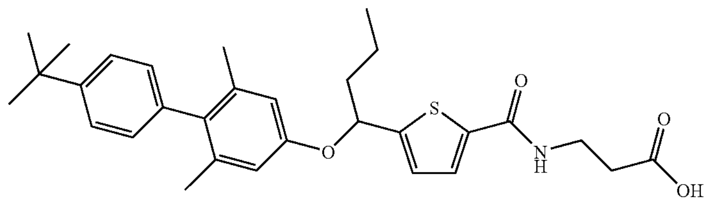 |
| X93 | 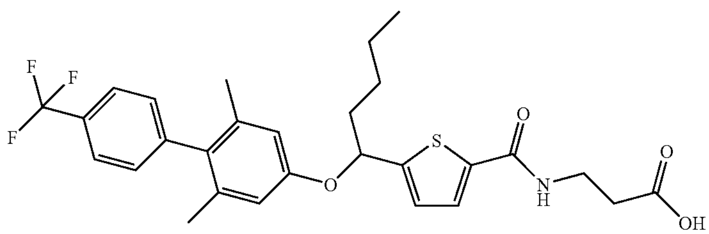 |
| X94 | 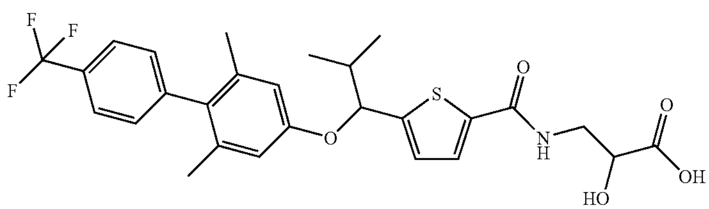 |
| X95 | 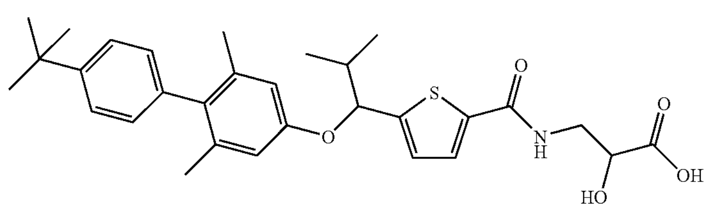 |
| X96 | 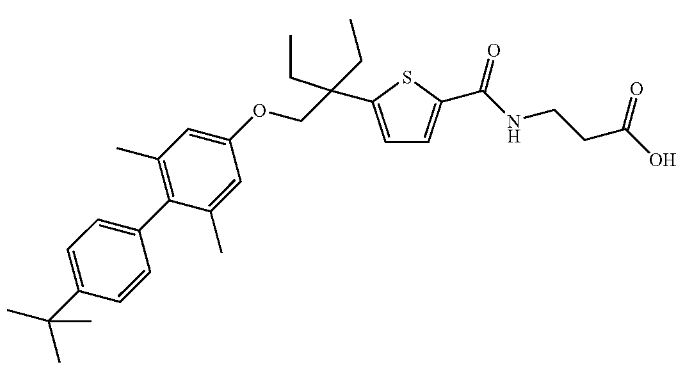 |

TABLE 1-continued
| Formula | Structure |
|---|---|
| X97 | 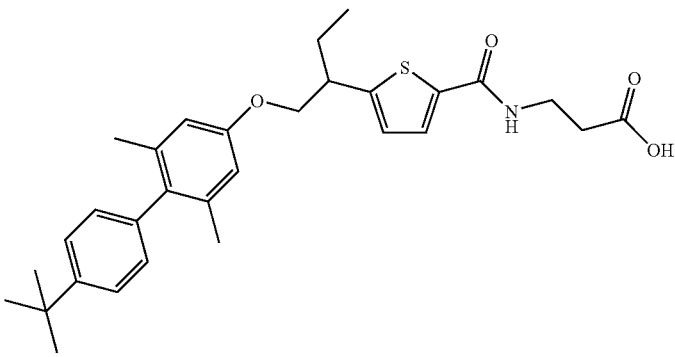 |
| X98 | 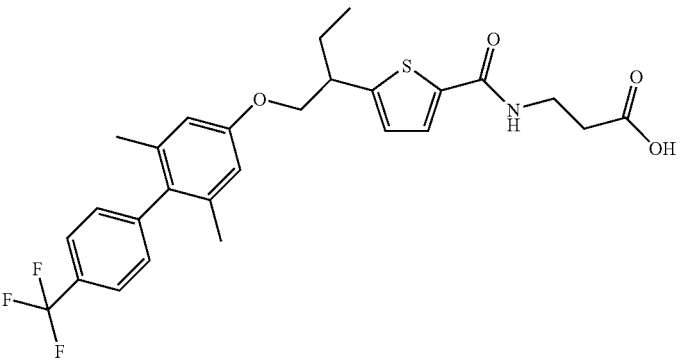 |
| X99 | 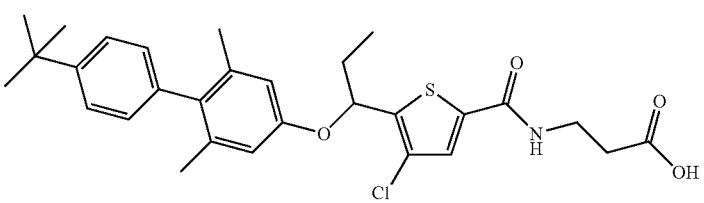 |
| X100 | 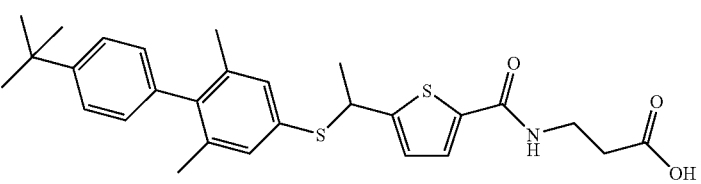 |
| X101 | 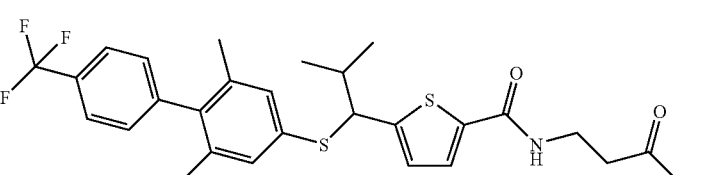 |
| X102 | 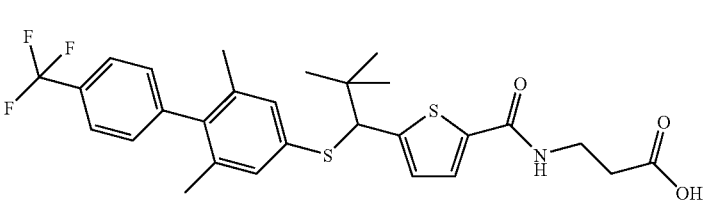 |

TABLE 1-continued

| Formula | Structure |
|---|---|
| X103 | 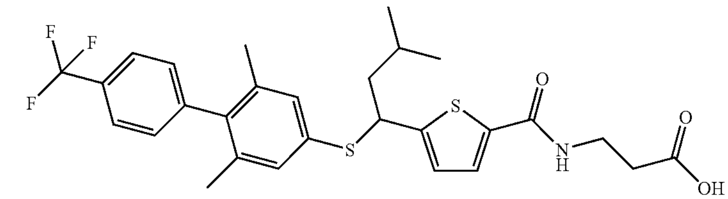 |
| X104 | 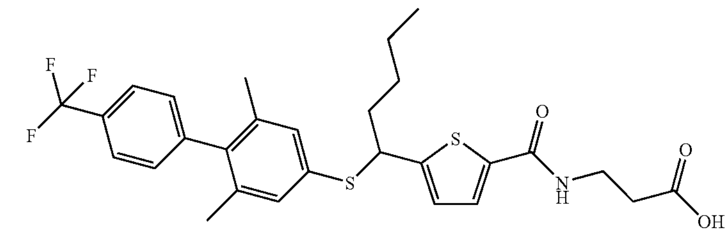 |
| X105 | 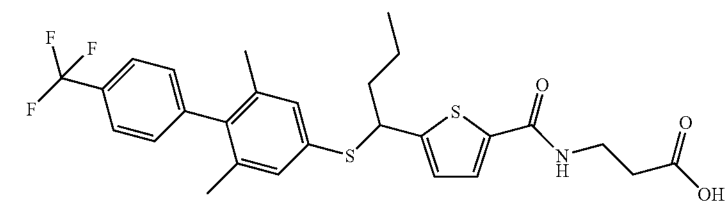 |
| X106 | 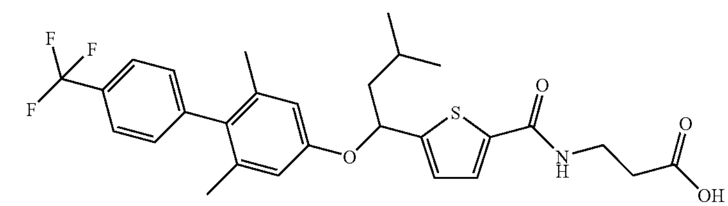 |
| X107 | 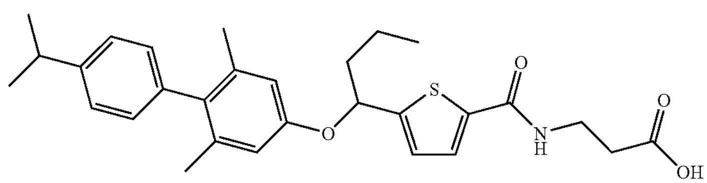 |
| X108 | 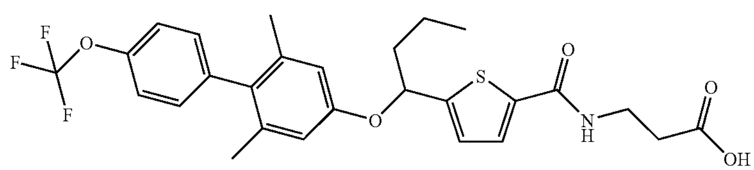 |
| X109 | 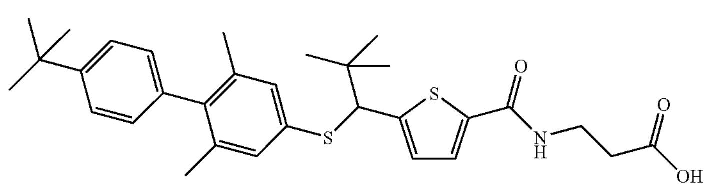 |
| X110 | 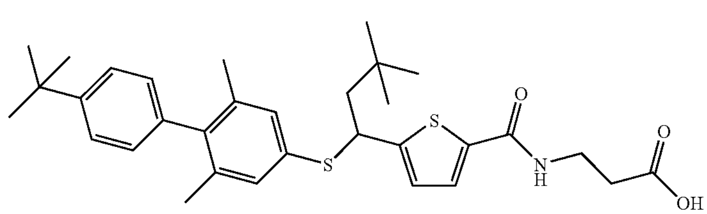 |

TABLE 1-continued

| Formula | Structure |
|---|---|
| X111 | 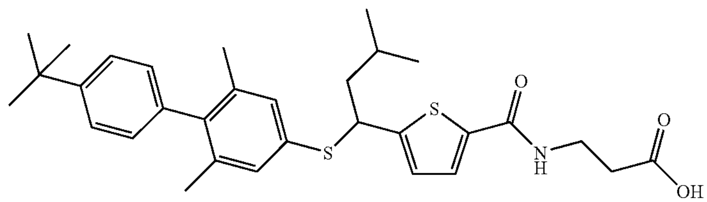 |
| X112 | 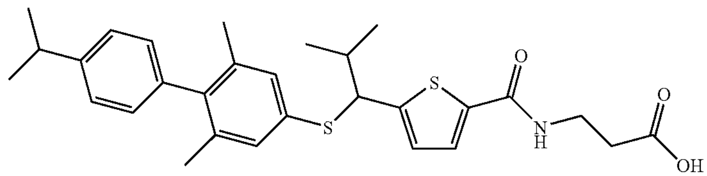 |
| X113 | 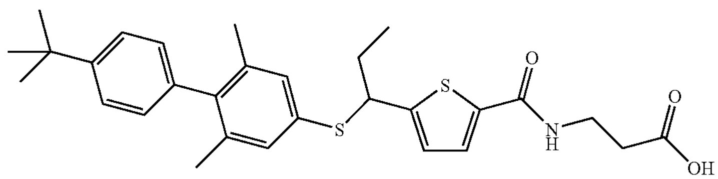 |
| X114 | 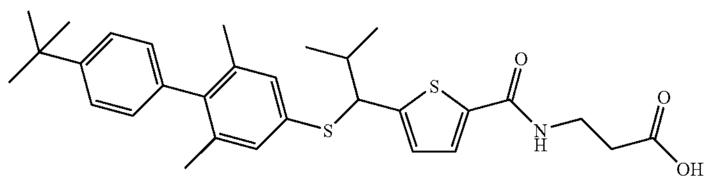 |
| X115 | 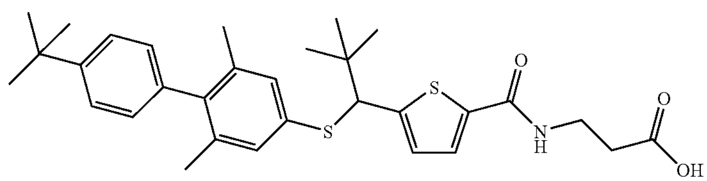 |
| X116 | 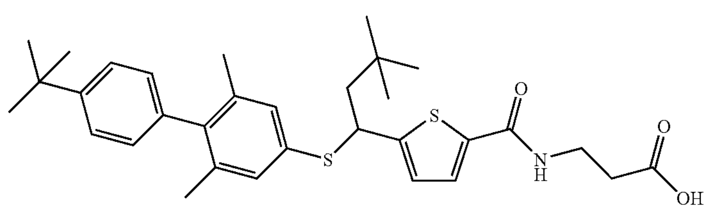 |
| X117 | 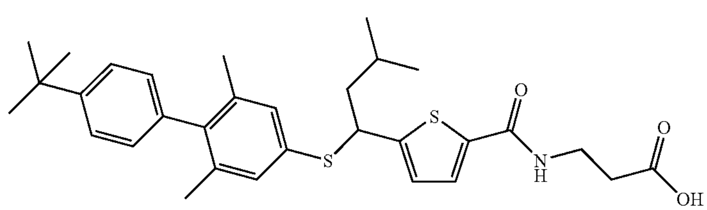 |
| X118 | 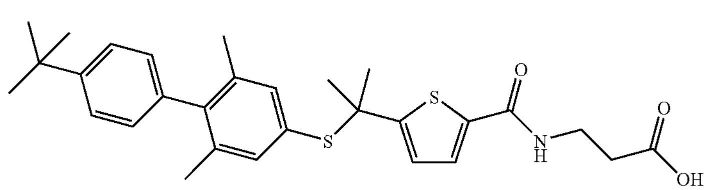 |

TABLE 1-continued
| Formula | Structure |
|---|---|
| X119 | 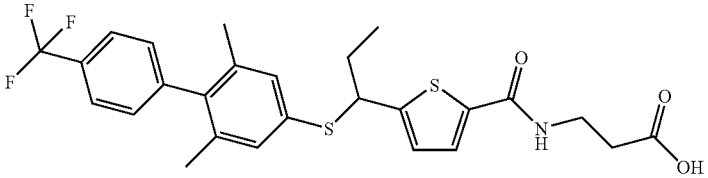 |
| X120 | 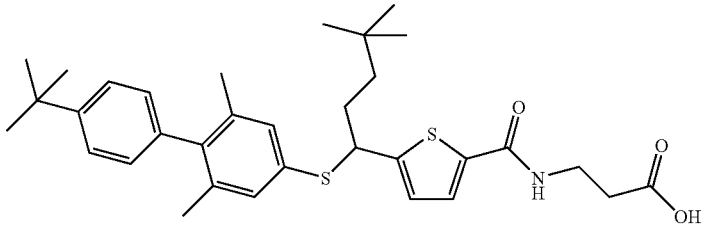 |
| X121 | 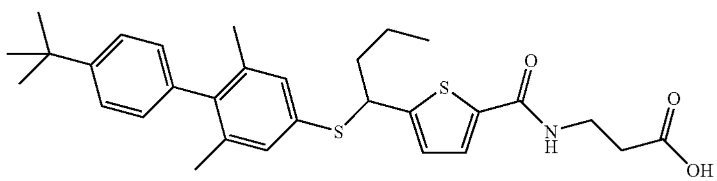 |
| X122 | 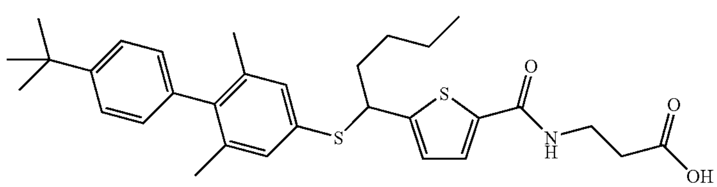 |
| X123 | 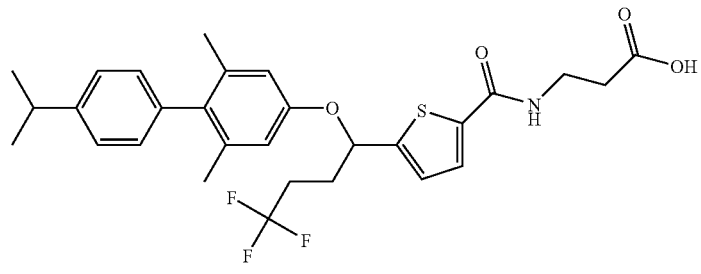 |
| X124 | 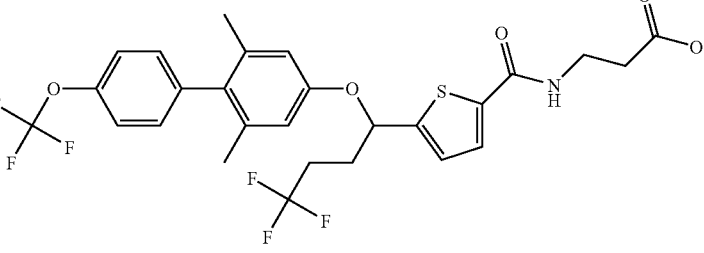 |

TABLE 1-continued

| Formula | Structure |
|---|---|
| X125 | 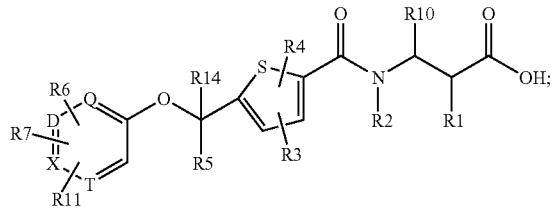 |
| X126 | 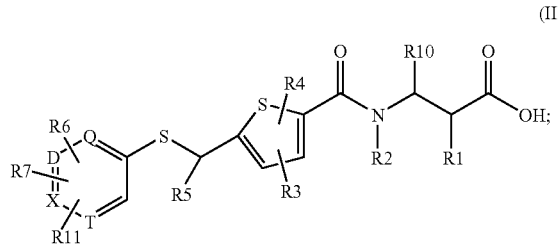 |

The following listing sets out several groups of preferred compounds. It will be understood that each of the listings may be combined with other listings to create additional groups of preferred embodiments. Other embodiments are, 1. A compound of Formula (II)

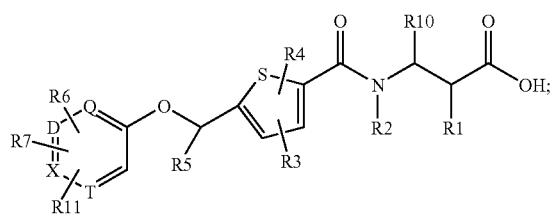

(II)

or a pharmaceutically acceptable salt thereof wherein Q, D, X, T and R1-R14 are defined as herein described.

2. A compound of Formula (III)

(III)

or a pharmaceutically acceptable salt thereof wherein Q, D, X, T and R1-R14 are defined as herein described.

3. A compound of Formula (IV)

(IV)

or a pharmaceutically acceptable salt thereof wherein Q, D, X, T and R1-R14 are defined as herein described.

Other Embodiments include compounds of formulae I-IV as follows;

4. wherein Y is —O—.
5. wherein Y is —S—.
6. wherein Y is —O—$CH_2$—.
7. wherein R1 is -hydrogen, —OH, or -halogen.
8. wherein R1 is hydrogen.
9. wherein R1 is —OH.
10. wherein R1 is halogen.
11. wherein R2 is -hydrogen, or —($C_1$-$C_3$)alkyl.
12. wherein R2 is hydrogen.
13. wherein R2 is —($C_1$-$C_3$)alkyl.
14. wherein R3 is -hydrogen, -halogen, —CN, —($C_1$-$C_7$)alkoxy, —($C_1$-$C_7$)alkyl, or —($C_2$-$C_7$)alkenyl.
15. wherein R3 is -hydrogen or -halogen.
16. wherein R4 is -hydrogen, -halogen, —CN, —($C_1$-$C_7$)alkoxy, —($C_1$-$C_7$)alkyl, or —($C_2$-$C_7$)alkenyl.
17. wherein R4 is -hydrogen or -halogen.
18. wherein R5 and R14 are independently -hydrogen, —($C_1$-$C_{12}$)alkyl, —($C_3$-$C_{12}$)cycloalkyl, —($C_3$-$C_{12}$)cycloalkyl-($C_1$-$C_{12}$)alkyl, -phenyl, -phenyl-phenyl-($C_1$-$C_{12}$)alkyl, -phenyl-($C_3$-$C_{12}$)cycloalkyl, -aryl, -aryl-($C_1$-$C_{12}$)alkyl, -heteroaryl, -heteroaryl-($C_1$-$C_{12}$)alkyl, —$(C_2-C_{12})$alkenyl, —$(C_3-C_{12})$cycloalkenyl, -heterocloalkyl, -heterocycloalkyl-$(C_1-C_{12})$alkyl, -aryl-$(C_2-C_{10})$alkenyl, -heteroaryl-$(C_2-C_{10})$alkenyl, —$(C_2-C_{12})$alkynyl, —$(C_8-C_{12})$cycloalkynyl, -aryl-$(C_2-C_{12})$alkynyl, -heteroaryl-$(C_2-C_{12})$alkynyl, wherein —$(C_1-C_{12})$alkyl, —$(C_3-C_{12})$cycloalkyl, -phenyl, -phenyl-phenyl-$(C_1-C_{12})$alkyl, -phenyl-$(C_3-C_{12})$cycloalkyl, -aryl, -aryl-$(C_1-C_{12})$alkyl, -heteroaryl, -heteroaryl-$(C_1-C_{12})$alkyl, -heterocycloalkyl, -heterocycloalkyl-$(C_1-C_{12})$alkyl, —$(C_2-C_{12})$alkenyl, —$(C_3-C_{12})$cycloalkenyl, -aryl-$(C_2-C_{10})$alkenyl, -heteroaryl-$(C_2-C_{10})$alkenyl, —$(C_2-C_{12})$alkynyl, —$(C_8-C_{12})$ cycloalkynyl, -aryl-$(C_2-C_{12})$alkynyl, or -heteroaryl-$(C_2-C_{12})$alkynyl are each optionally substituted with from one to three substituents each independently selected from the group consisting of -hydrogen, -hydroxy, -cyano, -nitro, -halo, -oxo, —$(C_1-C_7)$alkyl, —$(C_1-C_7)$alkyl-COOR12, —$(C_1-C_7)$alkoxy, —$(C_3-C_7)$cycloalkyl, -aryloxy, -aryl, -aryl-$(C_1-C_7)$alkyl, -heteroaryl,-heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

19. wherein R5 and R14 are independently -hydrogen, —$(C_1-C_{12})$alkyl, —$(C_3-C_{12})$cycloalkyl, -phenyl, -phenyl-phenyl-$(C_1-C_{12})$alkyl, -phenyl-$(C_3-C_{12})$cycloalkyl, -aryl, -aryl-$(C_1-C_{12})$alkyl, -heteroaryl, -heteroaryl-$(C_1-C_{12})$alkyl, —$(C_2-C_{12})$alkenyl, —$(C_3-C_{12})$cycloalkenyl, -heterocycloalkyl, -heterocycloalkyl-$(C_1-C_{12})$alkyl, -aryl-$(C_2-C_{10})$alkenyl, -heteroaryl-$(C_2-C_{10})$alkenyl, —$(C_2-C_{12})$alkynyl, —$(C_8-C_{12})$cycloalkynyl, -aryl-$(C_2-C_{12})$alkynyl, or -heteroaryl-$(C_2-C_{12})$alkynyl wherein optionally R5 and R14 may form a four, five, or six membered ring with the atom to which they are attached, and the ring so formed may optionally include one or two double bonds, and optionally may be substituted with up to four halogens.

20. wherein R5 and R14 are independently —$(C_1-C_{12})$alkyl, —$(C_3-C_{12})$cycloalkyl, -phenyl, -phenyl-phenyl-$(C_1-C_{12})$alkyl, -phenyl-$(C_3-C_{12})$cycloalkyl,-$(C_2-C_{12})$alkenyl, —$(C_3-C_{12})$cycloalkenyl, -heterocycloalkyl, -heterocycloalkyl-$(C_1-C_{12})$alkyl, —$(C_2-C_{12})$alkynyl, or —$(C_8-C_{12})$cycloalkynyl wherein optionally R5 and R14 may form a four, five, or six membered ring with the atom to which they are attached, and the ring so formed may optionally include one or two double bonds, and optionally may be substituted with up to four halogens.

21. wherein R5 and R14 are independently —$(C_1-C_{12})$alkyl, —$(C_3-C_{12})$cycloalkyl, —$(C_2-C_{12})$alkenyl, —$(C_3-C_{12})$cycloalkenyl, -heterocycloalkyl, -heterocycloalkyl-$(C_1-C_{12})$alkyl, —$(C_2-C_{12})$alkynyl, or —$(C_8-C_{12})$cycloalkynyl wherein optionally R5 and R14 may form a four, five, or six membered ring with the atom to which they are attached, and the ring so formed may optionally include one or two double bonds, and optionally may be substituted with up to four halogens.

22. wherein R6 and R7 are independently at each occurrence -hydrogen, -halogen, -hydroxy, —CN, —$(C_1-C_7)$alkoxy, —$(C_2-C_7)$alkenyl, —$(C_1-C_7)$alkyl, -aryl, -heteroaryl, —$(C_3-C_7)$cycloalkyl, —$(C_3-C_7)$heterocycloalkyl, wherein —$(C_2-C_7)$alkenyl, —$(C_1-C_7)$alkyl, —$(C_1-C_7)$alkoxy, -aryl, -heteroaryl, —$(C_3-C_7)$cycloalkyl, —$(C_3-C_7)$heterocycloalkyl, are each optionally substituted with from one to three substituents independently selected from the group consisting of -hydrogen, -hydroxy, -cyano, -nitro, -halo, -oxo, —$(C_1-C_7)$alkyl, —$(C_1-C_7)$alkyl-COOR12, —$(C_1-C_7)$alkoxy, —$(C_3-C_7)$cycloalkyl, -aryloxy, -aryl, -aryl-$(C_1-C_7)$alkyl, -heteroaryl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and —S(O)$_2$N(R12)$_2$; provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X; and wherein R6 and R7 may optionally form a six membered ring with the atoms to which they are attached, and the ring so formed may optionally contain up to two oxygens, and further the ring so formed may optionally be substituted with up to four halogens.

23. wherein R6 and R7 are independently at each occurrence -halogen, -hydroxy, —CN, —$(C_1-C_7)$alkoxy, —$(C_2-C_7)$alkenyl, —$(C_1-C_7)$alkyl, -aryl, -heteroaryl, —$(C_3-C_7)$cycloalkyl, —$(C_3-C_7)$heterocycloalkyl, wherein —$(C_2-C_7)$alkenyl, —$(C_1-C_7)$alkyl, —$(C_1-C_7)$alkoxy; -aryl, -heteroaryl, —$(C_3-C_7)$cycloalkyl, —$(C_3-C_7)$heterocycloalkyl, are each optionally substituted with from one to three substituents independently selected from the group consisting of -hydrogen, -hydroxy, -cyano, -nitro, -halo, -oxo, —$(C_1-C_7)$alkyl, —$(C_1-C_7)$alkyl-COOR12, —$(C_1-C_7)$alkoxy, —$(C_3-C_7)$cycloalkyl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and —S(O)$_2$N(R12)$_2$; provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X; and wherein R6 and R7 may optionally form a six membered ring with the atoms to which they are attached, and the ring so formed may optionally contain up to two oxygens, and further the ring so formed may optionally be substituted with up to four halogens.

24. wherein R6 and R7 are independently at each occurrence -hydrogen, -halogen, -hydroxy, —CN, —$(C_1-C_7)$alkoxy, —$(C_2-C_7)$alkenyl, —$(C_1-C_7)$alkyl, wherein —$(C_2-C_7)$alkenyl, —$(C_1-C_7)$alkyl, —$(C_1-C_7)$alkoxy, -aryl, -heteroaryl, —$(C_3-C_7)$cycloalkyl, —$(C_3-C_7)$heterocycloalkyl, provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X.

25. wherein R8 and R9 are independently at each occurrence -hydrogen, -hydroxy, —CN, -nitro, -halo, —$(C_1-C_7)$alkyl, —$(C_1-C_7)$alkoxy, —$(C_3-C_7)$cycloalkyl, -aryl, -aryl-$(C_1-C_7)$alkyl, -heteroaryl, -heteroaryl-$(C_1-C_7)$alkyl, -aryloxy, —C(O)R12, —COOR12, —OC(O)R12, —OS(O)$_2$R12, —N(R12)$_2$, —NR12C(O)R12, —NR12SO$_2$ R12, —SR12, —S(O)R12, —S(O)$_2$R12, and —S(O)$_2$N(R12)$_2$; and wherein —$(C_1-C_7)$alkyl, —$(C_1-C_7)$alkoxy, —$(C_3-C_7)$cycloalkyl, -aryl, -aryl-$(C_1-C_7)$alkyl, -heteroaryl, -heteroaryl-$(C_1-C_7)$alkyl, -aryloxy, are each optionally substituted with from one to three substituents independently selected from the group consisting of -hydrogen, -hydroxy, -cyano, -nitro, -halo, -oxo, —$(C_1-C_7)$alkyl, —$(C_1-C_7)$alkyl-COOR12, —(C$_1$-C$_7$)alkoxyl, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and —S(O)$_2$N(R12)$_2$.

26. wherein R8 and R9 are independently at each occurrence -hydrogen, -hydroxy, —CN, -nitro, -halo, —(C$_1$-C$_7$)alkyl, —(C$_1$-C$_7$)alkoxy, —(C$_3$-C$_7$)cycloalkyl, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, and —S(O)$_2$N(R12)$_2$; and wherein —(C$_1$-C$_7$)alkyl, —(C$_1$-C$_7$)alkoxy, —(C$_3$-C$_7$)cycloalkyl, are each optionally substituted with from one to three substituents independently selected from the group consisting of -hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxyl, —(C$_3$-C$_7$)cycloalkyl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and —S(O)$_2$N(R12)$_2$.

27. wherein R8 and R9 are independently at each occurrence -hydrogen, -hydroxy, —CN, -nitro, -halo, —(C$_1$-C$_7$)alkyl, —CF$_3$, —(C$_1$-C$_7$)alkoxy, —(C$_3$-C$_7$)cycloalkyl, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, and —S(O)$_2$N(R12)$_2$.

28. wherein R10 is independently -hydrogen, -halogen, —(C$_1$-C$_{12}$)alkyl, -cycloalkyl, -aryl, -aryl-(C$_1$-C$_7$)alkyl, -heteroaryl, -heteroaryl—(C$_1$-C$_7$)alkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_8$-C$_{12}$)cycloalkynyl, -aryl-(C$_2$-C$_{12}$)alkynyl, -heteroaryl-(C$_2$-C$_{12}$)alkynyl, and wherein —(C$_1$-C$_{12}$)alkyl, -cycloalkyl, -aryl, -aryl-(C$_1$-C$_7$)alkyl, -heteroaryl, -heteroaryl—(C$_1$-C$_7$)alkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_8$-C$_{12}$)cycloalkynyl, -aryl-(C$_2$-C$_{12}$)alkynyl, -heteroaryl-(C$_2$-C$_{12}$)alkynyl, are each optionally substituted with from one to three substituents each independently selected from the group consisting of -hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxyl, —(C$_3$-C$_7$)cycloalkyl, -aryloxy, -aryl, -aryl-C$_1$-C$_7$ alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$.

29. wherein R10 is -hydrogen, -halogen, —(C$_1$-C$_{12}$)alkyl, -cycloalkyl —(C$_2$-C$_{12}$)alkenyl, —(C$_3$-C$_{12}$)cycloalkenyl, -aryl-(C$_2$-C$_{10}$)alkenyl, —(C$_2$-C$_{12}$)alkynyl, —(C$_8$-C$_{12}$)cycloalkynyl.

30. wherein R10 is -hydrogen, -halogen, —(C$_1$-C$_{12}$)alkyl.

31. wherein R10 is —H.

32. wherein R11 is independently at each occurrence —H or

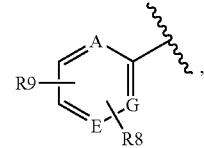

wherein the zig-zag mark represents the point of attachment to the R11 position in formulae I-IV, wherein A, G, and E independently represent carbon or nitrogen, provided that no more than two of A, G, and E are nitrogen; provided however that wherein A is nitrogen, then R8 or R9 are not attached to A, and provided that wherein G is nitrogen, then R8 or R9 are not attached to G, and provided that wherein E is nitrogen, then R8 or R9 are not attached to E; or

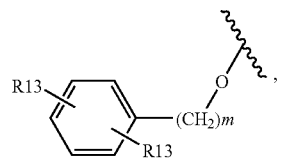

wherein the zig-zag mark represents the point of attachment to the R11 position in formulae I-IV, wherein m is an integer of 0, 1, 2, or 3, and when m is 0 then (CH$_2$)m is a bond, provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

33. wherein A, G, and E are carbon.
34. wherein one of A, G, or E is nitrogen.
35. wherein two of A, G, or E are nitrogen.
36. wherein R12 is independently at each occurrence -hydrogen, —(C$_1$-C$_7$)alkyl.
37. wherein R13 is independently at each occurrence -hydrogen, -halogen, —(C$_1$-C$_7$) alkyl, —CF$_3$, —OCF$_3$, —(C$_2$-C$_7$)alkenyl, wherein —(C$_1$-C$_7$)alkyl, —(C$_2$-C$_7$)alkenyl are each optionally substituted once with substituents independently selected from the group consisting of —CF$_3$, —OCF$_3$.
38. wherein Q, D, X and T independently represent carbon or nitrogen, provided that no more than two of Q, D, X and T are nitrogen.
39. wherein D, Q, X and T are carbon.
40. wherein X is carbon and R11 is attached to X.
41. wherein D is carbon and R11 is attached to D.
42. wherein X is carbon and R11 is attached to X and R11 is selected from the group consisting of

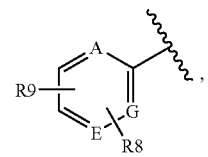

wherein the zig-zag mark represents the point of attachment to the R11 position in formula I, II, III, or IV, and wherein A, G, and E independently represent carbon or nitrogen, provided that no more than two of A, G, and E are nitrogen.

43. wherein X is carbon and R11 is attached to X and R11 is selected from the group consisting of

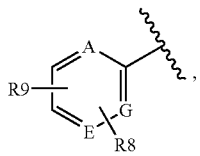

wherein the zig-zag mark represents the point of attachment to the R11 position in formula I, II, III, or IV, and wherein A, G, and E independently represent carbon or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, and —S(O)$_2$N(R12)$_2$.

44. wherein X is carbon and R11 is attached to X and R11 is selected from the group consisting of

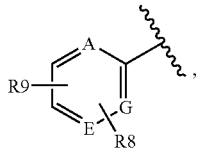

wherein the zig-zag mark represents the point of attachment to the R11 position in formula I, II, III, or IV, and wherein A, G, and E independently represent carbon or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl.

45. wherein X is carbon and R11 is attached to X and R11 is selected from the group consisting of

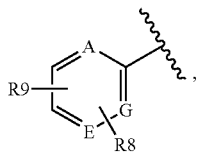

wherein the zig-zag mark represents the point of attachment to the R11 position in formula I, II, III, or IV and wherein A, G, and E are carbon.

46. wherein X is carbon and R11 is attached to X and R11 is selected from the group consisting of

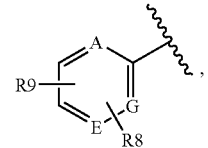

wherein the zig-zag mark represents the point of attachment to the R11 position in formula I, II, III, or IV, and wherein A, G, and E are carbon, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, and —S(O)$_2$N(R12)$_2$.

47. wherein X is carbon and R11 is attached to X and R11 is selected from the group consisting of

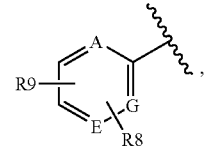

wherein the zig-zag mark represents the point of attachment to the R11 position in formula I, II, III, or IV, and wherein A, G, and E are carbon, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl.

48. wherein one of D, X, Q or T is nitrogen.
49. wherein D is nitrogen.
50. wherein X is nitrogen.
51. wherein Q is nitrogen.
52. wherein T is nitrogen.
53. wherein two of D, X, Q and T are nitrogen.
54. wherein D and T are nitrogen.
55. wherein Q and X are nitrogen.
56. wherein m is 0, 1, 2, or 3.
57. wherein ($CH_2$)m is a bond.
58. wherein ($CH_2$)m is —$CH_2$—.

Due to their interaction with the glucagon receptor, the present compounds are useful in the treatment of a wide range of conditions and disorders in which an interaction with the glucagon receptor is beneficial. These disorders and conditions are defined herein as "diabetic and other glucagon related metabolic disorders". One of skill in the art is able to identify "diabetic and other glucagon related metabolic disorders" by the involvement of glucagon receptor mediated signaling either in the pathophysiology of the disorder, or in the homeostatic response to the disorder. Thus, the compounds may find use for example to prevent, treat, or alleviate, diseases or conditions or associated symptoms or sequelae, of the endocrinological system, the central nervous system, the peripheral nervous system, the cardiovascular system, the pulmonary system, and the gastrointestinal system, while reducing and or eliminating one or more of the unwanted side effects associated with the current treatments. "Diabetic and other glucagon related metabolic disorders" include, but are not limited to, diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, syndrome X, type 1 diabetes, type 2 diabetes, hyperlipidemia, dyslipidemia, hypertriglycerideinia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

In addition, the present invention relates to a compound of Formulae I-IV, or a pharmaceutical salt thereof; for use in inhibiting the glucagon receptor; for use in inhibiting a glucagon receptor mediated cellular response in a mammal; for use in reducing the glycemic level in a mammal; for use in treating a disease arising from excessive glucagon; for use in diabetic and other glucagon related metabolic disorders in a mammal; and for use in treating diabetes, obesity, hyperglycemia, atherosclerosis, ischemic heart disease, stroke, neuropathy, and wound healing. Thus, the uses and methods of this invention encompass a prophylactic and therapeutic administration of a compound of Formulae I-IV.

The present invention is further related to the use of a compound of Formulae I-IV, or a pharmaceutical salt thereof; for the manufacture of a medicament for inhibiting the glucagon receptor; for the manufacture of a medicament for inhibiting a glucagon receptor mediated cellular response in a mammal; for the manufacture of a medicament for reducing the glycemic level in a mammal; for the manufacture of a medicament for treating a disease arising from excessive glucagon; for the manufacture of a medicament for treating diabetic and other glucagon related metabolic disorders in a mammal; and for the manufacture of a medicament for treating diabetes, obesity, hyperglycemia, atherosclerosis, ischemic heart disease, stroke, neuropathy, and wound healing.

The present invention further provides; a method of treating conditions resulting from excessive glucagon in a mammal; a method of inhibiting the glucagon receptor in a mammal; a method of inhibiting a glucagon receptor mediated cellular response in a mammal; a method of reducing the glycemic level in a mammal; a method of treating diabetic and other glucagon related metabolic disorders in a mammal; a method of treating diabetes, obesity, hyperglycemia, atherosclerosis, ischemic heart disease, stroke, neuropathy, and wound healing; comprising administering to a mammal in need of such treatment a glucagon receptor-inhibiting amount of a compound of Formulae I-IV or a pharmaceutically acceptable salt thereof.

The present invention provides a pharmaceutical composition which comprises a compound of Formulae I-IV, or a pharmaceutical salt thereof, and a pharmaceutically acceptable carrier, diluent, or excipient.

In addition, the present invention relates to a pharmaceutical composition which comprises a compound of Formulae I-IV, or a pharmaceutical salt thereof, and a pharmaceutically acceptable carrier, diluent, or excipient; adapted for use in inhibiting the glucagon receptor; adapted for use in inhibiting glucagon receptor mediated cellular responses; adapted for use in reducing the glycemic level in a mammal; adapted for use in treating diabetic and other glucagon related metabolic disorders in a mammal; adapted for use in preventing or treating diabetes, obesity, hyperglycemia, atherosclerosis, ischemic heart disease, stroke, neuropathy, and wound healing.

The present invention is further related to the use of a pharmaceutical composition which comprises a compound of Formulae I-IV, or a pharmaceutical salt thereof, and a pharmaceutically acceptable carrier, diluent, or excipient; for the manufacture of a medicament for inhibiting the glucagon receptor; for the manufacture of a medicament for inhibiting glucagon receptor mediated cellular responses; for the manufacture of a medicament for reducing the glycemic level in a mammal; for the manufacture of a medicament for treating diabetic and other glucagon related metabolic disorders in a mammal; and for the manufacture of a medicament for treating diabetes, obesity, hyperglycemia, atherosclerosis, ischemic heart disease, stroke, neuropathy, and wound healing.

The present invention further provides a method of treating conditions resulting from excessive glucagon in a mammal comprising administering to a mammal in need of such treatment a glucagon receptor inhibiting amount of a pharmaceutical composition which comprises a compound of Formulae I-IV, or a pharmaceutical salt thereof, and a pharmaceutically acceptable carrier, diluent, or excipient.

The present invention also provides; a method of selectively reducing the glycemic level in a mammal; a method of inhibiting hyperglycemia in a mammal; a method of treating diabetic and other glucagon related metabolic disorders in a mammal comprising administering to a mammal comprising administering to a mammal in need of such treatment a glucagon receptor inhibiting amount of a pharmaceutical composition which comprises a compound of Formulae I-IV, or a pharmaceutical salt thereof, and a pharmaceutically acceptable carrier, diluent, or excipient. Furthermore, a compound of Formulae I-IV may be applicable as diagnostic agents for identifying patients having a defect in the glucagon receptor, as a therapy to increase gastric acid secretions and to reverse intestinal hypomobility due to glucagon administration.

In addition, a pharmaceutical composition of Formulae I-IV can be useful in the treatment or prevention of a disorder or disease in which modulation of glucagon receptor activity has a beneficial effect. The present invention further provides an antagonist or inverse agonist of Formulae I-IV which is characterized by having greater affinity for the glucagon receptor as compared to the affinity for the GLP-1 receptor.

The present compounds are effective in lowering the blood glucose, both in the fasting and the postprandial stage. In still another embodiment of the invention the present compounds are used for the preparation of a pharmaceutical composition for the treatment of IGT. In a further embodiment of the invention the present compounds are used for the preparation of a pharmaceutical composition for the treatment of type 2 diabetes. In yet a further embodiment of the invention the present compounds are used for the preparation of a pharmaceutical composition for the delaying or prevention of the progression from IGT to type 2 diabetes. In yet another embodiment of the invention the present compounds are used for the preparation of a pharmaceutical composition for the delaying or prevention of the progression from non-insulin requiring type 2 diabetes to insulin requiring type 2 diabetes. In a further embodiment of the invention the present compounds are used for the preparation of a pharmaceutical composition for the treatment of type 1 diabetes. Such treatment is normally accompanied by insulin therapy. In yet a further embodiment of the invention the present compounds are used for the preparation of a pharmaceutical composition for the treatment of obesity. In still a further embodiment of the invention the present compounds are used for the preparation of a pharmaceutical composition for the treatment of disorders of the lipid metabolism. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise.

General terms used in the description of compounds, compositions, and methods herein described, bear their usual meanings. Throughout the instant application, the following terms have the indicated meanings: "GLP-1" means glucagon-like peptide 1. The term "glucagon receptor" means one or more receptors that interact specifically with glucagon to result in a biological signal. The term "GLP-1 receptor" means one or more receptors that interact specifically with glucagon-like peptide 1 to result in a biological signal.

The term "glucagon receptor antagonist" is defined as a compound of the present invention with the ability of to block cAMP production in response glucagon.

The term "glucagon receptor inverse agonist" is defined as a compound of the present invention with the ability of to inhibit the constitutive activity of glucagon receptor. The term "selective" antagonist or inverse agonist means a compound having greater affinity for the glucagon receptor as compared to the affinity for the GLP-1 receptor.

In the general formulae of the present document, the general chemical terms have their usual meanings. For example;

"Halogen" or "halo" means fluoro, chloro, bromo and iodo.

The term "alkyl," unless otherwise indicated, refers to those alkyl groups of a designated number of carbon atoms of either a straight or branched saturated configuration. "$(C_1$-$C_3)$alkyl" are one to three carbon atoms, such as methyl, ethyl, propyl, n-propyl, isopropyl, and the like and branched or isomeric forms thereof, and optionally may be substituted with one to three halogens or a designated number of substituents as set forth in the embodiments recited herein, "$(C_1$-$C_7)$alkyl" are one to seven carbon atoms such as methyl, ethyl, propyl, n-propyl, isopropyl, n-butyl, isobutyl, sec-butyl and tert-butyl, pentyl, isopentyl, hexyl, heptyl, and the like, and branched or isomeric forms thereof, and optionally may be substituted with one to three halogens or a designated number of substituents as set forth in the embodiments recited herein, and "$(C_1$-$C_{10})$alkyl" are one to ten carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein. "$(C_1$-$C_{12})$alkyl" are one to twelve carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein.

The term "$(C_3$-$C_{12})$cycloalkyl" refers to a saturated or partially saturated carbocycle containing one or more rings of from 3 to 12 carbon atoms, typically 3 to 7 carbon atoms optionally substituted with up to three halogens. Examples of $(C_3$-$C_{12})$ cycloalkyl include but are not limited to cyclopropyl, cyclobutyl, cyclopentyl, cyclohexyl and cycloheptyl, and the like. "$(C_3$-$C_7)$cycloalkyl" means a ring with three to seven carbon atoms such as cyclopropyl, cyclobutyl, cyclopentyl and cyclohexyl, cycloheptyl, and the like, optionally substituted with up to three halogens.

The term " $(C_1$-$C_7)$alkoxy" represents an alkyl group of one to seven carbon atoms attached through an oxygen bridge, such as methoxy, ethoxy, propoxy, isopropoxy, butoxy, tert-butoxy, pentoxy, and the like, and may be optionally substituted with three halogens or a designated number of substituents as set forth in the embodiments recited herein.

The terms "$(C_2$-$C_7)$alkenyl", "$(C_2$-$C_{10})$alkenyl", "$(C_2$-$C_{10})$alkylenyl", "$(C_2$-$C_{12})$alkenyl", or "$(C_2$-$C_{12})$alkylenyl" means hydrocarbon chains of the indicated number of carbon atoms, of either a straight or branched configuration, having at least one carbon-carbon double bond which may occur at any point along the chain, such as ethenyl, propenyl, butenyl, pentenyl, vinyl, alkyl, 2-butenyl and the like, and may be optionally substituted with one to three halogens or a designated number of substituents as set forth in the embodiments recited herein.

The term "$(C_3$-$C_{12})$ cycloalkenyl " refers to a partially saturated carbocycle containing one or more rings of from 3 to 12 carbon atoms, typically 3 to 7 carbon atoms optionally substituted with up to three halogens.

The term "$(C_2$-$C_{12})$alkynyl" means hydrocarbon chain of two to twelve carbon atoms of either a straight or branched configuration and having at least one carbon-carbon triple bond, which may occur at any point along the chain. Example of alkynyl is acetylene. Alkynyl as defined above may be optionally substituted with up to three halogens or the designated number of substituents as set forth in the embodiments recited herein.

The term "$(C_8$-$C_{12})$ cycloalkynyl" refers to a carbocycle containing one or more rings of from 8 to 12 carbon atoms, having at least one carbon-carbon triple bond which may occur at any point along the chain or ring, optionally substituted with up to three halogens. Cycloalkynyl as defined above may be optionally substituted with up to three halogens or the designated number of substituents as set forth in the embodiments recited herein.

As used herein, the terms "Aryl" or "aryl" include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl), which may contain one or more fused or non-fused phenyl rings, and includes, for example, phenyl, biphenyl, 1- or 2-naphthyl, 1,2-dihydronaphthyl, 1,2,3,4-tetrahydronaphthyl, and the like. In addition, the aryl group may be unsubstituted or may be optionally substituted with a designated number of substituents as set forth in the embodiments recited herein.

The term "aryloxy" refers to an aryl group that is linked to the parent molecule through an oxygen bridge. The term "aryloxy" includes, but is not limited to carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl), which may contain one or more fused or non-fused phenyl rings, and includes, for example, phenyl, biphenyl, 1- or 2-naphthyl, 1,2-dihydronaphthyl, 1,2,3,4-tetrahydronaphthyl, and the like linked to the parent molecule through an oxygen bridge.

The term "heteroaryl" group, as used herein, is an aryl ring system having at least one heteroatom such as nitrogen, sulfur or oxygen and includes monocyclic, bicyclic or tricyclic aromatic rings of 5- to 14-carbon atoms containing one or more heteroatoms selected from the group consisting of O, N, and S. The "heteroaryl" as defined above may be optionally substituted with a designated number of substituents as set forth in the embodiments recited herein. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroaryl" also includes, but is not limited to the following:

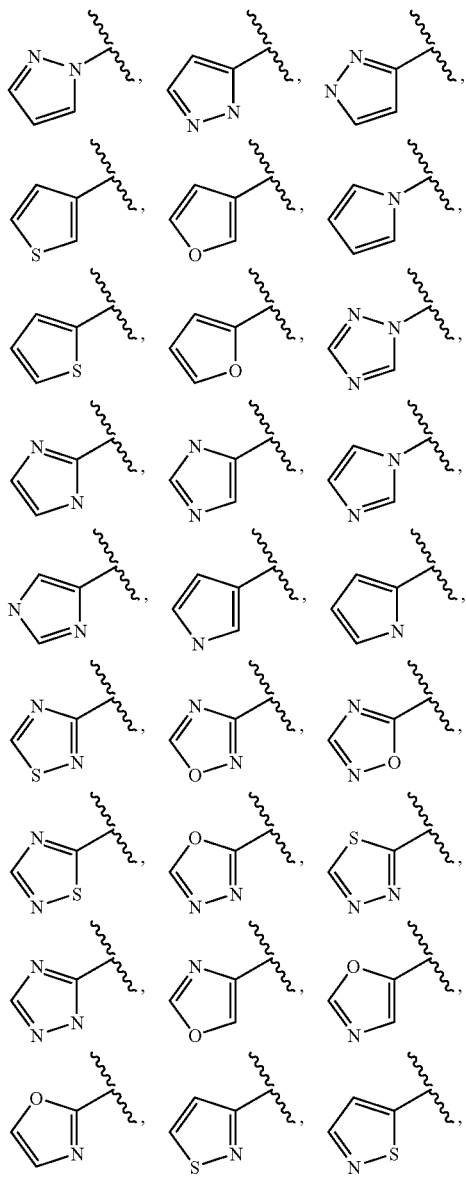

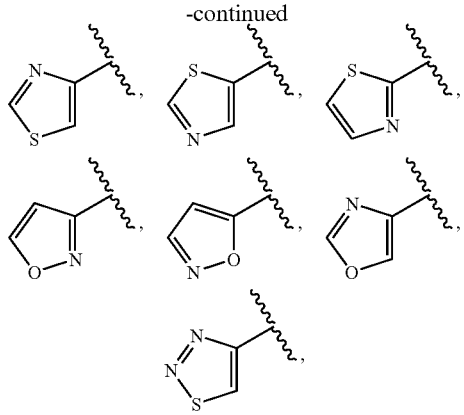

wherein the zig-zag mark, represents the point of attachment to the position indicated for heteroaryl in the parent molecule.

The term "arylalkyl" refers to an aryl alkyl group which is linked to the parent molecule through the alkyl group, which may be further optionally substituted with a designated number of substituents as set forth in the embodiment recited herein. Likewise, arylheteroalkyl means an aryl group linked to the parent molecule through the heteroalkyl group.

The term "acyl" refers to alkylcarbonyl species.

The term "heterocycloalkyl" refers to a non-aromatic ring which contains one or more oxygen, nitrogen or sulfur and includes a monocyclic, bicyclic or tricyclic non-aromatic ring of 3 to 14 carbon atoms containing one or more heteroatoms selected from O, N, or S. "—($C_3$-$C_7$) heterocycloalkyl" refers to a non-aromatic ring which contains one or more oxygen, nitrogen or sulfur and includes a monocyclic, bicyclic or tricyclic non-aromatic ring of 3 to 7 carbon atoms containing one or more heteroatoms selected from O, N, or S.

The term "optionally substituted" as used herein means that the groups in question are either unsubstituted or substituted with one or more of the substituents specified. When the groups in question are substituted with more than one substituent, the substituents may be the same or different.

Furthermore, when using the terms "independently", "independently are" and "independently selected from" it should be understood that the groups in question may be the same or different.

The term "patient" includes human and non-human animals, such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The term "a glucagon receptor mediated cellular response" includes various responses by mammalian cells to glucagon stimulation or glucagon receptor activity. For example "glucagon receptor mediated cellular responses" include but are not limited to release of glucose from liver, or other cells, in response to glucagon stimulation or glucagon receptor activity. One of ordinary skill in the art can readily identify other cellular responses mediated by glucagon receptor activity, for example by observing a change in the responsive cellular endpoint after contacting the cell with an effective dose of glucagon.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formulae I-IV and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

Certain of the above defined terms may occur more than once in the structural formulae, and upon such occurrence each term shall be defined independently of the other.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The compounds of the present invention may be chiral, and it is intended that any enantiomers, as separated, pure or partially purified enantiomers or racemic mixtures thereof are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of Formulae I-IV. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counter-clockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation " ▬ " refers to a bond that protrudes forward out of the plane of the page. The designation " ▪▪▪▪▪▪ " refers to a bond that protrudes backward out of the plane of the page. The designation " ∿∿ " refers to a bond wherein the stereochemistry is not defined.

The compounds of Formulae I-IV, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formulae I-IV may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formulae I-IV can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen," *Stereochemistry of Organic Compounds*," (Wiley-Interscience 1994), and European Patent Application No. EP-A-838448, published Apr. 29, 1998. Examples of resolutions include recrystallization techniques or chiral chromatography.

In general, the term "pharmaceutical" when used as an adjective means substantially non-toxic to living organisms. For example, the term "pharmaceutical salt" as used herein, refers to salts of the compounds of Formulae I-IV which are substantially non-toxic to living organisms. See, e.g., Berge, S. M, Bighley, L. D., and Monkhouse, D. C., "Pharmaceutical Salts," *J. Pharm. Sci.*, 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts such as lysine, arginine and ornithine. Typical pharmaceutical salts include those salts prepared by reaction of the compounds of Formulae I-IV with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formulae I-IV prepared by reaction of a compound of Formulae I-IV with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, ethanesulfonic acid, methanesulfonic acid, oxalic acid, p-bromophenylsulfonic acid, carbonic acid, succinic acid, citric acid, tartaric acid, benzoic acid, acetic acid and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The skilled artisan would appreciate that some compounds of Formulae I-IV may be acidic in nature and accordingly react with any of a number of inorganic and organic bases to form pharmaceutical base addition salts. The term "base addition salt" refers to a salt of a compound of Formulae I-IV prepared by reaction of a compound of Formula I, II, or III with a mineral or organic base. For exemplification of pharmaceutical base addition salts see, e.g., Berge, S. M, Bighley, L. D., and Monkhouse, D. C., *J. Pharm. Sci.*, 66:1, 1977. Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formulae I-IV. The potassium and sodium salt forms are particularly preferred. The present invention also contemplates pharmaceutical base addition salts of compounds of Formulae I-IV.

The pharmaceutical salts of the invention are typically formed by reacting a compound of Formulae I-IV with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

It should be recognized that the particular counterion forming a part of any salt of this invention is not of a critical nature, so long as the salt as a whole is pharmacologically acceptable and as long as the counterion does not contribute undesired qualities to the salt as a whole.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example $Asp^{B28}$ human insulin, U.S. Pat. No. 5,504,188 (Eli Lilly), for example $Lys^{B28}$ $pro^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide for example metformin.

In yet another embodiment of the invention the present compounds are administered in combination with a meglitinide for example repaglinide or nateglinide.

In still another embodiment of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer for example such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor for example voglibose, emiglitate, miglitol or acarbose.

In another embodiment of the invention the present compounds are administered in combination with an agent acting on the ATP-dependent potassium channel of the β-cells for example tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant).

In another embodiment the antiobesity agent is dexamphetamine or amphetamine.

In another embodiment the antiobesity agent is leptin.

In another embodiment the antiobesity agent is fenfluramine or exfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, SCE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of Formulae I-IV can be prepared by one of ordinary skill in the art following a variety of procedures, some of which are illustrated in the procedures and schemes set forth below. The particular order of steps required to produce the compounds of Formulae I-IV is dependent upon the particular compound being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formulae I-IV may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates (M+1) unless indicated otherwise. "MS(FD)" refers to field desorption mass spectrometry, "MS(IS)" refers to ion spray mass spectrometry, "MS(FIA)" refers to flow injection analysis mass spectrometry, "MS (FAB)" refers to fast atom bombardment mass spectrometry, "MS(EI)" refers to electron impact mass spectrometry, "MS (ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature.

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

GENERAL SCHEMES

Compounds of the present invention have been formed as specifically described in the examples. Furthermore, many compounds are prepared more generally using a) alkylation of an alcohol, phenol or thiophenol with a halide, b) a Mitsunobu protocol (O Mitsunobu, 1981 Synthesis, p1), and c) other methods known to the skilled artisan. Alternative synthesis methods may also be effective and known to the skilled artisan.

For example, an intermediate like A is alkylated with an alkylating agent B in the presence of a base (e.g. NaH, $K_2CO_3$, $Cs_2CO_3$ etc.). Hydrolysis in the presence of aqueous NaOH or LiOH gives the acid product.

Under certain circumstances, the synthetic sequence can be altered, where an intermediate like D is coupled with an aryl boronic acid or ester under Suzuki reaction conditions (Pd catalyst, base). Hydrolysis in the presence of aqueous NaOH or LiOH gives the acid product. If Y=S then the thiophenol A can also be coupled to the alcohol C using zinc iodide.

Scheme GZ1

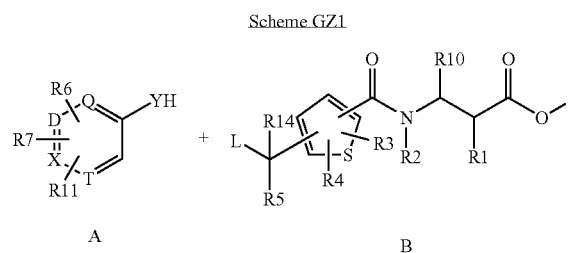

L = halide, mesylate, tosylate etc.

1) base 2) hydrolysis

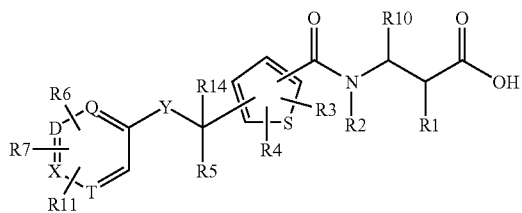

Alternatively, an intermediate like A is coupled with an alcohol C under Mitsunobu reaction conditions (DEAD/$PPh_3$, ADDP/$PBu_3$ etc.). Hydrolysis in the presence of aqueous NaOH or LiOH gives the acid product:

Scheme GZ2

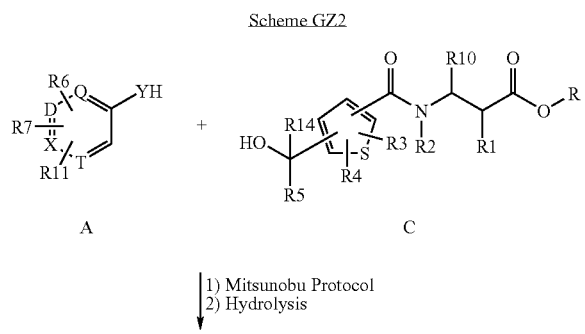

1) Mitsunobu Protocol
2) Hydrolysis

Scheme GZ3

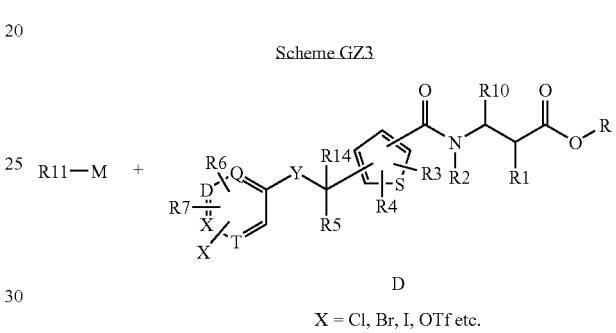

X = Cl, Br, I, OTf etc.

1) Cross-Coupling
2) Hydrolysis

The alcohol intermediates C can be made by A) reduction of the ketone with or without chiral auxiliary or B) alkylation of aldehyde with an organometallic reagent, e.g. Grignard reagent, or by C) direct alkylation of the thiophene.

Scheme GZ4

Method A

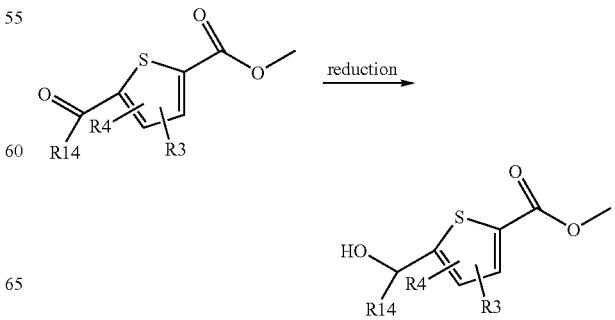

reduction

Method B

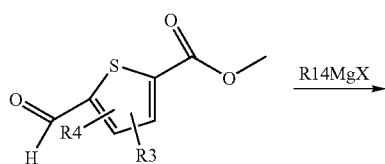

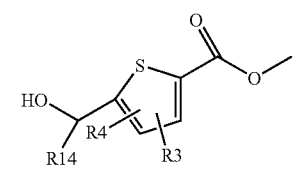

Method C

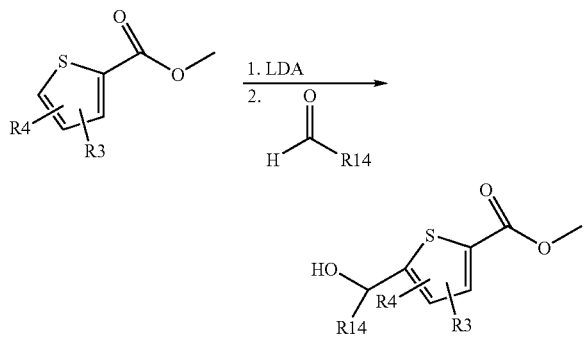

The biaryl phenol analogs can be made by a palladium catalyzed cross-coupling reaction:

Scheme GZ5

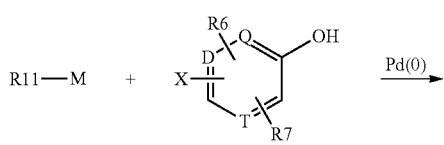

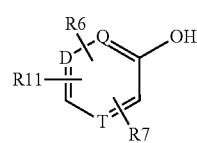

M = B(OR')$_2$, SnR'$_4$

A Wittig reaction is used to homobenzylic alcohol analogs as shown in Scheme GZ6:

Scheme GZ6

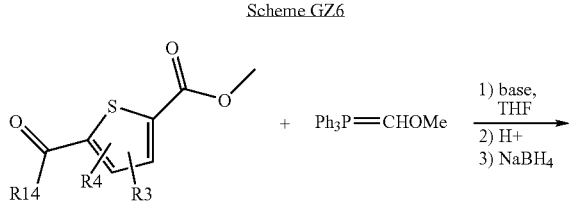

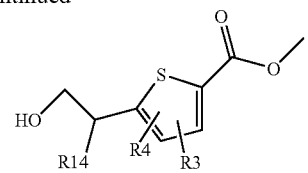

Alternatively, geminal-disubstituted homobenzylic alcohol analogs can be synthesized by bisalkylation of the thiophene ester and subsequent diisobutylaluminum hydride (Dibal-H) reduction to the alcohol. Lithiation of the thiazole is accomplished using tert-butyl lithium. The resulting anion is trapped with carbon dioxide and then esterified to provide the disubstituted homobenzylic analog.

The enantiomeric pure products are prepared either through A) chiral chromatography or B) Mitsunobu coupling between a phenol or thiophenol and a chiral alcohol that can be prepared using the methods known to the art.

PREPARATION AND EXAMPLES

The Examples provided herein are illustrative of the invention and are not intended to limit the scope of the claimed invention in any way.

Preparation 1

(R,S)-5-(1-Hydroxy-ethyl)-thiophene-2-carboxylic acid methyl ester

Step A

5-Acetyl-thiophene-2-carboxylic acid methyl ester

A solution of 5-acetyl-thiophene-2-carboxylic acid (1 g, 5.88 mmol) in DMF (24 mL) is treated with potassium carbonate (813 mg, 5.88 mmol), then iodomethane (0.368 mL, 5.88 mmol), and stirred for 60 h at rt. The reaction mixture is acidified and extracted into ethyl acetate twice. The combined organic layers are washed with brine, dried, filtered, and concentrated, then taken up in ethyl acetate, washed with saturated aqueous potassium carbonate, dried, filtered and concentrated to give 5-acetyl-thiophene-2-carboxylic acid methyl ester (653 mg).

Step B (R,S)-5-(1-Hydroxy-ethyl)-thiophene-2-carboxylic acid methyl ester

A solution of 5-acetyl-thiophene-2-carboxylic acid methyl ester (650 mg, 3.53 mmol) in THF (35 mL) is cooled to 0° C. under N₂, treated with sodium borohydride (54 mg, 1.44 mmol), warmed to rt, and stirred overnight. The reaction is quenched with aqueous buffer (pH=7), and extracted into ethyl acetate twice. Combined organic layers are washed with brine, dried, filtered, and concentrated. The crude product is applied to silica gel and eluted using hexanes with an ethyl acetate gradient from 0% to 60% to give the title compound (535 mg).

Preparation 2

(R,S)-5-(1-Hydroxy-propyl)-thiophene-2-carboxylic acid ethyl ester

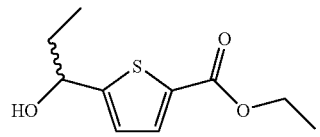

Step A

5-Formyl-thiophene-2-carboxylic acid ethyl ester

A solution of diisopropylamine (0.588 mL, 60 mmol) in THF (20 mL) under N₂ is cooled to −78° C. and treated with n-butyllithium (2.5 M in hexanes, 1.66 mL). The mixture is then warmed to 0° C. for 10 min, cooled back to −78° C., treated dropwise with a solution of thiophene-2-carboxylic acid ethyl ester (0.5 g, 3.2 mmol) in THF (12 mL), and stirred 5 min. N,N-dimethylformamide (0.324 mL, 4.16 mmol) is then added, and the reaction is allowed to warm to rt, while stirring overnight. Aqueous buffer (pH=7) is added, and the product is extracted into ethyl acetate (3×). Combined organic layers are dried, filtered, and concentrated. The resulting residue is applied to silica gel and eluted using hexanes with an ethyl acetate gradient from 0% to 40% to give 5-formyl-thiophene-2-carboxylic acid ethyl ester (325 mg).

Step B (R,S)-5-(1-Hydroxy-propyl)-thiophene-2-carboxylic acid ethyl ester

A solution of 5-formyl-thiophene-2-carboxylic acid ethyl ester (136 mg, 0.739 mmol) in THF (7.4 mL) under N₂ is cooled to 0° C., treated with ethylmagnesium bromide (3.0 M in Et₂O, 0.271 mL, 0.813 mmol), allowed to warm to rt, and stirred overnight. The reaction is then acidified, extracted into ethyl acetate (2×), dried, filtered, and concentrated. The resulting residue is applied to silica gel and eluted using hexanes with an ethyl acetate gradient from 0% to 40% to give the title compound (81 mg).

The following compounds are made in a substantially similar manner:

Preparation 3

(R,S)-5-(1-Hydroxy-butyl)-thiophene-2-carboxylic acid ethyl ester

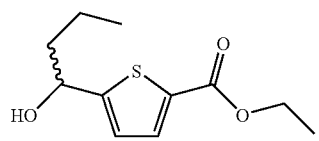

This compound is made by the general method as exemplified in Preparation 2 using 5-formyl-thiophene-2-carboxylic acid ethyl ester and n-propyl magnesium bromide as the starting materials.

Preparation 4

(R,S)-5-(1-Hydroxy-hexyl)-thiophene-2-carboxylic acid ethyl ester

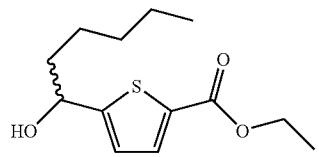

This compound is made by the general method as exemplified in Preparation 2 using 5-formyl-thiophene-2-carboxylic acid ethyl ester and n-pentyl magnesium bromide as the starting materials.

Preparation 5

(R,S)-5-(Cyclohexyl-hydroxy-methyl)-thiophene-2-carboxylic acid ethyl ester

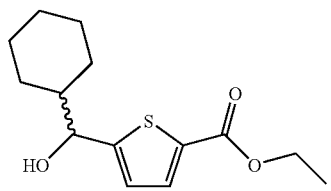

This compound is made by the general method as exemplified in Preparation 2 using 5-formyl-thiophene-2-carboxylic acid ethyl ester and cyclohexyl magnesium bromide as the starting materials.

Preparation 6

(R,S)-5-(1-Hydroxy-2,2-dimethyl-propyl)-thiophene-2-carboxylic acid ethyl ester

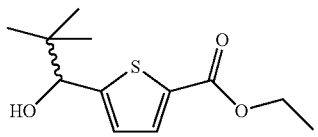

This compound is made by the general method as exemplified in Preparation 2 using 5-formyl-thiophene-2-carboxylic acid ethyl ester and t-butyl magnesium chloride as the starting materials.

Preparation 7

(R,S)-5-(1-Hydroxy-3,3-dimethyl-butyl)-thiophene-2-carboxylic acid ethyl ester

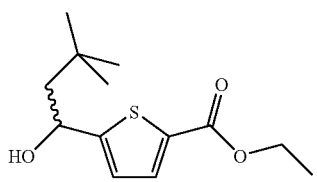

This compound is made by the general method as exemplified in Preparation 2 using 5-formyl-thiophene-2-carboxylic acid ethyl ester and neo-pentyl magnesium chloride as the starting materials.

Preparation 8

5-Hydroxymethyl-thiophene-2-carboxylic acid ethyl ester

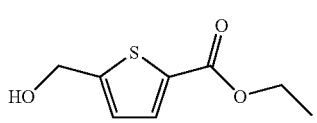

This material is the byproduct of Preparation 2, Step B.

Preparation 9

(R,S)-5-(1-Hydroxy-3-methyl-butyl)-thiophene-2-carboxylic acid ethyl ester

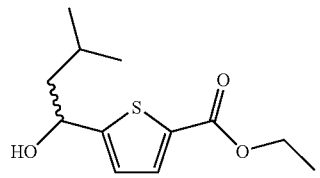

A solution of diisopropylamine (8.55 mL, 60 mmol) in THF (350 mL) under N$_2$ is cooled to −78° C. and treated with n-butyllithium (2.5 M in hexanes, 24 mL). The mixture is then warmed to 0° C. for 10 min, cooled back to −78° C., treated dropwise with a solution of thiophene-2-carboxylic acid ethyl ester (7.8 g, 50 mmol) in THF (150 mL), and stirred 5 min. 3-Methyl-butyraldehyde (6.48 mL, 60 mmol) is then added, and the reaction is allowed to warm to rt, while stirring overnight. Aqueous buffer (pH=7) is added, and the product is extracted into ethyl acetate (3×). Combined organic layers are dried, filtered, and concentrated. The resulting residue is applied to silica gel and eluted using hexanes with an ethyl acetate gradient from 0% to 60% to give the title compound (8.03 g).

Preparation 10

5-(1-Hydroxy-1-methyl-ethyl)-thiophene-2-carboxylic acid ethyl ester

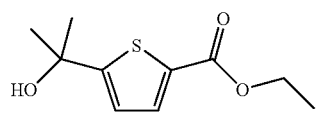

This compound is made substantially as described for Preparation 9.

Preparation 11

(R,S)-5-(1-Hydroxy-4-methyl-pentyl)-thiophene-2-carboxylic acid ethyl ester

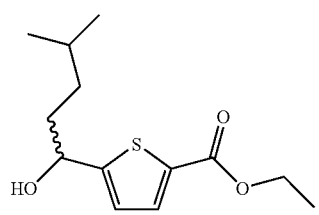

A solution of 5-formyl-thiophene-2-carboxylic acid ethyl ester (444 mg, 2.61 mmol) in THF (26 mL) under N₂ is cooled to -10° C., treated with boron trifluoride diethyl etherate (0.033 mL, 0.26 mmol) and 3-methylbutylzinc bromide (0.5 M solution in THF, 2.87 mmol, 5.73 mL), allowed to warm to rt, and stirred overnight. The reaction is then acidified, extracted into ethyl acetate (2×), dried, filtered, and concentrated. The resulting residue is applied to silica gel and eluted using hexanes with an ethyl acetate gradient from 0% to 50% to give the title compound (204 mg).

Preparation 12

(R,S)-5-(1-Hydroxy-2-methyl-propyl)-thiophene-2-carboxylic acid ethyl ester

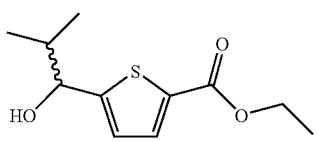

A solution of i-Pr₂NH (1.26 mL, 9.20 mmol) in THF (35 mL) at −78° C. is treated with n-BuLi (5.6 mL, 1.6M, 9.0 mmol) over the course of 3 minutes. The solution is warmed to rt for 10 min., then recooled to 78° C. Ethyl 2-thiophene carboxylate (1.00 mL, 7.44 mmol) is added dropwise and the resulting solution is stirred for 15 min., then isobutyraldehyde (0.81 mL, 9.14 mmol) is added and the reaction is warmed to rt and stirred overnight. The resulting solution is quenched with saturated NH₄Cl (25 mL) and extracted with EtOAc (2×50 mL). Combined extracts are washed with H₂O, brine, dried over MgSO₄, filtered, and concentrated. The residue is loaded onto silica gel and eluted with hexanes using a gradient of 0% to 30% EtOAc giving 5-(1-hydroxy-2-methyl-propyl)-thiophene-2-carboxylic acid ethyl ester (1.25 g, 73%) as a yellow oil. MS (ES): 211.1 [M+H−H₂O]⁺.

The following compounds are made in a substantially similar manner:

Preparation 13

(R,S)-5-(1-Hydroxy-ethyl)-thiophene-2-carboxylic acid ethyl ester

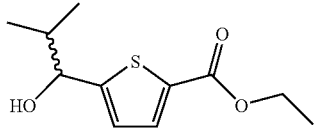

This compound is made by the general method as exemplified in Preparation 11 using acetaldehyde as the starting material. (10.98 g, 85% yield). MS (ES): 201.0 [M+H]⁺.

Preparation 14

(R,S)-5-(1-Hydroxy-butyl)-thiophene-2-carboxylic acid ethyl ester

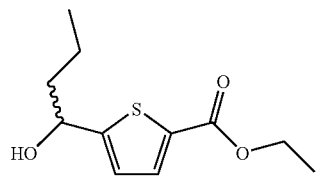

This compound is made by the general method as exemplified in Preparation 11 using butyraldehyde as the starting material. (9.92 g, 68% yield). MS (ES): 229.2 [M+H]⁺.

Preparation 15

(R,S)-5-(1-Hydroxy-3-methyl-butyl)-thiophene-2-carboxylic acid ethyl ester

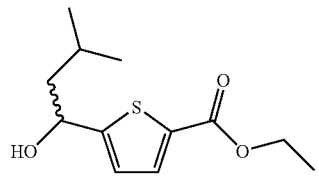

This compound is made by the general method as exemplified in Preparation 11 using 3-methyl-butyraldehyde as the starting material. (0.373 g, 21% yield). MS (ES): 225.1 [M+H−H₂O]⁺.

Preparation 16

(R,S)-5-(1-Hydroxy-pentyl)-thiophene-2-carboxylic acid ethyl ester

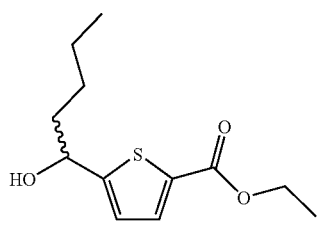

This compound is made by the general method as exemplified in Preparation 11 using pentanal as the starting material. (10.65 g, 69% yield). MS (ES): 243.1 [M+H]⁺.

Preparation 17

(R,S)-5-(1-Hydroxy-octyl)-thiophene-2-carboxylic acid ethyl ester

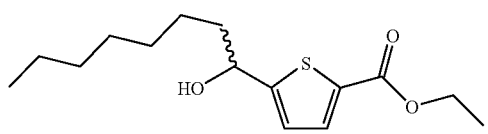

This compound is made by the general method as exemplified in Preparation 11 using octanal as the starting material. (0.467 g, 22% yield). MS (ES): 268.1 [M+H−H₂O]⁺.

Preparation 18

(R,S)-3-Chloro-5-(1-hydroxy-propyl)-thiophene-2-carboxylic acid ethyl ester

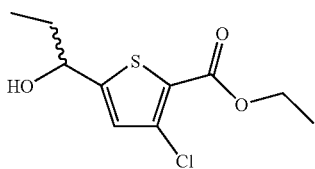

This compound is made by the general method as exemplified in Preparation 11 using 3-chloro-thiophene-2-carboxylic acid ethyl ester and propionaldehyde as the starting materials. (0.499 g, 37% yield).

Preparation 19

(R,S)-5-(1-Hydroxy-2,2-dimethyl-propyl)-thiophene-2-carboxylic acid ethyl ester

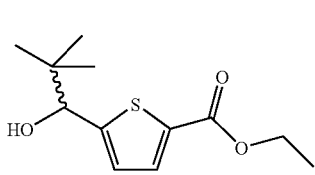

Preparation 20

(R,S)-5-(1-Hydroxy-3,3-dimethyl-butyl)-thiophene-2-carboxylic acid ethyl ester

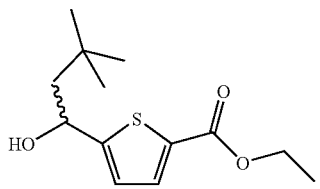

Preparation 21

(R,S)-5-(1-Hydroxy-3,3-dimethyl-butyl)-thiophene-3-carboxylic acid methyl ester

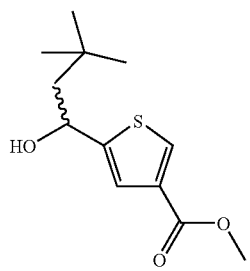

A solution of 5-formyl-thiophene-3-carboxylic acid methyl ester (0.504 g, 2.96 mmol) in Et₂O (30 mL) at 0° C. is treated with neopentyl magnesium chloride (7.1 mL, 0.5 M in Et₂O, 3.6 mmol) and stirred for 15 min. Solution warmed to rt and additional Et₂O (10 mL) added. The reaction mixture is stirred overnight at rt. after which it is poured into H₂O (30 mL) and extracted with EtOAc (3×50 mL). Combined extracts washed with brine, dried over MgSO₄, filtered, and concentrated. The residue is loaded onto silica gel and eluted using hexanes with an ethyl acetate gradient from 0% to 50%. The resulting mixture is then loaded onto C₁₈ and eluted using H₂O and a MeCN gradient from 15% to 100% giving (±)-5-(1-hydroxy-3,3-dimethyl-butyl)-thiophene-3-carboxylic acid methyl ester (0.316 g, 44%) as a light yellow syrup.

Preparation 22

(R,S)-4-Chloro-5-(1-hydroxy-propyl)-thiophene-2-carboxylic acid methyl ester

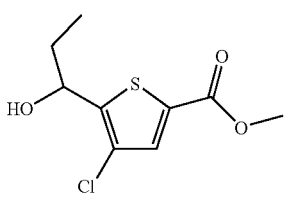

Step A 4,5-Dichloro-thiophene-2-carboxylic acid

A solution of i-Pr$_2$NH (1.80 mL, 12.9 mmol) in THF (65 mL) at −78° C. is treated with n-BuLi (7.8 mL, 1.6M, 12.5 mmol). The solution is warmed to 0° C. for 10 min., then recooled to −78° C. A solution of 2,3-dichlorothiophene (2.00 g, 13.1 mmol) in THF (3.0 mL) is added dropwise and the resulting solution is stirred for 40 min, then anhydrous CO$_{2(g)}$ is bubbled through the solution for 8 min. The reaction is warmed to rt and acidified with 1 N HCl (25 mL) and extracted with EtOAc (2×50 mL). Combined extracts are dried over MgSO$_4$, filtered, and concentrated giving 4,5-dichloro-thiophene-2-carboxylic acid (1.94 g, 75%) as a white solid. MS (ES): 197.0 [M+H]$^+$.

Step B

4-Chloro-5-(1-hydroxy-propyl)-thiophene-2-carboxylic acid methyl ester

A solution of 4,5-dichloro-thiophene-2-carboxylic acid in THF (25 mL) at −53° C. is treated with LiHMDS (2.5 mL, 1 M THF) and then cooled to −78° C. for 10 min. Tert-butyl lithium (3.2 mL, 1.7 M Pentane, 5.4 mmol) is added dropwise for 12 min., then treated with propanal (0.25 mL, 3.4 mmol). After 5 min. the reaction is warmed to rt and stirred overnight. The reaction mixture is then acidified with 1 N HCl (10 mL) and extracted with EtOAc (3×25 mL). Combined organic extracts are dried over MgSO$_4$, filtered, and concentrated to provide crude 4-chloro-5-(1-hydroxy-propyl)-thiophene-2-carboxylic acid as a brown syrup (0.280 g), which is used in the next step without further purification.

A solution of crude 4-chloro-5-(1-hydroxy-propyl)-thiophene-2-carboxylic acid (0.262 g) in dimethylformamide (6.0 mL) is treated with K$_2$CO$_3$ (0.502 g, 3.63 mmol) and iodomethane (0.17 mL, 2.73 mmol) and stirred overnight. The reaction mixture is then poured into H$_2$O (15 mL) and extracted with EtOAc (3×10 mL). Combined organic extracts are washed with brine (1×), dried over MgSO$_4$, filtered, and concentrated. The residue is loaded onto silica gel and eluted with hexanes using a gradient of 0% to 50% EtOAc to provide 4-chloro-5-(1-hydroxy-propyl)-thiophene-2-carboxylic acid methyl ester (87.6 mg, 15%-2 steps) as a yellow syrup. MS (ES): 216.9 [M+H]$^+$.

Preparation 23

5-(1-Ethyl-1-hydroxymethyl-propyl)-thiophene-2-carboxylic acid methyl ester

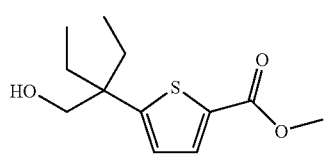

Step A

2-Ethyl-2-thiophen-2-yl-butyric acid methyl ester

A mixture of thiophen-2-yl-acetic acid methyl ester (3.00 g, 19.2 mmol) in DMF (85 mL) at 0° C. is treated with NaH (60% dispersion in mineral oil, 1.71 g, 42.8 mmol). After 5 min, iodoethane (3.5 mL, 43.8 mmol) is added. The reaction mixture is warmed to rt and stirred overnight. The mixture is cooled in a cold water bath and quenched with H$_2$O (150 mL). The mixture is extracted with EtOAc (3×100 mL). Combined extracts are washed with H$_2$O, brine, dried over MgSO$_4$, filtered, and concentrated. The residue is loaded onto silica gel and eluted with hexanes using a gradient of 0% to 50% EtOAc to provide 2-ethyl-2-thiophen-2-yl-butyric acid methyl ester 3.67 g, 909%) as a light yellow oil.

Step B

2-Ethyl-2-thiophen-2-yl-butan-1-ol

A solution of 2-methyl-2-thiophen-2-yl-propionic acid methyl ester (3.66 g, 17.2 mmol) in CH$_2$Cl$_2$ (85 mL) at 0° C. is treated with diisobutylaluminum hydrde (Dibal-H, 1.0 M PhMe, 38.0 mL, 384.0 mmol) and warmed to rt overnight. The reaction mixture is carefully poured into 1N tartaric acid (100 mL) and stirred for 3 d. The layers are separated and the aqueous layer is extracted with CH$_2$Cl$_2$ (100 mL). The combined extracts are dried over MgSO$_4$, filtered, and concentrated. The residue is loaded onto silica gel and eluted with hexanes using a gradient of 0% to 75% EtOAc to give 2-ethyl-2-thiophen-2-yl-butan-1-ol (2.87 g, 90%) as a pink oil.

Step C 5-(1-Ethyl-1-hydroxymethyl-propyl)-thiophene-2-carboxylic acid

A solution of 2-ethyl-2-thiophen-2-yl-butan-1-ol (2.87 g, 15.6 mmol) in THF (100 mL) is cooled to −78° C. and treated with t-BuLi (1.7M in pentane, 19.3 mL, 32.8 mmol) dropwise over 10 min. After stirring for 20 min, CO$_{2(g)}$ is bubbled through the solution for 3 min. The solution is then warmed to rt and stirred overnight. The reaction is acidified with 1N HCl (35 mL). The mixture is extracted with EtOAc (3×100 mL). The combined extracts are dried over MgSO$_4$, filtered, and concentrated. The residue is loaded onto C$_{18}$ resin and eluted with H$_2$O using a gradient of 15% to 100% MeCN to give 5-(1-ethyl-1-hydroxymethyl-propyl)-thiophene-2-carboxylic acid (0.7471 g, 21%) as a white solid. MS (ES): 227.1 [M−H]$^-$.

Step D 5-(1-Ethyl-1-hydroxymethyl-propyl)-thiophene-2-carboxylic acid methyl ester A solution of 5-(1-ethyl-1-hydroxymethyl-propyl)-thiophene-2-carboxylic acid (0.750 g, 3.28 mmol) in DMF (16.0 mL) is treated with K$_2$CO$_3$ (0.684 g, 6.00 mmol), iodomethane (0.27 mL, 4.34 mmol), and stirred at rt overnight. The mixture is poured into H$_2$O (30 mL) and extracted with EtOAc (3×30 mL). The combined extracts are washed with H$_2$O, brine, dried over MgSO$_4$, filtered, and concentrated. The residue is loaded onto silica gel and eluted with hexanes using a gradient of 0% to 75% EtOAc to give 5-(1-ethyl-1-hydroxymethyl-propyl)-thiophene-2-carboxylic acid methyl ester (0.571 g, 72%) as a clear syrup. MS (ES): 243.2 [M+H]$^+$.

The following compound is made in a substantially similar manner:

Preparation 24

(R,S)-5-(1-Hydroxymethyl-propyl)-thiophene-2-carboxylic acid methyl ester

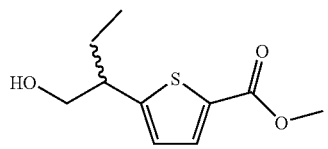

This compound is made by the general method as exemplified in Example 23 using 1 eq of sodium hydride and iodoethane as the starting materials in step A. MS (ES): 215.1 [M+H]$^+$.

Preparation 25

(R,S)-5-(1-Hydroxy-4,4-dimethyl-pentyl)-thiophene-2-carboxylic acid ethyl ester

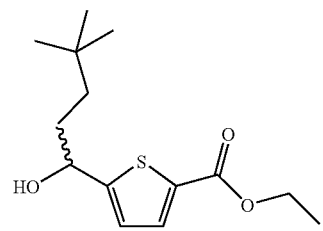

Step A

5-Formyl-thiophene-2-carboxylic acid ethyl ester

A solution of diisopropylamine (0.588 mL, 60 mmol) in THF (20 mL) under N$_2$ is cooled to −78° C. and treated with n-butyllithium (2.5 M in hexanes, 1.66 mL). The mixture is then warmed to 0° C. for 10 min, cooled back to −78° C., treated dropwise with a solution of thiophene-2-carboxylic acid ethyl ester (0.5 g, 3.2 mmol) in THF (12 mL), and stirred 5 min. N,N-Dimethylformamide (0.324 mL, 4.16 mmol) is then added, and the reaction is allowed to warm to rt, while stirring overnight. Aqueous buffer (pH=7) is added, and the product is extracted into ethyl acetate (3×). Combined organic layers are dried, filtered, and concentrated. The resulting residue is applied to silica gel and eluted using hexanes with an ethyl acetate gradient from 0% to 40% to give 5-formyl-thiophene-2-carboxylic acid ethyl ester (325 mg).

Step B 3,3-Dimethylbutylmagnesium bromide

In an oven-dried flask, a suspension of magnesium turnings (1.82 g, 75 mmol) in THF (40 mL) is treated with molecular iodine (254 mg, 1 mmol). To this mixture is added twenty drops of a solution of 3,3-dimethylbutyl bromide (7.14 mL, 50 mmol) in THF (10 mL) via a fitted separatory funnel. The resulting mixture is heated to reflux, followed by addition of the remaining 3,3-dimethylbutyl bromide solution. The reaction mixture is allowed to reflux for 1 h, cooled to rt, and used as is (1.0 M solution of 3,3-dimethylbutylmagnesium bromide in THF, 50 mmol).

Step C (R,S)-5-(1-Hydroxy-4,4-dimethyl-pentyl)-thiophene-2-carboxylic acid ethyl ester A solution of 5-formyl-thiophene-2-carboxylic acid ethyl ester (3.12 g, 16.9 mmol) in THF (169 mL) under N$_2$ is cooled to 0° C., treated with 3,3-dimethylbutylmagnesium bromide (1.0 M in THF; 16.9 mL, 16 9 mmol), allowed to warm to rt, and stirred overnight. The reaction is then acidified, extracted into ethyl acetate (2×), dried, filtered, and concentrated. The resulting residue is applied to silica gel and eluted using hexanes with an ethyl acetate gradient from 0% to 60% to give the title compound (730 mg).

Preparation 26

2,6-Dimethyl-4'-trifluoromethyl-biphenyl-4-ol

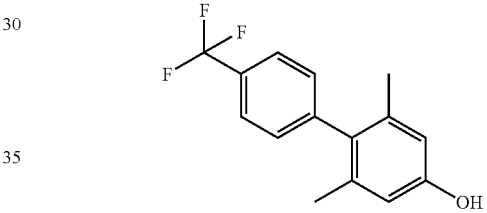

To a solution of 4-iodo-3,5-dimethyl-phenol (3.35 g, 13.5 mmol) in THF (81 ml) is added (4-trifluoromethyl)phenylboronic acid (3.35 g, 16.2 mmol), potassium fluoride (1.94 mg, 40.6 mmol), palladium(II) acetate (152 mg, 0.67 mmol), and (oxydi-2,1-phenylene)bis-(diphenylphosphine) (730 mg, 1.35 mmol). The reaction mixture is heated to reflux overnight. After cooling to rt, the reaction mixture is partitioned between ethyl acetate and water. The aqueous layer is back-extracted with ethyl acetate, the combined organic layers are dried and concentrated. The resulting residue is applied to silica gel and eluted using hexanes with an ethyl acetate gradient from 0% to 70% to give the title compound (3.3 g).

Preparation 27

4'-tert-Butyl-2,6-dimethyl-biphenyl-4-ol

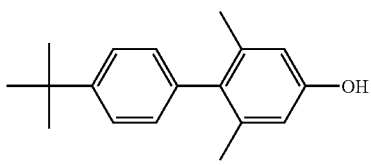

This compound is made in a substantially similar manner as exemplified in Preparation 26 staring from 4-tert-butyl-phenyl boronic acid and 4-bromo-3,5-dimethyl phenol.

Preparation 27

4'-tert-Butyl-2-methyl-biphenyl-4-ol

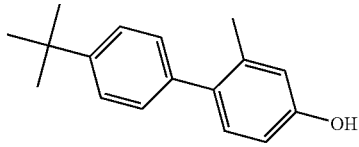

This compound is made by the general method as exemplified in Preparation 26 using 4-bromo-3-methyl-phenol and 4-tert-butyl-phenyl boronic acid as reagents.

Preparation 28

6-(4-tert-Butyl-phenyl)-pyridin-3-ol

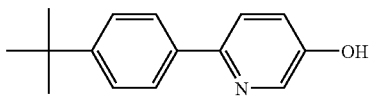

To a solution of 6-Chloro-pyridin-3-ol (3.10 g, 23.9 mmol) in toluene (30 ml) is added 4-tert-butyl-phenylboronic acid (5.46 g, 30.6 mmol), potassium fluoride (2.82 g, 47.9 mmol), and palladium tetrakis triphenylphosphine (1.20 g, 1.20 mmol). Water (15 mL) is added and the reaction mixture is heated to reflux overnight. After cooling to rt, the reaction mixture is partitioned between ethyl acetate and water. The aqueous layer is back-extracted with ethyl acetate, the combined organic layers are dried and concentrated. The resulting residue is applied to silica gel and eluted using hexanes with an ethyl acetate gradient to give the title compound (2.06 g).

Preparation 29

6-(4-Trifluoromethyl-phenyl)-pyridin-3-ol

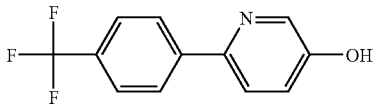

The titled compound is made in a manner substantially similar to Preparation 28 starting from the 6-chloro-pyridin-3-ol and 4-trifluoromethylphenyl boronic acid.

Preparation 30

4'-tert-Butyl-2,6-dimethyl-biphenyl-4-thiol

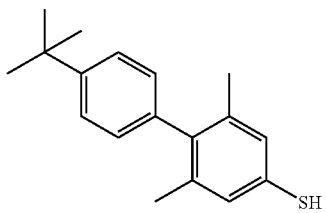

Step A

Dimethyl-thiocarbamic acid O-(4'-tert-butyl-2,6-dimethyl-biphenyl-4-yl)ester

To a solution of 4'-tert-butyl-2,6-dimethyl-biphenyl-4-ol (10 g, 37.3 mmol) in dioxane (157 ml) is added 4-dimethylaminopyridine (476 mg, 3.9 mmol), triethylamine (10 mL, 78.6 mmol), and dimethylthiocarbamoyl chloride (6.1 g, 49.1 mmol). The reaction mixture is heated to reflux overnight. After cooling to rt, the reaction mixture is partitioned between ethyl acetate and water. The aqueous layer is back-extracted with ethyl acetate, and the combined organic layers are dried and concentrated. The resulting residue is applied to silica gel and eluted using 20% ethyl acetate in hexanes to give dimethyl-thiocarbamic acid O-(4'-tert-butyl-2,6-dimethyl-biphenyl-4-yl)ester (12.2 g).

Step B

Dimethyl-thiocarbamic acid S-(4'-tert-butyl-2,6-dimethyl-biphenyl-4-yl)ester

A suspension of dimethyl-thiocarbamic acid 0-(4'-tert-butyl-2,6-dimethyl-biphenyl-4-yl) ester (12.1 g, 35.4 mmol) in tetradecane (80 mL) was heated at 245° C. for 16 h. After cooling to rt, a solid precipitate is filtered, washed with heptane, and dried under vacuum at 40° C. The resulting residue is applied to silica gel and eluted using hexanes with an ethyl acetate gradient from 0% to 60% to give dimethyl-thiocarbamic acid S-(4'-tert-butyl-2,6-dimethyl-biphenyl-4-yl)ester (8.86 g).

Step C

4'-tert-Butyl-2,6-dimethyl-biphenyl-4-thiol

To a solution of dimethyl-thiocarbamic acid S-(4'-tent-butyl-2,6-dimethyl-biphenyl-4-yl) ester (8.8 g, 25.8 mmol) in methanol (65 mL) is added sodium methoxide (1.39 g, 25.8 mmol). The reaction mixture is heated to reflux overnight. After cooling to rt, the reaction mixture is neutralized with 5N HCl, concentrated to 1/3 volume, treated with brine, and extracted into dichloromethane. The aqueous layer is back-extracted with dichloromethane, and the combined organic layers are dried and concentrated. The resulting residue is applied to silica gel and eluted using hexanes with an ethyl acetate gradient from 0% to 50% to give the title compound (5.84 g).

The following compounds are made in a substantially similar manner.

Preparation 31

2,6-Dimethyl-4'-trifluoromethyl-biphenyl-4-thiol

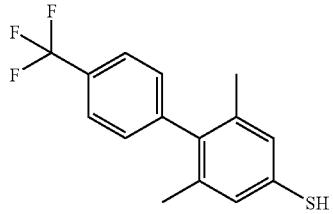

MS (ES): 281.1 [M−H]⁻.

Preparation 32

4'-Isopropyl-2,6-dimethyl-biphenyl-4-thiol

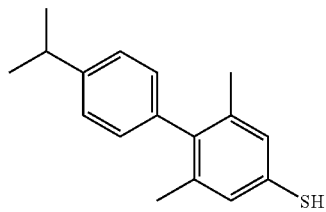

Preparation 33

(R,S)-3-({5-[1-(2,6-Dimethyl-4'-trifluoromethyl-biphenyl-4-yloxy)-ethyl]-thiophene-2-carbonyl}-amino)-propionic acid

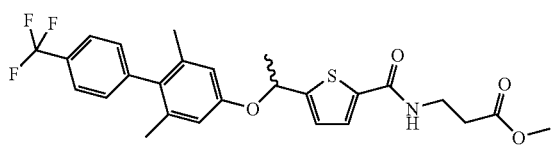

Step A (R,S)-5-[1-(2,6-Dimethyl-4'-trifluoromethyl-biphenyl-4-yloxy)-ethyl]-thiophene-2-carboxylic acid ethyl ester A mixture of (±)-5-(1-hydroxy-ethyl)-thiophene-2-carboxylic acid ethyl ester (0.402 g, 2.01 mmol), 2,6-dimethyl-4'-trifluoromethyl-biphenyl-4-ol (0.593 g, 2.23 mmol), and PPh₃ (0.798 g, 3.04 mmol) is dissolved in toluene (20 mL) and treated with 1,1'-(azodicarbonyl)dipiperidine (ADDP, 0.763 g, 3.02 mmol) and stirred overnight at rt. The mixture is diluted with MeOH until homogeneous and concentrated. The residue is loaded onto silica gel and eluted using hexanes with an ethyl acetate gradient from 0% to 40% giving (±)-5-[1-(2,6-Dimethyl-4'-trifluoromethyl-biphenyl-4-yloxy)-ethyl]-thiophene-2-carboxylic acid ethyl ester (0.638 g, 71%) as a clear syrup. MS (ES): 447.3 [M−H]⁻.

Step B (R,S)-5-[1-(2,6-Dimethyl-4'-trifluoromethyl-biphenyl-4-yloxy)-ethyl]-thiophene-2-carboxylic acid To a mixture of (±)-5-[1-(2,6-dimethyl-4'-trifluoromethyl-biphenyl-4-yloxy)-ethyl]-thiophene-2-carboxylic acid ethyl ester (0.636 g, 1.42 mmol) in THF (14 mL) is added lithium hydroxide (1N aqueous, 14 mL). The mixture is warmed to 70° C. and stirred overnight. The reaction mixture is acidified with 1N HCl (15 mL), extracted into ethyl acetate (3×25 mL), dried over MgSO₄, and concentrated, to provide (±)-5-[1-(2,6-dimethyl-4'-trifluoromethyl-biphenyl-4-yloxy)-ethyl]-thiophene-2-carboxylic acid (0.552 g, 92%) as a white foam. MS (ES): 419.2 [M−H]⁻.

Step C (R,S)-3-({5-[1-(2,6-dimethyl-4'-trifluoromethyl-biphenyl-4-yloxy)-ethyl]-thiophene-2-carbonyl}-amino)-propionic acid methyl ester To a mixture of (-±)-5-[1-(2,6-dimethyl-4'-trifluoromethyl-biphenyl-4-yloxy)-ethyl]-thiophene-2-carboxylic acid (0.545 g, 1.30 mmol), 3-amino-propionic acid methyl ester hydrochloride (0.199 g, 1.43 mmol), and 1-hydroxybenzotriazole hydrate (HOBt, 0.217 g, 1.60 mmol) in DMF (13.0 mL) is added N,N-diisopropylethylamine (0.67 mL, 3.84 mmol), then N-(3-dimethylaminopropyl)-N'-ethylcarbodiimide hydrochloride (EDCI, 0.330 g, 1.72 mmol) and stirred overnight. The reaction mixture is poured into H₂O (25 mL) and extracted with EtOAc (3×25 mL). Combined organic extracts are washed with H₂O, brine, dried over MgSO₄, filtered, and concentrated. The residue is loaded onto silica gel and eluted using hexanes with an ethyl acetate gradient from 0% to 75% to provide (±)-3-({5-[1-(2,6-dimethyl-4'-trifluoromethyl-biphenyl-4-yloxy)-ethyl]-thiophene-2-carbonyl}-amino)-propionic acid methyl ester (0.490 g, 75%) as a white foam. MS (ES): 504.3 [M−H]⁻.

The following compounds are made in a substantially similar manner:

Preparation 34

(R,S)-3-({5-[2-Methyl-1-(4'-trifluoromethyl-biphenyl-4-yloxy)-propyl]-thiophene-2-carbonyl}-amino)-propionic acid methyl ester

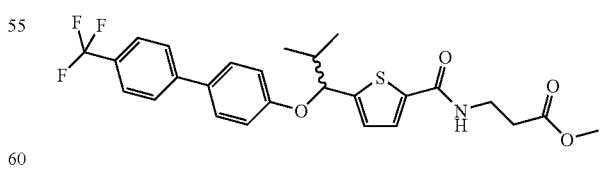

This compound is made by the general method as exemplified in Preparation 33 using 4'-trifluoromethyl-biphenyl-4-ol as the starting material. MS (ES): 504.2 [M−H]⁻. The racemic material (183 mg) is separated by chiral HPLC (column: Chiralpak AD 4.6×150 mm; eluent: 50% heptane:50% isopropanol; flow rate: 0.6 mL/min; UV absorbance wavelength: 270 nm) to provide chiral Isomer 1 (71 mg, 98.4% ee) and chiral Isomer 2 (74 mg, 99.8% ee).

Preparation 35

(R,S)-3-({5-[3-Methyl-1-(4'-trifluoromethyl-biphenyl-4-yloxy)-butyl]-thiophene-2-carbonyl}-amino)-propionic acid methyl ester

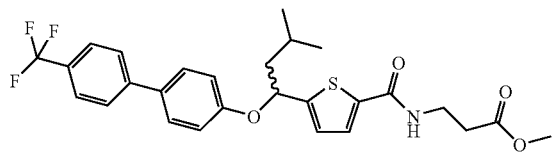

This compound is made by the general method as exemplified in Preparation 33 using 4'-trifluoromethyl-biphenyl-4-ol as the starting material. MS (ES): 518.3 [M−H]⁻.

Preparation 36

(R,S)-3-({5-[1-(4'-Trifluoromethyl-biphenyl-4-yloxy)-octyl]-thiophene-2-carbonyl}-amino)-propionic acid methyl ester

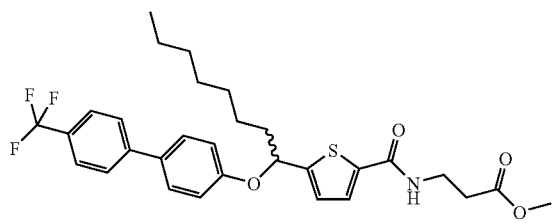

This compound is made by the general method as exemplified in Preparation 33 using 4'-trifluoromethyl-biphenyl-4-ol as the starting material. MS (ES): 560.2 [M−H]⁻. The racemic material (287 mg) is separated by chiral HPLC (column: Chiralpak AD 4.6×150 mm; eluent: 100% 3A ethanol; flow rate: 0.6 mL/min; UV absorbance wavelength: 270 nm) to provide chiral Isomer 1 (131 mg, 98.1% ee) and chiral Isomer 2 (125 mg, 98.3% ee).

Preparation 37

(R,S)-3-({5-[1-(4'-tert-Butyl-2,6-dimethyl-biphenyl-4-yloxy)-ethyl]-thiophene-2-carbonyl}-amino)-propionic acid methyl ester

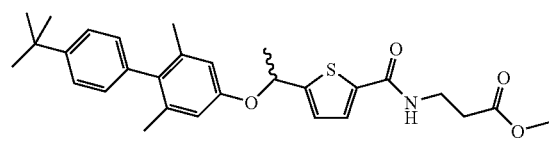

This compound is made by the general method as exemplified in Preparation 33 using 4'-tert-butyl-2,6-dimethyl-biphenyl-4-ol as the starting material. MS (ES): 492.1 [M−H]⁻.

Preparation 38

(R,S)-3-({3-Chloro-5-[1-(2,6-dimethyl-4'-trifluoromethyl-biphenyl-4-yloxy)-propyl]-thiophene-2-carbonyl}-amino)-propionic acid methyl ester

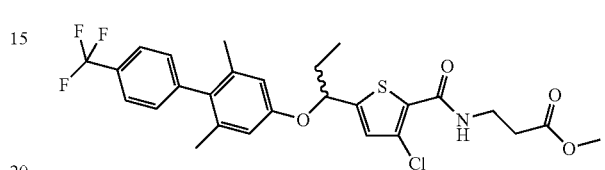

This compound is made by the general method as exemplified in Preparation 33 using 2,6-dimethyl-4'-trifluoromethyl-biphenyl-4-ol as the starting material. MS (ES): 552.2 [M−H]⁻.

Preparation 39

(R,S)-3-({3-Chloro-5-[1-(2-methyl-4'-trifluoromethyl-biphenyl-4-yloxy)-propyl]-thiophene-2-carbonyl}-amino)-propionic acid methyl ester

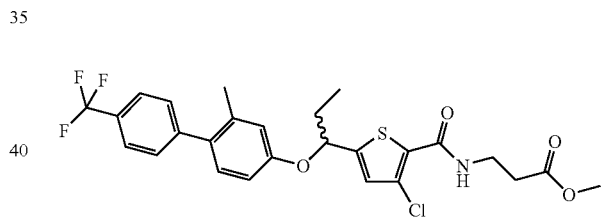

This compound is made by the general method as exemplified in Preparation 33 using 2-methyl-4'-trifluoromethyl-biphenyl-4-ol as the starting material. MS (ES): 538.2 [M−H]⁻.

Preparation 40

(R,S)-3-({5-[1-(2,6-Dimethyl-4'-trifluoromethyl-biphenyl-4-yloxy)-2-methyl-propyl]-thiophene-2-carbonyl}-amino)-propionic acid methyl ester

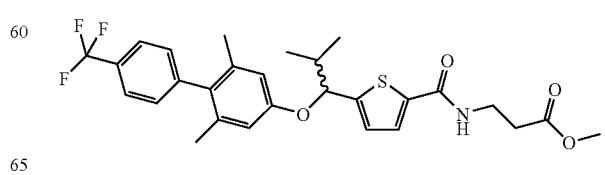

This compound is made by the general method as exemplified in Preparation 33 using 2,6-dimethyl-4'-trifluoromethyl-biphenyl-4-ol as the starting material. MS (ES): 532.2 [M−H]⁻.

Preparation 41

(R,S)-3-({5-[2-Methyl-1-(2-methyl-4'-trifluoromethyl-biphenyl-4-yloxy)-propyl]-thiophene-2-carbonyl}-amino)-propionic acid methyl ester

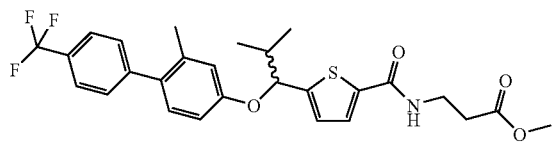

This compound is made by the general method as exemplified in Preparation 33 using 2-methyl-4'-trifluoromethyl-biphenyl-4-ol as the starting material. MS (ES): 518.1 [M−H]⁻.

Preparation 42

(R,S)-3-({5-[1-(4'-tert-Butyl-2,6-dimethyl-biphenyl-4-yloxy)-2-methyl-propyl]-thiophene-2-carbonyl}-amino)-propionic acid methyl ester

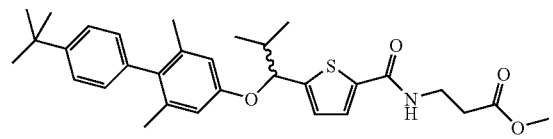

This compound is made by the general method as exemplified in Preparation 33 using 4'-tert-butyl-2,6-dimethyl-biphenyl-4-ol as the starting material. MS (ES): 522.3 [M+H]⁺. The racemic material (261 mg) is separated by chiral HPLC (column: Chiralpak OJ-H 4.6×150 mm; eluent: 100% MeOH; flow rate: 0.6 mL/min; UV absorbance wavelength: 270 nm) to provide chiral Isomer 1 (120 mg, 99.5% ee) and chiral Isomer 2 (119 mg, 100% ee).

Preparation 43

(R,S)-3-({5-[1-(4'-tert-Butyl-2-methyl-biphenyl-4-yloxy)-2-methyl-propyl]-thiophene-2-carbonyl}-amino)-propionic acid methyl ester

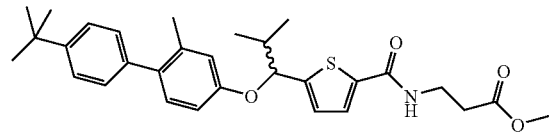

This compound is made by the general method as exemplified in Preparation 33 using 4'-tert-butyl-2-methyl-biphenyl-4-ol as the starting material. MS (ES): 506.2 [M−H]⁻. The racemic material (235 mg) is separated by chiral HPLC (column: Chiralpak AD-H 4.6×150 mm; eluent: 90% heptane: 10% isopropanol; flow rate: 0.6 mL/min; UV absorbance wavelength: 250 nm) to provide chiral Isomer 1 (105 mg, 99.8% ee) and chiral Isomer 2 (109 mg, 97.3% ee).

Preparation 44

(R,S)-3-({5-[1-(2,6-Dimethyl-4'-trifluoromethyl-biphenyl-4-yloxy)-butyl]-thiophene-2-carbonyl}-amino)-propionic acid methyl ester

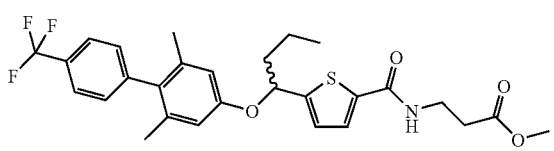

This compound is made by the general method as exemplified in Preparation 33 using 2,6-dimethyl-4'-trifluoromethyl-biphenyl-4-ol as the starting material. MS (ES): 532.1 [M−H]⁻.

Preparation 45

(R,S)-3-({5-[1-(2-Methyl-4'-trifluoromethyl-biphenyl-4-yloxy)-butyl]-thiophene-2-carbonyl}-amino)-propionic acid methyl ester

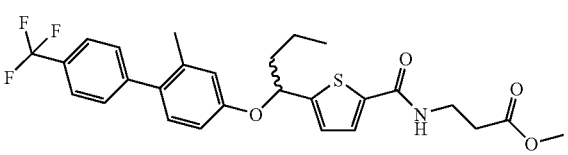

This compound is made by the general method as exemplified in Preparation 33 using 2-methyl-4'-trifluoromethyl-biphenyl-4-ol as the starting material. MS (ES): 518.2 [M−H]⁻.

Preparation 46

(R,S)-3-({5-[1-(4'-tert-Butyl-2,6-dimethyl-biphenyl-4-yloxy)-butyl]-thiophene-2-carbonyl}-amino)-propionic acid methyl ester

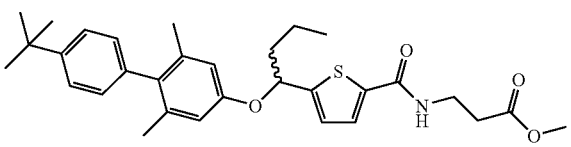

This compound is made by the general method as exemplified in Preparation 33 using 4'-tert-butyl-2,6-dimethyl-biphenyl-4-ol as the starting material. MS (ES): 522.5 [M+H]⁺.

Preparation 47

(R,S)-3-({5-[1-(4'-tert-Butyl-2-methyl-biphenyl-4-yloxy)-butyl]-thiophene-2-carbonyl}-amino)-propionic acid methyl ester

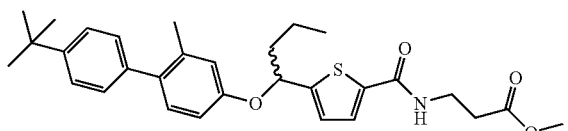

This compound is made by the general method as exemplified in Preparation 33 using 4'-tert-butyl-2-methyl-biphenyl-4-ol as the starting material. MS (ES): 508.5 [M+H]⁺.

Preparation 48

(R,S)-3-({5-[1-(2,6-Dimethyl-4'-trifluoromethyl-biphenyl-4-yloxy)-3,3-dimethyl-butyl]-thiophene-3-carbonyl}-amino)-propionic acid methyl ester

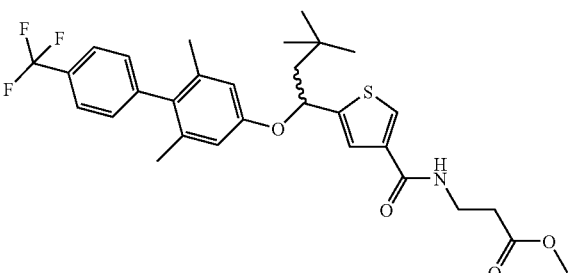

This compound is made by the general method as exemplified in Preparation 33 using 2,6-dimethyl-4'-trifluoromethyl-biphenyl-4-ol as the starting material. MS (ES): 560.3 [M−H]⁻. The racemic material (186 mg) is separated by chiral HPLC (column: Chiralpak AD-H 4.6×150 mm; eluent: 2.5% 3A ethanol: 2.5% MeOH: 95% Heptane; flow rate: 0.6 mL/min; UV absorbance wavelength: 250 nm) to provide chiral Isomer 1 (92 mg, 95.4% ee) and chiral Isomer 2 (83 mg, 100% ee).

Preparation 49

(R,S)-3-({5-[1-(2,6-Dimethyl-4'-trifluoromethyl-biphenyl-4-yloxy)-pentyl]-thiophene-2-carbonyl}-amino)-propionic acid methyl ester

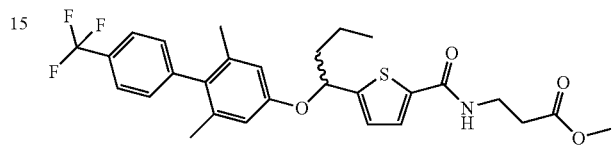

This compound is made by the general method as exemplified in Preparation 33 using 2,6-dimethyl-4'-trifluoromethyl-biphenyl-4-ol as the starting material. MS (ES): 546.3 [M−H]⁻.

Preparation 50

(R,S)-3-({5-[1-(2-Methyl-4'-trifluoromethyl-biphenyl-4-yloxy)-pentyl]-thiophene-2-carbonyl}-amino)-propionic acid methyl ester

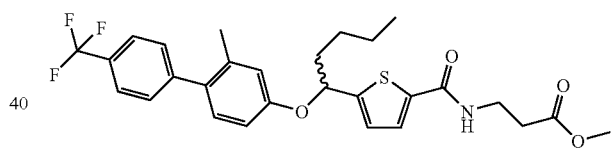

This compound is made by the general method as exemplified in Preparation 33 using 2-methyl-4'-trifluoromethyl-biphenyl-4-ol as the starting material. MS (ES): 532.3 [M−H]⁻.

Preparation 51

(R,S)-3-({5-[1-(4'-tert-Butyl-2,6-dimethyl-biphenyl-4-yloxy)-pentyl]-thiophene-2-carbonyl}-amino)-propionic acid methyl ester

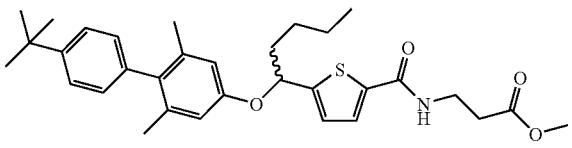

This compound is made by the general method as exemplified in Preparation 33 using 4'-tert-butyl-2,6-dimethyl-biphenyl-4-ol as the starting material. MS (ES): 534.2 [M−H]⁻.

Preparation 52

(R,S)-3-({5-[1-(4'-tert-Butyl-2-methyl-biphenyl-4-yloxy)-pentyl]-thiophene-2-carbonyl}-amino)-propionic acid methyl ester

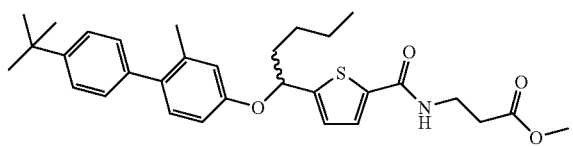

This compound is made by the general method as exemplified in Preparation 33 using 4'-tert-butyl-2-methyl-biphenyl-4-ol as the starting material. MS (ES): 520.3 [M−H]⁻.

Preparation 53

(R,S)-3-({5-[1-(4-Iodo-3,5-dimethyl-phenoxy)-propyl]-thiophene-2-carbonyl}-amino)-propionic acid methyl ester

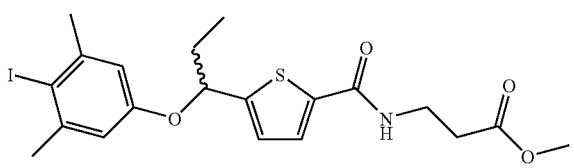

This compound is made by the general method as exemplified in Preparation 33 using 4-iodo-3,5-dimethyl-phenol as the starting material. MS (ES): 500.1 [M−H]⁻. The racemic material (2.122 g) is separated by chiral HPLC (column: Chiralpak OJ-H 4.6×150 mm; eluent: 100% MeOH; flow rate: 0.6 mL/min; UV absorbance wavelength: 280 nm) to provide chiral Isomer 1 (1.06 g, 99.7% ee) and chiral Isomer 2 (1.07 g, 99.4% ee), Preparation 54

(R,S)-3-({5-[1-(4-Iodo-3,5-dimethyl-phenoxy)-2-methyl-propyl]-thiophene-2-carbonyl}-amino)-propionic acid methyl ester

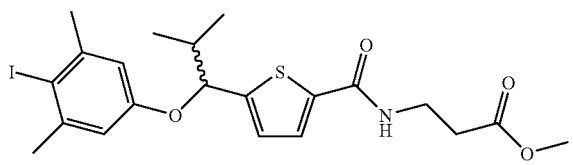

This compound is made by the general method as exemplified in Preparation 33 using 4-iodo-3,5-dimethyl-phenol as the starting material. MS (ES): 514.0 [M−H]⁻. The racemic material (1.793 g) is separated by chiral HPLC (column: Chiralpak OJ-H 4.6×150 mm; eluent: 100% MeOH; flow rate: 0.6 mL/min; UV absorbance wavelength: 270 nm) to provide chiral Isomer 1 (0.831 g, 99.7% ee) and chiral Isomer 2 (0.885 g, 98.6% ee).

Preparation 55

(R,S)-3-({5-[1-(4-Iodo-3,5-dimethyl-phenoxy)-butyl]-thiophene-2-carbonyl}-amino)-propionic acid methyl ester

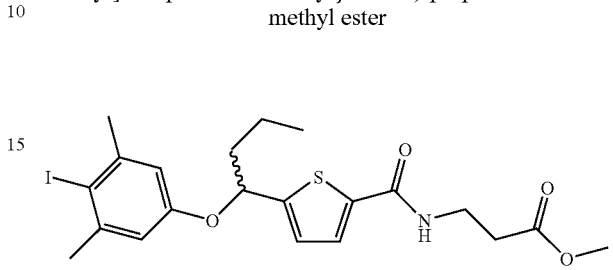

This compound is made by the general method as exemplified in Preparation 33 using 4-iodo-3,5-dimethyl-phenol as the starting material. MS (ES): 516.3 [M+H]⁺. The racemic material (1.697 g) is separated by chiral HPLC (column: Chiralpak AD-H 4.6×150 mm; eluent: 100% MeOH; flow rate: 0.6 mL/min; UV absorbance wavelength: 280 nm) to provide chiral Isomer 1 (0.733 g, 99.2% ee) and chiral Isomer 2 (0.820 g, 99.8% ee).

Preparation 56

5-[2-(2,6-Dimethyl-4'-trifluoromethyl-biphenyl-4-yloxy)-1,1-dimethyl-ethyl]-thiophene-2-carboxylic acid methyl ester

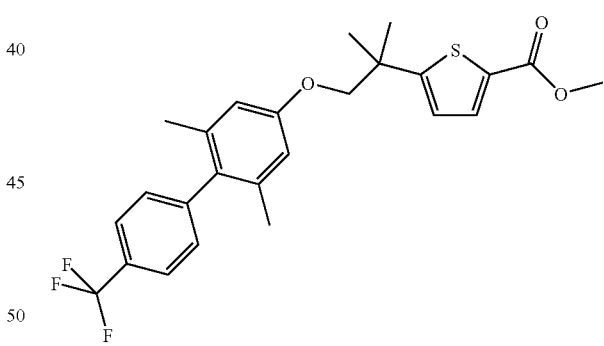

Step A

2-Methyl-2-thiophen-2-yl-propionic acid methyl ester

A mixture of thiophen-2-yl-acetic acid methyl ester (2.001 g, 12.81 mmol) in DMF (40 mL) at 0° C. is treated with NaH (60% dispersion in mineral oil, 1.144 g, 28.60 mmol). After 2 min., iodomethane (1.93 mL, 31.00 mmol) is added. The reaction mixture is warmed to rt and stirred overnight. The mixture is cooled in a cold water bath and quenched with H₂O (40 mL). The mixture is diluted with additional H₂O (40 mL) and extracted with EtOAc (3×50 mL). Combined extracts washed with H₂O, brine, dried over MgSO₄, filtered, and concentrated. The residue is loaded onto silica gel and eluted with hexanes using a gradient of 0% to 40% EtOAc to provide 2-methyl-2-thiophen-2-yl-propionic acid methyl ester (2.107 g, 89%) as a clear oil.
Step B 2-Methyl-2-thiophen-2-yl-propan-1-ol A solution of 2-methyl-2-thiophen-2-yl-propionic acid methyl ester (2.085 g, 11.32 mmol) in $CH_2Cl_2$ (55 mL) at 0° C. is treated with diisobutylaluminum hydrde (Dibal-H, 1.0 M PhMe, 24.0 mL, 24.0 mmol) and warmed to rt after 4 min. After 1.5 h the reaction mixture is cooled to 0° C. and quenched with 1N tartaric acid (50 mL) and stirred for 2 d. The layers are separated and the aqueous layer is extracted with $CH_2Cl_2$ (1×50 mL). The combined extracts are dried over $MgSO_4$, filtered, and concentrated. The residue is loaded onto silica gel and eluted with hexanes using a gradient of 0% to 75% EtOAc to give 2-methyl-2-thiophen-2-yl-propan-1-ol (1.494 g, 84%) as a clear oil.
Step C 5-(2-Hydroxy-1,1-dimethyl-ethyl)-thiophene-2-carboxylic acid A solution of 2-methyl-2-thiophen-2-yl-propan-1-ol (1.481 g, 9.476 mmol) in THF (70 mL) is cooled to −78° C. and treated with t-BuLi (1.7M in pentane, 11.7 mL, 19.9 mmol) dropwise over 14 min. After stirring for 15 min, $CO_{2(g)}$ is bubbled through the solution for 5 min. The solution is then warmed to rt and stirred overnight. The reaction is diluted with $H_2O$ and poured into 1N HCl (20 mL). The mixture is extracted with EtOAc (50 mL, 2×25 mL). The combined extracts are dried over $MgSO_4$, filtered, and conc. The residue is loaded onto $C_{18}$ and eluted with $H_2O$ using a gradient of 15% to 100% MeCN to give 5-(2-hydroxy-1,1-dimethyl-ethyl)-thiophene-2-carboxylic acid (0.511 g, 27%) as a white solid. MS (ES): 199.0 $[M-H]^-$.
Step D 5-(2-Hydroxy-1,1-dimethyl-ethyl)-thiophene-2-carboxylic acid methyl ester A solution of 5-(2-hydroxy-1,1-dimethyl-ethyl)-thiophene-2-carboxylic acid (0.495 g, 2.47 mmol) in DMF (12.0 mL) is treated with $K_2CO_3$ (0.515 g, 3.73 mmol), iodomethane (0.23 mL, 3.69 mmol), and stirred at rt overnight. The mixture is poured into $H_2O$ (25 mL) and extracted with EtOAc (3×25 mL). The combined extracts are washed with $H_2O$, brine, dried over $MgSO_4$, filtered, and concentrated. The residue is loaded onto silica gel and eluted with hexanes using a gradient of 0% to 75% EtOAc to give 5-(2-hydroxy-1,1-dimethyl-ethyl)-thiophene-2-carboxylic acid methyl ester (0.439 g, 83%). MS (ES): 215.1 $[M+H]^+$.
Step E 5-[2-(2,6-Dimethyl-4'-trifluoromethyl-biphenyl-4-yloxy)-1,1-dimethyl-ethyl]-thiophene-2-carboxylic acid methyl ester A mixture of 5-(2-hydroxy-1,1-dimethyl-ethyl)-thiophene-2-carboxylic acid methyl ester (0.436 g, 2.04 mmol), 2,6-dimethyl-4'-trifluoromethyl-biphenyl-4-ol (0.596 g, 2.24 mmol), and $PPh_3$ (0.793 g, 3.02 mmol) is dissolved in toluene (20 mL), treated with 1,1'-(azodicarbonyl)dipiperidine (ADDP, 0.763 g, 3.02 mmol), and stirred overnight at 80° C. The mixture is then cooled to rt, diluted with MeOH until homogeneous, and concentrated. The residue is loaded onto silica gel and eluted using hexanes with an ethyl acetate gradient from 0% to 40% to afford 5-[2-(2,6-dimethyl-4'-trifluoromethyl-biphenyl-4-yloxy)-1,1-dimethyl-ethyl]-thiophene-2-carboxylic acid methyl ester (0.394 g, 42%). MS (ES): 463.3 $[M+H]^+$.

The following compounds are made in a substantially similar manner:

Preparation 57

5-[1-(2,6-Dimethyl-4'-trifluoromethyl-biphenyl-4-yloxymethyl)-1-ethyl-propyl]-thiophene-2-carboxylic acid methyl ester

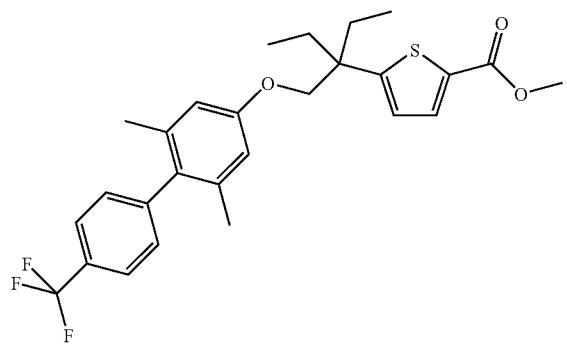

This compound is made by the general method as exemplified in Preparation 56 using iodoethane as the starting material. MS (ES): 491.3 $[M+H]^+$.

Preparation 58

5-[1-Allyl-1-(2,6-dimethyl-4'-trifluoromethyl-biphenyl-4-yloxymethyl)-but-3-enyl]-thiophene-2-carboxylic acid methyl ester

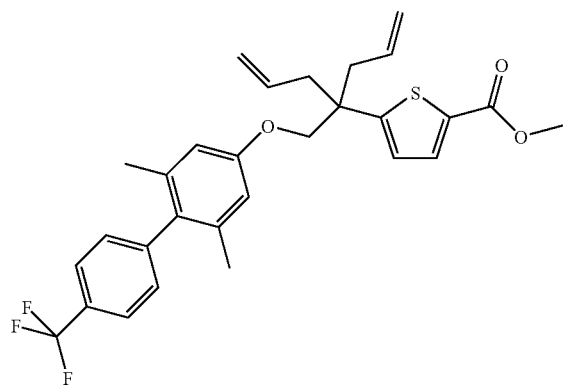

This compound is made by the general method as exemplified in Preparation 56 using allyl bromide as the starting material. MS (ES): 515.3 [M+H]+.

Preparation 59

3-({5-[1-Allyl-1-(2,6-dimethyl-4'-trifluoromethyl-biphenyl-4-yloxymethyl)-but-3-enyl]-thiophene-2-carbonyl}-amino)-propionic acid methyl ester

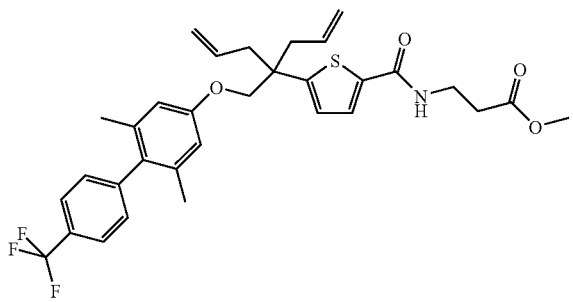

Step A

5-[1-allyl-1-(2,6-dimethyl-4'-trifluoromethyl-biphenyl-4-yloxymethyl)-but-3-enyl]-thiophene-2-carboxylic acid A solution of 5-[1-allyl-1-(2,6-dimethyl-4'-trifluoromethyl-biphenyl-4-yloxymethyl)-but-3-enyl]-thiophene-2-carboxylic acid methyl ester (0.186 g, 0.361 mmol) in THF (4.0 mL) is treated with LiOH (1N aqueous, 4.0 mL, 4.0 mmol), warmed to 70° C., and stirred overnight. The reaction mixture is cooled to rt., acidified with HCl (1N aqueous, 4.2 mL), and extracted with EtOAc (3×10 mL). The combined extracts are dried over MgSO4, filtered, and conc. to provide 5-[1-allyl-1-(2,6-dimethyl-4'-trifluoromethyl-biphenyl-4-yloxymethyl)-but-3-enyl]-thiophene-2-carboxylic acid (0.171 g, 94%) as a white foam. MS (ES): 501.4 [M+H]+.

Step B 3-({5-[1-Allyl-1-(2,6-dimethyl-4'-trifluoromethyl-biphenyl-4-yloxymethyl)-but-3-enyl]-thiophene-2-carbonyl}-amino)-propionic acid methyl ester To a mixture of 5-[1-allyl-1-(2,6-dimethyl-4'-trifluoromethyl-biphenyl-4-yloxymethyl)-but-3-enyl]-thiophene-2-carboxylic acid (0.1695 g, 0.338 mmol), 3-amino-propionic acid methyl ester hydrochloride (0.0533 g, 0.382 mmol), and 1-hydroxybenzotriazole hydrate (HOBt, 0.0561 g, 0.415 mmol) in DMF (3.5 mL) is added N, N-diisopropylethylamine (0.175 mL, 1.00 mmol), then N-(3-dimethylaminopropyl)-N'-ethylcarbodiimide hydrochloride (EDCI, 0.0836 g, 0.436 mmol) and stirred overnight. The reaction mixture is poured into H2O (10 mL) and extracted with EtOAc (3×10 mL). Combined organic extracts are washed with H2O, brine, dried over MgSO4, filtered, and concentrated. The residue is loaded onto silica gel and eluted using hexanes with an ethyl acetate gradient from 0% to 75% to provide 3-({5-[1-allyl-1-(2,6-dimethyl-4'-trifluoromethyl-biphenyl-4-yloxymethyl)-but-3-enyl]-thiophene-2-carbonyl}-amino)-propionic acid methyl ester (0.138 g, 70%) as a white foam. MS (ES): 584.3 [M–H]–.

The following compounds are made in a substantially similar manner:

Preparation 60

3-({5-[2-(2,6-Dimethyl-4'-trifluoromethyl-biphenyl-4-yloxy)-1,1-dimethyl-ethyl]-thiophene-2-carbonyl}-amino)-propionic acid methyl ester

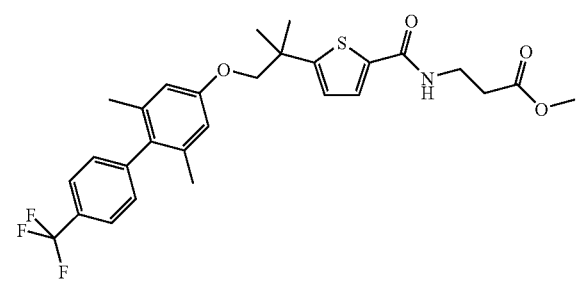

This compound is made by the general method as exemplified in Preparation 59 using 5-[2-(2,6-dimethyl-4'-trifluoromethyl-biphenyl-4-yloxy)-1,1-dimethyl-ethyl]-thiophene-2-carboxylic acid methyl ester as the starting material. MS (ES): 534.4 [M+H]+.

Preparation 61

3-({5-[1-(2,6-Dimethyl-4'-trifluoromethyl-biphenyl-4-yloxymethyl)-1-ethyl-propyl]-thiophene-2-carbonyl}-amino)-propionic acid methyl ester

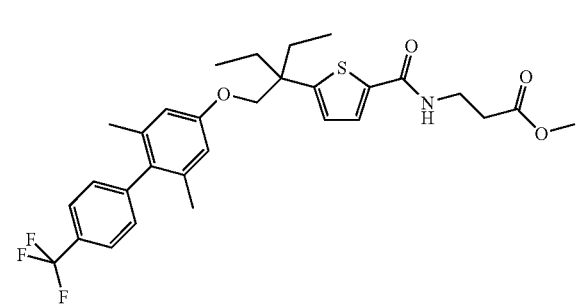

This compound is made by the general method as exemplified in Preparation 59 using 5-[1-(2,6-dimethyl-4'-trifluoromethyl-biphenyl-4-yloxymethyl)-1-ethyl-propyl]-thiophene-2-carboxylic acid methyl ester as the starting material. MS (ES): 562.5 [M+H]+.

Preparation 62

3-({5-[1-(2,6-Dimethyl-4'-trifluoromethyl-biphenyl-4-yloxymethyl)-cyclopent-3-enyl]-thiophene-2-carbonyl}-amino)-propionic acid methyl ester

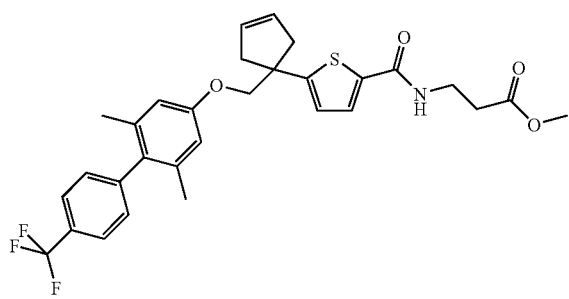

Step A

5-[1-(2,6-dimethyl-4'-trifluoromethyl-biphenyl-4-yloxymethyl)-cyclopent-3-enyl]-thiophene-2-carboxylic acid methyl ester A solution of 5-[1-allyl-1-(2,6-dimethyl-4'-trifluoromethyl-biphenyl-4-yloxymethyl)-but-3-enyl]-thiophene-2-carboxylic acid methyl ester (0.292 g, 0.567 mmol) in CH$_2$Cl$_2$ (270 mL) is treated with [1,3-bis-(2,4,6-trimethylphenyl)-2-imidazolidinylidene)dichloro(phenylmethylene)-(tricyclohexylphosphine)ruthenium] (0.0528 g, 0.0622 mmol) for 4 h and concentrated. The residue is loaded onto silica gel and eluted using hexanes with an ethyl acetate gradient from 0% to 40% to afford 5-[1-(2,6-dimethyl-4'-trifluoromethyl-biphenyl-4-yloxymethyl)-cyclopent-3-enyl]-thiophene-2-carboxylic acid methyl ester (0.240 g, 87%) as a colorless syrup. MS (ES): 487.4 [M+H]$^+$.

Step B

5-[1-(2,6-Dimethyl-4'-trifluoromethyl-biphenyl-4-yloxymethyl)-cyclopent-3-enyl]-thiophene-2-carboxylic acid A solution of 5-[1-(2,6-dimethyl-4'-trifluoromethyl-biphenyl-4-yloxymethyl)-cyclopent-3-enyl]-thiophene-2-carboxylic acid methyl ester (0.239 g, 0.492 mmol) in THF (5.0 mL) is treated with LiOH (1N aqueous, 5.0 mL, 5.0 mmol), warmed to 70° C., and stirred overnight. The reaction mixture is cooled to rt, acidified with HCl (1N aqueous, 5.2 mL), and extracted with EtOAc (3×10 mL). The combined extracts are dried over MgSO$_4$, filtered, and concentrated to provide 5-[1-(2,6-dimethyl-4'-trifluoromethyl-biphenyl-4-yloxymethyl)-cyclopent-3-enyl]-thiophene-2-carboxylic acid (0.210 g, 90%) as a yellow foam. MS (ES): 471.2 [M−H]$^-$.

Step C 3-({5-[1-(2,6-Dimethyl-4'-trifluoromethyl-biphenyl-4-yloxymethyl)-cyclopent-3-enyl]-thiophene-2-carbonyl}-amino)-propionic acid methyl ester To a mixture of 5-[1-(2,6-dimethyl-4'-trifluoromethyl-biphenyl-4-yloxymethyl)-cyclopent-3-enyl]-thiophene-2-carboxylic acid (0.204 g, 0.433 mmol), 3-amino-propionic acid methyl ester hydrochloride (0.0665 g, 0.476 mmol), and 1-hydroxybenzotriazole hydrate (HOBt, 0.0716 g, 0.530 mmol) in DMF (4.0 mL) is added N, N-diisopropylethylamine (0.240 mL, 1.37 mmol), then N-(3-dimethylaminopropyl)-N'-ethylcarbodiimide hydrochloride (EDCI, 0.106 g, 0.553 mmol) and stirred overnight. The reaction mixture is poured into H$_2$O (10 mL) and extracted with EtOAc (3×10 mL). Combined organic extracts are washed with H$_2$O, brine, dried over MgSO$_4$, filtered, and concentrated. The residue is loaded onto silica gel and eluted using hexanes with an ethyl acetate gradient from 0% to 75% to provide 3-({5-[1-(2,6-dimethyl-4'-trifluoromethyl-biphenyl-4-yloxymethyl)-cyclopent-3-enyl]-thiophene-2-carbonyl}-amino)-propionic acid methyl ester (0.158 g, 65%) as a white foam. MS (ES): 556.3 [M−H]$^-$.

Preparation 63

3-({5-[1-(2,6-Dimethyl-4'-trifluoromethyl-biphenyl-4-yloxymethyl)-cyclopentyl]-thiophene-2-carbonyl}-amino)-propionic acid methyl ester

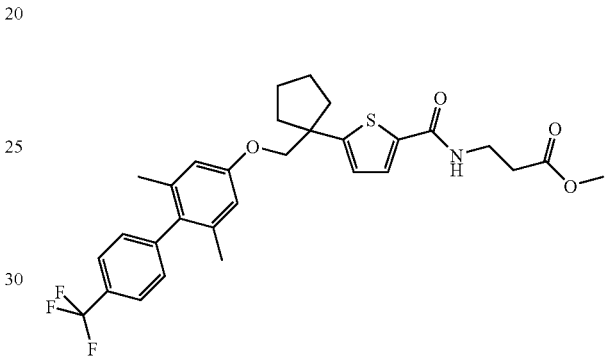

A solution of 3-({5-[1-(2,6-dimethyl-4'-trifluoromethyl-biphenyl-4-yloxymethyl)-cyclopent-3-enyl]-thiophene-2-carbonyl}-amino)-propionic acid methyl ester (0.0828 g, 0.148 mmol) in EtOH (2.0 mL) is treated with 10% palladium on carbon (16 mg), flushed with H$_2$, and stirred under 1 atm pressure for 50 min. The mixture is then filtered through Celite® and concentrated. to provide 3-({5-[1-(2,6-dimethyl-4'-trifluoromethyl-biphenyl-4-yloxymethyl)-cyclopentyl]-thiophene-2-carbonyl}-amino)-propionic acid methyl ester (0.0770 g, 93%) as a white foam. MS (ES): 558.3 [M−H]$^-$.

Preparation 64

3-({5-[1-(2,6-Dimethyl-4'-trifluoromethyl-biphenyl-4-yloxymethyl)-1-propyl-butyl]-thiophene-2-carbonyl}-amino)-propionic acid methyl ester

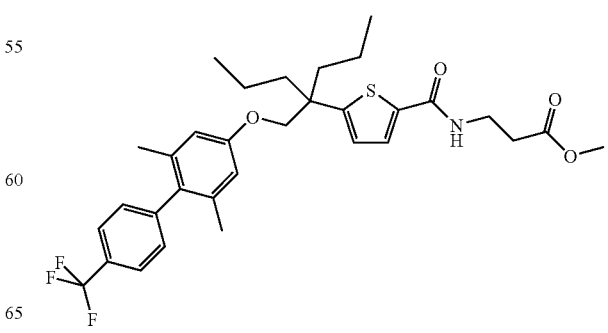

A solution of 3-({5-[1-allyl-1-(2,6-dimethyl-4'-trifluoromethyl-biphenyl-4-yloxymethyl)-but-3-enyl]-thiophene-2-carbonyl}-amino)-propionic acid methyl ester (0.0679 g, 0.116 mmol) in EtOH (2.0 mL) is treated with 10% palladium on carbon (12 mg), flushed with $H_2$, and stirred under 1 atm pressure for 2 h. The mixture is then filtered through Celite® and conc. to provide 3-({5-[1-(2,6-Dimethyl-4'-trifluoromethyl-biphenyl-4-yloxymethyl)-1-propyl-butyl]-thiophene-2-carbonyl}-amino)-propionic acid methyl ester (0.0591 g, 86%) as a white foam. MS (ES): 588.4 [M–H]⁻.

Preparation 65

(R,S)-5-(4,4,4-Trifluoro-1-hydroxy-butyl)-thiophene-2-carboxylic acid ethyl ester

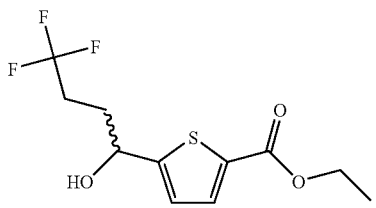

A solution of lithium diisopropyl amide (37.35 mL, 67.22 mmol) in tetrahydrofuran is cooled to −78° C., treated dropwise with a solution of thiophene-2-carboxylic acid ethyl ester (7.0 g, 44.81 mmol) in THF (100 mL), and stirred 5 min. 3-trifluoromethyl-butyraldehyde (9.81 g, 67.22 mmol) is then added, and the reaction is allowed to warm to rt while stirring overnight. Aqueous buffer (pH=7) is added, and the product is extracted into ethyl acetate (3×). Combined organic layers are dried, filtered, and concentrated. The resulting residue is applied to silica gel and eluted using hexanes with an ethyl acetate gradient from 0% to 60% to give the title compound (4.54 g).

Preparation 66

4-Bromo-3,5-dimethyl-benzenethiol

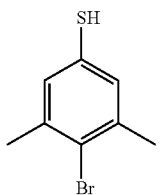

Step A

Dimethyl-thiocarbamic acid O-(4-bromo-3,5-dimethyl-phenyl)ester

4-Bromo-3,5-dimethyl-phenol (10.0 g, 50.01 mmol) was dissolved into dry dioxane (200 mL) and combined with 4-dimethylamino pyridine (1.0 g, 5.2 mmol), triethylamine (12.77 mL, 100.1 mmol), and dimethylamino-thiocarbomoyl chloride (7.69 g, 62.51 mmol). The reaction was heated to reflux under nitrogen. The reaction was monitored by TLC until all of the phenol was consumed, 20 h. After cooling to room temperature, the reaction was diluted with ethyl acetate (200 mL). Water (75 mL) was added and the two layers were separated. The organic layer was washed with brine (75 mL) then dried over anhydrous sodium sulfate. The solvent was removed and the residue was purified by column chromatography, (6.4 g or 55% yield).

Step B

Dimethyl-thiocarbamic acid S-(4-bromo-3,5-dimethyl-phenyl)ester

Dimethyl-thiocarbamic acid O-(4-bromo-3,5-dimethyl-phenyl)ester (6.4 g, 22.3 mmol) was diluted with 50 mL of tetradecane and heated to reflux under nitrogen. The reaction was monitored by TLC until all the conversion was complete, 20 h. The reaction was allowed to cool to room temperature and then loaded onto silica gel column and purified using flash column chromatography, yielding 5.78 g, or 90% of the target product.

Step C

4-Bromo-3,5-dimethyl-benzenethiol

Dimethyl-thiocarbamic acid S-(4-bromo-3,5-dimethyl-phenyl)ester (5.78 g, 20.14 mmol) was diluted with methanol (50 mL) and to this was added sodium methoxide (4.75 mL of 4.25M in methanol, 20.14 mmol). The reaction was heated to reflux under nitrogen and monitored by TLC. After complete conversion, 20 h., the reaction was allowed to cool to room temperature. The reaction was neutralized with 1N HCl (7.5 mL) and diluted with ethyl acetate (150 mL). The two phases were separated and the organic layer was washed with water (75 mL), then brine (75 mL). The organic layer was then dried over anhydrous sodium sulfate, then concentrated and loaded onto silica gel column. The title compound was purified using flash column chromatography, yielding 4.0 g, or 92%.

Preparation 67

(R,S)-5-[1-(4-Bromo-3,5-dimethyl-phenoxy)-4,4,4-trifluoro-butyl]-thiophene-2-carboxylic acid ethyl ester

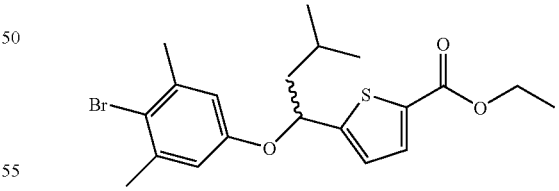

A solution of 4-bromo-3,5-dimethyl-phenol (3.29 g, 16.44 mmol) and (R,S)-5-(1-Hydroxy-3-methyl-butyl)-thiophene-2-carboxylic acid ethyl ester (3.0 g, 13.15 mmol) in toluene is degassed and filled with nitrogen for 3 times. Tributylphosphine (4.87 mL, 19.73 mmol) is added to the reaction mixture under nitrogen at 0° C., followed by addition of 1,1'-(azodicarbonyl)-dipiperidine (4.98 g, 19.73 mmol). The reaction mixture is allowed to warm to room temperature and stirred overnight, the mixture is loaded on silica gel column and purified by flash column chromatography, 4.1 g or 60% yield.

The following compounds are made in a substantially similar manner.

Preparation 68

(R,S)-5-[1-(4-Iodo-3,5-dimethyl-phenoxy)-4,4,4-trifluoro-butyl]-thiophene-2-carboxylic acid ethyl ester

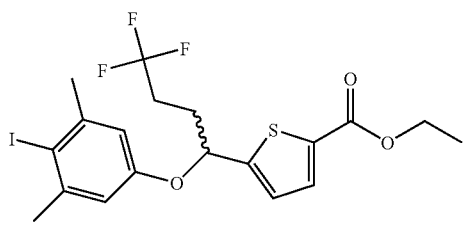

This compound is made by the general method as exemplified in Preparation 67 starting from the 4-iodo-3,5-dimethyl-phenol and 5-(4,4,4-Trifluoro-1-hydroxy-butyl)-thiophene-2-carboxylic acid ethyl ester.

Preparation 69

(R,S)-5-[1-(4-Bromo-3,5-dimethyl-phenylsulfanyl)-4,4,4-trifluoro-butyl]-thiophene-2-carboxylic acid ethyl ester

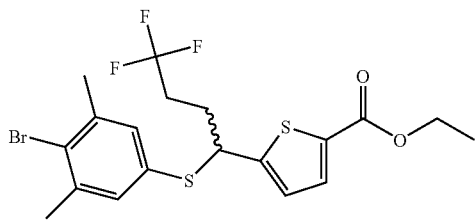

This compound is made by the general method as exemplified in Preparation 67 starting from 4-bromo-3,5-dimethyl-benzenethiol and 5-(4,4,4-trifluoro-1-hydroxy-butyl)-thiophene-2-carboxylic acid ethyl ester.

Preparation 70

(R,S)-5-[1-(4-Bromo-3,5-dimethyl-phenoxy)-3-methyl-butyl]-thiophene-2-carboxylic acid

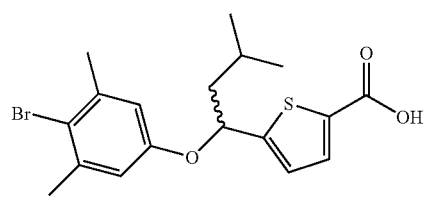

To a mixture of 5-[1-(4-bromo-3,5-dimethyl-phenoxy)-4,4,4-trifluoro-butyl]-thiophene-2-carboxylic acid ethyl ester (4.1 g, 9.67 mmol) in tetrahydrofuran (20 mL) is added sodium hydroxide (5N aqueous, 10 mL) at room temperature, brought to reflux under nitrogen, and stirred overnight. The reaction mixture is acidified by 5 N HCl (10 mL), extracted into ethyl acetate, dried and concentrated, then dried under vacuum, giving the title compound 3.7 g or 96.6% yield.

The following compounds are made in a substantially similar manner.

Preparation 71

(R,S)-5-[4,4,4-Trifluoro-1-(4-iodo-3,5-dimethyl-phenoxy)-butyl]-thiophene-2-carboxylic acid

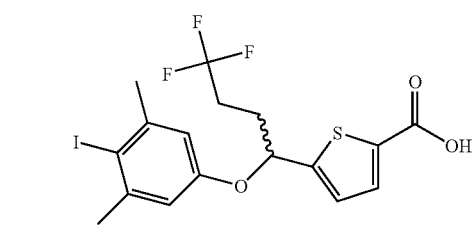

This compound is made by the general method as exemplified in Preparation 70 starting from 5-[1-(4-iodo-3,5-dimethyl-phenoxy)-4,4,4-trifluoro-butyl]-thiophene-2-carboxylic acid ethyl ester.

Preparation 72

(R,S)-5-[1-(4-Bromo-3,5-dimethyl-phenylsulfanyl)-4,4,4-trifluoro-butyl]-thiophene-2-carboxylic acid

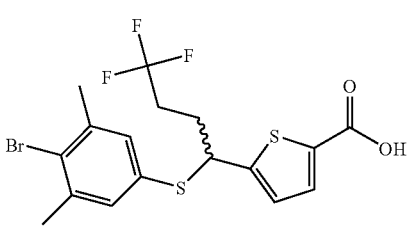

This compound is made by the general method as exemplified in Preparation 70 starting from 5-[1-(4-bromo-3,5-dimethyl-phenylsulfanyl)-4,4,4-trifluoro-butyl]-thiophene-2-carboxylic acid ethyl ester.

Preparation 73

(R,S)-3-({5-[1-(4-Bromo-3,5-dimethyl-phenoxy)-3-methyl-butyl]-thiophene-2-carbonyl}-amino)-propionic acid methyl ester

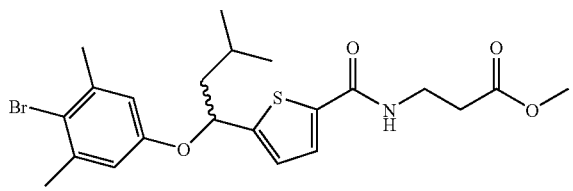

To a mixture of 5-[1-(4-bromo-3,5-dimethyl-phenoxy)-3-methyl-butyl]-thiophene-2-carboxylic acid (3.7 g, 9.34 mmol) in dichloromethane (40 mL) is added chlorodimethoxy-triazine (1.69 g, 9.62 mmol) and 4-methylmorpholine (1.08 mL, 9.81 mmol) under nitrogen. The reaction is allowed to stir under nitrogen at room temperature overnight. The beta-alanine methyl ester hydrochloride salt (1.85 g, 10.28 mmol) is then added to the reaction mixture, followed by addition of 4-methylmorpholine (2.16 mL, 19.62 mmol) and allowed to stir at room temperature. Some water (<10% volume) is added to help solubility. The reaction is monitored by HPLC, and upon complete consumption of the acid, the reaction is diluted with dichloromethane. The reaction is diluted with water and rinsed with 1N HCl. Upon acidification, the two layers are separated. The organic layer is washed with brine, dried over anhydrous sodium sulfate, and concentrated. Flash column chromatography gave the pure compound, 4.2 g or 93.4% yield.

The following compounds are made in a substantially similar manner.

Preparation 74

(R,S)-3-({5-[4,4,4-Trifluoro-1-(4-iodo-3,5-dimethyl-phenoxy)-butyl]thiophene-2-carbonyl}-amino)-propionic acid methyl ester

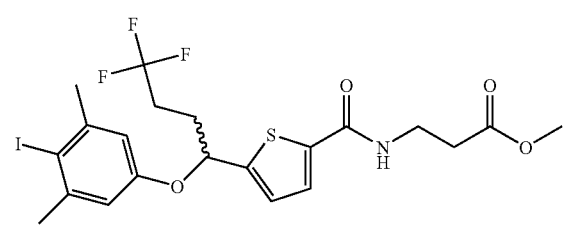

This compound is made by the general method as exemplified in Preparation 73 starting from 5-[4,4,4-trifluoro-1-(4-iodo-3,5-dimethyl-phenoxy)-butyl]-thiophene-2-carboxylic acid.

Preparation 75

3-({5-[4,4,4-Trifluoro-1-(4-iodo-3,5-dimethyl-phenoxy)-butyl]-thiophene-2-carbonyl}-amino)-propionic acid methyl ester, Isomer 1

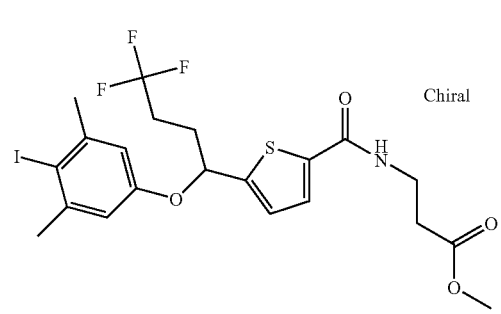

Procedure AA, Chiral Separation

The (R,S)-3-({5-[4,4,4-trifluoro-1-(4-iodo-3,5-dimethyl-phenoxy)-butyl]-thiophene-2-carbonyl}-amino)-propionic acid methyl ester was resolved on a Chiralpak AD-H column (0.46×15.0 cm) with a flow rate of 0.6 mL/min. and detection at 270 nm. Eluted with 3A alcohol solvent and concentrated the fractions to provide a pure enantiomer ester (chiral isomer 1, 99% ee).

The following enantiomeric pure compounds were obtained by a procedure similar to chiral separation Procedure AA using Chiralcel OD-H column (4.6×250 mm), or Chiralpak AD-H column (4.6×150 mm), or using Chiralcel OJ column (4.6×250 mm):

Preparation 76

3-({5-[4,4,4-Trifluoro-1-(4-iodo-3,5-dimethyl-phenoxy)-butyl]-thiophene-2-carbonyl}-amino)-propionic acid methyl ester, Isomer 2

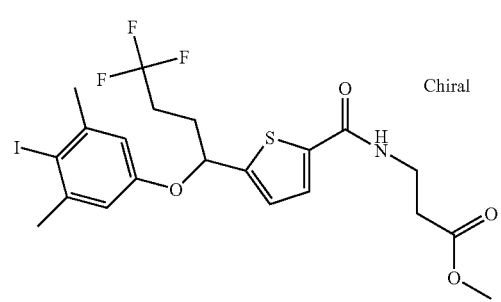

Preparation 77

3-({5-[4,4,4-Trifluoro-1-(4'-isopropyl-2,6-dimethyl-biphenyl-4-yloxy)-butyl]-thiophene-2-carbonyl}-amino)-propionic acid methyl ester, Isomer 2

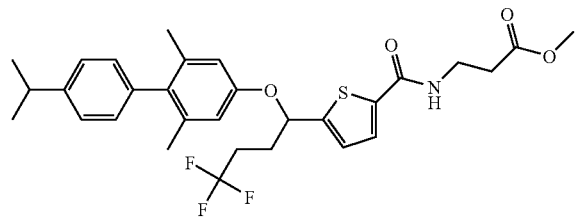

3-({5-[4,4,4-Trifluoro-1-(4-iodo-3,5-dimethyl-phenoxy)-butyl]-thiophene-2-carbonyl}-amino)-propionic acid methyl ester (300 mg, 0.53 mmol) was dissolved in toluene (1.5 mL), followed by palladium tetrakis triphenylphosphine (30 mg, 0.03 mmol), 4-isopropyl-phenyl boronic acid (173 mg, 1.05 mmol), and potassium fluoride (61.2 mg, 1.05 mmol). The reaction was purged with nitrogen and heated to reflux, then water (1.5 mL) was added. The reaction was monitored by HPLC, and upon completion, allowed to cool to room temperature. The reaction was diluted with EtOAc and then Celite® added, followed by water. This mixture was then filtered through a pad of Celite®. The solution was separated in a separatory funnel and the organic layer was washed with 0.1N sodium hydroxide, water, and brine. The organic layer was dried over anhydrous sodium sulfate and concentrated. The product was purified by flash column chromatography (225 mg). MS(ES): 562.3 [M+H]+.

The following compounds are made in a substantially similar manner.

Preparation 78

3-({5-[4,4,4-Trifluoro-1-(4'-isopropyl-2,6-dimethyl-biphenyl-4-yloxy)-butyl]-thiophene-2-carbonyl}-amino)-propionic acid methyl ester, Isomer 1

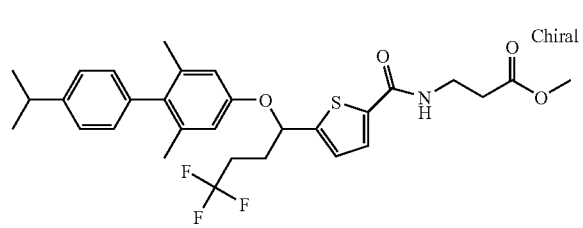

MS(ES): 562.3 [M+H]+.

Preparation 79

3-({5-[1-(2,6-Dimethyl-4'-trifluoromethoxy-biphenyl-4-yloxy)-4,4,4-trifluoro-butyl]-thiophene-2-carbonyl}-amino)-propionic acid methyl ester, Isomer 1

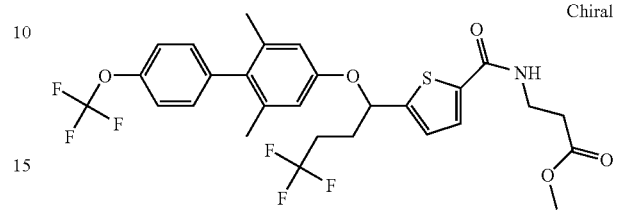

This compound is made by the general method as exemplified in Preparation 77 using 3-({5-[4,4,4-trifluoro-1-(4-iodo-3,5-dimethyl-phenoxy)-butyl]-thiophene-2-carbonyl}-amino)-propionic acid methyl ester - chiral Isomer 1 and 4-trifluoromethoxy-phenyl boronic acid as the starting materials. MS(ES): 604.3 [M+H]+.

Preparation 80

3-({5-[1-(2,6-Dimethyl-4'-trifluoromethoxy-biphenyl-4-yloxy)-4,4,4-trifluoro-butyl]-thiophene-2-carbonyl}-amino)-propionic acid methyl ester, Isomer 2

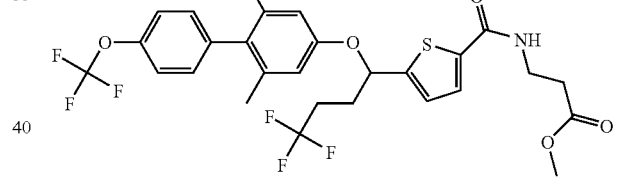

MS(ES): 604.3 [M+H]+.

Preparation 81

3-({5-[1-(4'-Ethyl-2,6-dimethyl-biphenyl-4-yloxy)-4,4,4-trifluoro-butyl]-thiophene-2-carbonyl}-amino)-propionic acid methyl ester, Isomer 1

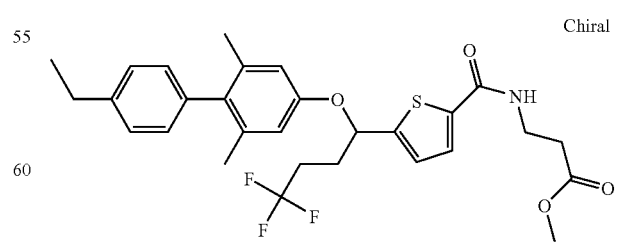

This compound is made by the general method as exemplified in Preparation 77 using 3-({5-[4,4,4-trifluoro-1-(4-iodo-3,5-dimethyl-phenoxy)-butyl]-thiophene-2-carbonyl}- amino)-propionic acid methyl ester - chiral Isomer 1 and 4-ethyl-phenyl boronic acid as the starting materials. MS(ES): 548.3 [M+H]+.

Preparation 82

3-({5-[1-(4'-Ethyl-2,6-dimethyl-biphenyl-4-yloxy)-4,4,4-trifluoro-butyl]-thiophene-2-carbonyl}-amino)-propionic acid methyl ester, Isomer 2

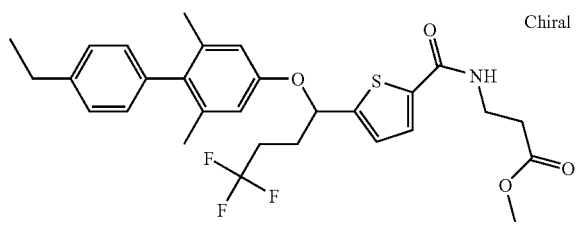

MS(ES): 548.3 [M+H]+.

Preparation 83

(R,S)-3-({5-[1-(4-Bromo-3,5-dimethyl-phenylsulfanyl)-4,4,4-trifluoro-butyl]-thiophene-2-carbonyl}-amino)-propionic acid methyl ester

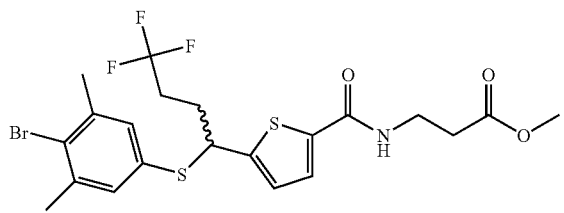

This compound is made by the general method as exemplified in Preparation 73 starting from the 5-[1-(4-bromo-3,5-dimethyl-phenylsulfanyl)-4,4,4-trifluoro-butyl]-thiophene-2-carboxylic acid.

Preparation 84

3-({5-[1-(4-Bromo-3,5-dimethyl-phenylsulfanyl)-4,4,4-trifluoro-butyl]-thiophene-2-carbonyl}-amino)-propionic acid methyl ester, Isomer 1

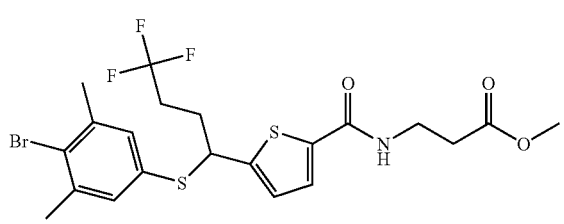

The racemic material was resolved using a procedure similar the chiral separation of Procedure AA, to obtain the pure enantiomer esters of Isomer 1 and Isomer 2 (Preparation 85).

Preparation 85

3-({5-[1-(4-Bromo-3,5-dimethyl-phenylsuffanyl)-4,4,4-trifluoro-butyl]-thiophene-2-carbonyl}-amino)-propionic acid methyl ester, Isomer 2

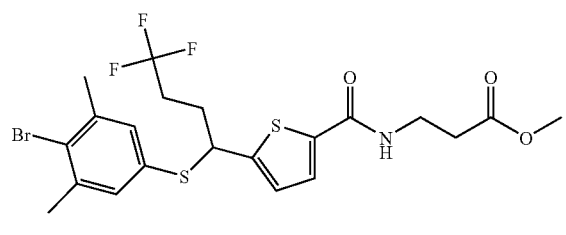

Preparation 86

3-({5-[1-(4'-tert-Butyl-2,6-dimethyl-biphenyl-4-yl-sulfanyl)-4,4,4-trifluoro-butyl]-thiophene-2-carbonyl}-amino)-propionic acid methyl ester, Isomer 2

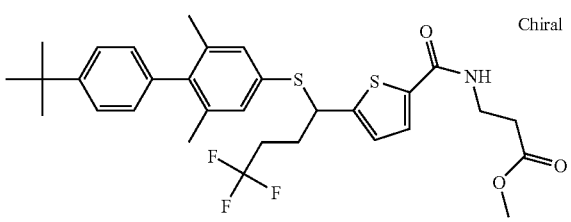

This compound is made by the general method as exemplified in Preparation 77 using 3-({5-[1-(4-bromo-3,5-dimethyl-phenylsulfanyl)-4,4,4-trifluoro-butyl]-thiophene-2-carbonyl}-amino)-propionic acid methyl ester chiral Isomer 2 and 4-t-butyl-phenyl boronic acid as the starting materials. MS(ES): 592.2 [M+H]+.

Preparation 87

3-({5-[1-(4'-tert-Butyl-2,6-dimethyl-biphenyl-4-yl-sulfanyl)-4,4,4-trifluoro-butyl]-thiophene-2-carbonyl}-amino)-propionic acid methyl ester, Isomer 1

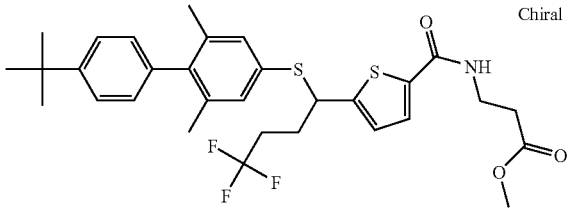

This compound is made by the general method as exemplified in Preparation 77 using 3-({5-[1-(4-bromo-3,5-dimethyl-phenylsulfanyl)-4,4,4-trifluoro-butyl]-thiophene-2- carbonyl}-amino)-propionic acid methyl ester chiral Isomer 1 and 4-t-butyl-phenyl boronic acid as the starting materials. MS(ES): 592.2 [M+H]+.

Preparation 88

(R,S)-5-[1-(4'-tert-Butyl-2,6-dimethyl-biphenyl-4-yloxy)-4,4,4-trifluoro-butyl]-thiophene-2-carboxylic acid ethyl ester

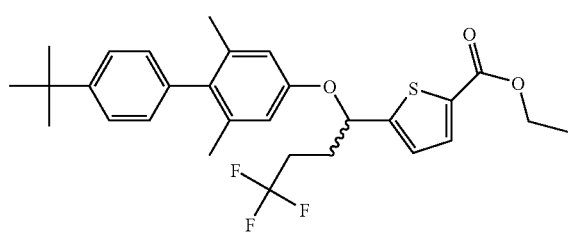

A solution of 4'-tert-butyl-2,6-dimethyl-biphenyl-4-ol (563 mg, 2.22 mmol) and (R,S)5-(4,4,4-trifluoro-1-hydroxy-butyl)-thiophene-2-carboxylic acid ethyl ester (500 mg, 1.77 mmol) in toluene is degassed and filled with nitrogen for 3 times. Tributylphosphine (0.66 mL, 2.66 mmol) is added to the reaction mixture under nitrogen at 0° C., followed by addition of 1,1'-(azodicarbonyl)-dipiperidine (671 mg, 2.66 mmol). The reaction mixture is allowed to warm to room temperature and stirred overnight, the mixture is loaded on silica gel column and purified by flash column chromatography, 862 mg or 94% yield.

The following compounds are made in a substantially similar manner.

Preparation 89

(R,S)-5-[1-(2,6-Dimethyl-4'-trifluoromethyl-biphenyl-4-yloxy)-4,4,4-trifluoro-butyl]-thiophene-2-carboxylic acid ethyl ester

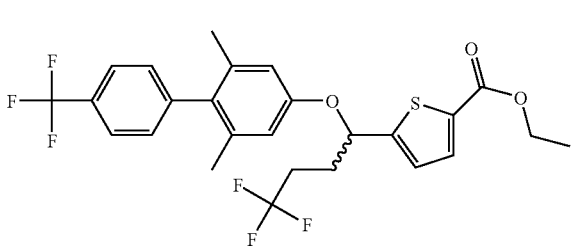

Starting from the 2,6-dimethyl-4'-trifluoromethyl-biphenyl-4-ol and (R,S)5-(4,4,4-trifluoro-1-hydroxy-butyl)-thiophene-2-carboxylic acid ethyl ester.

Preparation 90

(R,S)-5-[1-(4'-tert-Butyl-2,6-dimethyl-biphenyl-4-yloxy)-4,4,4-trifluoro-butyl]-thiophene-2-carboxylic acid To a mixture of 5-[1-(4'-tert-butyl-2,6-dimethyl-biphenyl-4-yloxy)-4,4,4-trifluoro-butyl]-thiophene-2-carboxylic acid ethyl ester (800 mg, 1.54 mmol) in tetrahydrofuran (10 mL) is added sodium hydroxide (5N aqueous, 5 mL) at room temperature, brought to reflux under nitrogen, and stirred overnight. The reaction mixture is acidified by 5 N HCl (5 mL), extracted into ethyl acetate, dried and concentrated, then dried under vacuum, giving the title compound 747 mg or 98.7% yield.

The following compounds are made in a substantially similar manner.

Preparation 91

(R,S)-5-[1-(2,6-Dimethyl-4'-trifluoromethyl-biphenyl-4-yloxy)-4,4,4-trifluoro-butyl]-thiophene-2-carboxylic acid

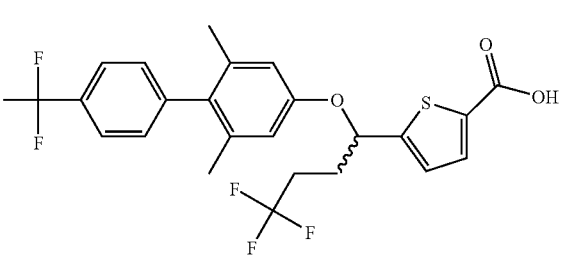

This compound is made by the general method as exemplified in Preparation 90 starting from 5-[1-(2,6-dimethyl-4'- trifluoromethyl-biphenyl-4-yloxy)-4,4,4-trifluoro-butyl]-thiophene-2-carboxylic acid ethyl ester.

Preparation 92

(R,S)-3-({5-[1-(4'-tert-Butyl-2,6-dimethyl-biphenyl-4-yloxy)-4,4,4-trifluoro-butyl]-thiophene-2-carbonyl}-amino)-propionic acid methyl ester

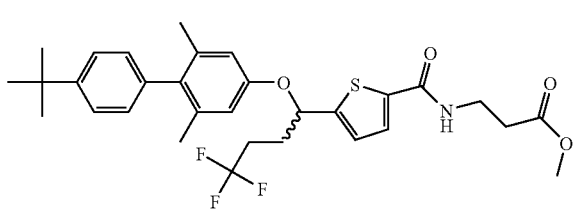

To a mixture of 5-[1-(4'-tert-butyl-2,6-dimethyl-biphenyl-4-yloxy)-4,4,4-trifluoro-butyl]-thiophene-2-carboxylic acid (747 mg, 1.52 mmol) in dichloromethane (10 mL) is added chloro-dimethoxy-triazine (276 mg, 1.57 mmol) and 4-methylmorpholine (0.180 mL, 1.6 mmol) under nitrogen. The reaction is allowed to stir under nitrogen at room temperature overnight. The beta-alanine methyl ester hydrochloride salt (302 mg, 1.57 mmol) is then added to the reaction mixture, followed by addition of 4-methylmorpholine (0.360 mL, 3.20 mmol) and allowed to stir at room temperature. Some water (<10% volume) is added to help solubility. The reaction is monitored by HPLC, and upon complete consumption of the acid, the reaction is diluted with dichloromethane. The reaction is diluted with water and rinsed with 1N HCl. Upon acidification, the two layers are separated. The organic layer is washed with brine, dried over anhydrous sodium sulfate, and concentrated. Flash column chromatography gave the pure compound, 252 mg or 28.8% yield.

The following compounds are made in a substantially similar manner.

Preparation 93

(R,S)-3-({5-[1-(2,6-Dimethyl-4'-trifluoromethyl-biphenyl-4-yloxy)-4,4,4-trifluoro-butyl]-thiophene-2-carbonyl}-amino)-propionic acid methyl ester

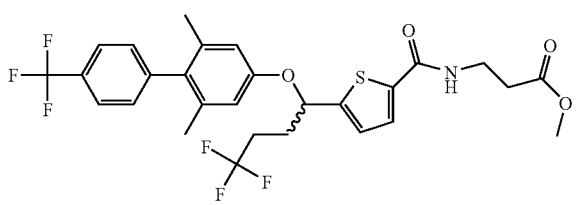

This compound is made by the general method as exemplified in Preparation 92 from 5-[1-(2,6-dimethyl-4'-trifluoromethyl-biphenyl-4-yloxy)-4,4,4-trifluoro-butyl]-thiophene-2-carboxylic acid.

Preparation 94

(R,S)-3-({5-[1-(4'-tert-Butyl-2,6-dimethyl-biphenyl-4-yloxy)-ethyl]-thiophene-2-carbonyl}-amino)-propionic acid methyl ester Step A (R,S)-5-[1-(4'-tert-Butyl-2,6-dimethyl-biphenyl-4-yloxy)-ethyl]-thiophene-2-carboxylic acid ethyl ester A mixture of (±)-5-(1-hydroxy-ethyl)-thiophene-2-carboxylic acid ethyl ester (0.416 g, 2.08 mmol), 4'-tert-butyl-2,6-dimethyl-biphenyl-4-ol (0.561 g, 2.20 mmol), and $PPh_3$ (0.787 g, 3.00 mmol) is dissolved in toluene (19 mL) and treated with 1,1'-(azodicarbonyl)dipiperidine (ADDP, 0.760 g, 3.01 mmol) and stirred overnight at rt. The mixture is diluted with MeOH until homogeneous and conc. The residue is loaded onto silica gel and eluted using hexanes with an ethyl acetate gradient from 0% to 40% giving (±)-5-[1-(4'-tert-butyl-2,6-dimethyl-biphenyl-4-yloxy)-ethyl]-thiophene-2-carboxylic acid ethyl ester (0.604 g, 671%) as a clear syrup.

Step B (R,S)-5-[1-(4'-tert-Butyl-2,6-dimethyl-biphenyl-4-yloxy)-ethyl]-thiophene-2-carboxylic acid To a mixture of (±)-5-[1-(4'-tert-butyl-2,6-dimethyl-biphenyl-4-yloxy)-ethyl]-thiophene-2-carboxylic acid ethyl ester (0.603 g, 1.38 mmol) in THF (14 mL) is added lithium hydroxide (1N aqueous, 14 mL). The mixture is warmed to 70° C. and stirred overnight. The reaction mixture is acidified with 1N HCl (15 mL), extracted into ethyl acetate (3×25 mL), dried over $MgSO_4$, and concentrated, to provide (±)-5-[1-(4'-tert-butyl-2,6-dimethyl-biphenyl-4-yloxy)-ethyl]-thiophene-2-carboxylic acid (0.554 g, 98%) as a white foam. MS (ES): 407.3 [M–H]⁻.

Step C (R,S)-3-({5-[1-(4'-tert-Butyl-2,6-dimethyl-biphenyl-4-yloxy)-ethyl]-thiophene-2-carbonyl}-amino)-propionic acid methyl ester To a mixture of (±)-5-[1-(4'-tert-butyl-2,6-dimethyl-biphenyl-4-yloxy)-ethyl]-thiophene-2-carboxylic acid (0.546 g, 1.34 mmol), 3-amino-propionic acid methyl ester hydrochloride (0.204 g, 1.46 mmol), and 1-hydroxybenzotriazole hydrate (HOBt, 0.217 g, 1.60 mmol) in DMF (12.3 mL) is added N, N-diisopropylethylamine (0.70 mL, 4.01 mmol), then N-(3-dimethylaminopropyl)-N'-ethylcarbodiimide hydrochloride (EDCI, 0.333 g, 1.74 mmol) and stirred overnight. The reaction mixture is poured into $H_2O$ (25 mL) and extracted with EtOAc (3×25 mL). Combined organic extracts are washed with H₂O, brine, dried over MgSO₄, filtered, and concentrated. The residue is loaded onto silica gel and eluted using hexanes with an ethyl acetate gradient from 0% to 75% to provide (±)-3-({5-[1-(4'-tert-butyl-2,6-dimethyl-biphenyl-4-yloxy)-ethyl]-thiophene-2-carbonyl}-amino)-propionic acid methyl ester (0.472 g, 71%) as a white solid. MS (ES): 492.1 [M–H]⁻. The racemic material is separated by chiral HPLC (column: Chiralpak OD-H 4.6×150 mm; eluent: 10:90 3A alcohol/Heptane; flow rate: 0.6 mL/min; UV absorbance wavelength: 270 nm) to provide Isomer 1 (0.180 g, 98.3% ee) and Isomer 2 (0.190 g, 96.7% ee).

The following compounds are made in a substantially similar manner:

Preparation 95

(R,S)-3-({5-[1-(4-Iodo-3,5-dimethyl-phenoxy)-2-methyl-propyl]-thiophene-2-carbonyl}-amino)-propionic acid methyl ester

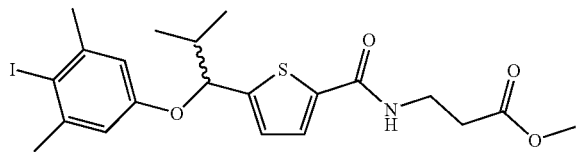

This compound is made by the general method as exemplified in Preparation 94, Step A using 4-iodo-3,5-dimethyl-phenol and 5-(1-hydroxy-2-methyl-propyl)-thiophene-2-carboxylic acid ethyl ester as the starting materials to provide (±)-3-({5-[1-(4-iodo-3,5-dimethyl-phenoxy)-2-methyl-propyl]-thiophene-2-carbonyl}-amino)-propionic acid methyl ester (1.796 g) as a white solid. MS (ES): 514.0 [M–H]⁻. The racemic material is separated by chiral HPLC (column: Chiralpak OJ-H 4.6×150 mm; eluent: 100% MeOH; flow rate: 0.6 mL/min; UV absorbance wavelength: 270 nm) to provide Isomer 1 (0.885 g, 98.67% ee) and Isomer 2 (0.831 g, 99.7% ee).

Preparation 96

(R,S)-3-({5-[1-(2,6-Dimethyl-4'-trifluoromethyl-biphenyl-4-yloxy)-2-methyl-propyl]-thiophene-2-carbonyl}-amino)-2R-hydroxy-propionic acid methyl ester

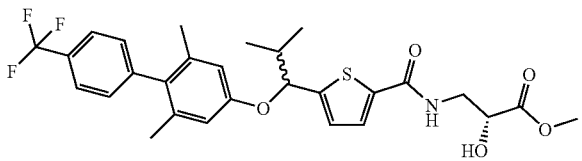

This compound is made by the general method as exemplified in Preparation 94 using 2,6-dimethyl-4'-trifluoromethyl-biphenyl-4-ol as the starting material in Step A and 2R-hydroxy-propionic acid methyl ester in Step C to provide (±)-3-({5-[1-(2,6-Dimethyl-4'-trifluoromethyl-biphenyl-4-yloxy)-2-methyl-propyl]-thiophene-2-carbonyl}-amino)-2R-hydroxy-propionic acid methyl ester hydrochloride salt (0.291 g) as a white foam. MS (ES): 548.2 [M–H]⁻. The diastereomeric material is separated by chiral HPLC (column: Chiralpak OJ-H 4.6×150 mm; eluent: 100% MeOH; flow rate: 0.6 mL/min; UV absorbance wavelength: 280 nm) to provide Isomer 1 (0.113 g, 99% de) and Isomer 2 (0.107 g, 99% de).

Preparation 97

(R,S)-3-({5-[1-(4'-tert-Butyl-2,6-dimethyl-biphenyl-4-yloxy)-2-methyl-propyl]-thiophene-2-carbonyl}-amino)-2R-hydroxy-propionic acid methyl ester

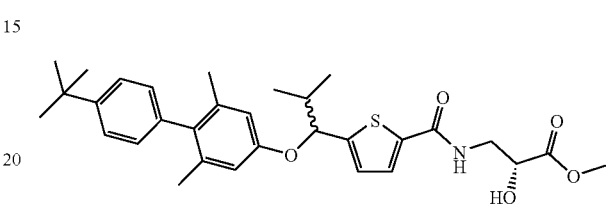

This compound is made by the general method as exemplified in Preparation 94 using 4'-tert-butyl-2,6-dimethyl-biphenyl-4-ol as the starting material in Step A and 2R-hydroxy-propionic acid methyl ester hydrochloride salt in Step C to provide (±)-3-({5-[1-(4'-tert-Butyl-2,6-dimethyl-biphenyl-4-yloxy)-2-methyl-propyl]-thiophene-2-carbonyl}-amino)-2-hydroxy-propionic acid methyl ester (0.327 g) as a white/tan solid. MS (ES): 536.3 [M–H]⁻. The diastereomeric material is separated by chiral HPLC (column: Chiralpak OJ-H 4.6×150mm; eluent: 100% MeOH; flow rate: 0.6 mL/min; UV absorbance wavelength: 280 nm) to provide Isomer 1 (0.132 g, >99% de) and Isomer 2 (0.127 g, >99% de).

Preparation 98

(R,S)-3-({5-[1-(2,6-Dimethyl-4'-trifluoromethyl-biphenyl-4-yloxy)-2-methyl-propyl]-thiophene-2-carbonyl}-amino)-2S-hydroxy-propionic acid ethyl ester

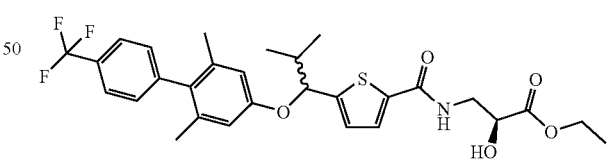

This compound is made by the general method as exemplified in Preparation 94 using 2,6-dimethyl-4'-trifluoromethyl-biphenyl-4-ol as the starting material in Step A and 2S-hydroxy-propionic acid ethyl ester hydrochloride salt in Step C to provide (±)-3-({5-[1-(2,6-Dimethyl-4'-trifluoromethyl-biphenyl-4-yloxy)-2-methyl-propyl]-thiophene-2-carbonyl}-amino)-2S-hydroxy-propionic acid methyl ester (0.387 g) as a white foam. MS (ES): 562.2 [M–H]⁻. The diastereomeric material is separated by chiral HPLC (column: Chiralpak OJ-H 4.6×150 mm; eluent: 100% MeOH;

flow rate: 0.6 mL/min; UV absorbance wavelength: 280 nm) to provide Isomer 1 (0.1573 g, >99% de) and Isomer 2 (0.149 g, 98.9% de).

Preparation 99

(R,S)-3-({5-[1-(4'-tert-Butyl-2,6-dimethyl-biphenyl-4-yloxy)-2-methyl-propyl]-thiophene-2-carbonyl}-amino)-2S-hydroxy-propionic acid ethyl ester

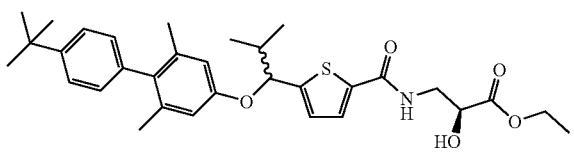

This compound is made by the general method as exemplified in Preparation 94 using 4'-tert-butyl-2,6-dimethyl-biphenyl-4-ol as the starting material in Step A and 2S-hydroxy-propionic acid ethyl ester hydrochloride salt in Step C to provide (±)-3-({5-[1-(4'-tert-butyl-2,6-dimethyl-biphenyl-4-yloxy)-2-methyl-propyl]-thiophene-2-carbonyl}-amino)-2-hydroxy-propionic acid ethyl ester (0.326 g) as a white foam. MS (ES): 550.3 [M−H]⁻. The diastereomeric material is separated by chiral HPLC (column: Chiralpak OJ-H 4.6× 150 mm; eluent: 100% MeOH; flow rate: 0.6 mL/min; UV absorbance wavelength: 280 nm) to provide Isomer 1 (0.127 g, 99% de) and Isomer 2 (0.116 g, >99% de).

Preparation 100

(R,S)-3-({5-[1-(4'-tert-Butyl-2-methyl-biphenyl-4-yloxy)-butyl]-thiophene-2-carbonyl}-amino)-propionic acid methyl ester

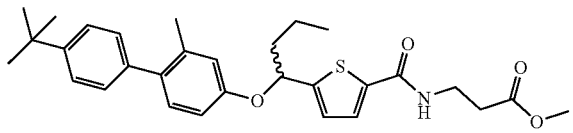

This compound is made by the general method as exemplified in Preparation 94 using 4'-tert-butyl-2-methyl-biphenyl-4-ol in Step A and 3-amino-propionic acid methyl ester hydrochloride salt in Step C as the starting materials to provide (±)-3-({5-[1-(4'-tert-Butyl-2-methyl-biphenyl-4-yloxy)-butyl]-thiophene-2-carbonyl}-amino)-propionic acid methyl ester (0.398 g) as a white solid. MS (ES): 508.5 [M+H]⁺. The racemic material is separated by chiral HPLC (column: Chiralpak AD-H 4.6×150 mm; eluent: 85:15 Heptane/IPA; flow rate: 0.6 mL/min; UV absorbance wavelength: 260 nm) to provide Isomer 1 (0.170 g, 99% ee) and Isomer 2 (0.147 g, 96.2% ee).

Preparation 101

(R,S)-3-({5-[1-(4'-tert-Butyl-2,6-dimethyl-biphenyl-4-yloxy)-butyl]-thiophene-2-carbonyl}-amino)-propionic acid methyl ester This compound is made by the general method as exemplified in Preparation 94 using 4'-tert-butyl-2,6-dimethyl-biphenyl-4-ol in Step A and 3-amino-propionic acid methyl ester hydrochloride salt in Step C as the starting materials to provide (±)-3-({5-[1-(4'-tert-Butyl-2,6-dimethyl-biphenyl-4-yloxy)-butyl]-thiophene-2-carbonyl}-amino)-propionic acid methyl ester (0.434 g) as a white solid. MS (ES): 522.5 [M+H]⁺. The racemic material is separated by chiral HPLC (column: Chiralpak OD-H 4.6×150 mm; eluent: 5:95 3A alcohol/Heptane; flow rate: 0.6 mL/min; UV absorbance wavelength: 270 nm) to provide Isomer 1 (0.187 g, 97.0% ee) and Isomer 2 (0.167 g, 92.8% ee).

Preparation 102

(R,S)-3-({5-[1-(2,6-Dimethyl-4'-trifluoromethyl-biphenyl-4-yloxy)-pentyl]-thiophene-2-carbonyl}-amino)-propionic acid methyl ester

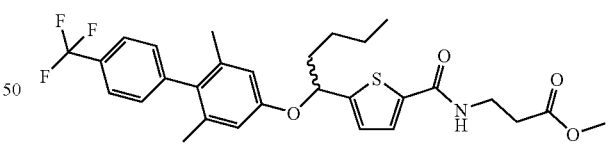

This compound is made by the general method as exemplified in Preparation 94 using 2,6-dimethyl-4'-trifluoromethyl-biphenyl-4-ol in Step A and 3-amino-propionic acid methyl ester hydrochloride salt in Step C as the starting materials to provide (±)-3-({5-[1-(2,6-dimethyl-4'-trifluoromethyl-biphenyl-4-yloxy)-pentyl]thiophene-2-carbonyl}-amino)-propionic acid methyl ester (0.391 g) as a clear syrup. MS (ES): 546.3 [M−H]⁻. The racemic material is separated by chiral HPLC (column: Chiralpak OD-H 4.6×150 mm; eluent: 10:90 IPA/Heptane; flow rate: 0.6 mL/min; UV absor- Preparation 103

3-({5-[1-(4'-tert-Butyl-2,6-dimethyl-biphenyl-4-yloxymethyl)-1-ethyl-propyl]-thiophene-2-carbonyl}-amino)-propionic acid methyl ester

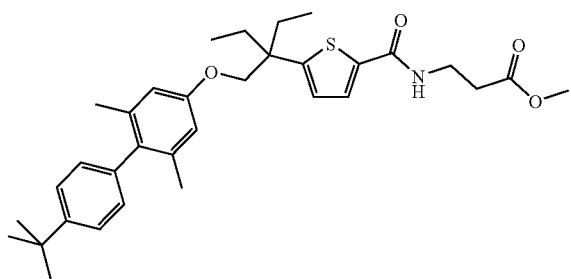

This compound is made by the general method as exemplified in Preparation 94 using 4'-tert-butyl-2,6-dimethyl-biphenyl-4-ol and 5-(1-ethyl-1-hydroxymethyl-propyl)-thiophene-2-carboxylic acid methyl ester in Step A and 3-amino-propionic acid methyl ester hydrochloride salt in Step C as the starting materials to provide 3-({5-[1-(4'-test-butyl-2,6-dimethyl-biphenyl-4-yloxymethyl)-1-ethyl-propyl]-thiophene-2-carbonyl}-amino)-propionic acid methyl ester (0.189 g) as a white solid.

Preparation 104

(R,S)-3-({5-[1-(4'-tert-Butyl-2,6-dimethyl-biphenyl-4-yloxymethyl)-propyl]-thiophene-2-carbonyl}-amino)-propionic acid methyl ester

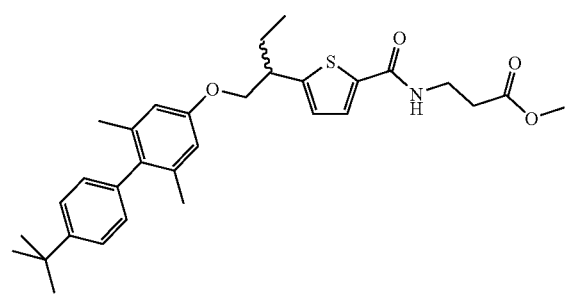

This compound is made by the general method as exemplified in Preparation 94 using 4'-tert-butyl-2,6-dimethyl-biphenyl-4-ol and 5-(1-hydroxymethyl-propyl)-thiophene-2-carboxylic acid methyl ester in Step A and 3-amino-propionic acid methyl ester hydrochloride salt in Step C as the starting materials to provide (±)-3-({5-[1-(4'-tert-butyl-2,6-dimethyl-biphenyl-4-yloxymethyl)-propyl]-thiophene-2-carbonyl}-amino)-propionic acid methyl ester (0.213 g) as a white solid. MS (ES): 520.3 [M–H]⁻. The racemic material is separated by chiral HPLC (column: Chiralpak AD-H 4.6×150 mm; eluent: 20:80 IPA/supercritical CO₂; flow rate: 5 mL/min; UV absorbance wavelength: 270 nm) to provide Isomer 1 (0.155 g, 99.0% ee) and Isomer 2 (0.117 g, 98.5% ee).

Preparation 105

(R,S)-3-({5-[1-(2,6-Dimethyl-4'-trifluoromethyl-biphenyl-4-yloxymethyl)-propyl]-thiophene-2-carbonyl}-amino)-propionic acid methyl ester

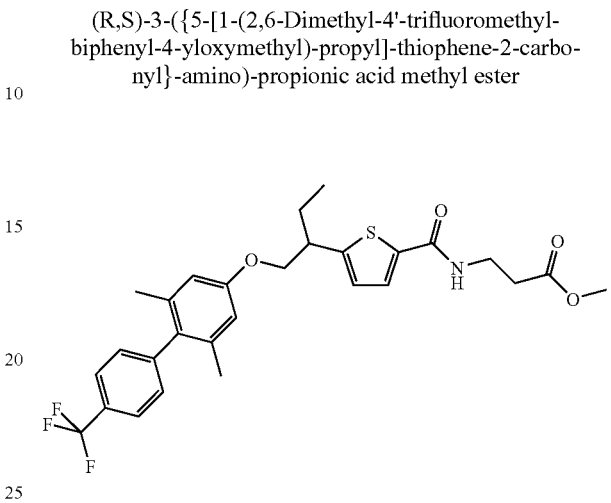

This compound is made by the general method as exemplified in Preparation 94 using 2,6-dimethyl-4'-trifluoromethyl-biphenyl-4-ol and 5-(1-hydroxymethyl-propyl)-thiophene-2-carboxylic acid methyl ester in Step A and 3-amino-propionic acid methyl ester hydrochloride salt in Step C as the starting materials to provide (±)-3-({5-[1-(2,6-dimethyl-4'-trifluoromethyl-biphenyl-4-yloxymethyl)-propyl]-thiophene-2-carbonyl}-amino)-propionic acid methyl ester (0.225 g) as a white solid. MS (ES): 532.3 [M–H]⁻. The racemic material is separated by chiral HPLC (column: Chiralpak AD-H 4.6×150 mm; eluent: 20:80 IPA/supercritical CO₂; flow rate: 5 mL/min; UV absorbance wavelength: 270 nm) to provide Isomer 1 (0.049 g, >99% ee) and Isomer 2 (0.049 g, 96.8% ee).

Preparation 106

(R,S)-3-({4-Chloro-5-[1-(2,6-dimethyl-4'-trifluoromethyl-biphenyl-4-yloxy)-propyl]-thiophene-2-carbonyl}-amino)-propionic acid methyl ester

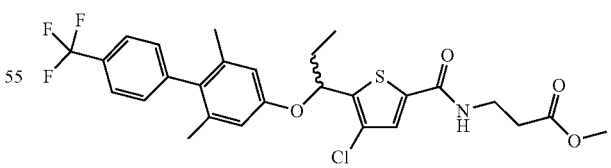

This compound is made by the general method as exemplified in Preparation 94 using 2,6-dimethyl-4'-trifluoromethyl-biphenyl-4-ol and 4-chloro-5-(1-hydroxy-propyl)-thiophene-2-carboxylic acid methyl ester in Step A and 3-amino-propionic acid methyl ester hydrochloride salt in Step C as the starting materials to provide (±)-3-({4-chloro-5-[1-(2,6-dimethyl-4'-trifluoromethyl-biphenyl-4-yloxy)- propyl]-thiophene-2-carbonyl}-amino)-propionic acid methyl ester (0.094 g) as a white foam. MS (ES): 552.2 [M−H]⁻.

Preparation 107

(R,S)-3-({5-[1-(2,6-Dimethyl-4'-trifluoromethyl-biphenyl-4-ylsulfanyl)-2-methyl-propyl]-thiophene-2-carbonyl}-amino)-propionic acid methyl ester

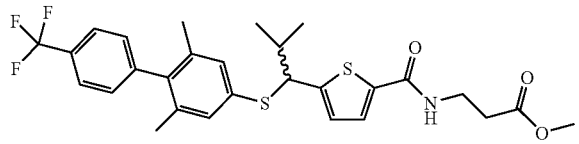

Step A (R,S)-5-[1-(2,6-Dimethyl-4'-trifluoromethyl-biphenyl-4-ylsulfanyl)-2-methyl-propyl]-thiophene-2-carboxylic acid ethyl ester A solution of (±)-5-(1-hydroxy-2-methyl-propyl)-thiophene-2-carboxylic acid ethyl ester (0.321 g, 1.41 mmol) and 4'-tert-butyl-2,6-dimethyl-biphenyl-4-thiol (0.427 g, 1.51 mmol) in 1,2-dichloroethane (13 mL) is treated with zinc iodide (0.474 g, 1.48 mmol) and stirred overnight at rt. The reaction mixture is then partitioned between water and dichloromethane. The reaction mixture is filtered and concentrated. The resulting residue is applied to silica gel and eluted using hexanes with an ethyl acetate gradient from 0% to 40% to give (±)-5-[1-(2,6-dimethyl-4'-trifluoromethyl-biphenyl-4-ylsulfanyl)-2-methyl-propyl]-thiophene-2-carboxylic acid ethyl ester (0.469, 70% g) as a clear syrup. MS (ES): 481.1 [M+H]⁺.

Step B (R,S)-5-[1-(2,6-Dimethyl-4'-trifluoromethyl-biphenyl-4-ylsulfanyl)-2-methyl-propyl]-thiophene-2-carboxylic acid To a mixture of (±)-5-[1-(2,6-dimethyl-4'-trifluoromethyl-biphenyl-4-ylsulfanyl)-2-methyl-propyl]-thiophene-2-carboxylic acid ethyl ester (0.458 g, 0.961 mmol) in THF (9.0 mL) is added lithium hydroxide (1N aqueous, 9.0 mL). The mixture is warmed to 70° C. and stirred overnight. The reaction mixture is cooled to rt, acidified with 1N HCl (9.5 mL), extracted into ethyl acetate (3×25 mL), dried over MgSO₄, and concentrated to provide (±)-5-[1-(2,6-dimethyl-4'-trifluoromethyl-biphenyl-4-ylsulfanyl)-2-methyl-propyl]-thiophene-2-carboxylic acid (0.431 g, 96%) as a white foam. MS (ES): 463.2 [M−H]⁻.

Step C (R,S)-3-({5-[1-(2,6-Dimethyl-4'-trifluoromethyl-biphenyl-4-ylsulfanyl)-2-methyl-propyl]-thiophene-2-carbonyl}-amino)-propionic acid methyl ester To a mixture of (±)-5-[1-(2,6-dimethyl-4'-trifluoromethyl-biphenyl-4-ylsulfanyl)-2-methyl-propyl]-thiophene-2-carboxylic acid (0.420 g, 0.905 mmol), 3-amino-propionic acid methyl ester hydrochloride (0.148 g, 1.06 mmol), and 1-hydroxybenzotriazole hydrate (HOBt, 0.151 g, 1.12 mmol) in DMF (9.0 mL) is added N,N-diisopropylethylamine (0.49 mL, 2.81 mmol), then N-(3-dimethylaminopropyl)-N'-ethyl-carbodiimide hydrochloride (EDCI, 0.0.228 g, 1.19 mmol) and stirred overnight. The reaction mixture is poured into H₂O (25 mL) and extracted with EtOAc (3×25 mL). Combined organic extracts are washed with H₂O, brine, dried over MgSO₄, filtered, and concentrated. The residue is loaded onto silica gel and eluted using hexanes with an ethyl acetate, gradient from 0% to 75% to provide (±)-3-({5-[1-(2,6-dimethyl-4'-trifluoromethyl-biphenyl-4-ylsulfanyl)-2-methyl-propyl]-thiophene-2-carbonyl}-amino)-propionic acid methyl ester (0.347 g, 70%) as a white foam. MS (ES): 548.1 [M−H]⁻. The racemic material is separated by chiral HPLC (column: Chiralpak AD-H 4.6×150 mm; eluent: 10:90 3A alcohol/Heptane; flow rate: 0.6 mL/min; UV absorbance wavelength: 280 nm) to provide Isomer 1 (0.126 g, >99% ee) and Isomer 2 (0.119 g, 94.5% ee).

The following compounds are made in a substantially similar manner.

Preparation 108

(R,S)-3-({5-[1-(4'-tert-Butyl-2,6-dimethyl-biphenyl-4-ylsulfanyl)-ethyl]-thiophene-2-carbonyl}-amino)-propionic acid methyl ester

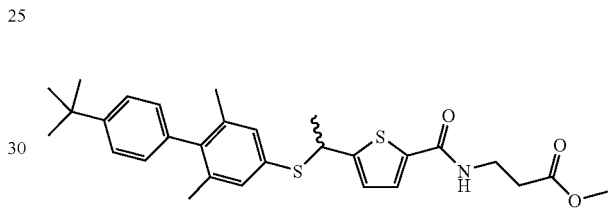

This compound is made by the general method as exemplified in Preparation 107 using 4'-tert-butyl-2,6-dimethyl-biphenyl-4-thiol and (±)-5-(1-hydroxy-ethyl)-thiophene-2-carboxylic acid ethyl ester in Step A and 3-amino-propionic acid methyl ester hydrochloride salt in Step C as the starting materials to provide (±)-3-({5-[1-(4'-tert-butyl-2,6-dimethyl-biphenyl-4-ylsulfanyl)-ethyl]-thiophene-2-carbonyl}-amino)-propionic acid methyl ester (0.279 g) as a white foam. MS (ES): 508.3 [M−H]⁻.

Preparation 109

(R,S)-3-({5-[1-(2,6-Dimethyl-4'-trifluoromethyl-biphenyl-4-ylsulfanyl)-2,2-dimethyl-propyl]-thiophene-2-carbonyl}-amino)-propionic acid methyl ester

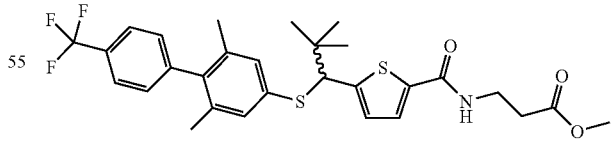

This compound is made by the general method as exemplified in Preparation 107 using (±)-5-(1-hydroxy-2,2-dimethyl-propyl)-thiophene-2-carboxylic acid ethyl ester in Step A and 3-amino-propionic acid methyl ester hydrochloride salt in Step C as the starting materials to provide (±)-3-({5-[1-(2,6-dimethyl-4'-trifluoromethyl-biphenyl-4-ylsulfanyl)-2,2-dimethyl-propyl]-thiophene-2-carbonyl}-amino)-propionic acid methyl ester (0.168 g) as a white foam. MS (ES):

562.1 [M−H]⁻. The racemic material is separated by chiral HPLC (column: Chiralpak AD-H 4.6×150 mm; eluent: 5:95:0.2 EtOH/Heptane/DMEA (dimethylethyl amine); flow rate: 0.6 mL/min; UV absorbance wavelength: 270 nm) to provide Isomer 1 (0.059 g, >99% ee) and Isomer 2 (0.053 g, 95% ee).

Preparation 110

(R,S)-3-({5-[1-(2,6-Dimethyl-4'-trifluoromethyl-biphenyl-4-ylsulfanyl)-3-methyl-butyl]-thiophene-2-carbonyl}-amino)-propionic acid methyl ester

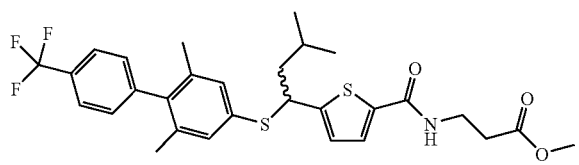

This compound is made by the general method as exemplified in Preparation 107 using (±)-5-(1-hydroxy-3-methyl-butyl)-thiophene-2-carboxylic acid ethyl ester in Step A and 3-amino-propionic acid methyl ester hydrochloride salt in Step C as the starting materials to provide (±)-3-({5-[1-(2,6-dimethyl-4'-trifluoromethyl-biphenyl-4-ylsulfanyl)-3-methyl-butyl]-thiophene-2-carbonyl}-amino)-propionic acid methyl ester (0.191 g) as a white foam. MS (ES): 562.1 [M−H]⁻.

Preparation 111

(R,S)-3-({5-[1-(2,6-Dimethyl-4'-trifluoromethyl-biphenyl-4-ylsulfanyl)-3,3-dimethyl-butyl]-thiophene-2-carbonyl}-amino)-propionic acid methyl ester

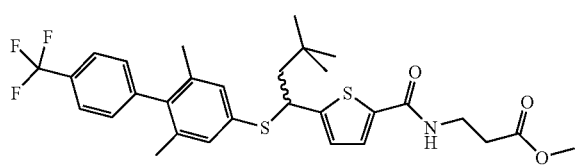

This compound is made by the general method as exemplified in Example 107 using (±)-5-(1-hydroxy-3,3-dimethyl-butyl)-thiophene-2-carboxylic acid ethyl ester in Step A and 3-Amino-propionic acid methyl ester hydrochloride salt in Step C as the starting materials to provide (±)-3-({5-[1-(2,6-dimethyl-4'-trifluoromethyl-biphenyl-4-ylsulfanyl)-3,3-dimethyl-butyl]-thiophene-2-carbonyl}-amino)-propionic acid methyl ester (0.362 g) as a white foam. MS (ES): 576.2 [M−H]⁻.

Preparation 112

(R,S)-3-({5-[1-(2,6-Dimethyl-4'-trifluoromethyl-biphenyl-4-ylsulfanyl)-pentyl]-thiophene-2-carbonyl}-amino)-propionic acid methyl ester

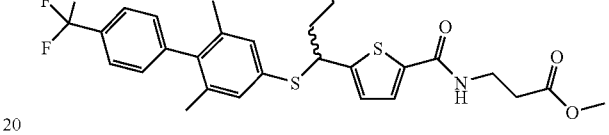

This compound is made by the general method as exemplified in Preparation 107 using (±)-5-(1-hydroxy-pentyl)-thiophene-2-carboxylic acid ethyl ester in Step A and 3-amino-propionic acid methyl ester hydrochloride salt in Step C as the starting materials to provide (±)-3-({5-[1-(2,6-dimethyl-4'-trifluoromethyl-biphenyl-4-ylsulfanyl)-pentyl]-thiophene-2-carbonyl}-amino)-propionic acid methyl ester (0.314 g) as a white foam. MS (ES): 562.3 [M−H]⁻.

Preparation 113

(R,S)-3-({5-[1-(2,6-Dimethyl-4'-trifluoromethyl-biphenyl-4-ylsulfanyl)-butyl]-thiophene-2-carbonyl}-amino)-propionic acid methyl ester

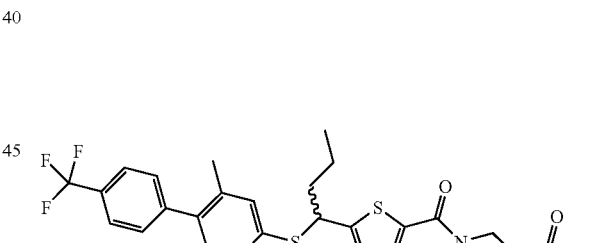

This compound is made by the general method as exemplified in Preparation 107 using (±)-5-(1-hydroxy-butyl)-thiophene-2-carboxylic acid ethyl ester in Step A and 3-amino-propionic acid methyl ester hydrochloride salt in Step C as the starting materials to provide (±)-3-({5-[1-(2,6-dimethyl-4'-trifluoromethyl-biphenyl-4-ylsulfanyl)-butyl]-thiophene-2-carbonyl}-amino)-propionic acid methyl ester (0.163 g) as a white foam. MS (ES): 548.0 [M−H]⁻. The racemic material is separated by chiral HPLC (column: Chiralpak AD-H 4.6×150 mm; eluent: 15:85:0.2 EtOH/Heptane/DMEA (dimethylethyl amine); flow rate: 0.6 mL/min;

UV absorbance wavelength: 270 nm) to provide Isomer 1 (0.0769 g, 98.3% ee) and Isomer 2 (0.100 g, 96.6% ee).

Preparation 114

3-({5-[1-(2,6-Dimethyl-4'-trifluoromethoxy-biphenyl-4-yloxy)-2-methyl-propyl]-thiophene-2-carbonyl}-amino)-propionic acid methyl ester, Isomer 2

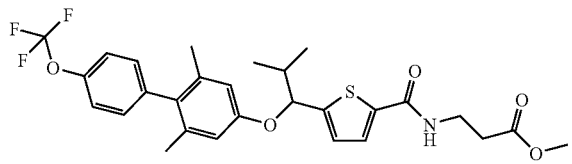

To a mixture of 3-({5-[1-(4-iodo-3,5-dimethyl-phenoxy)-2-methyl-propyl]-thiophene-2-carbonyl}-amino)-propionic acid methyl ester (Isomer 2) (0.304 g, 0.5902 mmol), (4-trifluoromethoxy)phenylboronic acid (0.153 g, 0.743 mmol), and potassium fluoride (0.0869 g, 1.807 mmol) in THF (6.0 ml) is added palladium(II) acetate (30.2 mg, 0.134 mmol), and (oxydi-2,1-phenylene)bis-(diphenylphosphine) (141 mg, 0.261 mmol). The reaction mixture is heated to reflux overnight. The reaction mixture is cooled to rt and poured into $H_2O$ (10 mL) and diluted with EtOAc (10 mL). The resulting yellow emulsion is removed by vacuum filtration through a pad of Celite®. The layers are separated and the aqueous layer is extracted with EtOAc (2×10 mL). Combined extracts are washed with brine (1×), dried over $MgSO_4$, filtered, and concentrated. The residue is loaded onto silica gel and eluted using hexanes with an ethyl acetate gradient from 0% to 75% giving a mixture of product and starting material. This material is then loaded onto $C_{18}$ and eluted using $H_2O$ with an MeCN gradient from 15% to 100% giving 3-({5-[1-(2,6-dimethyl-4'-trifluoromethoxy-biphenyl-4-yloxy)-2-methyl-propyl]-thiophene-2-carbonyl}-amino)-propionic acid methyl ester (Isomer 2) (0.126 g, 39%) as a white foam. MS (ES): 508.44 [M+H]⁺.

The following compound is prepared in a substantially similar manner.

Preparation 115

3-({5-[1-(4'-Isopropyl-2,6-dimethyl-biphenyl-4-yloxy)-2-methyl-propyl]-thiophene-2-carbonyl}-amino)-propionic acid methyl ester, Isomer 2

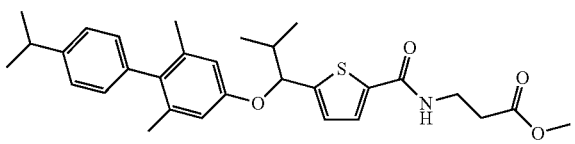

This compound is made by the general method as exemplified in Preparation 114 using 4-isopropyl phenylboronic acid as the starting material to provide 3-({5-[1-(4'-isopropyl-2,6-dimethyl-biphenyl-4-yloxy)-2-methyl-propyl]-thiophene-2-carbonyl}-amino)-propionic acid methyl ester (Isomer 2) (0.091 g) as a white solid. MS (ES): 550.3 [M+H]⁺.

Example 1

(R,S)-3-({5-[1-(4'-Trifluoromethyl-biphenyl-4-yloxy)-propyl]-thiophene-2-carbonyl}-amino)-propionic acid

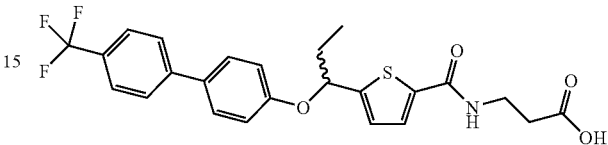

Step A (R,S)-5-[1-(4'-Trifluoromethyl-biphenyl-4-yloxy)-propyl]-thiophene-2-carboxylic acid ethyl ester To a solution of (R,S)-5-(1-hydroxy-propyl)-thiophene-2-carboxylic acid ethyl ester (74.3 mg, 0.35 mmol) in toluene (3.5 mL) is added 1,1'-(azodicarbonyl)dipiperidine (ADDP, 131 mg, 0.52 mmol) at room temperature, followed by the addition of triphenylphosphine (137 mg, 0.52 mmol) and 4'-trifluoromethyl-biphenyl-4-ol (83 mg, 0.35 mmol). The reaction mixture is stirred overnight. The mixture is treated with water, extracted into ethyl acetate, dried and concentrated, then loaded onto silica gel and eluted using hexanes with an ethyl acetate gradient from 0% to 65% giving (R,S)-5-[1-(4'-trifluoromethyl-biphenyl-4-yloxy)-propyl]-thiophene-2-carboxylic acid ethyl ester (87 mg). MS (ES): 433.1 [M–H]⁻.

Step B (R,S)-5-[1-(4-Trifluoromethyl-biphenyl-4-yloxy)-propyl]-thiophene-2-carboxylic acid To a mixture of (R,S)-5-[1-(4'-trifluoromethyl-biphenyl-4-yloxy)-propyl]-thiophene-2-carboxylic acid ethyl ester (85 mg, 0.195 mmol) in ethanol (2.0 mL) is added sodium hydroxide (5N aqueous, 0.196 mL) at room temperature, and stirred overnight. The reaction mixture is acidified by 1N HCl (0.198 mL), extracted into ethyl acetate, dried and concentrated, then dried under vacuum, giving (R,S)-5-[1-(4'-trifluoromethyl-biphenyl-4-yloxy)-propyl]-thiophene-2-carboxylic acid (59 mg). MS (ES): 405.1 [M–H]⁻.

Step C (R,S)-3-({5-[1-(4'-Trifluoromethyl-biphenyl-4-yloxy)-propyl]-thiophene-2-carbonyl}-amino)-propionic acid methyl ester To a mixture of (R,S)-5-[1-(4'-trifluoromethyl-biphenyl-4-yloxy)-propyl]-thiophene-2-carboxylic acid (56 mg, 0.138 mmol) in DMF (1.4 mL) is added 3-amino-propionic acid methyl ester hydrochloride(19.3 mg, 0.138 mmol), 1-hydroxybenzotriazole hydrate (23 mg, 0.166 mmol), and diisopropylethylamine (0.048 mL, 0.276 mmol) at room temperature, and stirred 10 min. The mixture is then treated with N-(3-dimethylaminopropyl)-N'-ethylcarbodiimide hydrochloride (53 mg, 0.276 mmol), and stirred overnight. The reaction mixture is treated with 0.1N HCl and extracted into ethyl acetate twice. The combined organic layers are washed with brine, dried and concentrated, and dried under vacuum to give (R,S)-3-({5-[1-(4'-trifluoromethyl-biphenyl-4-yloxy)-propyl]-thiophene-2-carbonyl}-amino)-propionic acid methyl ester (81 mg). MS (ES): 464.1 [M+H]+.

Step D (R,S)-3-({5-[1-(4-Trifluoromethyl-biphenyl-4-yloxy)-propyl]-thiophene-2-carbonyl}-amino)-propionic acid To a mixture of (R,S)-3-({5-[1-(4'-trifluoromethyl-biphenyl-4-yloxy)-propyl]-thiophene-2-carbonyl}-amino)-propionic acid methyl ester (61.3 mg, 0.125 mmol) in methanol (0.662 mL) is added sodium hydroxide (5N aqueous, 0.126 mL) at room temperature, and stirred overnight. The reaction mixture is acidified by 1 N HCl (0.662 mL), extracted into dichloromethane, dried and concentrated, then dried under vacuum, giving the title compound (56 mg). MS (ES): 478.1 [M+H]+.

The following compounds are made in a substantially similar manner.

Example 2

(R,S)-3-({5-[1-(4-Trifluoromethyl-biphenyl-4-yloxy)-butyl]-thiophene-2-carbonyl}-amino)-propionic acid This compound is made by the general method as exemplified in Example 1 using (R,S)-5-(1-hydroxy-butyl)-thiophene-2-carboxylic acid ethyl ester and 4'-trifluoromethyl-biphenyl-4-ol as the starting materials. MS(ES): 492.1 [M+H]+.

Example 3

(R,S)-3-({5-[1-(4-Trifluoromethyl-biphenyl-4-yloxy)-ethyl]-thiophene-2-carbonyl}-amino)-propionic acid This compound is made by the general method as exemplified in Example 1 using (R,S)-5-(1-hydroxy-ethyl)-thiophene-2-carboxylic acid ethyl ester and 4'-trifluoromethyl-biphenyl-4-ol as the starting materials. MS (ES): 464.1 [M+H]+.

Example 4

(R,S)-3-({5-[1-(4'-Trifluoromethyl-biphenyl-4-yloxy)-hexyl]-thiophene-2-carbonyl}-amino)-propionic acid

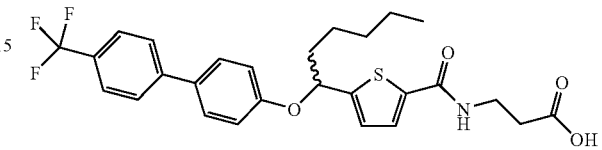

This compound is made by the general method as exemplified in Example 1 using (R,S)-5-(1-hydroxy-hexyl)-thiophene-2-carboxylic acid ethyl ester and 4'-trifluoromethyl-biphenyl-4-ol as the starting materials. MS (ES): 520.2 [M+H]+.

Example 5

(R,S)-3-({5-[Cyclohexyl-(4'-trifluoromethyl-biphenyl-4-yloxy)-methyl]-thiophene-2-carbonyl}-amino)-propionic acid

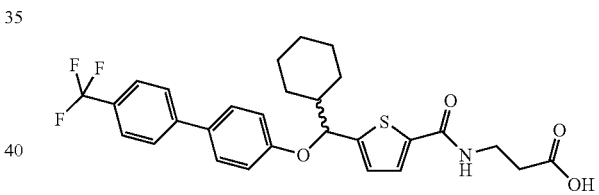

This compound is made by the general method as exemplified in Example 1 using (R,S)-5-(cyclohexyl-hydroxy-methyl)-thiophene-2-carboxylic acid ethyl ester and 4'-trifluoromethyl-biphenyl-4-ol as the starting materials. MS (ES): 532.3 [M+H]+.

Example 6

(R,S)-3-({5-[2,2-Dimethyl-1-(4'-trifluoromethyl-biphenyl-4-yloxy)-propyl]-thiophene-2-carbonyl}-amino)-propionic acid

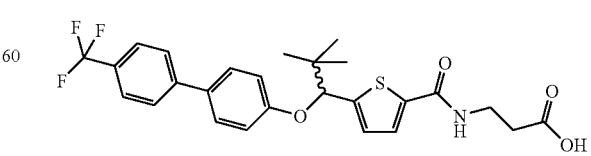

This compound is made by the general method as exemplified in Example 1 using (R,S)-5-(1-hydroxy-2,2-dimethylpropyl)-thiophene-2-carboxylic acid ethyl ester and 4'-trifluoromethyl-biphenyl-4-ol as the starting materials. MS (ES): 506.3 [M+H]⁺.

Example 7

(R,S)-3-({5-[3,3-Dimethyl-1-(4'-trifluoromethyl-biphenyl-4-yloxy)-butyl]-thiophene-2-carbonyl}-amino)-propionic acid

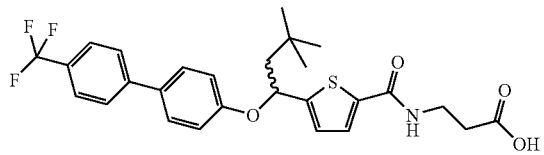

This compound is made by the general method as exemplified in Example 1 using (R,S)-5-(1-hydroxy-3,3-dimethyl-butyl)-thiophene-2-carboxylic acid ethyl ester and 4'-trifluoromethyl-biphenyl-4-ol as the starting materials. MS (ES): 520.3 [M+H]⁺.

Example 8

(R,S)-3-({5-[4-Methyl-1-(4-trifluoromethyl-biphenyl-4-yloxy)-pentyl]-thiophene-2-carbonyl}-amino)-propionic acid

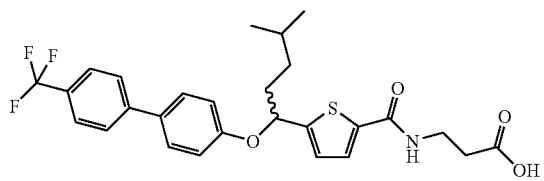

This compound is made by the general method as exemplified in Example 1 using (R,S)-5-(1-hydroxy-4-methyl-pentyl)-thiophene-2-carboxylic acid ethyl ester and 4'-trifluoromethyl-biphenyl-4-ol as the starting materials. MS (ES): 542.3 [M+Na]⁺.

Example 9

(R,S)-3-({5-[1-(2,6-Dimethyl-4'-trifluoromethyl-biphenyl-4-yloxy)-2,2-dimethyl-propyl]-thiophene-2-carbonyl}-amino)-propionic acid

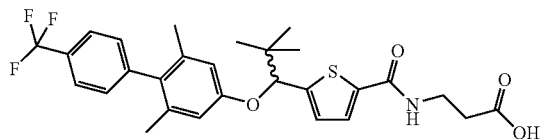

This compound is made by the general method as exemplified in Example 1 using (R,S)-5-(1-hydroxy-4-methyl-pentyl)-thiophene-2-carboxylic acid ethyl ester and 2,6-dimethyl-4'-trifluoromethyl-biphenyl-4-ol as the starting materials. MS (ES): 534.3 [M+H]⁺.

Example 10

(R,S)-3-({5-[1-(2,6-Dimethyl-4'-trifluoromethyl-biphenyl-4-yloxy)-3,3-dimethyl-butyl]-thiophene-2-carbonyl}-amino)-propionic acid

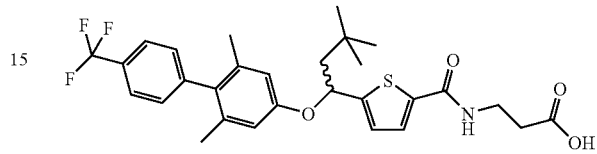

This compound is made by the general method as exemplified in Example 1 using (R,S)-5-(1-hydroxy-3,3-dimethyl-butyl)-thiophene-2-carboxylic acid ethyl ester and 2,6-dimethyl-4'-trifluoromethyl-biphenyl-4-ol as the starting materials. MS (ES): 548.3 [M+H]⁺.

Example 11

(R,S)-3-({5-[3,3-Dimethyl-1-(2-methyl-4'-trifluoromethyl-biphenyl-4-yloxy)-butyl]-thiophene-2-carbonyl}-amino)-propionic acid

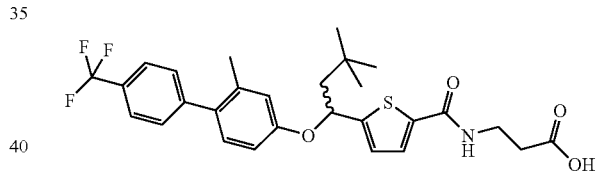

This compound is made by the general method as exemplified in Example 1 using (R,S)-5-(1-hydroxy-3,3-dimethyl-butyl)-thiophene-2-carboxylic acid ethyl ester and 2-methyl-4'-trifluoromethyl-biphenyl-4-ol as the starting materials. MS (ES): 534.3 [M+H]⁺.

Example 12

(R,S)-3-({5-[1-(4'-tert-Butyl-2-methyl-biphenyl-4-yloxy)-3,3-dimethyl-butyl]-thiophene-2-carbonyl}-amino)-propionic acid

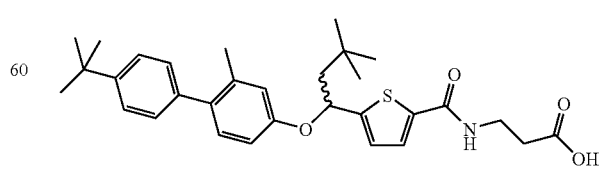

This compound is made by the general method as exemplified in Example 1 using (R,S)-5-(1-hydroxy-3,3-dimethylbutyl)-thiophene-2-carboxylic acid ethyl ester and 4'-tert-butyl-2-methyl-biphenyl-4-ol as the starting materials. MS (ES): 522.3 [M+H]⁺.

Example 13

(R,S)-3-[(5-{3,3-Dimethyl-1-[6-(4-trifluoromethyl-phenyl)-pyridin-3-yloxy]-butyl}-thiophene-2-carbonyl)-amino]-propionic acid

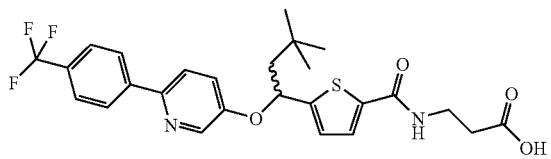

This compound is made by the general method as exemplified in Example 1 using (R,S)-5-(1-hydroxy-3,3-dimethyl-butyl)-thiophene-2-carboxylic acid ethyl ester and 6-(4-trifluoromethyl-phenyl)-pyridin-3-ol as the starting materials. MS (ES): 521.3 [M+H]⁺.

Example 14

(R,S)-3-[(5-{1-[6-(4-tert-Butyl-phenyl)-pyridin-3-yloxy]-3,3-dimethyl-butyl}-thiophene-2-carbonyl)-amino]-propionic acid

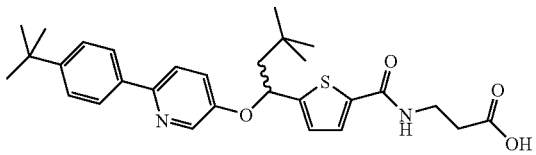

This compound is made by the general method as exemplified in Example 1 using (R,S)-5-(1-hydroxy-3,3-dimethyl-butyl)-thiophene-2-carboxylic acid ethyl ester and 6-(4-tert-butyl-phenyl)-pyridin-3-ol as the starting materials. MS (ES): 509.3 [M+H]⁺.

Example 15

(R,S)-3-({5-[1-(4'-tert-Butyl-2-methyl-biphenyl-4-yloxy)-2,2-dimethyl-propyl]-thiophene-2-carbonyl}-amino)-propionic acid

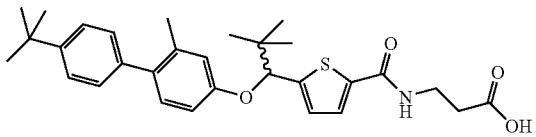

This compound is made by the general method as exemplified in Example 1 using (R,S)-5-(1-hydroxy-2,2-dimethyl-propyl)-thiophene-2-carboxylic acid ethyl ester and 4'-tert-butyl-2-methyl-biphenyl-4-ol as the starting materials. MS (ES): 508.3 [M+H]⁺.

Example 16

(R,S)-3-({5-[2,2-Dimethyl-1-(2-methyl-4'-trifluoromethyl-biphenyl-4-yloxy)-propyl]-thiophene-2-carbonyl}-amino)-propionic acid

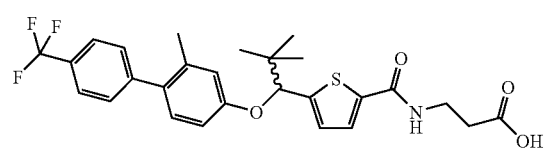

This compound is made by the general method as exemplified in Example 1 using (R,S)-5-(1-hydroxy-2,2-dimethyl-propyl)-thiophene-2-carboxylic acid ethyl ester and 2-methyl-4'-trifluoromethyl-biphenyl-4-ol as the starting materials. MS (ES): 520.3 [M+H]⁺.

Example 17

(R,S)-3-({5-[1-(4'-tert-Butyl-2-methyl-biphenyl-4-yloxy)-propyl]-thiophene-2-carbonyl}-amino)-propionic acid

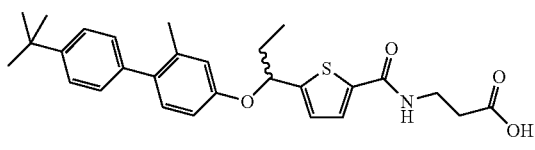

This compound is made by the general method as exemplified in Example 1 using (R,S)-5-(1-hydroxy-propyl)-thiophene-2-carboxylic acid ethyl ester and 4'-tert-butyl-2-methyl-biphenyl-4-ol as the starting materials. MS (ES): 480.2 [M+H]⁺.

Example 18

(R,S)-3-({5-[1-(2-Methyl-4'-trifluoromethyl-biphenyl-4-yloxy)-propyl]-thiophene-2-carbonyl}-amino)-propionic acid

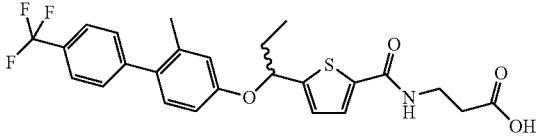

This compound is made by the general method as exemplified in Example 1 using (R,S)-5-(1-hydroxy-propyl)- thiophene-2-carboxylic acid ethyl ester and 2-methyl-4'-trifluoromethyl-biphenyl-4-ol as the starting materials. MS (ES): 492.1 [M+H]⁺.

Example 19

(R,S)-3({5-[1-(2,6-Dimethyl-4'-trifluoromethyl-biphenyl-4-yloxy)-propyl]-thiophene-2-carbonyl}-amino)-propionic acid

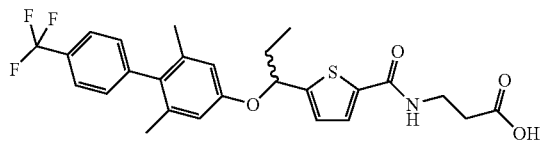

This compound is made by the general method as exemplified in Example 1 using (R,S)-5-(1-hydroxy-propyl)-thiophene-2-carboxylic acid ethyl ester and 2,6-dimethyl-4'-trifluoromethyl-biphenyl-4-ol as the starting materials. MS (ES): 506.2 [M+H]⁺.

Example 20

(R,S)-3-({5-[1-(4'-tert-Butyl-2,6-dimethyl-biphenyl-4-yloxy)-propyl]-thiophene-2-carbonyl}-amino)-propionic acid

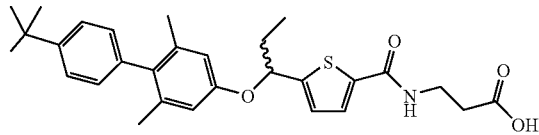

This compound is made by the general method as exemplified in Example 1 using (R,S)-5-(1-hydroxy-propyl)-thiophene-2-carboxylic acid ethyl ester and 4'-tert-butyl-2,6-dimethyl-biphenyl-4-ol as the starting materials. MS (ES): 494.2 [M+H]⁺.

Example 21

(R,S)-3-({5-[1-(2,6-Dimethyl-4'-trifluoromethyl-biphenyl-4-yloxy)-3-methyl-butyl]-thiophene-2-carbonyl}-amino)-propionic acid

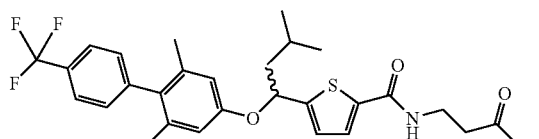

This compound is made by the general method as exemplified in Example 1 using (R,S)-5-(1-hydroxy-3-methyl-butyl)-thiophene-2-carboxylic acid ethyl ester and 2,6-dimethyl-4'-trifluoromethyl-biphenyl-4-ol as the starting materials. MS (ES): 534.4 [M+H]⁺.

Example 22

(R,S)-3-({5-[1-(4'-tert-Butyl-2,6-dimethyl-biphenyl-4-yloxy)-2,2-dimethyl-propyl]-thiophene-2-carbonyl}-amino)-propionic acid

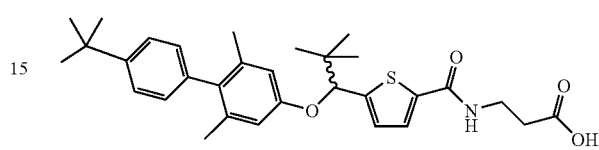

This compound is made by the general method as exemplified in Example 1 using (R,S)-5-(1-hydroxy-2,2-dimethyl-propyl)-thiophene-2-carboxylic acid ethyl ester and 4'-tert-butyl-2,6-dimethyl-biphenyl-4-ol as the starting materials. MS (ES): 522.4 [M+H]⁺.

Example 23

3-{[5-(4'-tert-Butyl-2,6-dimethyl-biphenyl-4-yloxymethyl)-thiophene-2-carbonyl]-amino}-propionic acid

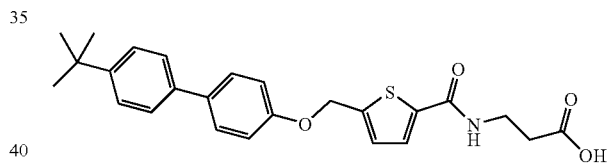

This compound is made by the general method as exemplified in Example 1 using 5-hydroxymethyl-thiophene-2-carboxylic acid ethyl ester and 4'-tert-butyl-2,6-dimethyl-biphenyl-4-ol as the starting materials. MS (ES): 466.3 [M+H]⁺.

Example 24

(R,S)-3-({5-[3-Methyl-1-(2-methyl-4'-trifluoromethyl-biphenyl-4-yloxy)-butyl]-thiophene-2-carbonyl}-amino)-propionic acid

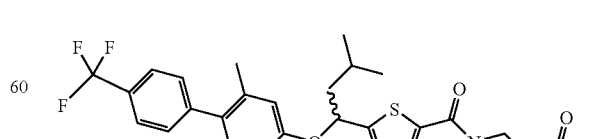

This compound is made by the general method as exemplified in Example 1 using (R,S)-5-(1-hydroxy-3-methyl-butyl)-thiophene-2-carboxylic acid ethyl ester and 2-methyl-4'-trifluoromethyl-biphenyl-4-ol as the starting materials. MS (ES): 520.0 [M+H]⁺.

Example 25

(R,S)-3-({5-[1-(4'-tert-Butyl-2-methyl-biphenyl-4-yloxy)-3-methyl-butyl]-thiophene-2-carbonyl}-amino)-propionic acid

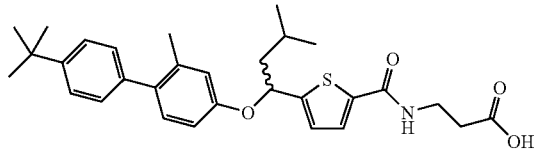

This compound is made by the general method as exemplified in Example 1 using (R,S)-5-(1-hydroxy-3-methyl-butyl)-thiophene-2-carboxylic acid ethyl ester and 4'-tert-butyl-2-methyl-biphenyl-4-ol as the starting materials. MS (ES): 508.3 [M+H]⁺.

Example 26

3-({5-[1-(4-Trifluoromethyl-biphenyl-4-yloxy)-ethyl]-thiophene-2-carbonyl}-amino)-propionic acid, Isomer 1

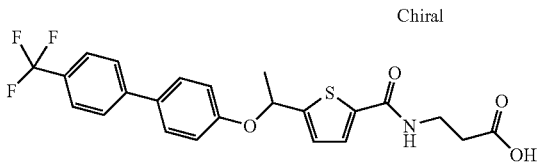

Step A

3-{(5-[1-(4'-Trifluoromethyl-biphenyl-4-yloxy)-ethyl]-thiophene-2-carbonyl}-amino)-propionic acid methyl ester, Isomer 1

(R,S)-3-({5-[1-(4'-Trifluoromethyl-biphenyl-4-yloxy)-ethyl]-thiophene-2-carbonyl}-amino)-propionic acid methyl ester (375 mg) is separated by chiral HPLC (column: Chiralpak AD 4.6×150 mm; eluent: 100% 3A ethanol; flow rate: 0.6 mL/min; UV absorbance wavelength: 280 nm) to provide 3-({5-[1-(4'-trifluoromethyl-biphenyl-4-yloxy)-ethyl]-thiophene-2-carbonyl}-amino)-propionic acid methyl ester (chiral Isomer 1) (51 mg).

Step B 3-({5-[1-(4'-Trifluoromethyl-biphenyl-4-yloxy)-ethyl]-thiophene-2-carbonyl}-amino)-propionic acid, Isomer 1

A solution of 3-({5-[1-(4'-trifluoromethyl-biphenyl-4-yloxy)-ethyl]-thiophene-2-carbonyl}-amino)-propionic acid methyl ester (chiral Isomer 1) (170 mg, 0.356 mmol) in methanol (7.1 mL) is treated with 5N NaOH (0.712 mL) and shaken at rt for 2 h. The reaction is neutralized with 1N HCl (0.748 mL), and extracted into ethyl acetate (2×). The combined organic layers are dried and concentrated, giving the title compound (142 mg). MS (ES): 464.2 [M+H]⁺.

The following compounds are made in a substantially similar manner.

Example 27

3-({5-[1-(4'-Trifluoromethyl-biphenyl-4-yloxy)-ethyl]-thiophene-2-carbonyl}-amino)-propionic acid, Isomer 2

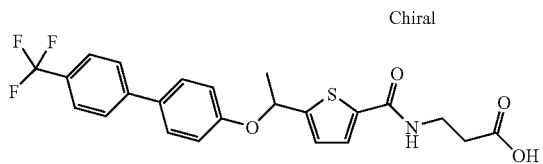

This compound is made by the general method as exemplified in Example 26 using 3-({5-[1-(4'-trifluoromethyl-biphenyl-4-yloxy)-ethyl]-thiophene-2-carbonyl}-amino)-propionic acid methyl ester (Isomer 2) as the starting material. MS (ES): 464.2 [M+H]⁺.

Example 28

3-({5-[1-(4'-Trifluoromethyl-biphenyl-4-yloxy)-propyl]-thiophene-2-carbonyl}-amino)-propionic acid, Isomer 1

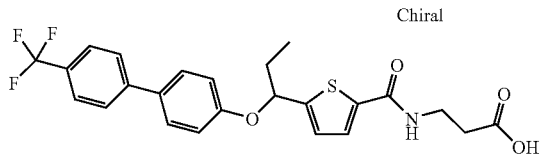

This compound is made by the general method as exemplified in Example 26 using 3-({5-[1-(4'-trifluoromethyl-biphenyl-4-yloxy)-propyl]-thiophene-2-carbonyl}-amino)-propionic acid methyl ester (Isomer 1) as the starting material. MS (ES): 478.2 [M+H]⁺.

Example 29

3-({5-[1-(4'-Trifluoromethyl-biphenyl-4-yloxy)-propyl]-thiophene-2-carbonyl}-amino)-propionic acid, Isomer 2

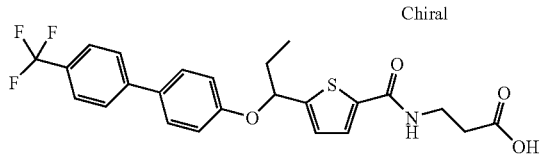

This compound is made by the general method as exemplified in Example 26 using 3-({5-[1-(4'-trifluoromethyl-biphenyl-4-yloxy)-propyl]-thiophene-2-carbonyl}-amino)- propionic acid methyl ester (Isomer 2) as the starting material. MS (ES): 478.2 [M+H]⁺.

Example 30

3-({5-[1-(4'-Trifluoromethyl-biphenyl-4-yloxy)-butyl]thiophene-2-carbonyl}-amino)-propionic acid, Isomer 1

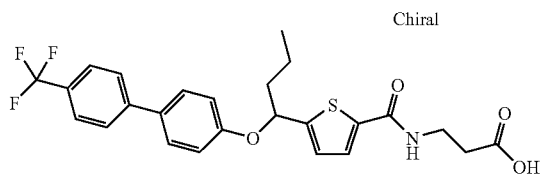

This compound is made by the general method as exemplified in Example 26 using 3-({5-[1-(4'-trifluoromethyl-biphenyl-4-yloxy)-butyl]-thiophene-2-carbonyl}-amino)-propionic acid methyl ester (Isomer 1) as the starting material. MS (ES): 492.2 [M+H]⁺.

Example 31

3-({5-[1-(4'-Trifluoromethyl-biphenyl-4-yloxy)-butyl]-thiophene-2-carbonyl}-amino)-propionic acid, Isomer 2

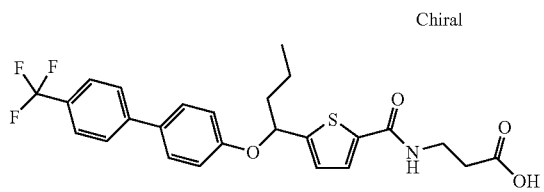

This compound is made by the general method as exemplified in Example 26 using 3-({5-[1-(4'-trifluoromethyl-biphenyl-4-yloxy)-butyl]-thiophene-2-carbonyl}-amino)-propionic acid methyl ester (Isomer 2) as the starting material. MS (ES): 492.2 [M+H]⁺.

Example 32

3-({5-[2,2-Dimethyl-1-(4'-trifluoromethyl-biphenyl-4-yloxy)-propyl]-thiophene-2-carbonyl}-amino)-propionic acid, Isomer 1

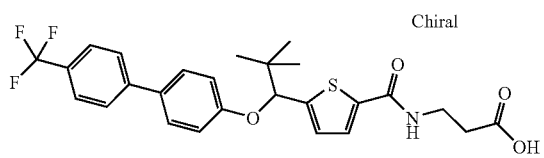

This compound is made by the general method as exemplified in Example 26 using 3-({5-[2,2-dimethyl-1-(4'-trifluoromethyl-biphenyl-4-yloxy)-propyl]-thiophene-2-carbonyl}-amino)-propionic acid methyl ester (isomer 1) as the starting material. MS (ES): 506.2 [M+H]⁺.

Example 33

3-({5-[2,2-Dimethyl-1-(4'-trifluoromethyl-biphenyl-4-yloxy)-propyl]-thiophene-2-carbonyl}-amino)-propionic acid, Isomer 2

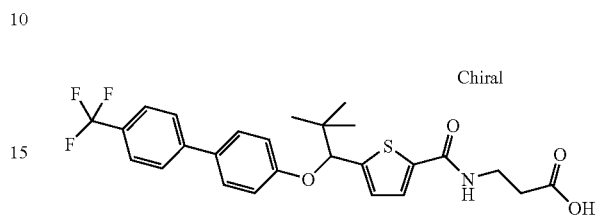

This compound is made by the general method as exemplified in Example 26 using 3-({5-[2,2-dimethyl-1-(4'-trifluoromethyl-biphenyl-4-yloxy)-propyl]-thiophene-2-carbonyl}-amino)-propionic acid methyl ester (isomer 2) as the starting material. MS (ES): 506.2 [M+H]⁺.

Example 34

3-({5-[3,3-Dimethyl-1-(4'-trifluoromethyl-biphenyl-4-yloxy)-butyl]-thiophene-2-carbonyl}-amino)-propionic acid, Isomer 1

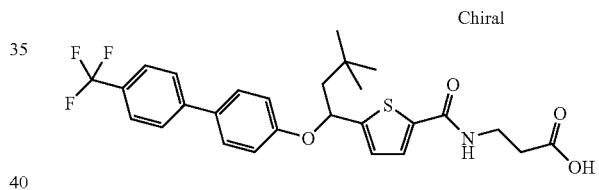

This compound is made by the general method as exemplified in Example 26 using 3-({5-[3,3-dimethyl-1-(4'-trifluoromethyl-biphenyl-4-yloxy)-butyl]-thiophene-2-carbonyl}-amino)-propionic acid methyl ester (isomer 1) as the starting material. MS (ES): 520.3 [M+H]⁺.

Example 35

3-({5-[3,3-Dimethyl-1-(4'-trifluoromethyl-biphenyl-4-yloxy)-butyl]-thiophene-2-carbonyl}-amino)-propionic acid, Isomer 2

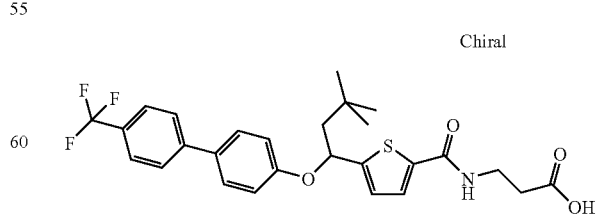

This compound is made by the general method as exemplified in Example 26 using 3-({5-[3,3-Dimethyl-1-(4'-trifluoromethyl-biphenyl-4-yloxy)-butyl]-thiophene-2-carbonyl}-amino)-propionic acid methyl ester (isomer 2) as the starting material. MS (ES): 520.3 [M+H]+.

Example 36

3-({5-[2,2-Dimethyl-1-(2-methyl-4'-trifluoromethyl-biphenyl-4-yloxy)-propyl]-thiophene-2-carbonyl}-amino)-propionic acid, Isomer 1

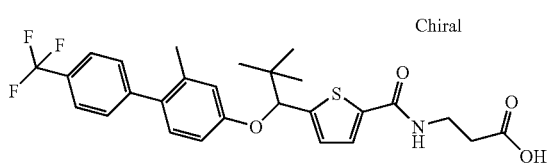

Step A 3-({5-[2,2-Dimethyl-1-(2-methyl-4'-trifluoromethyl-biphenyl-4-yloxy)-propyl]-thiophene-2-carbonyl}-amino)-propionic acid methyl ester (chiral Isomer 1)

(R,S)-3-({5-[2,2-Dimethyl-1-(2-methyl-4'-trifluoromethyl-biphenyl-4-yloxy)-propyl]-thiophene-2-carbonyl}-amino)-propionic acid methyl ester (93.4 mg) is separated by chiral HPLC (column: Chiralpak AD 4.6×150 mm; eluent: 10% ethanol in heptane; flow rate: 1.0 mL/min; UV absorbance wavelength: 225 nm) to provide 3-({5-[2,2-dimethyl-1-(2-methyl-4'-trifluoromethyl-biphenyl-4-yloxy)-propyl]-thiophene-2-carbonyl}-amino)-propionic acid methyl ester (chiral Isomer 1) (36 mg).

Step B 3-({5-[2,2-Dimethyl-1-(2-methyl-4'-trifluoromethyl-biphenyl-4-yloxy)-propyl]-thiophene-2-carbonyl}-amino)-propionic acid (chiral Isomer 1)

A solution of 3-({5-[2,2-dimethyl-1-(2-methyl-4'-trifluoromethyl-biphenyl-4-yloxy)-propyl]-thiophene-2-carbonyl}-amino)-propionic acid methyl ester (chiral Isomer 1) (36 mg, 0.067 mmol) in methanol (1.0 mL) is treated with 5N NaOH (0.067 mL) and shaken at rt overnight. The reaction is neutralized with 1N HCl (0.068 mL), and extracted into ethyl acetate (2×). The combined organic layers are dried and concentrated, giving the title compound (21.6 mg). MS (ES): 520.3 [M+H]+.

The following compounds are made in a substantially similar manner.

Example 37

3-({5-[2,2-Dimethyl-1-(2-methyl-4'-trifluoromethyl-biphenyl-4-yloxy)-propyl]-thiophene-2-carbonyl}-amino)-propionic acid, Isomer 2

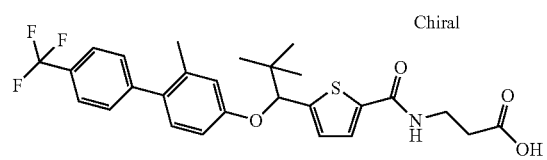

This compound is made by the general method as exemplified in Example 36 using 3-({5-[2,2-dimethyl-1-(2-methyl-4'-trifluoromethyl-biphenyl-4-yloxy)-propyl]-thiophene-2-carbonyl}-amino)-propionic acid methyl ester (isomer 2) as the starting material. MS (ES): 520.4 [M+H]+.

Example 38

3-({5-[1-(4'-tert-Butyl-2-methyl-biphenyl-4-yloxy)-propyl]-thiophene-2-carbonyl}-amino)-propionic acid, Isomer 1

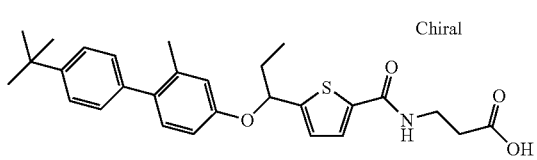

This compound is made by the general method as exemplified in Example 36 using 3-({5-[1-(4'-tert-butyl-2-methyl-biphenyl-4-yloxy)-propyl]-thiophene-2-carbonyl}-amino)-propionic acid methyl ester (isomer 1) as the starting material. MS (ES): 480.4 [M+H]+.

Example 39

3-({5-[1-(4'-tert-Butyl-2-methyl-biphenyl-4-yloxy)-propyl]-thiophene-2-carbonyl}-amino)-propionic acid, Isomer 2

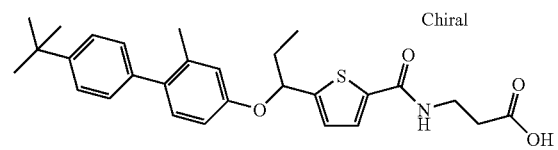

This compound is made by the general method as exemplified in Example 36 using 3-({5-[1-(4'-tert-butyl-2-methyl-biphenyl-4-yloxy)-propyl]-thiophene-2-carbonyl}-amino)-propionic acid methyl ester (isomer 2) as the starting material. MS (ES): 480.4 [M+H]+.

Example 40

3-({5-[3,3-Dimethyl-1-(2-methyl-4'-trifluoromethyl-biphenyl-4-yloxy)-butyl]-thiophene-2-carbonyl}-amino)-propionic acid, Isomer 1

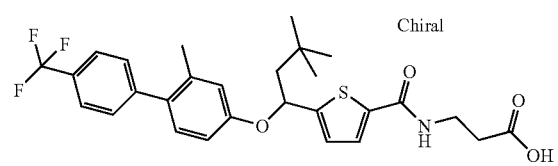

This compound is made by the general method as exemplified in Example 36 using 3-({5-[3,3-dimethyl-1-(2-methyl-4'-trifluoromethyl-biphenyl-4-yloxy)-butyl]-thiophene- 2-carbonyl}-amino)-propionic acid methyl ester (isomer 1) as the starting material. MS (ES): 534.3 [M+H]⁺.

Example 41

3-({5-[3,3-Dimethyl-1-(2-methyl-4'-trifluoromethyl-biphenyl-4-yloxy)-butyl]-thiophene-2-carbonyl}-amino)-propionic acid, Isomer 2

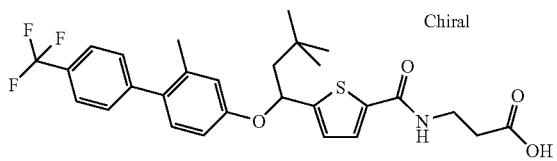

This compound is made by the general method as exemplified in Example 36 using 3-({5-[3,3-dimethyl-1-(2-methyl-4'-trifluoromethyl-biphenyl-4-yloxy)-butyl]-thiophene-2-carbonyl}-amino)-propionic acid methyl ester (isomer 2) as the starting material. MS (ES): 534.3 [M+H]⁺.

Example 42

3-({5-[3,3-Dimethyl-1-(2-methyl-4'-trifluoromethyl-biphenyl-4-yloxy)-butyl]-thiophene-2-carbonyl}-amino)-propionic acid, Isomer 1

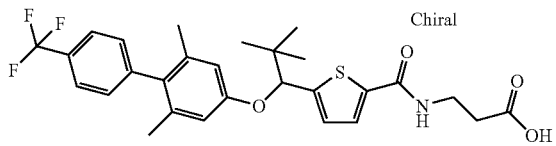

This compound is made by the general method as exemplified in Example 36 using 3-({5-[3,3-dimethyl-1-(2-methyl-4'-trifluoromethyl-biphenyl-4-yloxy)-butyl]-thiophene-2-carbonyl}-amino)-propionic acid methyl ester (isomer 1) as the starting material. MS (ES): 534.3 [M+H]⁺.

Example 43

3-({5-[3,3-Dimethyl-1-(2-methyl-4'-trifluoromethyl-biphenyl-4-yloxy)-butyl]-thiophene-2-carbonyl}-amino)-propionic acid, Isomer 2

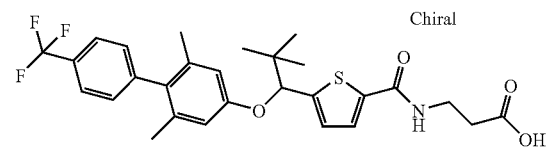

This compound is made by the general method as exemplified in Example 36 using 3-({5-[3,3-dimethyl-1-(2-methyl-4'-trifluoromethyl-biphenyl-4-yloxy)-butyl]-thiophene-2-carbonyl}-amino)-propionic acid methyl ester (isomer 2) as the starting material. MS (ES): 534.3 [M+H]⁺.

Example 44

3-({5-[1-(2,6-Dimethyl-4'-trifluoromethyl-biphenyl-4-yloxy)-propyl]-thiophene-2-carbonyl}-amino)-propionic acid, Isomer 1

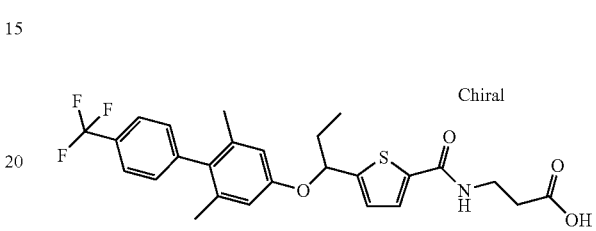

Step A 3-({5-[1-(2,6-Dimethyl-4'-trifluoromethyl-biphenyl-4-yloxy)-propyl]-thiophene-2-carbonyl}-amino)-propionic acid methyl ester (chiral Isomer 1)

To a solution of 3-({5-[1-(4-iodo-3,5-dimethyl-phenoxy)-propyl]-thiophene-2-carbonyl}-amino)-propionic acid methyl ester (chiral Isomer 1) (187.3 g, 0.347 mmol) in THF (3.7 ml) is added (4-trifluoromethyl)phenylboronic acid (92.5 g, 0.449 mmol), potassium fluoride (53.9 mg, 1.12 mmol), palladium(II) acetate (4.3 mg, 0.019 mmol), and (oxydi-2,1-phenylene)bis-(diphenylphosphine) (20 mg, 0.037 mmol). The reaction mixture is heated to reflux overnight. After cooling to rt, the reaction mixture is partitioned between ethyl acetate and water. The aqueous layer is back-extracted with ethyl acetate, the combined organic layers are dried and concentrated, then loaded onto C₁₈ and eluted using acetonitrile with a water gradient from 15% to 100% giving 3-({5-[1-(2,6-dimethyl-4'-trifluoromethyl-biphenyl-4-yloxy)-propyl]-thiophene-2-carbonyl}-amino)-propionic acid methyl ester (chiral Isomer 1) (81.1 mg). MS (ES): 520.4 [M+H]⁺.

Step B 3-({5-[1-(2,6-Dimethyl-4'-trifluoromethyl-biphenyl-4-yloxy)-propyl]-thiophene-2-carbonyl}-amino)-propionic acid (chiral Isomer 1)

A solution of 3-({5-[1-(2,6-dimethyl-4'-trifluoromethyl-biphenyl-4-yloxy)-propyl]-thiophene-2-carbonyl}-amino)-propionic acid methyl ester (chiral Isomer 1) (79.6 mg, 0.153 mmol) in methanol (1.54 mL) is treated with 5N NaOH (0.154 mL) and shaken at rt overnight. The reaction is neutralized with 1N HCl (0.158 mL), and extracted into ethyl acetate (2×). The combined organic layers are dried and concentrated, giving the title compound (76 mg). MS (ES): 506.4 [M+H]⁺.

Example 45

3-({5-[1-(2,6-Dimethyl-4'-trifluoromethyl-biphenyl-4-yloxy)-propyl]-thiophene-2-carbonyl}-amino)-propionic acid, Isomer 2

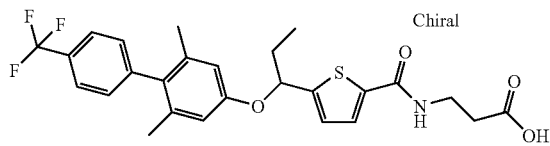

This compound is made by the general method as exemplified in Example 44 using 3-({5-[1-(4-iodo-3,5-dimethyl-phenoxy)-propyl]-thiophene-2-carbonyl}-amino)-propionic acid methyl ester (isomer 1) and (4-trifluoromethyl)phenylboronic acid as the starting materials. MS (ES): 506.3 [M+H]$^+$.

Example 46

3-({5-[1-(4'-tert-Butyl-2,6-dimethyl-biphenyl-4-yloxy)-propyl]-thiophene-2-carbonyl}-amino)-propionic acid, Isomer 1

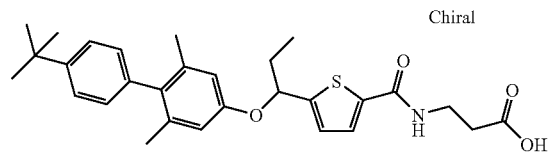

This compound is made by the general method as exemplified in Example 44 using 3-({5-[1-(4-iodo-3,5-dimethyl-phenoxy)-propyl]-thiophene-2-carbonyl}-amino)-propionic acid methyl ester (isomer 1) and (4-tert-butyl)phenylboronic acid as the starting materials. MS (ES): 494.4 [M+H]$^+$.

Example 47

(R,S)-3-({5-[2-Methyl-1-(4'-trifluoromethyl-biphenyl-4-yloxy)-propyl]-thiophene-2-carbonyl}-amino)-propionic acid

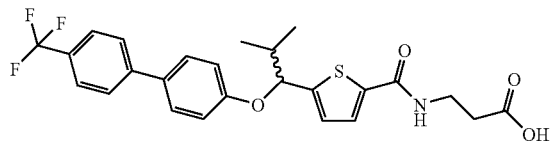

To a solution of (±)-3-({5-[1-(2,6-dimethyl-4'-trifluoromethyl-biphenyl-4-yloxy)-ethyl]-thiophene-2-carbonyl}-amino)-propionic acid methyl ester (0.0887 mg, 0.175 mmol) in THF (2.0 mL) is added lithium hydroxide (1N aqueous, 2.0 mL) at rt and stirred overnight. The reaction mixture is acidified with 1 N HCl (2.4 mL), extracted with EtOAc (3×10 mL), dried over MgSO$_4$, filtered, and conc. to provide the title compound (0.0788 g, 92%). MS (ES): 492.0 [M+H]$^+$.

The following compounds are made in a substantially similar manner:

Example 48

(R,S)-3-({5-[2-Methyl-1-(4'-trifluoromethyl-biphenyl-4-yloxy)-propyl]-thiophene-2-carbonyl}-amino)-propionic acid

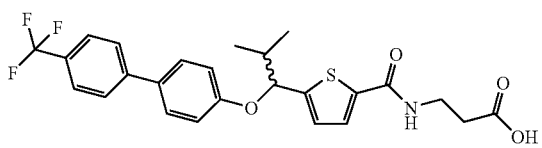

This compound is made by the general method as exemplified in Example 47 using 3-({5-[2-methyl-1-(4'-trifluoromethyl-biphenyl-4-yloxy)-propyl]-thiophene-2-carbonyl}-amino)-propionic acid methyl ester (chiral Isomer 1) as the starting material. MS (ES): 492.2 [M+H]$^+$.

Example 49

3-({5-[2-Methyl-1-(4'-trifluoromethyl-biphenyl-4-yloxy)-propyl]-thiophene-2-carbonyl}-amino)-propionic acid, Isomer 1

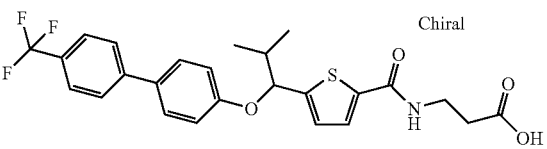

This compound is made by the general method as exemplified in Example 47 using 3-({5-[2-methyl-1-(4'-trifluoromethyl-biphenyl-4-yloxy)-propyl]-thiophene-2-carbonyl}-amino)-propionic acid methyl ester (chiral Isomer 2) as the starting material. MS (ES): 492.2 [M+H]$^+$.

Example 50

(R,S)-3-({5-[3-Methyl-1-(4'-trifluoromethyl-biphenyl-4-yloxy)-butyl]-thiophene-2-carbonyl}-amino)-propionic acid, Isomer 2

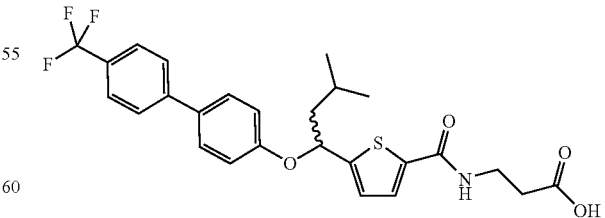

This compound is made by the general method as exemplified in Example 47 using (±)-3-({5-[3-methyl-1-(4'-trifluoromethyl-biphenyl-4-yloxy)-butyl]-thiophene-2-carbonyl}-amino)-propionic acid methyl ester as the starting material. MS (ES): 506.2 [M+H]$^+$.

Example 51

(R,S)-3-({5-[1-(4'-Trifluoromethyl-biphenyl-4-yloxy)-octyl]-thiophene-2-carbonyl}-amino)-propionic acid

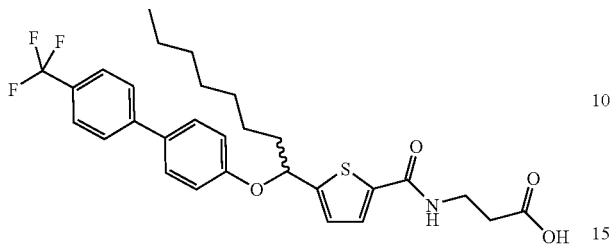

This compound is made by the general method as exemplified in Example 47 using (±)-3-({5-[1-(4'-trifluoromethyl-biphenyl-4-yloxy)-octyl]-thiophene-2-carbonyl}-amino)-propionic acid methyl ester as the starting material. MS (ES): 548.3 [M+H]+.

Example 52

3-({5-[1-(4'-Trifluoromethyl-biphenyl-4-yloxy)-octyl]-thiophene-2-carbonyl}-amino)-propionic acid, Isomer 1

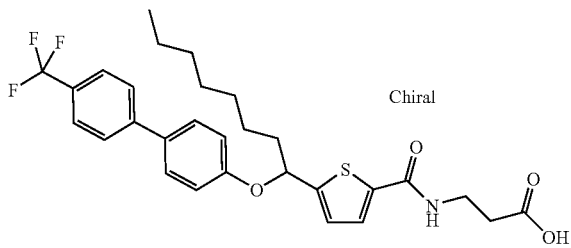

This compound is made by the general method as exemplified in Example 47 using 3-({5-[1-(4'-trifluoromethyl-biphenyl-4-yloxy)-octyl]-thiophene-2-carbonyl}-amino)-propionic acid methyl ester (chiral Isomer 1) as the starting material. MS (ES): 548.2 [M+H]+.

Example 53

3-({5-[1-(4-Trifluoromethyl-biphenyl-4-yloxy)-octyl]-thiophene-2-carbonyl}-amino)-propionic acid, Isomer 2

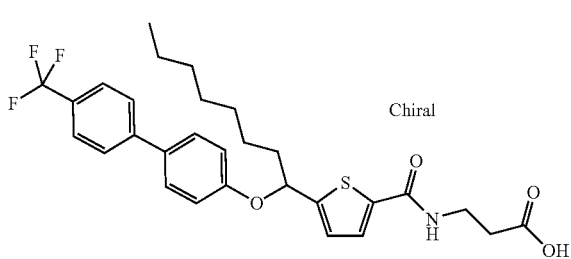

This compound is made by the general method as exemplified in Example 47 using 3-({5-[1-(4'-trifluoromethyl-biphenyl-4-yloxy)-octyl]-thiophene-2-carbonyl}-amino)-propionic acid methyl ester (chiral Isomer 2) as the starting material. MS (ES): 548.2 [M+H]+.

Example 54

(R,S)-3-({5-[1-(2,6-Dimethyl-4'-trifluoromethyl-biphenyl-4-yloxy)-3,3-dimethyl-butyl]-thiophene-2-carbonyl}-amino)-propionic acid

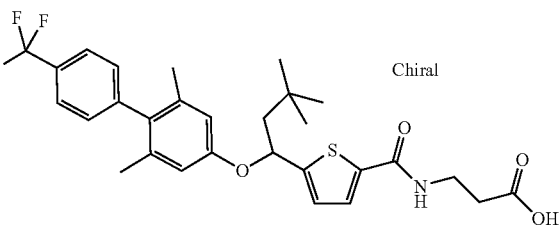

This compound is made by the general method as exemplified in Example 47 using (±)-3-({5-[1-(2,6-dimethyl-4'-trifluoromethyl-biphenyl-4-yloxy)-3,3-dimethyl-butyl]-thiophene-2-carbonyl}-amino)-propionic acid methyl ester as the starting material. MS (ES): 548.3 [M+H]+.

Example 55

3-({5-[1-(2,6-Dimethyl-4'-trifluoromethyl-biphenyl-4-yloxy)-3,3-dimethyl-butyl]-thiophene-2-carbonyl}-amino)-propionic acid, Isomer 1)

This compound is made by the general method as exemplified in Example 47 using 3-({5-[1-(2,6-dimethyl-4'-trifluoromethyl-biphenyl-4-yloxy)-3,3-dimethyl-butyl]-thiophene-2-carbonyl}-amino)-propionic acid methyl ester (chiral Isomer 1) as the starting material. MS (ES): 548.3 [M+H]+.

Example 56

3-({5-[1-(2,6-Dimethyl-4'-trifluoromethyl-biphenyl-4-yloxy)-3,3-dimethyl-butyl]-thiophene-2-carbonyl}-amino)-propionic acid, Isomer 2

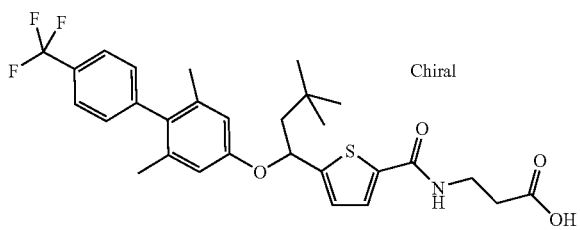

This compound is made by the general method as exemplified in Example 47 using 3-({5-[1-(2,6-dimethyl-4'-trifluoromethyl-biphenyl-4-yloxy)-3,3-dimethyl-butyl]-thiophene-2-carbonyl}-amino)-propionic acid methyl ester (chiral Isomer 2) as the starting material. MS (ES): 548.3 [M+H]+.

Example 57

(R,S)-3-({3-Chloro-5-[1-(2,6-dimethyl-4'-trifluoromethyl-biphenyl-4-yloxy)-propyl]-thiophene-2-carbonyl}-amino)-propionic acid

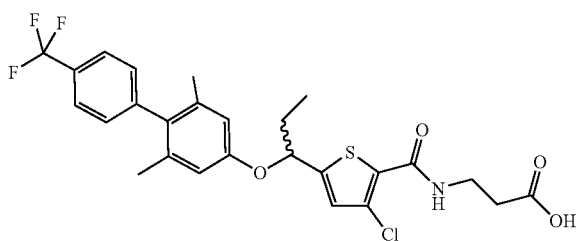

This compound is made by the general method as exemplified in Example 47 using (±)-3-({3-chloro-5-[1-(2,6-dimethyl-4'-trifluoromethyl-biphenyl-4-yloxy)-propyl]-thiophene-2-carbonyl}-amino)-propionic acid methyl ester as the starting material. MS (ES): 538.1 [M–H]−.

Example 58

(R,S)-3-({5-[1-(4'-tert-Butyl-2,6-dimethyl-biphenyl-4-yloxy)-4,4,4-trifluoro-butyl]-thiophene-2-carbonyl}-amino)-propionic acid

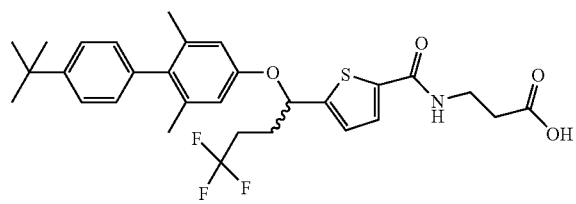

To a mixture of (R,S)-3-({5-[1-(4'-tert-butyl-2,6-dimethyl-biphenyl-4-yloxy)-4,4,4-trifluoro-butyl]-thiophene-2-carbonyl}-amino)-propionic acid methyl ester (50 mg, 0.09 mmol) in tetrahydrofuran (1.0 mL) is added sodium hydroxide (5N aqueous, 1.0 mL) at room temperature, and stirred overnight. The reaction mixture is acidified by 5N HCl (1.0 mL), extracted into ethyl acetate, dried and concentrated, then dried under vacuum, giving the title compound (45 mg). MS (ES): 562.0 [M–H]−.

Example 59

(R,S)-3-({5-[1-(2,6-Dimethyl-4'-trifluoromethyl-biphenyl-4-yloxy)-2-methyl-propyl]-thiophene-2-carbonyl}-amino)-propionic acid

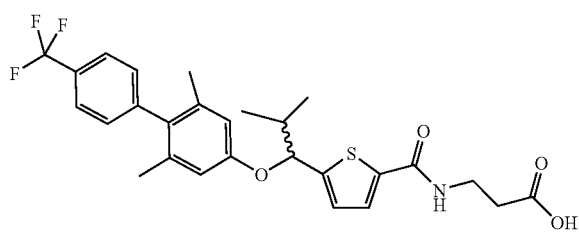

This compound is made by the general method as exemplified in Example 47 using (±)-3-({5-[1-(2,6-dimethyl-4'-trifluoromethyl-biphenyl-4-yloxy)-2-methyl-propyl]-thiophene-2-carbonyl}-amino)-propionic acid methyl ester as the starting material. MS (ES): 518.1 [M–H]−.

Example 60

(R,S)-3-({5-[2-Methyl-1-(2-methyl-4'-trifluoromethyl-biphenyl-4-yloxy)-propyl]-thiophene-2-carbonyl}-amino)-propionic acid

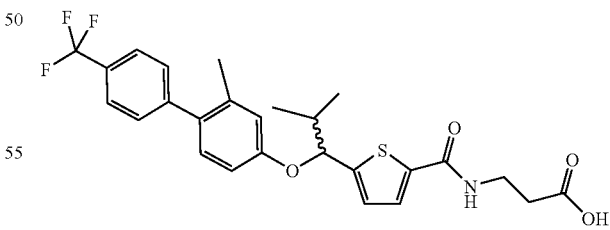

This compound is made by the general method as exemplified in Example 47 using (±)-3-({5-[2-methyl-1-(2-methyl-4'-trifluoromethyl-biphenyl-4-yloxy)-propyl]- thiophene-2-carbonyl}-amino)-propionic acid methyl ester as the starting material. MS (ES): 504.1 [M−H]⁻.

Example 61

(R,S)-3-({5-[1-(2,6-Dimethyl-4'-trifluoromethyl-biphenyl-4-yloxy)-butyl]-thiophene-2-carbonyl}-amino)-propionic acid

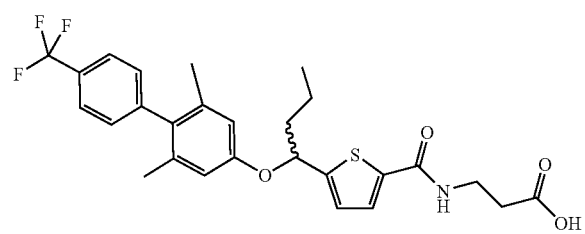

This compound is made by the general method as exemplified in Example 47 using (±)-3-({5-[1-(2,6-dimethyl-4'-trifluoromethyl-biphenyl-4-yloxy)-butyl]-thiophene-2-carbonyl}-amino)-propionic acid methyl ester as the starting material. MS (ES): 518.1 [M−H]⁻.

Example 62

(R,S)-3-({5-[1-(2-Methyl-4'-trifluoromethyl-biphenyl-4-yloxy)-butyl]-thiophene-2-carbonyl}-amino)-propionic acid

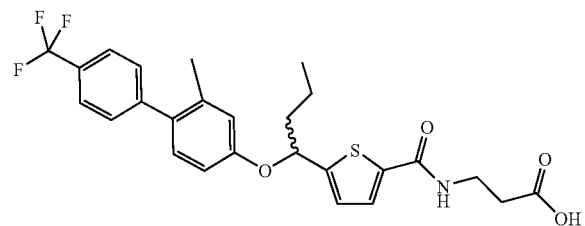

This compound is made by the general method as exemplified in Example 47 using (±)-3-({5-[1-(2-methyl-4'-trifluoromethyl-biphenyl-4-yloxy)-butyl]-thiophene-2-carbonyl}-amino)-propionic acid methyl ester as the starting material. MS (ES): 504.1 [M−H]⁻.

Example 63

(R,S)-3-({5-[1-(4'-tert-Butyl-2,6-dimethyl-biphenyl-4-yloxy)-2-methyl-propyl]-thiophene-2-carbonyl}-amino)-propionic acid

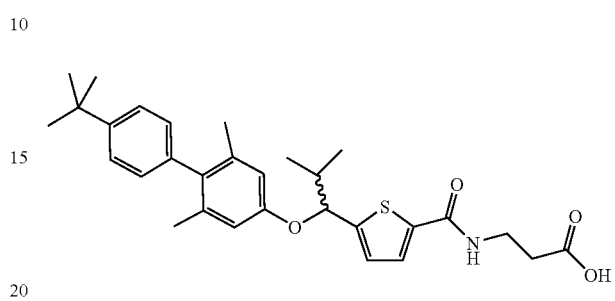

This compound is made by the general method as exemplified in Example 47 using (±)-3-({5-[1-(4'-tert-butyl-2,6-dimethyl-biphenyl-4-yloxy)-2-methyl-propyl]-thiophene-2-carbonyl}-amino)-propionic acid methyl ester as the starting material. MS (ES): 506.2 [M−H]⁻.

Example 64

3-({5-[1-(4'-tert-Butyl-2,6-dimethyl-biphenyl-4-yloxy)-2-methyl-propyl]-thiophene-2-carbonyl}-amino)-propionic acid, Isomer 1

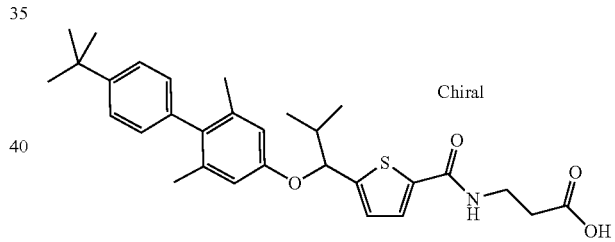

This compound is made by the general method as exemplified in Example 47 using 3-({5-[1-(4'-tert-butyl-2,6-dimethyl-biphenyl-4-yloxy)-2-methyl-propyl]-thiophene-2-carbonyl}-amino)-propionic acid methyl ester (chiral Isomer 1) as the starting material. MS (ES): 506.2 [M−H]⁻.

Example 65

3-({5-[1-(4'-tert-Butyl-2,6-dimethyl-biphenyl-4-yloxy)-2-methyl-propyl]-thiophene-2-carbonyl}-amino)-propionic acid, Isomer 2

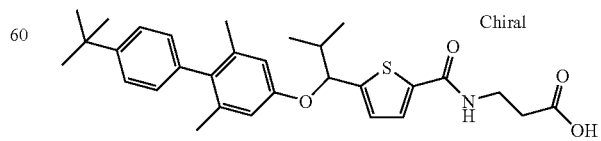

This compound is made by the general method as exemplified in Example 47 using 3-({5-[1-(4'-tert-butyl-2,6-dimethyl-biphenyl-4-yloxy)-2-methyl-propyl]-thiophene-2-carbonyl}-amino)-propionic acid methyl ester (chiral Isomer 2) as the starting material. MS (ES): 506.2 [M–H]⁻.

Example 66

(R,S)-3-({5-[1-(4'-tert-Butyl-2-methyl-biphenyl-4-yloxy)-2-methyl-propyl]-thiophene-2-carbonyl}-amino)-propionic acid

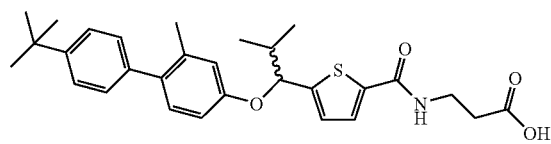

This compound is made by the general method as exemplified in Example 47 using (±)-3-({5-[1-(4'-tert-butyl-2-methyl-biphenyl-4-yloxy)-2-methyl-propyl]-thiophene-2-carbonyl}-amino)-propionic acid methyl ester as the starting material. MS (ES): 492.2 [M–H]⁻.

Example 67

3-({5-[1-(4'-tert-Butyl-2-methyl-biphenyl-4-yloxy)-2-methyl-propyl]-thiophene-2-carbonyl}-amino)-propionic acid, Isomer 1

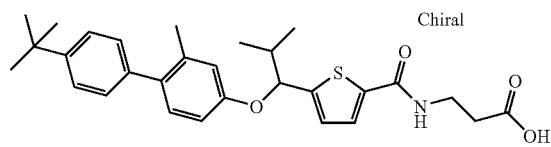

This compound is made by the general method as exemplified in Example 47 using 3-({5-[1-(4'-tert-butyl-2-methyl-biphenyl-4-yloxy)-2-methyl-propyl]-thiophene-2-carbonyl}-amino)-propionic acid methyl ester (chiral Isomer 1) as the starting material. MS (ES): 492.3 [M–H]⁻.

Example 68

3-({5-[1-(4'-tert-Butyl-2-methyl-biphenyl-4-yloxy)-2-methyl-propyl]-thiophene-2-carbonyl}-amino)-propionic acid, chiral Isomer 2

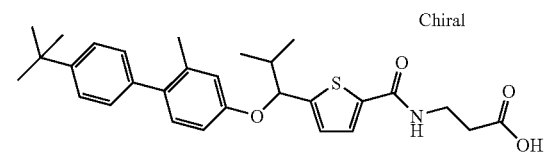

This compound is made by the general method as exemplified in Example 47 using 3-({5-[1-(4'-tert-butyl-2-methyl-biphenyl-4-yloxy)-2-methyl-propyl]-thiophene-2-carbo-nyl}-amino)-propionic acid methyl ester (chiral Isomer 2) as the starting material. MS (ES): 492.3 [M–H]⁻.

Example 69

(R,S)-3-({5-[1-(4'-tert-Butyl-2,6-dimethyl-biphenyl-4-yloxy)-butyl]-thiophene-2-carbonyl}-amino)-propionic acid

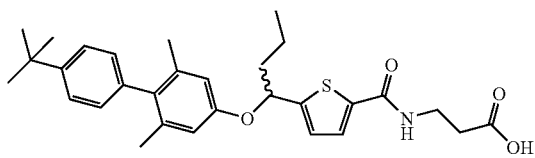

This compound is made by the general method as exemplified in Example 47 using (±)-3-({5-[1-(4'-tert-butyl-2,6-dimethyl-biphenyl-4-yloxy)-butyl]-thiophene-2-carbonyl}-amino)-propionic acid methyl ester as the starting material. MS (ES): 506.3 [M–H]⁻.

Example 70

(R,S)-3-({5-[1-(4'-tert-Butyl-2-methyl-biphenyl-4-yloxy)-butyl]-thiophene-2-carbonyl}-amino)-propionic acid

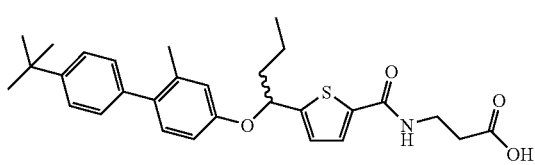

This compound is made by the general method as exemplified in Example 47 using (±)-3-({5-[1-(4'-tert-butyl-2-methyl-biphenyl-4-yloxy)-butyl]-thiophene-2-carbonyl}-amino)-propionic acid methyl ester as the starting material. MS (ES): 492.3 [M–H]⁻.

Example 71

(R,S)-3-({5-[1-(2,6-Dimethyl-4'-trifluoromethyl-biphenyl-4-yloxy)-ethyl]-thiophene-2-carbonyl}-amino)-propionic acid

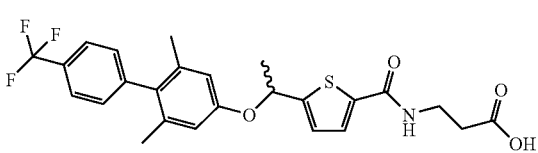

This compound is made by the general method as exemplified in Example 47 using (±)-3-({5-[1-(2,6-dimethyl-4'-trifluoromethyl-biphenyl-4-yloxy)-ethyl]-thiophene-2-car-

Example 72

(R,S)-3-({5-[1-(4'-tert-Butyl-2,6-dimethyl-biphenyl-4-yloxy)-ethyl]-thiophene-2-carbonyl}-amino)-propionic acid

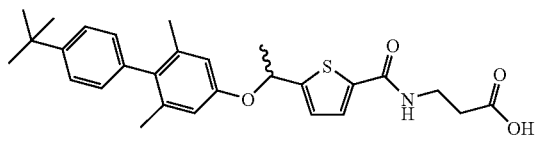

This compound is made by the general method as exemplified in Example 47 using (±)-3-({5-[1-(4'-tert-butyl-2,6-dimethyl-biphenyl-4-yloxy)-ethyl]-thiophene-2-carbonyl}-amino)-propionic acid methyl ester as the starting material. MS (ES): 480.2 [M+H]$^+$.

Example 73

(R,S)-3-({5-[1-(2,6-Dimethyl-4'-trifluoromethyl-biphenyl-4-yloxy)-pentyl]-thiophene-2-carbonyl}-amino)-propionic acid

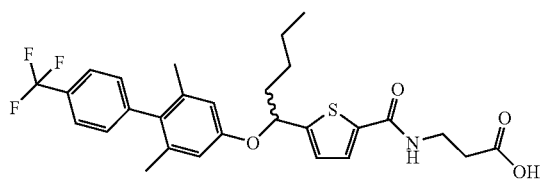

This compound is made by the general method as exemplified in Example 47 using (±)-3-({5-[1-(2,6-dimethyl-4'-trifluoromethyl-biphenyl-4-yloxy)-pentyl]-thiophene-2-carbonyl}-amino)-propionic acid methyl ester as the starting material. MS (ES): 534.2 [M+H]$^+$.

Example 74

(R,S)-3-({5-[1-(2-Methyl-4'-trifluoromethyl-biphenyl-4-yloxy)-pentyl]-thiophene-2-carbonyl}-amino)-propionic acid

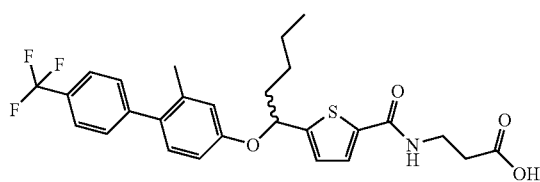

This compound is made by the general method as exemplified in Example 47 using (±)-3-({5-[1-(2-methyl-4'-trifluoromethyl-biphenyl-4-yloxy)-pentyl]-thiophene-2-carbonyl}-amino)-propionic acid methyl ester as the starting material. MS (ES): 492.0 [M+H]$^+$.

Example 75

(R,S)-3-({5-[1-(4'-tert-Butyl-2,6-dimethyl-biphenyl-4-yloxy)-pentyl]-thiophene-2-carbonyl}-amino)-propionic acid

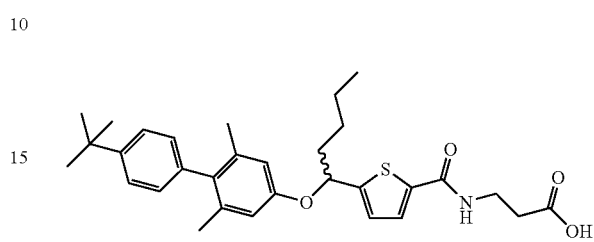

This compound is made by the general method as exemplified in Example 47 using (±)-3-({5-[1-(4'-tert-butyl-2,6-dimethyl-biphenyl-4-yloxy)-pentyl]-thiophene-2-carbonyl}-amino)-propionic acid methyl ester as the starting material. MS (ES): 522.2 [M+H]$^+$.

Example 76

(R,S)-3-({5-[1-(4'-tert-Butyl-2-methyl-biphenyl-4-yloxy)-pentyl]-thiophene-2-carbonyl}-amino)-propionic acid

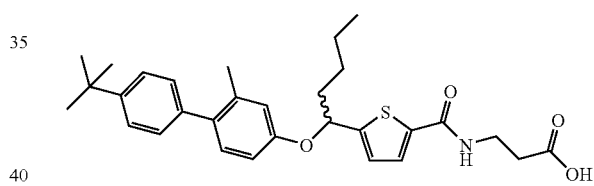

This compound is made by the general method as exemplified in Example 47 using (±)-3-({5-[1-(4'-tert-butyl-2-methyl-biphenyl-4-yloxy)-pentyl]-thiophene-2-carbonyl}-amino)-propionic acid methyl ester as the starting material. MS (ES): 508.3 [M+H]$^+$.

Example 77

3-({5-[2-(2,6-Dimethyl-4'-trifluoromethyl-biphenyl-4-yloxy)-1,1-dimethyl-ethyl]-thiophene-2-carbonyl}-amino)-propionic acid

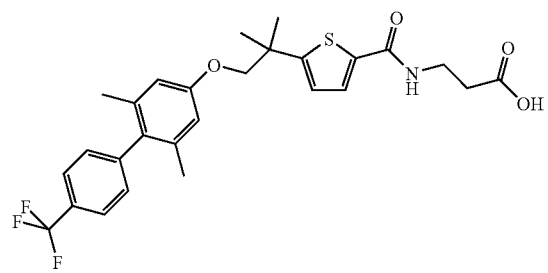

This compound is made by the general method as exemplified in Example 47 using 3-({5-[2-(2,6-dimethyl-4'-trifluoromethyl-biphenyl-4-yloxy)-1,1-dimethyl-ethyl]-thiophene-2-carbonyl}-amino)-propionic acid methyl ester as the starting material. MS (ES): 520.0 [M+H]+.

Example 78

3-({5-[1-(2,6-Dimethyl-4'-trifluoromethyl-biphenyl-4-yloxymethyl)-1-ethyl-propyl]-thiophene-2-carbonyl}-amino)-propionic acid

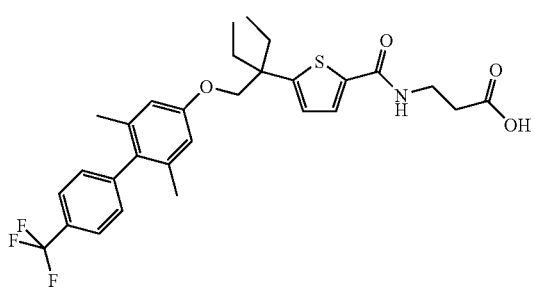

This compound is made by the general method as exemplified in Example 47 using 3-({5-[1-(2,6-dimethyl-4'-trifluoromethyl-biphenyl-4-yloxymethyl)-1-ethyl-propyl]-thiophene-2-carbonyl}-amino)-propionic acid methyl ester as the starting material. MS (ES): 548.0 [M+H]+.

Example 79

3-({5-[1-(2,6-Dimethyl-4'-trifluoromethyl-biphenyl-4-yloxymethyl)-1-propyl-butyl]-thiophene-2-carbonyl}-amino)-propionic acid

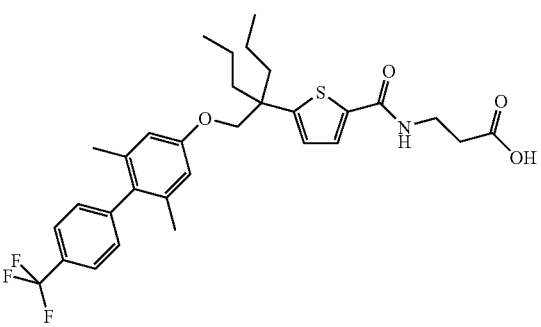

This compound is made by the general method as exemplified in Example 47 using 3-({5-[1-(2,6-dimethyl-4'-trifluoromethyl-biphenyl-4-yloxymethyl)-1-propyl-butyl]-thiophene-2-carbonyl}-amino)-propionic acid methyl ester as the starting material. MS (ES): 576.2 [M+H]+.

Example 80

3-({5-[1-Allyl-1-(2,6-dimethyl-4'-trifluoromethyl-biphenyl-4-yloxymethyl)-but-3-enyl]-thiophene-2-carbonyl}-amino)-propionic acid

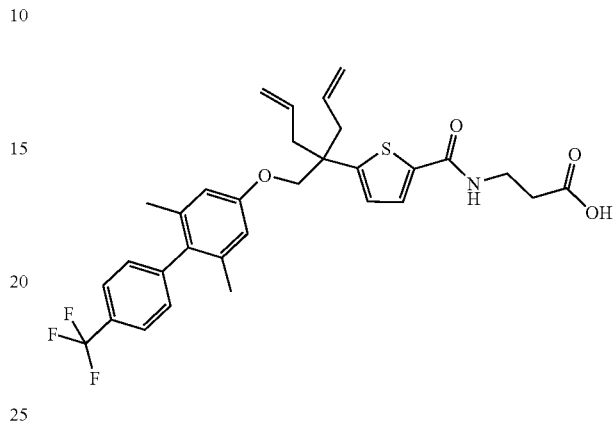

This compound is made by the general method as exemplified in Example 47 using 3-({5-[1-allyl-1-(2,6-dimethyl-4'-trifluoromethyl-biphenyl-4-yloxymethyl)-but-3-enyl]-thiophene-2-carbonyl}-amino)-propionic acid methyl ester as the starting material. MS (ES): 572.0 [M+H]+.

Example 81

3-({5-[1-(2,6-Dimethyl-4'-trifluoromethyl-biphenyl-4-yloxymethyl)-cyclopent-3-enyl]-thiophene-2-carbonyl}-amino)-propionic acid

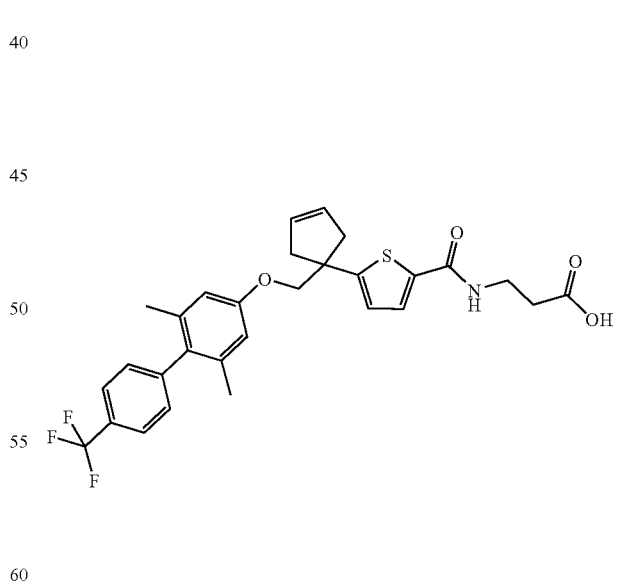

This compound is made by the general method as exemplified in Example 47 using 3-({5-[1-(2,6-dimethyl-4'-trifluoromethyl-biphenyl-4-yloxymethyl)-cyclopent-3-enyl]- thiophene-2-carbonyl}-amino)-propionic acid methyl ester as the starting material. MS (ES): 544.0 [M+H]+.

Example 82

3-({5-[1-(2,6-Dimethyl-4'-trifluoromethyl-biphenyl-4-yloxymethyl)-cyclopentyl]-thiophene-2-carbonyl}-amino)-propionic acid

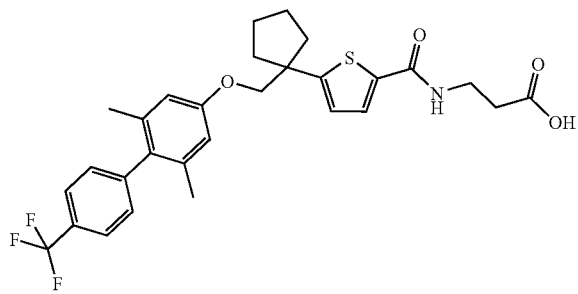

This compound is made by the general method as exemplified in Example 47 using 3-({5-[1-(2,6-dimethyl-4'-trifluoromethyl-biphenyl-4-yloxymethyl)-cyclopentyl]-thiophene-2-carbonyl}-amino)-propionic acid methyl ester as the starting material. MS (ES): 546.0 [M+H]+.

Example 83

(R,S)-3-({5-[1-(4-Bromo-3,5-dimethyl-phenoxy)-3-methyl-butyl]-thiophene-2-carbonyl}-amino)-propionic acid

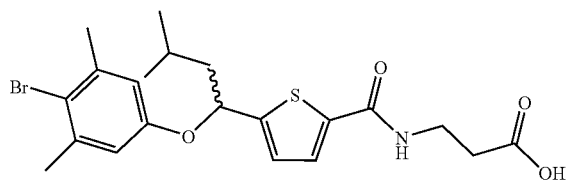

This compound is made in a manner substantially similar to Example 47 starting with (±)-3-({5-[1-(4-bromo-3,5-dimethyl-phenoxy)-3-methyl-butyl]-thiophene-2-carbonyl}-amino)-propionic acid methyl ester MS(ES): 470.2 [M+H]+.

Example 84

(R,S)-3-({5-[1-(3,5-Dimethyl-phenoxy)-3-methyl-butyl]-thiophene-2-carbonyl}-amino)-propionic acid

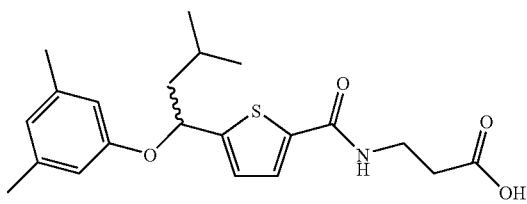

This compound is made in a manner substantially similar to Example 47 starting from (±)-3-({5-[1-(3,5-dimethyl-phenoxy)-3-methyl-butyl]-thiophene-2-carbonyl}-amino)-propionic acid methyl ester. MS(ES): 390.2 [M+H]+.

Example 85

(R,S)-3-({5-[1-(4-Bromo-3,5-dimethyl-phenylsulfanyl)-4,4,4-trifluoro-butyl]-thiophene-2-carbonyl}-amino)-propionic acid

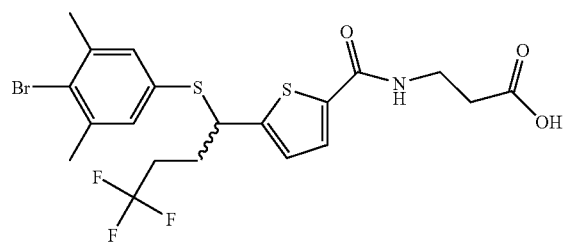

This compound is made in a manner substantially similar to Example 47 starting from (±)-3-({5-[1-(4-bromo-3,5-dimethyl-phenylsulfanyl)-4,4,4-trifluoro-butyl]-thiophene-2-carbonyl}-amino)-propionic acid methyl ester. MS(ES): 523.7, 535.8 [M+H]+.

Example 86

3-({5-[1-(2,6-Dimethyl-4'-trifluoromethyl-biphenyl-4-yloxy)-2-methyl-propyl]-thiophene-2-carbonyl}-amino)-propionic acid, Isomer 1

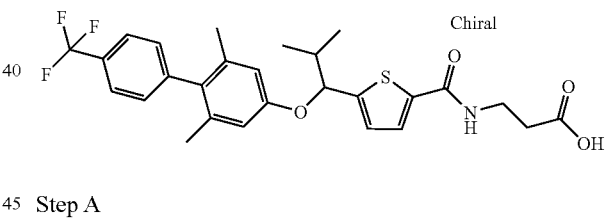

Step A 3-({5-[1-(2,6-Dimethyl-4'-trifluoromethyl-biphenyl-4-yloxy)-2-methyl-propyl]-thiophene-2-carbonyl}-amino)-propionic acid methyl ester To a mixture of 3-({5-[1-(4-iodo-3,5-dimethyl-phenoxy)-2-methyl-propyl]-thiophene-2-carbonyl}-amino)-propionic acid methyl ester (chiral Isomer 1) (0.218 g, 0.422 mmol), (4-trifluoromethyl)phenylboronic acid (0.110 g, 0.536 mmol), and potassium fluoride (0.0628 g, 1.306 mmol) in THF (4.07 ml) is added palladium(II) acetate (5.5 mg, 0.024 mmol), and (oxydi-2,1-phenylene)bis-(diphenylphosphine) (25.8 mg, 0.0479 mmol). The reaction mixture is heated to reflux overnight. Additional palladium(II) acetate (13.5 mg, 0.0601 mmol), and (oxydi-2,1-phenylene)bis-(diphenylphosphine) (55.7 mg, 0.103 mmol) and THF (4.0 mL) added. Reaction heated at relux overnight. The reaction mixture is cooled to rt, conc., loaded onto silica gel and eluted using hexanes with an ethyl acetate gradient from 0% to 80% giving a mixture of product and starting material. This material is then loaded onto $C_{18}$ and eluted using $H_2O$ with an MeCN gradient from 35% to 100% giving 3-({5-[1-(2,6- dimethyl-4'-trifluoromethyl-biphenyl-4-yloxy)-2-methyl-propyl]-thiophene-2-carbonyl}-amino)-propionic acid methyl ester (0.0392 g, 17%) as a white foam. MS (ES): 534.4 [M+H]+.

Step B 3-({5-[1-(2,6-Dimethyl-4'-trifluoromethyl-biphenyl-4-yloxy)-propyl]-thiophene-2-carbonyl}-amino)-propionic acid To a solution of 3-({5-[1-(2,6-dimethyl-4'-trifluoromethyl-biphenyl-4-yloxy)-2-methyl-propyl]-thiophene-2-carbonyl}-amino)-propionic acid methyl ester (0.0390 mg, 0.0731 mmol) in THF (2.0 mL) is added lithium hydroxide (1N aqueous, 2.0 mL) at rt and stirred overnight. The reaction mixture is acidified with 1 N HCl (2.4 mL), extracted with EtOAc (3×10 mL), dried over MgSO4, filtered, and conc. to provide the title compound (0.0356 g, 94%). MS (ES): 520.0 [M+H]+.

The following compounds are made in a substantially similar manner:

Example 87

3-({5-[1-(2,6-Dimethyl-4'-trifluoromethyl-biphenyl-4-yloxy)-2-methyl-propyl]-thiophene-2-carbonyl}-amino)-propionic acid, Isomer 2

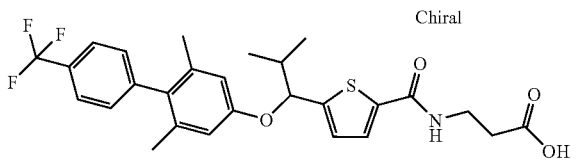

This compound is made by the general method as exemplified in Example 86 using 3-({5-[1-(4-iodo-3,5-dimethyl-phenoxy)-2-methyl-propyl]-thiophene-2-carbonyl}-amino)-propionic acid methyl ester (chiral Isomer 2) as the starting material. MS (ES): 520.0 [M+H]+.

Example 88

(R,S)-3-({5-[1-(2,6-Dimethyl-biphenyl-4-yloxy)-3-methyl-butyl]-thiophene-2-carbonyl}-amino)-propionic acid

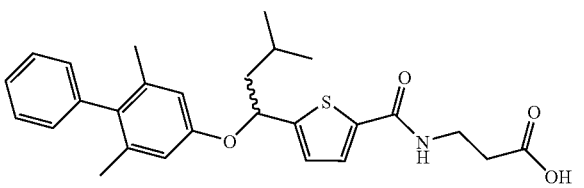

Step A (R,S)-3-({5-[1-(2,6-Dimethyl-biphenyl-4-yloxy)-3-methyl-butyl]-thiophene-2-carbonyl}-amino)-propionic acid ethyl ester To a solution of 3-({5-[1-(4-bromo-3,5-dimethyl-phenoxy)-3-methyl-butyl]-thiophene-2-carbonyl}-amino)-propionic acid methyl ester (158 mg, 0.330 mmol) in toluene (1.5 mL) is added potassium fluoride (38.1 mg, 0.660 mmol), phenyl boronic acid (80 mg, 0.66 mmol), and palladium tetrakis triphenyl phosphine (19 mg, 0.02 mmol). Water (1 mL) is added and the reaction mixture is heated to reflux overnight. After cooling to rt, the reaction mixture is partitioned between ethyl acetate and water. The aqueous layer is back-extracted with ethyl acetate, the combined organic layers are dried and concentrated. The resulting residue is applied to silica gel and eluted using hexanes with an ethyl acetate gradient to give the title compound (2.06 g). MS (ES): 478.2 [M−H]−.

Step B (R,S)-3-({5-[1-(2,6-Dimethyl-biphenyl-4-yloxy)-3-methyl-butyl]-thiophene-2-carbonyl}-amino)-propionic acid To a mixture of (R,S)-5-[1-(4'-trifluoromethyl-biphenyl-4-yloxy)-propyl]-thiophene-2-carboxylic acid ethyl ester from the previous step in tetrahydrofuran (1.0 mL) is added sodium hydroxide (5N aqueous, 1.0 mL) at room temperature, and stirred overnight. The reaction mixture is acidified by 5N HCl (1.0 mL), extracted into ethyl acetate, dried and concentrated, then dried under vacuum, giving the title compound (50 mg). MS (ES): 464.0 [M−H]−.

The following compounds are made in a substantially similar manner.

Example 89

(R,S)-3-({5-[1-(4'-tert-Butyl-2,6-dimethyl-biphenyl-4-yloxy)-3-methyl-butyl]-thiophene-2-carbonyl}-amino)-propionic acid

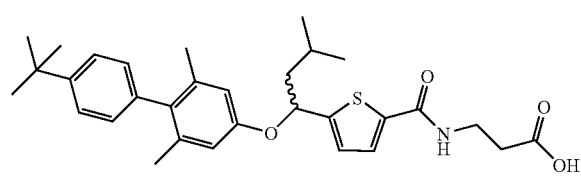

This compound is made by the general method as exemplified in Example 88 using 4-t-Bu-phenyl boronic acid as the reagent in Step A. MS(ES): 522.7 [M+H]+.

Example 90

(R,S)-3-({5-[1-(2,6-Dimethyl-2'-trifluoromethyl-biphenyl-4-yloxy)-3-methyl-butyl]-thiophene-2-carbonyl}-amino)-propionic acid

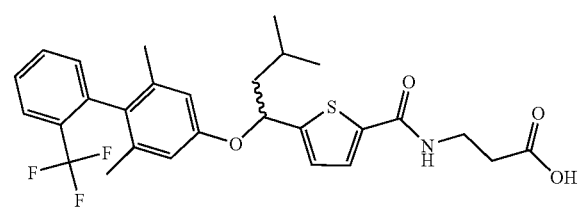

This compound is made by the general method as exemplified in Example 88 using 2-trifluoromethylphenyl boronic acid as the reagent in Step A. MS(ES): 534.2 [M+H]+.

Example 91

(R,S)-3-({5-[1-(2,6-Dimethyl-3'-trifluoromethyl-biphenyl-4-yloxy)-3-methyl-butyl]-thiophene-2-carbonyl}-amino)-propionic acid

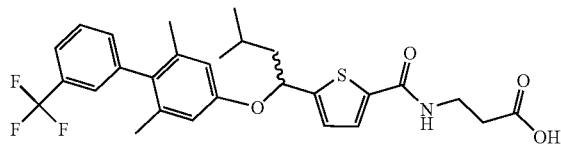

This compound is made by the general method as exemplified in Example 88 using 3-trifluoromethylphenyl boronic acid as the reagent in Step A. MS(ES): 534.2 [M+H]+.

Example 92

(R,S)-3-({5-[1-(4'-Ethyl-2,6-dimethyl-biphenyl-4-yloxy)-3-methyl-butyl]-thiophene-2-carbonyl}-amino)-propionic acid

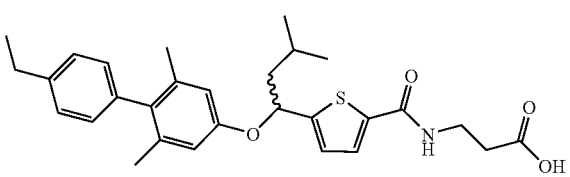

This compound is made by the general method as exemplified in Example 88 using 4-ethylphenyl boronic acid as the reagent in Step A. MS(ES): 494.2 [M+H]+.

Example 93

(R,S)-3-({5-[3-Methyl-1-(2,6,4'-trimethyl-biphenyl-4-yloxy)-butyl]-thiophene-2-carbonyl}-amino)-propionic acid

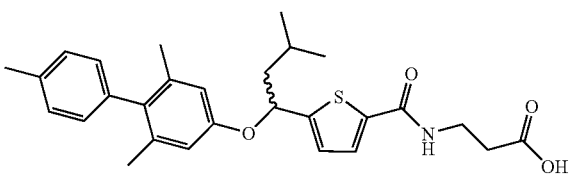

This compound is made by the general method as exemplified in Example 88 using 4-methylphenyl boronic acid as the reagent in Step A. MS(ES): 480.0 [M+H]+.

Example 94

(R,S)-3-({5-[1-(4'-Isopropyl-2,6-dimethyl-biphenyl-4-yloxy)-3-methyl-butyl]-thiophene-2-carbonyl}-amino)-propionic acid

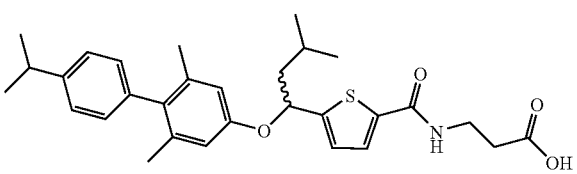

This compound is made by the general method as exemplified in Example 88 using 4-isopropylphenyl boronic acid as the reagent in Step A. MS(ES): 508.0 [M+H]+.

Example 95

(R,S)-3-({5-[1-(2,6-Dimethyl-4'-pentyl-biphenyl-4-yloxy)-3-methyl-butyl]-thiophene-2-carbonyl}-amino)-propionic acid

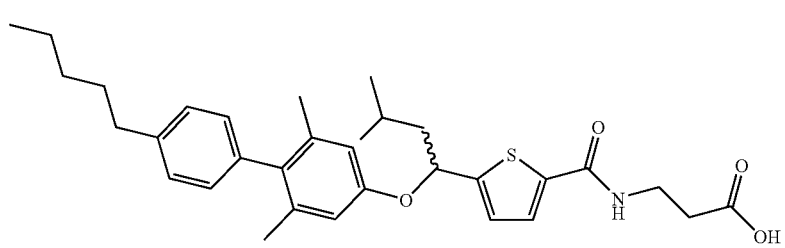

This compound is made by the general method as exemplified in Example 88 using 4-n-pentylphenyl boronic acid as the reagent in Step A. MS(ES): 536.0 [M+H]⁺.

Example 96

(R,S)-3-({5-[1-(4'-Cyclohexyl-2,6-dimethyl-biphenyl-4-yloxy)-3-methyl-butyl]-thiophene-2-carbonyl}-amino)-propionic acid

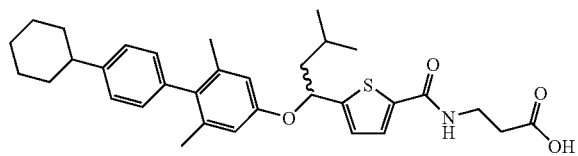

This compound is made by the general method as exemplified in Example 88 using 4-cyclohexylphenyl boronic acid as the reagent in Step A. MS(ES): 548.0 [M+H]⁺.

Example 97

(R,S)-3-({5-[1-(4'-Cyano-2,6-dimethyl-biphenyl-4-yloxy)-3-methyl-butyl]-thiophene-2-carbonyl}-amino)-propionic acid

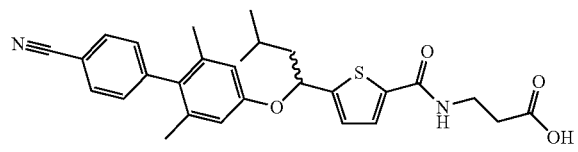

This compound is made by the general method as exemplified in Example 88 using 4-cyanophenyl boronic acid as the reagent in Step A. MS(ES): 492.1 [M+H]⁺.

Example 98

(R,S)-3-({5-[1-(2,6-Dimethyl-4'-trifluoromethoxy-biphenyl-4-yloxy)-3-methyl-butyl]-thiophene-2-carbonyl}-amino)-propionic acid

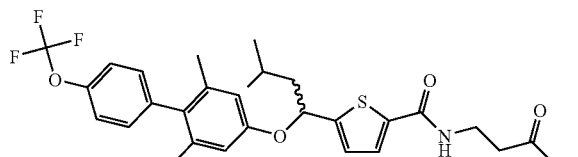

This compound is made by the general method as exemplified in Example 88 using 4-trifluoromethoxyphenyl boronic acid as the reagent in Step A. MS(ES): 550.0 [M+H]⁺.

Example 99

(R,S)-3-({5-[1-(4'-Dimethylamino-2,6-dimethyl-biphenyl-4-yloxy)-3-methyl-butyl]-thiophene-2-carbonyl}-amino)-propionic acid

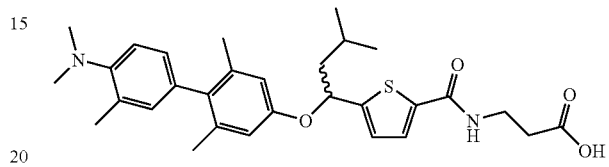

This compound is made by the general method as exemplified in Example 88 using 4-n-n-dimethylphenyl boronic acid as the reagent in Step A. MS(ES): 509.2 [M+H]⁺.

Example 100

(R,S)-3-[(5-{1-[4-(5-Acetyl-thiophen-2-yl)-3,5-dimethyl-phenoxy]-3-methyl-butyl}-thiophene-2-carbonyl)-amino]-propionic acid

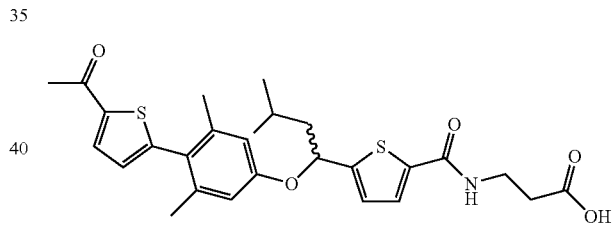

This compound is made by the general method as exemplified in Example 88 using 5-acetyl-2-thiophenyl boronic acid as the reagent in Step A. MS(ES): 514.0 [M+H]⁺.

Example 101

(R,S)-3-[(5-{1-[4-(5-Cyano-thiophen-2-yl)-3,5-dimethyl-phenoxy]-3-methyl-butyl}-thiophene-2-carbonyl)-amino]-propionic acid

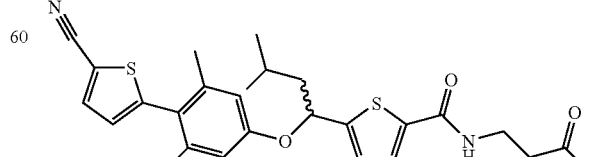

This compound is made by the general method as exemplified in Example 88 using 5-cyano-2-thiophenyl boronic acid as the reagent in Step A. MS(ES): 497.0 [M+H]+.

Example 102

(R,S)-3-({5-[1-(3,5-Dimethyl-4-thiophen-3-yl-phenoxy)-3-methyl-butyl]-thiophene-2-carbonyl}-amino)-propionic acid

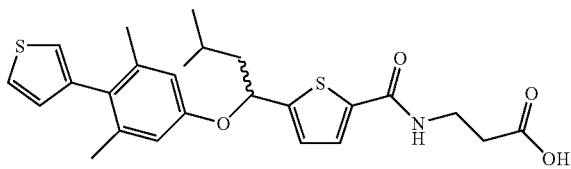

This compound is made by the general method as exemplified in Example 88 using 2-thiophenyl boronic acid as the reagent in Step A. MS(ES): 472.0 [M+H]+.

Example 103

(R,S)-3-({5-[1-(4'-tert-Butyl-2,6-dimethyl-biphenyl-4-ylsulfanyl)-4,4,4-trifluoro-butyl]-thiophene-2-carbonyl}-amino)-propionic acid

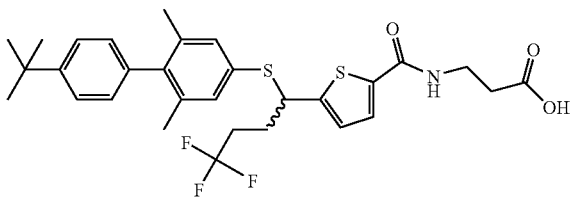

This compound is made by the general method as exemplified in Example 88 using 4-t-butylphenyl boronic acid and methyl-3({5-[1-(4-bromo-3,5-dimethyl-phenylsulfanyl)-4,4,4-trifluoro-butyl]-thiophene-2-carbonyl}-amino)-propionic acid as the starting materials in Step A. MS(ES): 578.0 [M+H]+.

Example 104

(R,S)-3-({5-[1-(2,6-Dimethyl-4'-trifluoromethyl-biphenyl-4-ylsulfanyl)-4,4,4-trifluoro-butyl]-thiophene-2-carbonyl}-amino)-propionic acid

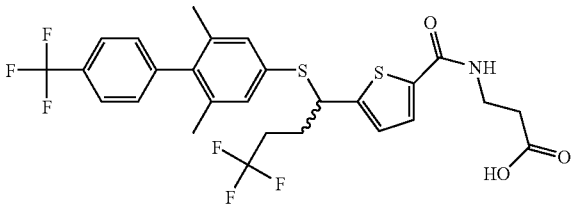

This compound is made by the general method as exemplified in Example 88 using 4-trifluromethyl boronic acid and methyl-3({5-[1-(4-bromo-3,5-dimethyl-phenylsulfanyl)-4,4,4-trifluoro-butyl]-thiophene-2-carbonyl}-amino)-propionic acid as the starting materials in Step A. MS(ES): 590.2 [M+H]+.

Example 105

(R,S)-3-({5-[1-(2,6-Dimethyl-4'-trifluoromethyl-biphenyl-4-yloxy)-4,4,4-trifluoro-butyl]-thiophene-2-carbonyl}-amino)-propionic acid

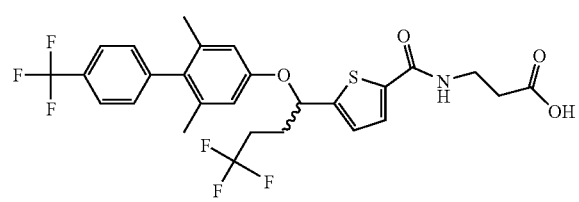

This compound is made by the general method as exemplified in Example 58 using (±)-3-({5-[1-(2,6-Dimethyl-4'-trifluoromethyl-biphenyl-4-yloxy)-4,4,4-trifluoro-butyl]-thiophene-2-carbonyl}-amino)-propionic acid methyl ester as the starting material. MS(ES): 574.0 [M+H]+.

Procedure BB, Chiral Separation

The (R,S)-3-({5-[1-(4'-tert-Butyl-2,6-dimethyl-biphenyl-4-yloxy)-4,4,4-trifluoro-butyl]-thiophene-2-carbonyl}-amino)-propionic acid methyl ester was resolved on a Chiralpak AD-H column (0.46×15.0 cm) with a flow rate of 0.6 mL/min. and detection at 270 nm. Eluted with isopropyl alcohol in heptane with 0.2% dimethyl-ethylamine and concentrated the fractions to provide a pure enantiomer ester (chiral isomer 1, 97.3% ee). Hydrolysis of the pure enantiomer of the ester provided the title compound as a white solid. MS (ES): 577.34 (M++1), 575.34 (M+−1), the structure was also confirmed by proton NMR.

The following enantiomeric pure compounds were obtained by a chiral separation procedure similar to Procedure BB, using Chiralcel OD-H column (4.6×250 mm), Chiralpak AD-H column (4.6×150 mm), or using Chiralcel OJ column (4.6×250 mm):

Example 106

3-({5-[1-(4'-tert-Butyl-2,6-dimethyl-biphenyl-4-yloxy)-4,4,4-trifluoro-butyl]-thiophene-2-carbonyl}-amino)-propionic acid, Isomer 1

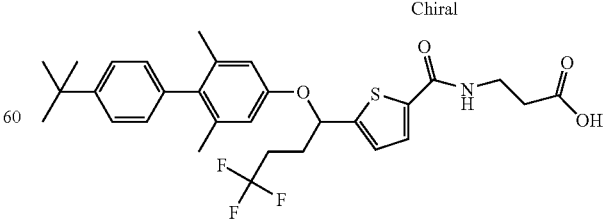

This compound is made by the general method as exemplified in Example 58 using 3-({5-[1-(4'-tert-butyl-2,6-dimethyl-biphenyl-4-yloxy)-4,4,4-trifluoro-butyl]-thiophene-2-carbonyl}-amino)-propionic acid methyl ester, chiral Isomer 1 as the starting material. MS(ES): 562.0 [M+H]+.

Example 107

3-({5-[1-(4'-tert-Butyl-2,6-dimethyl-biphenyl-4-yloxy)-4,4,4-trifluoro-butyl]-thiophene-2-carbonyl}-amino)-propionic acid, Isomer 2

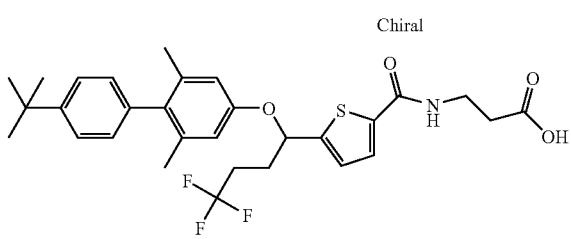

This compound is made by the general method as exemplified in Example 58 using 3-({5-[1-(4'-tert-butyl-2,6-dimethyl-biphenyl-4-yloxy)-4,4,4-trifluoro-butyl]-thiophene-2-carbonyl}-amino)-propionic acid methyl ester, chiral Isomer 2 as the starting material. MS(ES): 562.0 [M+H]+.

Example 108

3-({5-[1-(2,6-Dimethyl-4'-trifluoromethyl-biphenyl-4-yloxy)-4,4,4-trifluoro-butyl]-thiophene-2-carbonyl}-amino)-propionic acid, Isomer 1

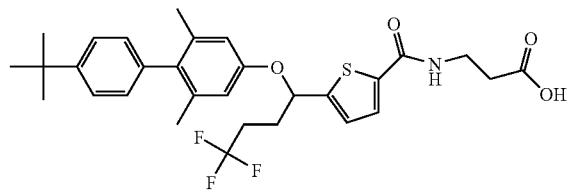

This compound is made by the general method as exemplified in Example 58 using 3-({5-[1-(2,6-dimethyl-4'-trifluoromethyl-biphenyl-4-yloxy)-4,4,4-trifluoro-butyl]-thiophene-2-carbonyl}-amino)-propionic acid methyl ester, chiral Isomer 1 as the starting material. MS(ES): 574.0 [M+H]+.

Example 109

3-({5-[1-(2,6-Dimethyl-4'-trifluoromethyl-biphenyl-4-yloxy)-4,4,4-trifluoro-butyl]-thiophene-2-carbonyl}-amino)-propionic acid, Isomer 2

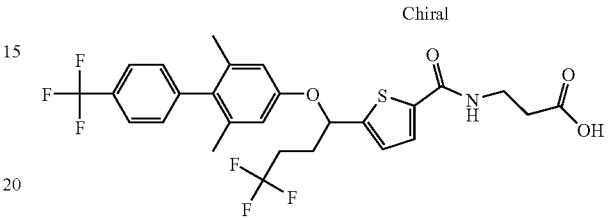

This compound is made by the general method as exemplified in Example 58 using 3-({5-[1-(2,6-dimethyl-4'-trifluoromethyl-biphenyl-4-yloxy)-4,4,4-trifluoro-butyl]-thiophene-2-carbonyl}-amino)-propionic acid methyl ester, chiral Isomer 2 as the starting material. MS(ES): 574.0 [M+H]+.

Example 110

3-({5-[1-(2,6-Dimethyl-4'-trifluoromethoxy-biphenyl-4-yloxy)-2-methyl-propyl]-thiophene-2-carbonyl}-amino)-propionic acid, Isomer 2

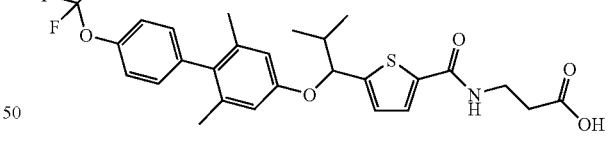

To a solution of 3-({5-[1-(2,6-Dimethyl-4'-trifluoromethoxy-biphenyl-4-yloxy)-2-methyl-propyl]-thiophene-2-carbonyl}-amino)-propionic acid methyl ester (Isomer 2) in tetrahydrofuran (2.0 mL) is added 1 N LiOH (2.0 mL) and stirred overnight. The reaction mixture is acidified with 1 N HCl (2.2 mL) and extracted with EtOAc (3×10 mL). Combined extracts are dried over MgSO4, filtered, and concentrated to provide 3-({5-[1-(2,6-dimethyl-4'-trifluoromethoxy-biphenyl-4-yloxy)-2-methyl-propyl]-thiophene- 2-carbonyl}-amino)-propionic acid (Isomer 2) (0.101 g, 89%) as a white foam. MS (ES): 536.0 [M+H]+.

Example 111

3-({5-[1-(4'-Isopropyl-2,6-dimethyl-biphenyl-4-yloxy)-2-methyl-propyl]-thiophene-2-carbonyl}-amino)-propionic acid, Isomer 2

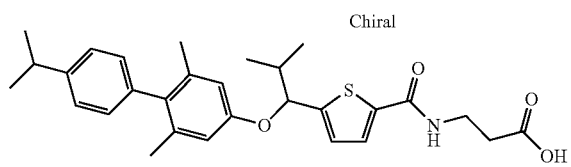

This compound is made by the general method as exemplified in Example 110 using 3-({5-[1-(4'-isopropyl-2,6-dimethyl-biphenyl-4-yloxy)-2-methyl-propyl]-thiophene-2-carbonyl}-amino)-propionic acid methyl ester (Isomer 2) as the starting material. MS (ES): 494.2 [M+H]+.

Example 112

(R,S)-3-({5-[1-(4'-tert-Butyl-2,6-dimethyl-biphenyl-4-yloxy)-2-methyl-propyl]-thiophene-2-carbonyl}-amino)-2R-hydroxy-propionic acid

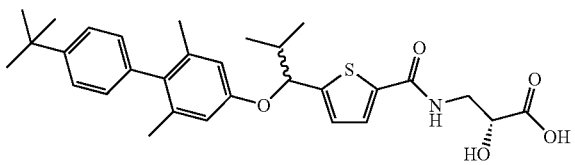

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2-hydroxy-propionic acid methyl ester as the starting material. MS (ES): 524.3 [M+H]+.

Example 113

(R,S)-3-({5-[1-(2,6-Dimethyl-4'-trifluoromethyl-biphenyl-4-yloxy)-2-methyl-propyl]-thiophene-2-carbonyl}-amino)-2S-hydroxy-propionic acid

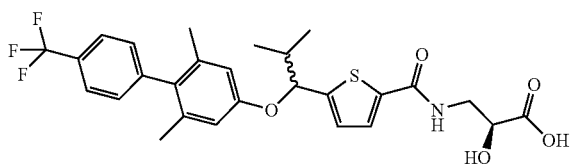

This compound is made by the general method as exemplified in Example 110 using 3-({5-[1-(2,6-dimethyl-4'-trifluoromethyl-biphenyl-4-yloxy)-2-methyl-propyl]-thiophene-2-carbonyl}-amino)-2R-hydroxy-propionic acid methyl ester as the starting material. MS (ES): 536.0 [M+H]+.

Example 114

(R,S)-3-({5-[1-(4'-tert-Butyl-2,6-dimethyl-biphenyl-4-yloxy)-2-methyl-propyl]-thiophene-2-carbonyl}-amino)-2S-hydroxy-propionic acid

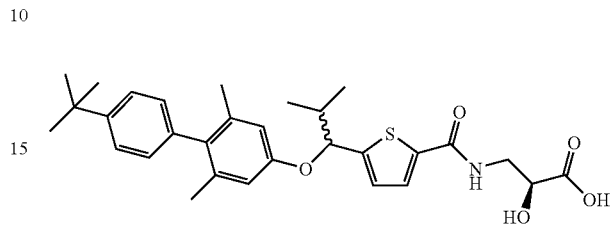

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2S-hydroxy-propionic acid ethyl ester as the starting material. MS (ES): 524.3 [M+H]+.

Example 115

3-({5-[1-(4'-tert-Butyl-2-methyl-biphenyl-4-yloxy)-butyl]-thiophene-2-carbonyl}-amino)-propionic acid, Isomer 1

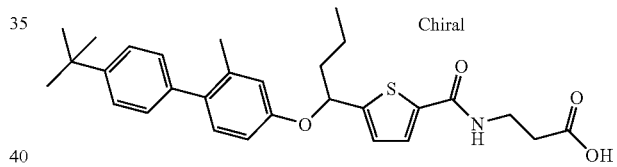

This compound is made by the general method as exemplified in Example 110 using 3-({5-[1-(4'-tert-butyl-2-methyl-biphenyl-4-yloxy)-butyl]-thiophene-2-carbonyl}-amino)-propionic acid methyl ester (isomer 1) as the starting material. MS (ES): 494.2 [M+H]+.

Example 116

3-({5-[1-(4'-tert-Butyl-2-methyl-biphenyl-4-yloxy)-butyl]-thiophene-2-carbonyl}-amino)-propionic acid, Isomer 2

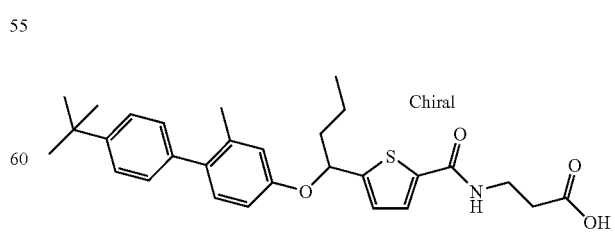

This compound is made by the general method as exemplified in Example 110 using 3-({5-[1-(4'-tert-butyl-2-methyl-biphenyl-4-yloxy)-butyl]-thiophene-2-carbonyl}- amino)-propionic acid methyl ester (isomer 2) as the starting material. MS (ES): 494.2 [M+H]⁺.

Example 117

3-({5-[1-(4'-tert-Butyl-2,6-dimethyl-biphenyl-4-yloxy)-ethyl]-thiophene-2-carbonyl}-amino)-propionic acid, Isomer 1

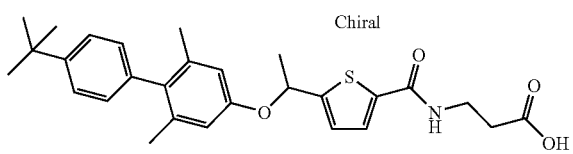

This compound is made by the general method as exemplified in Example 110 using 3-({5-[1-(4'-tert-butyl-2,6-dimethyl-biphenyl-4-yloxy)-ethyl]-thiophene-2-carbonyl}-amino)-propionic acid methyl ester (isomer 1) as the starting material. MS (ES): 480.2 [M+H]⁺.

Example 118

3-({5-[1-(4'-tert-Butyl-2,6-dimethyl-biphenyl-4-yloxy)-ethyl]-thiophene-2-carbonyl}-amino)-propionic acid, Isomer 2

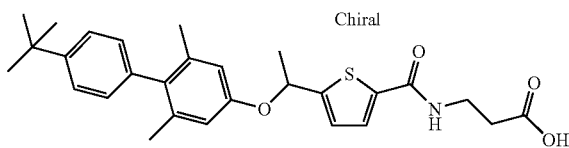

This compound is made by the general method as exemplified in Example 110 using 3-({5-[1-(4'-tert-butyl-2,6-dimethyl-biphenyl-4-yloxy)-ethyl]-thiophene-2-carbonyl}-amino)-propionic acid methyl ester (isomer 2) as the starting material. MS (ES): 480.2 [M+H]⁺.

Example 119

3-({5-[1-(4'-tert-Butyl-2,6-dimethyl-biphenyl-4-yloxy)-butyl]-thiophene-2-carbonyl}-amino)-propionic acid, Isomer 1

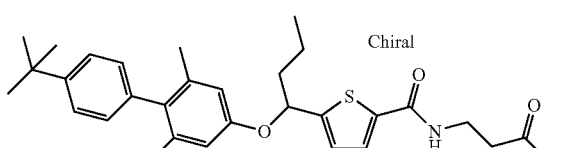

This compound is made by the general method as exemplified in Example 110 using 3-({5-[1-(4'-tert-butyl-2,6-dimethyl-biphenyl-4-yloxy)-butyl]-thiophene-2-carbonyl}-amino)-propionic acid methyl ester (isomer 1) as the starting material. MS (ES): 508.3 [M+H]⁺.

Example 120

3-({5-[1-(4'-tert-Butyl-2,6-dimethyl-biphenyl-4-yloxy)-butyl]-thiophene-2-carbonyl}-amino)-propionic acid, Isomer 2

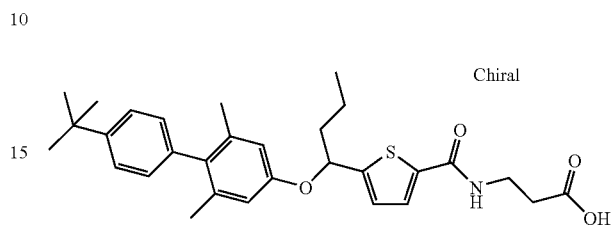

This compound is made by the general method as exemplified in Example 110 using 3-({5-[1-(4'-tert-butyl-2,6-dimethyl-biphenyl-4-yloxy)-butyl]-thiophene-2-carbonyl}-amino)-propionic acid methyl ester (isomer 2) as the starting material. MS (ES): 508.3 [M+H]⁺.

Example 121

3-({5-[1-(2,6-Dimethyl-4'-trifluoromethyl-biphenyl-4-yloxy)-pentyl]-thiophene-2-carbonyl}-amino)-propionic acid, Isomer 1

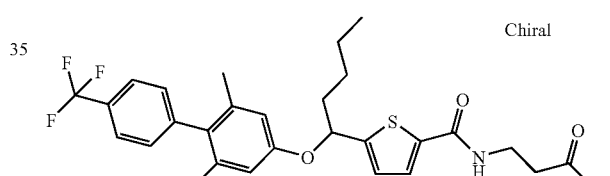

This compound is made by the general method as exemplified in Example 110 using 3-({5-[1-(2,6-dimethyl-4'-trifluoromethyl-biphenyl-4-yloxy)-pentyl]-thiophene-2-carbonyl}-amino)-propionic acid methyl ester (isomer 1) as the starting material. MS (ES): 534.2 [M+H]⁺.

Example 122

3-({5-[1-(2,6-Dimethyl-4'-trifluoromethyl-biphenyl-4-yloxy)-pentyl]-thiophene-2-carbonyl}-amino)-propionic acid, Isomer 2

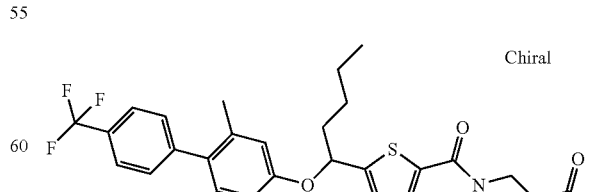

This compound is made by the general method as exemplified in Example 110 using 3-({5-[1-(2,6-dimethyl-4'-trifluoromethyl-biphenyl-4-yloxy)-pentyl]-thiophene-2-carbonyl}-amino)-propionic acid methyl ester (isomer 2) as the starting material. MS (ES): 534.0 [M+H]+.

Example 123

3-({5-[1-(2,6-Dimethyl-4'-trifluoromethyl-biphenyl-4-yloxy)-2-methyl-propyl]-thiophene-2-carbonyl}-amino)-2R-hydroxy-propionic acid, Isomer 1

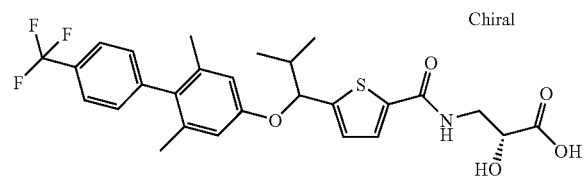

This compound is made by the general method as exemplified in Example 110 using 3-({5-[1-(2,6-dimethyl-4'-trifluoromethyl-biphenyl-4-yloxy)-2-methyl-propyl]-thiophene-2-carbonyl}-amino)-2R-hydroxy-propionic acid methyl ester (isomer 1) as the starting material. MS (ES): 536.0 [M+H]+.

Example 124

3-({5-[1-(2,6-Dimethyl-4'-trifluoromethyl-biphenyl-4-yloxy)-2-methyl-propyl]-thiophene-2-carbonyl}-amino)-2R-hydroxy-propionic acid, Isomer 2

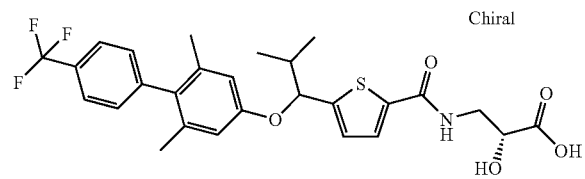

This compound is made by the general method as exemplified in Example 110 using 3-({5-[1-(2,6-dimethyl-4'-trifluoromethyl-biphenyl-4-yloxy)-2-methyl-propyl]-thiophene-2-carbonyl}-amino)-2R-hydroxy-propionic acid methyl ester (isomer 2) as the starting material. MS (ES): 536.0 [M+H]+.

Example 125

3-({5-[1-(2,6-Dimethyl-4'-trifluoromethyl-biphenyl-4-yloxy)-2-methyl-propyl]-thiophene-2-carbonyl}-amino)-2S-hydroxy-propionic acid, Isomer 1

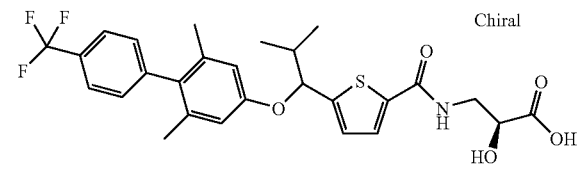

This compound is made by the general method as exemplified in Example 110 using 3-({5-[1-(2,6-dimethyl-4'-trifluoromethyl-biphenyl-4-yloxy)-2-methyl-propyl]-thiophene-2-carbonyl}-amino)-2R-hydroxy-propionic acid ethyl ester (isomer 1) as the starting material. MS (ES): 536.0 [M+H]+.

Example 126

3-({5-[1-(2,6-Dimethyl-4'-trifluoromethyl-biphenyl-4-yloxy)-2-methyl-propyl]-thiophene-2-carbonyl}-amino)-2S-hydroxy-propionic acid, Isomer 2

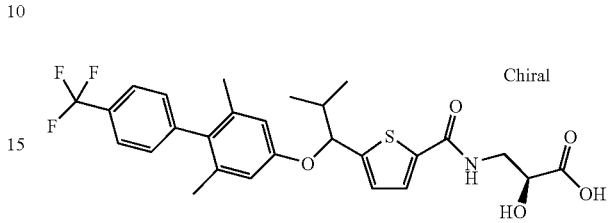

This compound is made by the general method as exemplified in Example 110 using 3-({5-[1-(2,6-dimethyl-4'-trifluoromethyl-biphenyl-4-yloxy)-2-methyl-propyl]-thiophene-2-carbonyl}-amino)-2R-hydroxy-propionic acid ethyl ester (isomer 2) as the starting material. MS (ES): 536.0 [M+H]+.

Example 127

3-({5-[1-(4'-tert-Butyl-2,6-dimethyl-biphenyl-4-yloxy)-2-methyl-propyl]-thiophene-2-carbonyl}-amino)-2R-hydroxy-propionic acid, Isomer 1

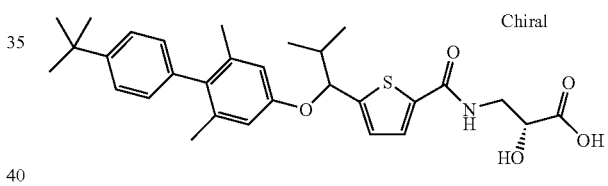

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2R-hydroxy-propionic acid methyl ester (isomer 1) as the starting material. MS (ES): 524.3 [M+H]+.

Example 128

3-({5-[1-(4'-tert-Butyl-2,6-dimethyl-biphenyl-4-yloxy)-2-methyl-propyl]-thiophene-2-carbonyl}-amino)-2R-hydroxy-propionic acid, Isomer 2

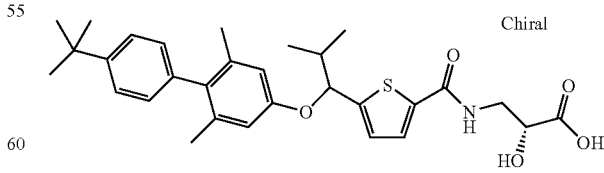

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2R-hydroxy-propionic acid methyl ester (isomer 2) as the starting material. MS (ES): 524.3 [M+H]+.

Example 129

3-({5-[1-(4'-tert-Butyl-2,6-dimethyl-biphenyl-4-yloxy)-2-methyl-propyl]-thiophene-2-carbonyl}-amino)-2S-hydroxy-propionic acid, Isomer 1

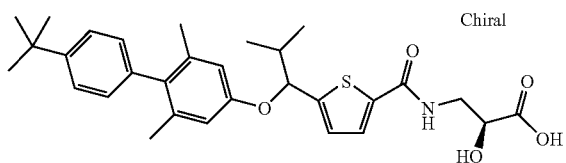

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2S-hydroxy-propionic acid ethyl ester (isomer 1) as the starting material. MS (ES): 524.3 [M+H]$^+$.

Example 130

3-({5-[1-(4'-tert-Butyl-2,6-dimethyl-biphenyl-4-yloxy)-2-methyl-propyl]-thiophene-2-carbonyl}-amino)-2S-hydroxy-propionic acid, Isomer 2

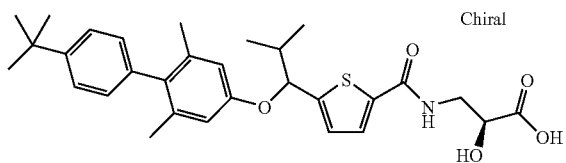

This compound is made by the general method as exemplified in Example 110 using 3-({5-[1-(4'-tert-butyl-2,6-dimethyl-biphenyl-4-yloxy)-2-methyl-propyl]-thiophene-2-carbonyl}-amino)-2S-hydroxy-propionic acid ethyl ester (isomer 2) as the starting material. MS (ES): 524.3 [M+H]$^+$.

Example 131

3-({5-[1-(4'-tert-Butyl-2,6-dimethyl-biphenyl-4-yloxymethyl)-1-ethyl-propyl]-thiophene-2-carbonyl}-amino)-propionic acid

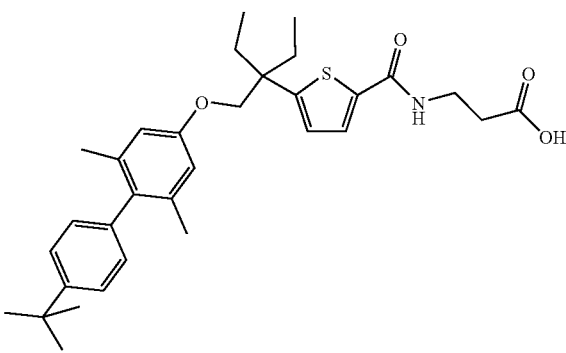

This compound is made by the general method as exemplified in Example 110 using 3-({5-[1-(4'-tert-butyl-2,6-dimethyl-biphenyl-4-yloxymethyl)-1-ethyl-propyl]-thiophene-2-carbonyl}-amino)-propionic acid methyl ester as the starting material. MS (ES): 536.2 [M+H]$^+$.

Example 132

(R,S)-3-({5-[1-(4'-tert-Butyl-2,6-dimethyl-biphenyl-4-yloxymethyl)-propyl]-thiophene-2-carbonyl}-amino)-propionic acid

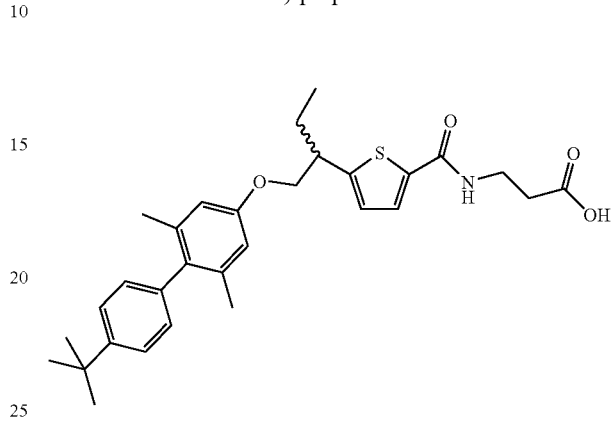

This compound is made by the general method as exemplified in Example 110 using 3-({5-[1-(4'-tert-butyl-2,6-dimethyl-biphenyl-4-yloxymethyl)-propyl]-thiophene-2-carbonyl}-amino)-propionic acid methyl ester as the starting material. MS (ES): 508.3 [M+H]$^+$.

Example 133

(R,S)-3-({5-[1-(2,6-Dimethyl-4'-trifluoromethyl-biphenyl-4-yloxymethyl)-propyl]-thiophene-2-carbonyl}-amino)-propionic acid

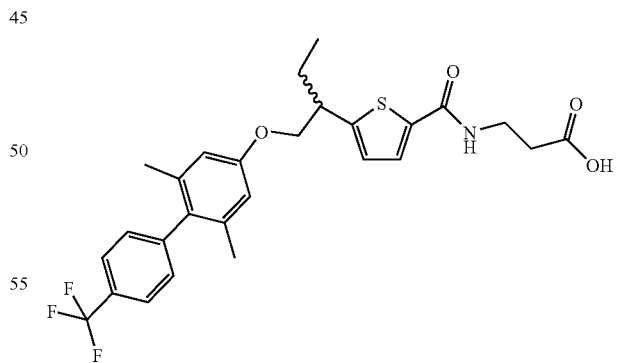

This compound is made by the general method as exemplified in Example 110 using 3-({5-[1-(2,6-dimethyl-4'-trifluoromethyl-biphenyl-4-yloxymethyl)-propyl]-thiophene-2- carbonyl}-amino)-propionic acid methyl ester as the starting material. MS (ES): 520.2 [M+H]⁺.

Example 134

3-({5-[1-(4'-tert-Butyl-2,6-dimethyl-biphenyl-4-yloxymethyl)-propyl]-thiophene-2-carbonyl}-amino)-propionic acid, Isomer 1

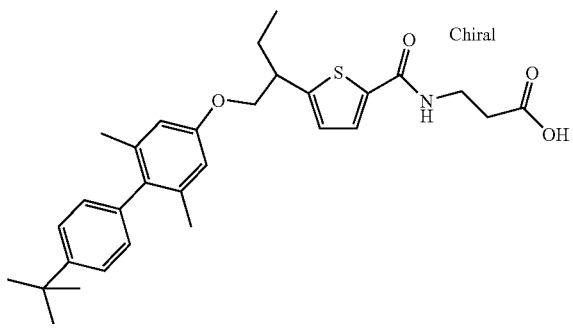

This compound is made by the general method as exemplified in Example 110 using 3-({5-[1-(4'-tert-butyl-2,6-dimethyl-biphenyl-4-yloxymethyl)-propyl]-thiophene-2-carbonyl}-amino)-propionic acid methyl ester (isomer 1) as the starting material. MS (ES): 508.3 [M+H]⁺.

Example 135

3-({5-[1-(4'-tert-Butyl-2,6-dimethyl-biphenyl-4-yloxymethyl)-propyl]-thiophene-2-carbonyl}-amino)-propionic acid, Isomer 2

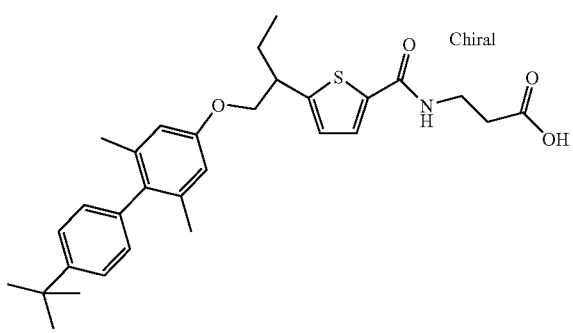

This compound is made by the general method as exemplified in Example 110 using 3-({5-[1-(4'-tert-butyl-2,6-dimethyl-biphenyl-4-yloxymethyl)-propyl]-thiophene-2-carbonyl}-amino)-propionic acid methyl ester (isomer 2) as the starting material. MS (ES): 508.3 [M+H]⁺.

Example 136

3-({5-[1-(2,6-Dimethyl-4'-trifluoromethyl-biphenyl-4-yloxymethyl)-propyl]-thiophene-2-carbonyl}-amino)-propionic acid, Isomer 1

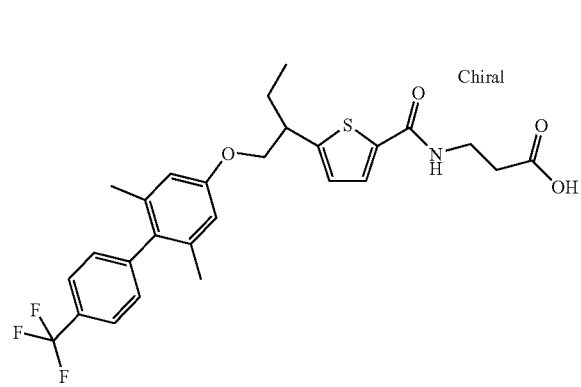

This compound is made by the general method as exemplified in Example 110 using 3-({5-[1-(2,6-dimethyl-4'-trifluoromethyl-biphenyl-4-yloxymethyl)-propyl]-thiophene-2-carbonyl}-amino)-propionic acid methyl ester (isomer 1) as the starting material. MS (ES): 520.0 [M+H]⁺.

Example 137

3-({5-[1-(2,6-Dimethyl-4'-trifluoromethyl-biphenyl-4-yloxymethyl)-propyl]-thiophene-2-carbonyl}-amino)-propionic acid, Isomer 2

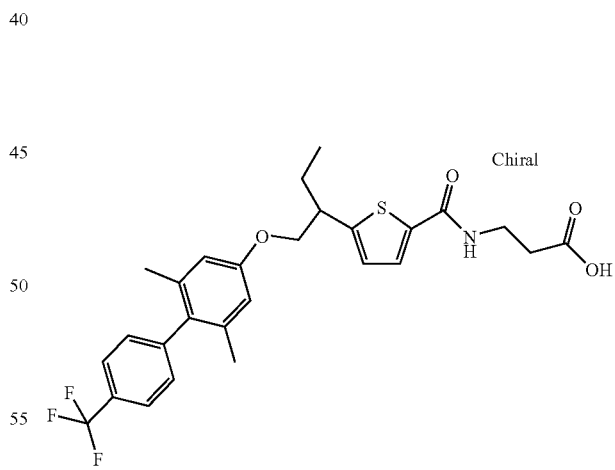

This compound is made by the general method as exemplified in Example 110 using 3-({5-[1-(2,6-dimethyl-4'-trifluoromethyl-biphenyl-4-yloxymethyl)-propyl]-thiophene-2- carbonyl}-amino)-propionic acid methyl ester (isomer 2) as the starting material. MS (ES): 520.0 [M+H]⁺.

Example 138

(R,S)-3-({5-[1-(4'-tert-Butyl-2,6-dimethyl-biphenyl-4-yloxy)-propyl]-4-chloro-thiophene-2-carbonyl}-amino)-propionic acid

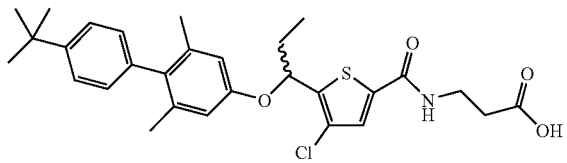

This compound is made by the general method as exemplified in Example 110 using 3-({5-[1-(4'-tert-butyl-2,6-dimethyl-biphenyl-4-yloxy)-propyl]-4-chloro-thiophene-2-carbonyl}-amino)-propionic acid methyl ester as the starting material. MS (ES): 528.0 [M+H]⁺.

Example 139

(R,S)-3-({5-[1-(4'-tert-Butyl-2,6-dimethyl-biphenyl-4-ylsulfanyl)-ethyl]-thiophene-2-carbonyl}-amino)-propionic acid

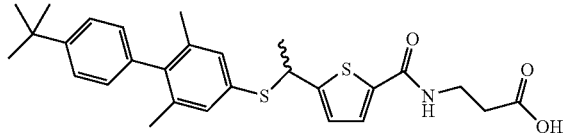

This compound is made by the general method as exemplified in Example 110 using 3-({5-[1-(4'-tert-butyl-2,6-dimethyl-biphenyl-4-ylsulfanyl)-ethyl]-thiophene-2-carbonyl}-amino)-propionic acid methyl ester as the starting material. MS (ES): 496.3 [M+H]⁺.

Example 140

(R,S)-3-({5-[1-(4'-tert-Butyl-2,6-dimethyl-biphenyl-4-ylsulfanyl)-ethyl]-thiophene-2-carbonyl}-amino)-propionic acid

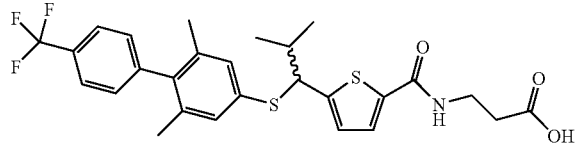

This compound is made by the general method as exemplified in Example 110 using 3-({5-[1-(4'-tert-butyl-2,6-dim-ethyl-biphenyl-4-ylsulfanyl)-ethyl]-thiophene-2-carbonyl}-amino)-propionic acid methyl ester as the starting material. MS (ES): 536.0 [M+H]⁺.

Example 141

(R,S)-3-({5-[1-(2,6-Dimethyl-4'-trifluoromethyl-biphenyl-4-ylsulfanyl)-2,2-dimethyl-propyl]-thiophene-2-carbonyl}-amino)-propionic acid This compound is made by the general method as exemplified in Example 110 using 3-({5-[1-(2,6-dimethyl-4'-trifluoromethyl-biphenyl-4-ylsulfanyl)-2,2-dimethyl-propyl]-thiophene-2-carbonyl}-amino)-propionic acid methyl ester as the starting material. MS (ES): 550.0 [M+H]⁺.

Example 142

(R,S)-3-({5-[1-(2,6-Dimethyl-4'-trifluoromethyl-biphenyl-4-ylsulfanyl)-3-methyl-butyl]-thiophene-2-carbonyl}-amino)-propionic acid This compound is made by the general method as exemplified in Example 110 using 3-({5-[1-(2,6-dimethyl-4'-trifluoromethyl-biphenyl-4-ylsulfanyl)-3-methyl-butyl]-thiophene-2-carbonyl}-amino)-propionic acid methyl ester as the starting material. MS (ES): 550.0 [M+H]⁺.

Example 143

3-({5-[1-(4'-tert-Butyl-2,6-dimethyl-biphenyl-4-ylsulfanyl)-ethyl]-thiophene-2-carbonyl}-amino)-propionic acid, Isomer 1

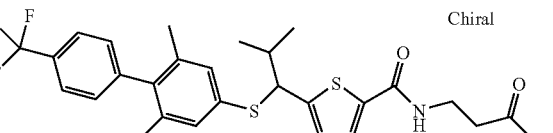

This compound is made by the general method as exemplified in Example 110 using 3-({5-[1-(4'-tert-butyl-2,6-dimethyl-biphenyl-4-ylsulfanyl)-ethyl]-thiophene-2-carbonyl}- amino)-propionic acid methyl ester (isomer 1) as the starting material. MS (ES): 536.0 [M+H]⁺.

Example 144

3-({5-[1-(4'-tert-Butyl-2,6-dimethyl-biphenyl-4-yl-sulfanyl)-ethyl]-thiophene-2-carbonyl}-amino)-propionic acid, Isomer 2

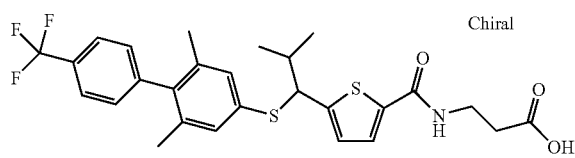

This compound is made by the general method as exemplified in Example 110 using 3-({5-[1-(4'-tert-butyl-2,6-dimethyl-biphenyl-4-ylsulfanyl)-ethyl]-thiophene-2-carbonyl}-amino)-propionic acid methyl ester (isomer 2) as the starting material. MS (ES): 536.0 [M+H]⁺.

Example 145

3-({5-[1-(2,6-Dimethyl-4'-trifluoromethyl-biphenyl-4-ylsulfanyl)-2,2-dimethyl-propyl]-thiophene-2-carbonyl}-amino)-propionic acid, Isomer 1

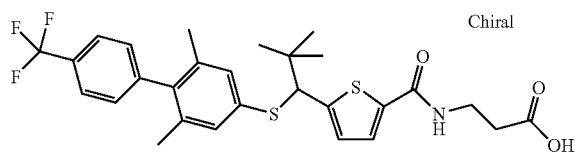

This compound is made by the general method as exemplified in Example 110 using 3-({5-[1-(2,6-dimethyl-4'-trifluoromethyl-biphenyl-4-ylsulfanyl)-2,2-dimethyl-propyl]-thiophene-2-carbonyl}-amino)-propionic acid methyl ester (isomer 1) as the starting material. MS (ES): 550.0 [M+H]⁺.

Example 146

3-({5-[1-(2,6-Dimethyl-4'-trifluoromethyl-biphenyl-4-ylsulfanyl)-2,2-dimethyl-propyl]-thiophene-2-carbonyl}-amino)-propionic acid, Isomer 2

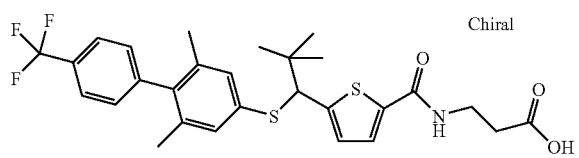

This compound is made by the general method as exemplified in Example 110 using 3-({5-[1-(2,6-dimethyl-4'-trifluoromethyl-biphenyl-4-ylsulfanyl)-2,2-dimethyl-propyl]- thiophene-2-carbonyl}-amino)-propionic acid methyl ester (isomer 2) as the starting material. MS (ES): 550.0 [M+H]⁺.

Example 147

(R,S)-3-({5-[1-(2,6-Dimethyl-4'-trifluoromethyl-biphenyl-4-ylsulfanyl)-3,3-dimethyl-butyl]thiophene-2-carbonyl}-amino)-propionic acid

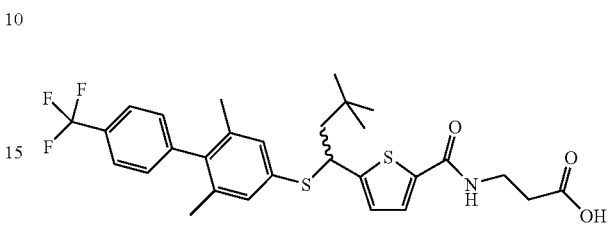

This compound is made by the general method as exemplified in Example 110 using 3-({5-[1-(2,6-dimethyl-4'-trifluoromethyl-biphenyl-4-ylsulfanyl)-3,3-dimethyl-butyl]-thiophene-2-carbonyl}-amino)-propionic acid methyl ester as the starting material. MS (ES): 564.0 [M+H]⁺.

Example 148

(R,S)-3-({5-[1-(2,6-Dimethyl-4'-trifluoromethyl-biphenyl-4-ylsulfanyl)-pentyl]-thiophene-2-carbonyl}-amino)-propionic acid

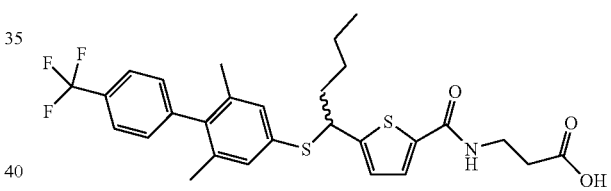

This compound is made by the general method as exemplified in Example 110 using 3-({5-[1-(2,6-dimethyl-4'-trifluoromethyl-biphenyl-4-ylsulfanyl)-pentyl]-thiophene-2-carbonyl}-amino)-propionic acid methyl ester as the starting material. MS (ES): 550.0 [M+H]⁺.

Example 149

(R,S)-3-({5-[1-(2,6-Dimethyl-4'-trifluoromethyl-biphenyl-4-ylsulfanyl)-butyl]-thiophene-2-carbonyl}-amino)-propionic acid

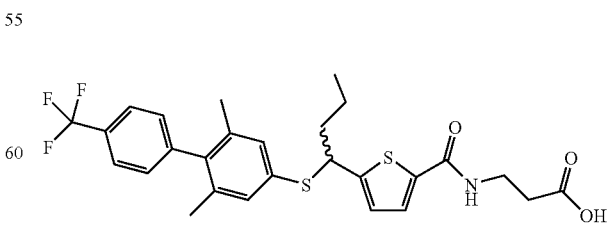

This compound is made by the general method as exemplified in Example 110 using 3-({5-[1-(2,6-dimethyl-4'-trifluoromethyl-biphenyl-4-ylsulfanyl)-butyl]-thiophene-2-carbonyl}-amino)-propionic acid methyl ester as the starting material. MS (ES): 536.0 [M+H]+.

Example 150

3-({5-[1-(2,6-Dimethyl-4'-trifluoromethyl-biphenyl-4-ylsulfanyl)-butyl]-thiophene-2-carbonyl}-amino)-propionic acid, Isomer 1

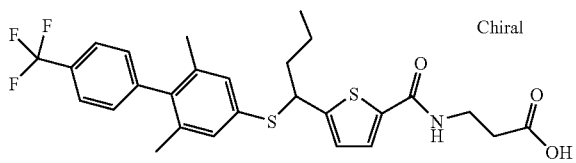

This compound is made by the general method as exemplified in Example 110 using 3-({5-[1-(2,6-dimethyl-4'-trifluoromethyl-biphenyl-4-ylsulfanyl)-butyl]-thiophene-2-carbonyl}-amino)-propionic acid methyl ester (isomer 1) as the starting material. MS (ES): 536.0 [M+H]+.

Example 151

3-({5-[1-(2,6-Dimethyl-4'-trifluoromethyl-biphenyl-4-ylsulfanyl)-butyl]-thiophene-2-carbonyl}-amino)-propionic acid, Isomer 2

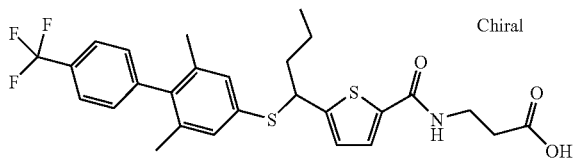

This compound is made by the general method as exemplified in Example 110 using 3-({5-[1-(2,6-dimethyl-4'-trifluoromethyl-biphenyl-4-ylsulfanyl)-butyl]-thiophene-2-carbonyl}-amino)-propionic acid methyl ester (isomer 2) as the starting material. MS (ES): 535.8 [M+H]+.

Example 152

3-({5-[1-(2,6-Dimethyl-4'-trifluoromethyl-biphenyl-4-yloxy)-3-methyl-butyl]-thiophene-2-carbonyl}-amino)-propionic acid, Isomer 1

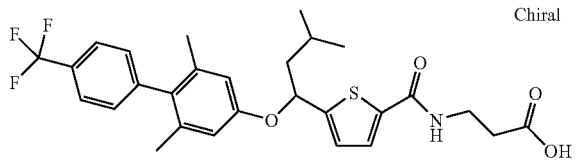

Step A 3-({5-[1-(2,6-Dimethyl-4'-trifluoromethyl-biphenyl-4-yloxy)-3-methyl-butyl]-thiophene-2-carbonyl}-amino)-propionic acid methyl ester (Isomer 1)

(R,S)-3-({5-[1-(2,6-Dimethyl-4'-trifluoromethyl-biphenyl-4-yloxy)-3-methyl-butyl]-thiophene-2-carbonyl}-amino)-propionic acid methyl ester (190 mg) is separated by chiral HPLC (column: Chiralpak AD 4.6×150 mm; eluent: 100% 3A ethanol; flow rate: 0.6 mL/min; UV absorbance wavelength: 280 nm) to provide 3-({5-[3-methyl-1-(4'-trifluoromethyl-biphenyl-4-yloxy)-butyl]-thiophene-2-carbonyl}-amino)-propionic acid methyl ester (Isomer 1) (91 mg).

Step B 3-({5-[1-(2,6-Dimethyl-4'-trifluoromethyl-biphenyl-4-yloxy)-3-methyl-butyl]-thiophene-2-carbonyl}-amino)-propionic acid (Isomer 1)

A solution of 3-({5-[1-(2,6-dimethyl-4'-trifluoromethyl-biphenyl-4-yloxy)-3-methyl-butyl]-thiophene-2-carbonyl}-amino)-propionic acid methyl ester (Isomer 1) (91 mg, 0.166 mmol) in methanol (1.66 mL) is treated with 5N NaOH (0.166 mL) and shaken at rt for 2 h. The reaction is neutralized with 1N HCl (0.170 mL), and extracted into ethyl acetate (2×). The combined organic layers are dried and concentrated, giving the title compound (142 mg). MS (ES): 534.4 [M+H]+.

The following compounds are made in a substantially similar manner.

Example 153

3-({5-[1-(2,6-Dimethyl-4'-trifluoromethyl-biphenyl-4-yloxy)-3-methyl-butyl]-thiophene-2-carbonyl}-amino)-propionic acid, Isomer 2

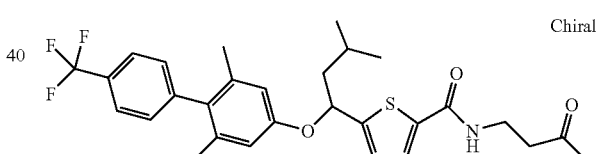

MS (ES): 534.4 [M+H]+.

Example 154

3-({5-[1-(4'-tert-Butyl-2,6-dimethyl-biphenyl-4-yloxy)-2,2-dimethyl-propyl]-thiophene-2-carbonyl}-amino)-propionic acid, Isomer 1

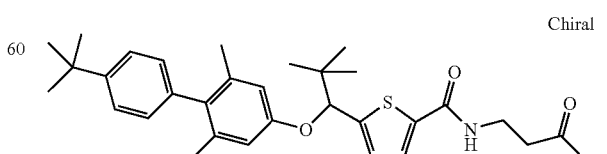

MS (ES): 522.4 [M+H]+.

Example 155

3-({5-[1-(4'-tert-Butyl-2,6-dimethyl-biphenyl-4-yloxy)-2,2-dimethyl-propyl]-thiophene-2-carbonyl}-amino)-propionic acid, Isomer 2

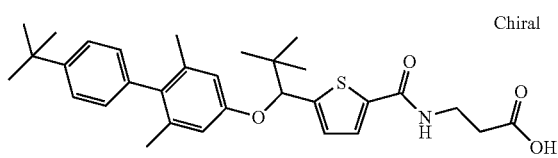

MS (ES): 522.5 [M+H]$^+$.

Example 156

3-({5-[1-(4'-tert-Butyl-2,6-dimethyl-biphenyl-4-yloxy)-propyl]-thiophene-2-carbonyl}-amino)-propionic acid, Isomer 2

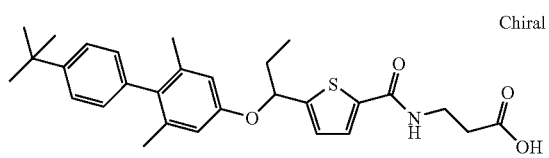

Step A

3-({5-[1-(4'-tert-Butyl-2,6-dimethyl-biphenyl-4-yloxy)-propyl]-thiophene-2-carbonyl}-amino)-propionic acid methyl ester, Isomer 2

To a solution of 3-({5-[1-(4-iodo-3,5-dimethyl-phenoxy)-propyl]-thiophene-2-carbonyl}-amino)-propionic acid methyl ester (Isomer 2) (203.5 mg, 0.406 mmol) in THF (4.1 ml) is added (4-trifluoromethyl)phenylboronic acid (87 mg, 0.487 mmol), potassium fluoride (59 mg, 1.22 mmol), palladium(II) acetate (18 mg, 0.081 mmol), and (oxydi-2,1-phenylene)bis-(diphenylphosphine) (86 mg, 0.16 mmol). The reaction mixture is heated to reflux overnight. After cooling to rt, the reaction mixture is partitioned between ethyl acetate and water. The aqueous layer is back-extracted with ethyl acetate, the combined organic layers are dried and concentrated, then loaded onto C$_{18}$ and eluted using acetonitrile with a water gradient from 15% to 100% giving 3-{5-[1-(4'-tert-butyl-2,6-dimethyl-biphenyl-4-yloxy)-propyl]-thiophene-2-carbonyl}-amino)-propionic acid methyl ester (Isomer 1) (93 mg).

Step B

3-({5-[1-(4'-tert-Butyl-2,6-dimethyl-biphenyl-4-yloxy)-propyl]-thiophene-2-carbonyl}-amino)-propionic acid, Isomer 2

A solution of 3-({5-[1-(4'-tert-butyl-2,6-dimethyl-biphenyl-4-yloxy)-propyl]-thiophene-2-carbonyl}-amino)-propionic acid methyl ester (Isomer 2) (90.2 mg, 0.178 mmol) in methanol (1.8 mL) is treated with 5N NaOH (0.178 mL) and shaken at rt overnight. The reaction is neutralized with 1N HCl (0.182 mL), and extracted into ethyl acetate (2×). The combined organic layers are dried and concentrated, giving the title compound (70.5 mg). MS (ES): 494.3 [M+H]$^+$.

The following compounds are made in a substantially similar manner.

Example 157

3-({5-[1-(2,6-Dimethyl-4'-trifluoromethyl-biphenyl-4-yloxy)-butyl]-thiophene-2-carbonyl}-amino)-propionic acid, Isomer 2

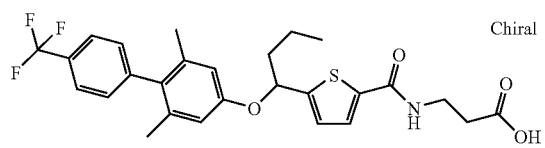

MS (ES): 520.4 [M+H]$^+$.

Example 158

3-({5-[1-(2,6-Dimethyl-4'-trifluoromethyl-biphenyl-4-yloxy)-butyl]-thiophene-2-carbonyl}-amino)-propionic acid, Isomer 1

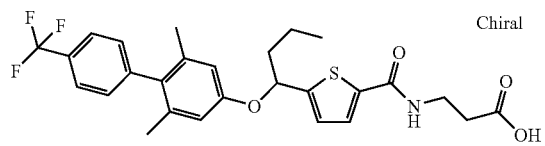

MS (ES): 520.4 [M+H]$^+$.

Example 159

3-({5-[1-(4'-Isopropyl-2,6-dimethyl-biphenyl-4-yloxy)-butyl]-thiophene-2-carbonyl}-amino)-propionic acid, Isomer 2

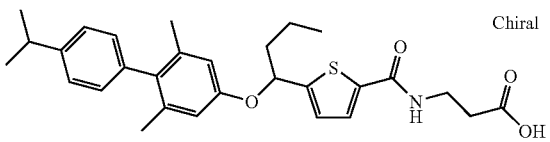

MS (ES): 494.4 [M+H]$^+$.

Example 160

3-({5-[1-(4'-Isopropyl-2,6-dimethyl-biphenyl-4-yloxy)-butyl]-thiophene-2-carbonyl}-amino)-propionic acid, Isomer 1

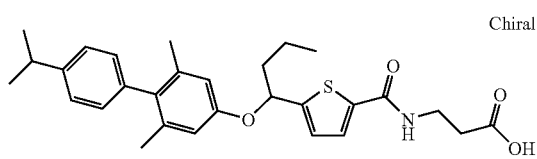

MS (ES): 494.4 [M+H]⁺.

Example 161

3-({5-[1-(2,6-Dimethyl-4'-trifluoromethoxy-biphenyl-4-yloxy)-butyl]-thiophene-2-carbonyl}-amino)-propionic acid, Isomer 2

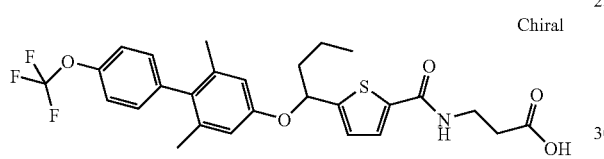

MS (ES): 536.4 [M+H]⁺.

Example 162

3-({5-[1-(2,6-Dimethyl-4'-trifluoromethoxy-biphenyl-4-yloxy)-butyl]-thiophene-2-carbonyl}-amino)-propionic acid, Isomer 1

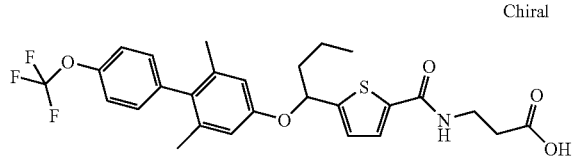

MS (ES): 536.4 [M+H]⁺.

Example 163

3-({5-[1-(4'-tert-Butyl-2,6-dimethyl-biphenyl-4-yl-sulfanyl)-2,2-dimethyl-propyl]-thiophene-2-carbonyl}-amino)-propionic acid, Isomer 1

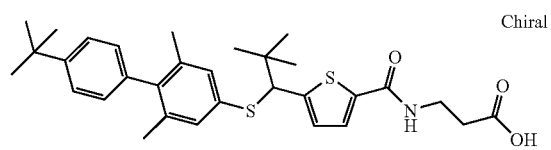

MS (ES): 538.2 [M+H]⁺.

Example 164

3-({5-[1-(4'-tert-Butyl-2,6-dimethyl-biphenyl-4-yl-sulfanyl)-2,2-dimethyl-propyl]-thiophene-2-carbonyl}-amino)-propionic acid, Isomer 2

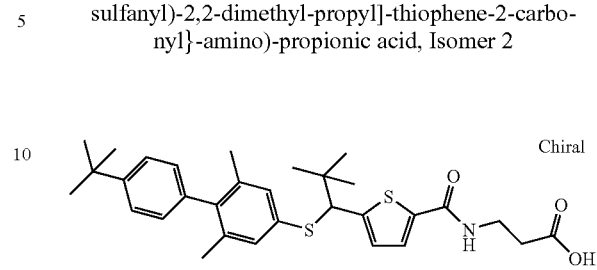

MS (ES): 538.2 [M+H]⁺.

Example 165

3-({5-[1-(4'-tert-Butyl-2,6-dimethyl-biphenyl-4-yl-sulfanyl)-3,3-dimethyl-butyl]-thiophene-2-carbonyl}-amino)-propionic acid, Isomer 2

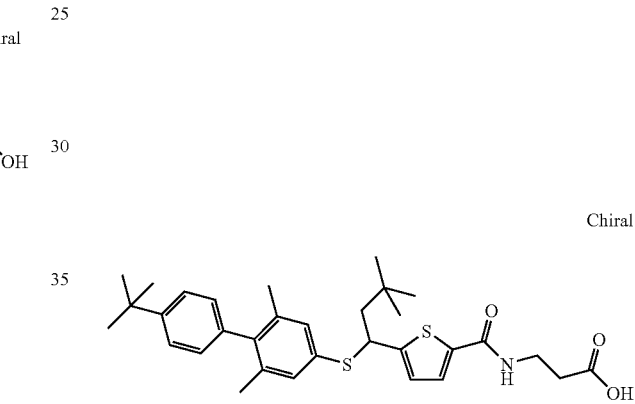

MS (ES): 552.2 [M+H]⁺.

Example 166

3-({5-[1-(4'-tert-Butyl-2,6-dimethyl-biphenyl-4-yl-sulfanyl)-3-methyl-butyl]-thiophene-2-carbonyl}-amino)-propionic acid, Isomer 1

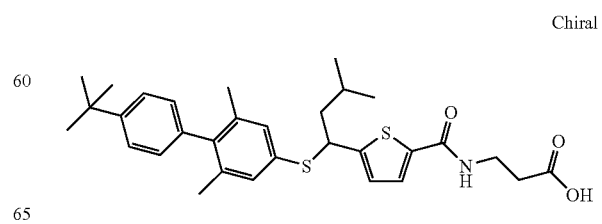

MS (ES): 538.3 [M+H]⁺.

Example 167

3-({5-[1-(4'-tert-Butyl-2,6-dimethyl-biphenyl-4-yl-sulfanyl)-3-methyl-butyl]-thiophene-2-carbonyl}-amino)-propionic acid, Isomer 2

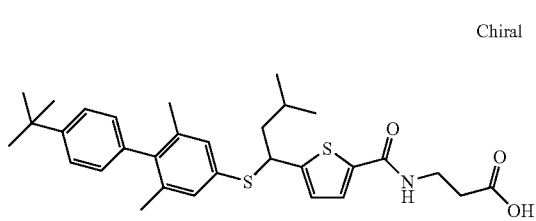

MS (ES): 538.3 [M+H]$^+$.

Example 168

3-({5-[1-(4'-Isopropyl-2,6-dimethyl-biphenyl-4-yl-sulfanyl)-2-methyl-propyl]-thiophene-2-carbonyl}-amino)-propionic acid, Isomer 1

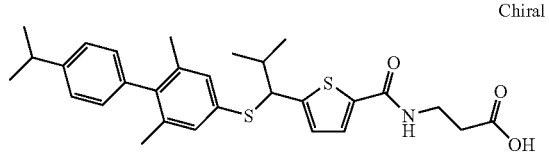

MS (ES): 510.3 [M+H]$^+$.

Example 169

3-({5-[1-(4'-Isopropyl-2,6-dimethyl-biphenyl-4-yl-sulfanyl)-2-methyl-propyl]-thiophene-2-carbonyl}-amino)-propionic acid, Isomer 2

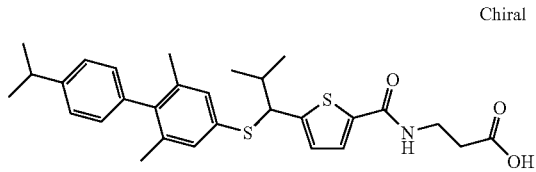

MS (ES): 510.3 [M+H]$^+$.

Example 170

3-({5-[1-(4'-tert-Butyl-2,6-dimethyl-biphenyl-4-yl-sulfanyl)-propyl]-thiophene-2-carbonyl}-amino)-propionic acid, Isomer 1

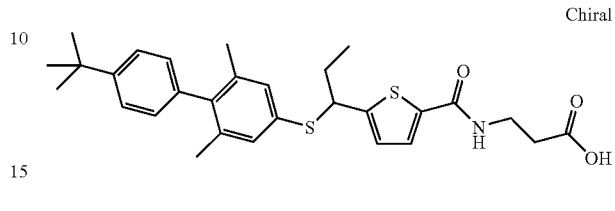

MS (ES): 510.3 [M+H]$^+$.

Example 171

3-({5-[1-(4'-tert-Butyl-2,6-dimethyl-biphenyl-4-yl-sulfanyl)-propyl]-thiophene-2-carbonyl}-amino)-propionic acid, Isomer 2

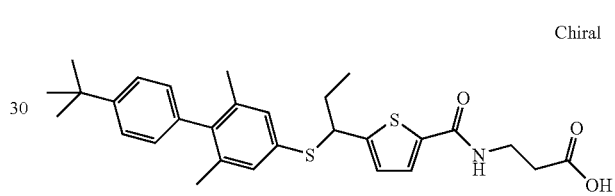

MS (ES): 510.3 [M+H]$^+$.

Example 172

(R,S)-3-({5-[1-(4'-tert-Butyl-2,6-dimethyl-biphenyl-4-ylsulfanyl)-2-methyl-propyl]-thiophene-2-carbonyl}-amino)-propionic acid

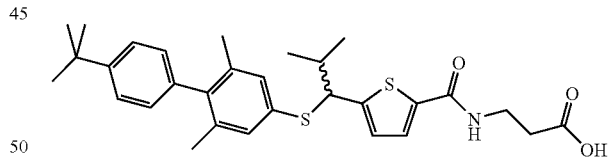

Step A (R,S)-3-({5-[1-(4'-tert-Butyl-2,6-dimethyl-biphenyl-4-ylsulfanyl)-2-methyl-propyl]-thiophene-2-carbonyl}-amino)-propionic acid methyl ester A solution of (R,S)-3-{[5-(1-hydroxy-2-methyl-propyl)-thiophene-2-carbonyl]-amino}-propionic acid methyl ester (355.8 mg, 1.25 mmol) and 4-bromo-3,5-dimethyl-benzenethiol (509 mg, 1.88 mmol) in 1,2-dichloroethane (5 mL) is treated with zinc iodide (399 mg, 1.25 mmol) and stirred overnight at it. The reaction mixture is then partitioned between water and dichloromethane. The aqueous layer is back-extracted with dichloromethane, and the combined organic layers are dried, filtered, and concentrated. The resulting residue is applied to silica gel and eluted using hexanes with an ethyl acetate gradient from 0% to 70% to give (R,S)-3-({5-[1-(4-bromo-3,5-dimethyl-phenylsulfanyl)-2-methyl-propyl]-thiophene-2-carbonyl}-amino)-propionic acid methyl ester (336 mg).

Step B (R,S)-3-({5-[1-(4'-tert-Butyl-2,6-dimethyl-biphenyl-4-ylsulfanyl)-2-methyl-propyl]-thiophene-2-carbonyl}-amino)-propionic acid methyl ester To a solution of (R,S)-3-({5-[1-(4-bromo-3,5-dimethyl-phenylsulfanyl)-2-methyl-propyl]-thiophene-2-carbonyl}-amino)-propionic acid methyl ester (244 mg, 0.504 mmol) in THF (5 ml) is added (4-tert-butyl)phenylboronic acid (269 mg, 1.512 mmol), potassium fluoride (73 mg, 1.512 mmol), palladium(II) acetate (23 mg, 0.101 mmol), and (oxydi-2,1-phenylene)bis-(diphenylphosphine) (109 mg, 0.202 mmol). The reaction mixture is heated to reflux overnight. After cooling to rt the reaction mixture is partitioned between ethyl acetate and water. The aqueous layer is back-extracted with ethyl acetate, the combined organic layers are dried and concentrated, then loaded onto $C_{18}$ and eluted using acetonitrile with a water gradient from 15% to 100% giving (R,S)-3-({5-[1-(4'-tert-butyl-2,6-dimethyl-biphenyl-4-ylsulfanyl)-2-methyl-propyl]-thiophene-2-carbonyl}-amino)-propionic acid methyl ester (83 mg).

Step C (R,S)-3-({5-[1-(4'-tert-Butyl-2,6-dimethyl-biphenyl-4-ylsulfanyl)-2-methyl-propyl]-thiophene-2-carbonyl}-amino)-propionic acid A solution of (R,S)-3-({5-[1-(4'-tert-butyl-2,6-dimethyl-biphenyl-4-ylsulfanyl)-2-methyl-propyl]-thiophene-2-carbonyl}-amino)-propionic acid methyl ester (77.7 mg, 0.144 mmol) in methanol (1.5 mL) is treated with 5N NaOH (0.144 mL) and shaken at rt overnight. The reaction is neutralized with 1N HCl (0.148 mL), and extracted into ethyl acetate (2×). The combined organic layers are dried and concentrated, giving the title compound (74.5 mg). MS (ES): 524.3 [M+H]⁺.

The following compound is made in a substantially similar manner.

Example 173

(R,S)-3-({5-[1-(4'-tert-Butyl-2,6-dimethyl-biphenyl-4-ylsulfanyl)-2,2-dimethyl-propyl]-thiophene-2-carbonyl}-amino)-propionic acid

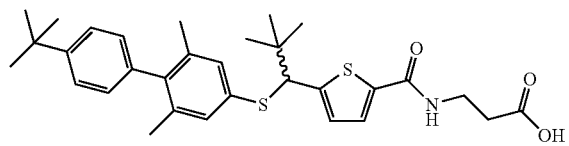

MS (ES): 538.3 [M+H]⁺.

Example 174

(R,S)-3-({5-[1-(4'-tert-Butyl-2,6-dimethyl-biphenyl-4-ylsulfanyl)-3,3-dimethyl-butyl]-thiophene-2-carbonyl}-amino)-propionic acid

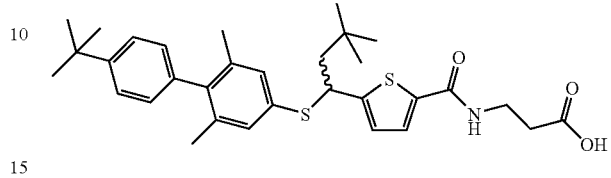

Step A (R,S)-5-[1-(4-Bromo-3,5-dimethyl-phenylsulfanyl)-3,3-dimethyl-butyl]-thiophene-2-carboxylic acid ethyl ester A solution of (R,S)-5-(1-hydroxy-3,3-dimethyl-butyl)-thiophene-2-carboxylic acid ethyl ester (766.7 mg, 2.99 mmol) and 4-bromo-3,5-dimethyl-benzenethiol (1.2 mg, 4.49 mmol) in 1,2-dichloroethane (12 mL) is treated with zinc iodide (951 mg, 2.99 mmol) and stirred overnight at it The reaction mixture is then partitioned between water and dichloromethane. The aqueous layer is back-extracted with dichloromethane, and the combined organic layers are dried, filtered, and concentrated. The resulting residue is applied to $C_{18}$ and eluted using acetonitrile with a water gradient from 15% to 100% giving to give (R,S)-5-[1-(4-bromo-3,5-dimethyl-phenylsulfanyl)-3,3-dimethyl-butyl]-thiophene-2-carboxylic acid ethyl ester (1.12 g).

Step B (R,S)-5-[1-(4-Bromo-3,5-dimethyl-phenylsulfanyl)-3,3-dimethyl-butyl]-thiophene-2-carboxylic acid To a mixture of (R,S)-5-[1-(4-bromo-3,5-dimethyl-phenylsulfanyl)-3,3-dimethyl-butyl]-thiophene-2-carboxylic acid ethyl ester (1.101 g, 2.42 mmol) in ethanol (24.2 mL) is added 5N NaOH (2.42 mL) at room temperature, and stirred overnight. The reaction mixture is acidified by 1N HCl (2.46 mL), extracted into ethyl acetate, dried and concentrated, then dried under vacuum, giving (R,S)-5-[1-(4-bromo-3,5-dimethyl-phenylsulfanyl)-3,3-dimethyl-butyl]-thiophene-2-carboxylic acid (896.2 mg).

Step C (R,S)-3-({5-[1-(4-Bromo-3,5-dimethyl-phenylsulfanyl)-3,3-dimethyl-butyl]-thiophene-2-carbonyl}-amino)-propionic acid methyl ester To a mixture of (R,S)-5-[1-(4-bromo-3,5-dimethyl-phenylsulfanyl)-3,3-dimethyl-butyl]-thiophene-2-carboxylic acid (886.5 mg, 2.07 mmol) in DMF (21 mL) is added 3-amino-propionic acid methyl ester hydrochloride(346 mg, 2.48 mmol), 1-hydroxybenzotriazole hydrate (335 mg, 2.48 mmol), and diisopropylethylamine (0.724 mL, 4.14 mmol) at room temperature, and stirred 10 min. The mixture is then treated with N-(3-dimethylaminopropyl)-N'-ethylcarbodiimide hydrochloride (794 mg, 4.14 mmol), and stirred overnight. The reaction mixture is treated with 0.1N HCl and extracted into ethyl acetate twice. The combined organic layers are washed with brine, dried and concentrated, and dried under vacuum to give (R,S)-3-({5-[1-(4-bromo-3,5-dimethyl-phenylsulfanyl)-3,3-dimethyl-butyl]-thiophene-2-carbonyl}-amino)-propionic acid methyl ester (885 mg).

Step D (R,S)-3-({5-[1-(4'-tert-Butyl-2,6-dimethyl-biphenyl-4-ylsulfanyl)-3,3-dimethyl-butyl]-thiophene-2-carbonyl}-amino)-propionic acid methyl ester To a solution of (R,S)-3-({5-[1-(4-bromo-3,5-dimethyl-phenylsulfanyl)-3,3-dimethyl-butyl]-thiophene-2-carbonyl}-amino)-propionic acid methyl ester (749.1 mg, 1.46 mmol) in THF (14.6 ml) is added (4-tert-butyl)phenylboronic acid (780 mg, 4.38 mmol), potassium fluoride (211 mg, 4.38 mmol), palladium(II) acetate (131 mg, 0.584 mmol), and (oxydi-2,1-phenylene)bis-(diphenylphosphine) (629 mg, 0.584 mmol). The reaction mixture is heated to reflux overnight. After cooling to rt, the reaction mixture is partitioned between ethyl acetate and water. The aqueous layer is back-extracted with ethyl acetate, the combined organic layers are dried and concentrated, then loaded onto $C_{-18}$ and eluted using acetonitrile with a water gradient from 15% to 100% giving (R,S)-3-({5-[1-(4'-tert-butyl-2,6-dimethyl-biphenyl-4-ylsulfanyl)-3,3-dimethyl-butyl]-thiophene-2-carbonyl}-amino)-propionic acid methyl ester (274.7 mg).

Step E (R,S)-3-({5-[1-(4'-tert-Butyl-2,6-dimethyl-biphenyl-4-ylsulfanyl)-3,3-dimethyl-butyl]-thiophene-2-carbonyl}-amino)-propionic acid To a mixture of (R,S)-3-({5-[1-(4'-tert-butyl-2,6-dimethyl-biphenyl-4-ylsulfanyl)-3,3-dimethyl-butyl]-thiophene-2-carbonyl}-amino)-propionic acid methyl ester (31 mg, 0.055 mmol) in methanol (0.548 mL) is added 5N NaOH (0.055 mL) at room temperature, and stirred overnight. The reaction mixture is acidified by 1N HCl (0.056 mL), extracted into ethyl acetate, dried and concentrated, then dried under vacuum, giving the title compound (28.8 mg).

MS (ES): 552.2 [M+H]$^+$.

The following compounds are made in a substantially similar manner.

Example 175

(R,S)-3-({5-[1-(4'-tert-Butyl-2,6-dimethyl-biphenyl-4-ylsulfanyl)-3-methyl-butyl]-thiophene-2-carbonyl}-amino)-propionic acid

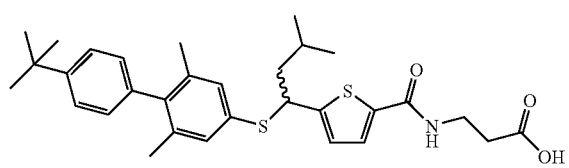

MS (ES): 538.3 [M+H]$^+$.

Example 176

3-({5-[1-(4'-tert-Butyl-2,6-dimethyl-biphenyl-4-ylsulfanyl)-1-methyl-ethyl]-thiophene-2-carbonyl}-amino)-propionic acid

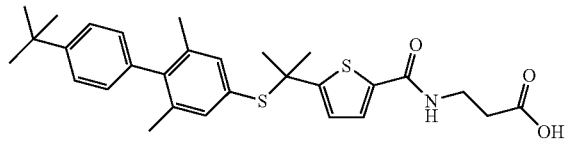

MS (ES): 510.4 [M+H]$^+$.

Example 177

(R,S)-3-({5-[1-(2,6-Dimethyl-4'-trifluoromethyl-biphenyl-4-ylsulfanyl)-propyl]-thiophene-2-carbonyl}-amino)-propionic acid

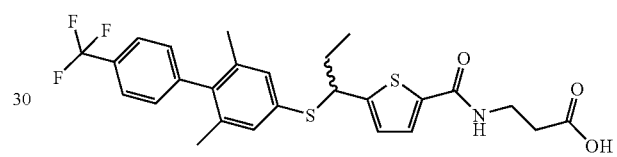

Step A (R,S)-5-[1-(2,6-Dimethyl-4'-trifluoromethyl-biphenyl-4-ylsulfanyl)-propyl]-thiophene-2-carboxylic acid ethyl ester A solution of (R,S)-5-(1-hydroxy-propyl)-thiophene-2-carboxylic acid ethyl ester (467.6 mg, 2.18 mmol) and 4'-trifluoromethyl-2,6-dimethyl-biphenyl-4-thiol (923 mg, 3.27 mmol) in 1,2-dichloroethane (8.72 mL) is treated with zinc iodide (694 mg, 2.18 mmol) and stirred overnight at rt. The reaction mixture is then partitioned between water and dichloromethane. The aqueous layer is back-extracted with dichloromethane, and the combined organic layers are dried, filtered, and concentrated. The resulting residue is applied to silica gel and eluted using hexanes with an ethyl acetate gradient from 0% to 40% to give (R,S)-5-[1-(2,6-dimethyl-4'-trifluoromethyl-biphenyl-4-ylsulfanyl)-propyl]-thiophene-2-carboxylic acid ethyl ester (846.8 mg).

Step B (R,S)-5-[1-(2,6-Dimethyl-4'-trifluoromethyl-biphenyl-4-ylsulfanyl)-propyl]-thiophene-2-carboxylic acid To a mixture of (R,S)-5-[1-(2,6-dimethyl-4'-trifluoromethyl-biphenyl-4-ylsulfanyl)-propyl]-thiophene-2-carboxylic acid ethyl ester (114 mg, 0.238 mmol) in ethanol (2.4 mL) is added 5N NaOH (0.238 mL) at room temperature, and stirred overnight. The reaction mixture is acidified by 1N HCl (0.242 mL), extracted into ethyl acetate, dried and concentrated, then dried under vacuum, giving (R,S)-5-[1-(2,6-dimethyl-4'-trifluoromethyl-biphenyl-4-ylsulfanyl)-propyl]-thiophene-2-carboxylic acid (107 mg).

Step C (R,S)-3-({5-[1-(2,6-Dimethyl-4'-trifluoromethyl-biphenyl-4-ylsulfanyl)-propyl]-thiophene-2-carbonyl}-amino)-propionic acid methyl ester To a mixture of (R,S)-5-[1-(2,6-dimethyl-4'-trifluoromethyl-biphenyl-4-ylsulfanyl)-propyl]-thiophene-2-carboxylic acid (107 mg, 0.237 mmol) in DMF (2.4 mL) is added 3-amino-propionic acid methyl ester hydrochloride(40 mg, 0.284 mmol), 1-hydroxybenzotriazole hydrate (38.4 mg, 0.284 mmol), and diisopropylethylamine (0.083 mL, 0.474 mmol) at room temperature, and stirred 10 min. The mixture is then treated with N-(3-dimethylaminopropyl)-N'-ethylcarbodiimide hydrochloride (91 mg, 0.284 mmol), and stirred overnight. The reaction mixture is treated with 0.1N HCl and extracted into ethyl acetate twice. The combined organic layers are washed with brine, dried and concentrated, and dried under vacuum to give (R,S)-3-({5-[1-(2,6-dimethyl-4'-trifluoromethyl-biphenyl-4-ylsulfanyl)-propyl]-thiophene-2-carbonyl}-amino)-propionic acid methyl ester (81 mg).

Step D (R,S)-3-({5-[1-(2,6-Dimethyl-4'-trifluoromethyl-biphenyl-4-ylsulfanyl)-propyl]-thiophene-2-carbonyl}-amino)-propionic acid To a mixture of (R,S)-3-({5-[1-(2,6-dimethyl-4'-trifluoromethyl-biphenyl-4-ylsulfanyl)-propyl]-thiophene-2-carbonyl}-amino)-propionic acid methyl ester (86 mg, 0.161 mmol) in methanol (1.6 mL) is added 5N NaOH (0.162 mL) at room temperature, and stirred overnight. The reaction mixture is acidified by 1N HCl (0.166 mL), extracted into ethyl acetate, dried and concentrated, then dried under vacuum, giving the title compound (75 mg). MS (ES): 522.1 [M+H]$^+$.

The following compounds are made in a substantially similar manner.

Example 178

(R,S)-3-({5-[1-(4'-tert-Butyl-2,6-dimethyl-biphenyl-4-ylsulfanyl)-propyl]-thiophene-2-carbonyl}-amino)-propionic acid

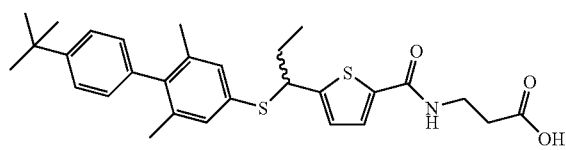

MS (ES): 510.2 [M+H]$^+$.

Example 179

(R,S)-3-({5-[1-(4'-tert-Butyl-2,6-dimethyl-biphenyl-4-ylsulfanyl)-4,4-dimethyl-pentyl]thiophene-2-carbonyl}-amino)-propionic acid

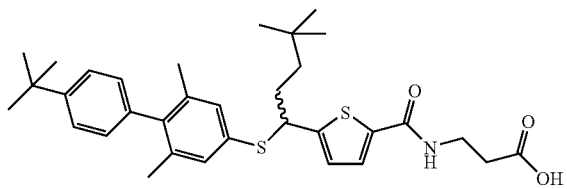

MS (ES): 566.2 [M+H]$^+$.

Example 180

(R,S)-3-({5-[1-(4'-Isopropyl-2,6-dimethyl-biphenyl-4-ylsulfanyl)-2-methyl-propyl]-thiophene-2-carbonyl}-amino)-propionic acid

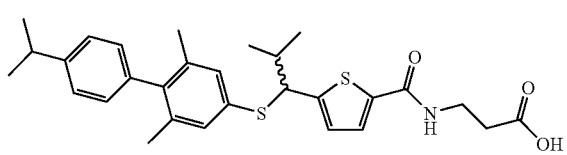

MS (ES): 510.2 [M+H]$^+$.

Example 181

(R,S)-3-({5-[1-(4'-tert-Butyl-2,6-dimethyl-biphenyl-4-ylsulfanyl)-butyl]-thiophene-2-carbonyl}-amino)-propionic acid

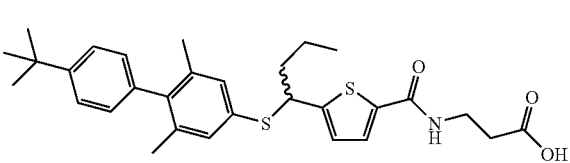

MS (ES): 524.3 [M+H]$^+$.

Example 182

(R,S)-3-({5-[1-(4'-tert-Butyl-2,6-dimethyl-biphenyl-4-ylsulfanyl)-pentyl]-thiophene-2-carbonyl}-amino)-propionic acid

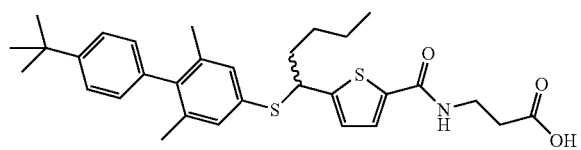

MS (ES): 538.3 [M+H]⁺.

The following compounds are made in a substantially similar manner as in Example 177, Step D, from the appropriate methyl ester.

Example 183

3-({5-[4,4,4-Trifluoro-1-(4'-isopropyl-2,6-dimethyl-biphenyl-4-yloxy)-butyl]-thiophene-2-carbonyl}-amino)-propionic acid, Isomer 1

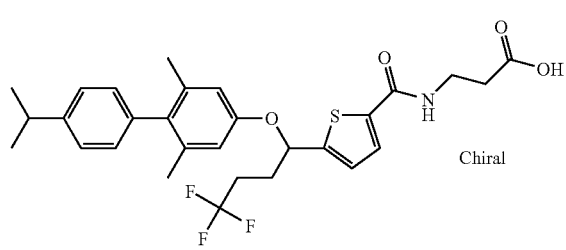

MS(ES): 548.3 [M+H]⁺.

Example 184

3-({5-[4,4,4-Trifluoro-1-(4'-isopropyl-2,6-dimethyl-biphenyl-4-yloxy)-butyl]-thiophene-2-carbonyl}-amino)-propionic acid, Isomer 2

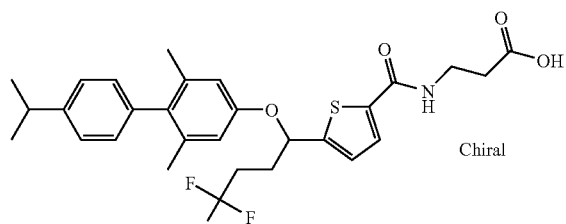

MS(ES): 548.3 [M+H]⁺.

Example 185

3-({5-[1-(2,6-Dimethyl-4'-trifluoromethoxy-biphenyl-4-yloxy)-4,4,4-trifluoro-butyl]-thiophene-2-carbonyl}-amino)-propionic acid, Isomer 1

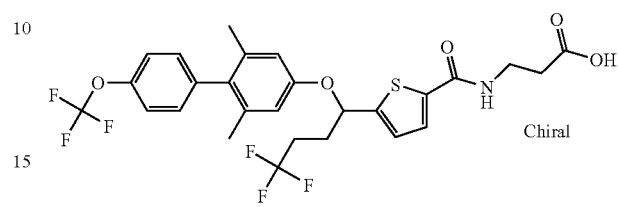

MS(ES): 590.2 [M+H]⁺.

Example 186

3-({5-[1-(2,6-Dimethyl-4'-trifluoromethoxy-biphenyl-4-yloxy)-4,4,4-trifluoro-butyl]-thiophene-2-carbonyl}-amino)-propionic acid, Isomer 2

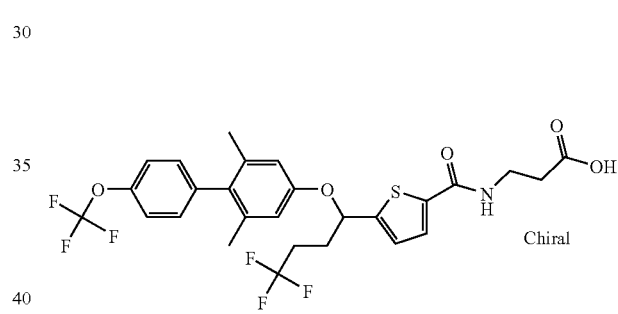

MS(ES): 590.2 [M+H]⁺.

Example 187

3-({5-[1-(4'-Ethyl-2,6-dimethyl-biphenyl-4-yloxy)-4,4,4-trifluoro-butyl]-thiophene-2-carbonyl}-amino)-propionic acid, Isomer 1

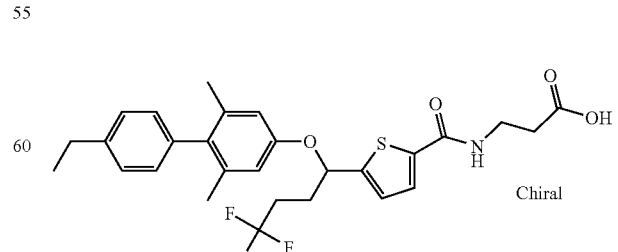

MS(ES): 534.2 [M+H]⁺.

Example 188

3-({5-[1-(4'-Ethyl-2,6-dimethyl-biphenyl-4-yloxy)-4,4,4-trifluoro-butyl]-thiophene-2-carbonyl}-amino)-propionic acid, Isomer 2

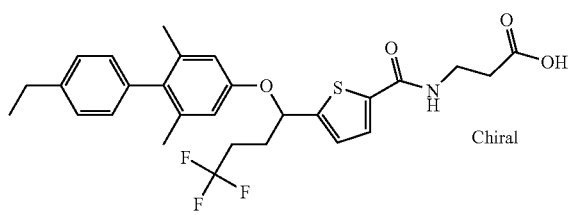

MS(ES): 534.2 [M+H]⁺.

Example 189

3-({5-[1-(4'-tert-Butyl-2,6-dimethyl-biphenyl-4-yl-sulfanyl)-4,4,4-trifluoro-butyl]-thiophene-2-carbonyl}-amino)-propionic acid, Isomer 1

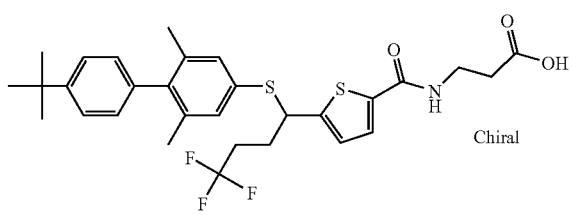

MS(ES): 578.3 [M+H]⁺.

Example 190

3-({5-[1-(4'-tert-Butyl-2,6-dimethyl-biphenyl-4-yl-sulfanyl)-4,4,4-trifluoro-butyl]-thiophene-2-carbonyl}-amino)-propionic acid, Isomer 2

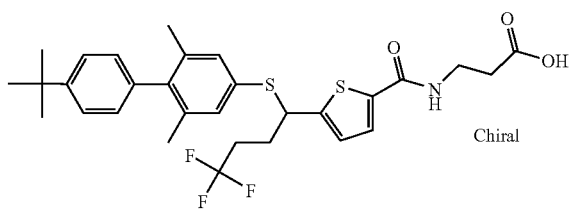

MS(ES): 578.3 [M+H]⁺.

The compound of Formulae I-IV is preferably formulated in a unit dosage form prior to administration. Therefore, yet another embodiment of the present invention is a pharmaceutical composition comprising a compound of Formulae I-IV and one or more pharmaceutically acceptable carriers, diluents or excipients.

The present pharmaceutical compositions are prepared by known procedures using well-known and readily available ingredients. In making the formulations of the present invention, the active ingredient (Formulae I-IV compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the pharmacological and therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

PHARMACOLOGICAL METHODS

In the following section binding assays as well as functional assays useful for evaluating the efficiency of the compounds of the invention are described.

Binding of compounds to the glucagon receptor may be determined in a competition binding assay using the cloned human glucagon receptor. Antagonism may be determined as the ability of the compounds to inhibit the amount of cAMP formed in the presence of 5 nM glucagon.

Glucagon Receptor (hGlucR) Binding Assay

The receptor binding assay uses cloned human glucagon receptor (Lok S, Kuijper J L, Jelinek L J, Kramer J M, Whitmore T E, Sprecher C A, Mathewes S, Grant F J, Biggs S H, Rosenberg G B, et al. Gene 140 (2), 203-209 (1994)) isolated from 293HEK membranes. The hGlucR cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA was transfected into 293 HEK cells and selected with 200 ug/ml Hygromycin.

Crude plasma membranes are prepared using cells from suspension culture. The cells are lysed on ice in hypotonic buffer containing 25 mM Tris HCL, pH 7.5, 1 mM MgCl2, DNAse1, 20 u/ml, and Roche Complete Inhibitors-without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots at −80 degree C. freezer until needed.

Glucagon is radioiodinated by I-125-lactoperoxidase procedure and purified by reversed phase HPLC at Perkin-Elmer/NEN (NEX207). The specific activity is 2200 Ci/mmol. Kd determination is performed by homologous competition instead of saturation binding due to high propanol content in the I-125 glucagon material. The Kd is estimated to be 3 nM and is used to calculate Ki values for all compounds tested.

The binding assays are carried out using a Scintillation Proximity Assay (Amersham) with WGA beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon is dissolved in 0.01 N HCl at 1 mg/ml and immediately frozen at −80 degrees C. in 30 ul aliquots. The glucagon aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon (NSB at 1 uM final). 50 ul of I-125 glucagon (0.15 nM final in reaction), 50 ul of membranes (300 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon binding in the presence of compound. The absolute EC50 dose of compound is derived by non-linear regression of percent specific binding of I-125-glucagon vs. the dose of compound added. The EC50 dose is converted to Ki using the Cheng-Prusoff equation (Cheng Y., Prusoff W. H., Biochem. Pharmacol. 22, 3099-3108, 1973).

Glucagon—Like—Peptide 1 (Glp1-R) Receptor Binding Assay

The receptor binding assay uses cloned human glucagon-like peptide 1 receptor (hGlp1-R) (Graziano M P, Hey P J, Borkowski D, Chicchi G G, Strader C D, Biochem Biophys Res Commun. 1993 Oct. 15;196(1):141-6) isolated from 293HEK membranes. The hGlp1-R cDNA is subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA is transfected into 293 HEK cells and selected with 200 ug/ml Hygromycin.

Crude plasma membrane is prepared using cells from suspension culture. The cells are lysed on ice in hypotonic buffer containing 25 mM Tris HCL, pH 7.5, 1 mM MgCl2, DNAse, 20 u/ml, and Roche Complete Inhibitors without EDTA. The cell suspension is homogenized with a glass dounce homogenizer using a Teflon pestle for 25 strokes. The homogenate is centrifuged at 4 degrees C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4 degrees C. The membrane pellet is resuspended in homogenization buffer and stored as frozen aliquots in −80 degree C. freezer until use.

Glucagaon-like peptide 1 (Glp-1) is radioiodinated by the I-125-lactoperoxidase procedure and purified by reversed phase HPLC at Perkin-Elmer/NEN (NEX308). The specific activity is 2200 Ci/mmol. Kd determination is performed by homologous competition instead of saturation binding due to high propanol content in the I-125 Glp-1 material. The Kd is estimated to be 3 nM and is used to calculate Ki values for all compounds tested.

The binding assays are carried out using a Scintillation Proximity Assay (Amersham) with wheat germ agglutinin (WGA) beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon-like peptide 1 is dissolved in PBS at 1 mg/ml and immediately frozen at −80 degrees C. in 30 ul aliquots. The glucagon-like peptide aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon-like peptide 1 (NSB at 1 uM final). 50 ul of I-125 glucagon-like peptide 1 (0.15 nM final in reaction), 50 ul of membranes (600 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon-like peptide 1 binding in the presence of compound. The absolute EC50 dose of compound is derived by non-linear regression of percent specific binding of I-125-glucagon-like peptide 1 vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Stimulated cAMP Functional Antagonist Assay

The cAMP functional assay uses the same cloned human glucagon receptor cell line isolated for the hGlucR binding assay described above. Cells are stimulated with a mixture of an EC80 dose of glucagon in the presence of compound. The cAMP generated within the cell is quantitated using an Amplified Luminescent Proximity Homogeneous Assay, Alpha Screen, from Perkin Elmer (6760625R). Briefly, cAMP within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinlyated cAMP-Donor bead complex occurs and decreases the signal.

Glucagon is dissolved in 0.01 N HCl at 1 mg/ml and immediately frozen at −80 degrees C. in 30 ul aliquots. The glucagon aliquot is diluted and used in the functional assay within an hour. Cells are harvested from sub-confluent tissue culture dishes with Enzyme-Free Cell Dissociation Solution, (Specialty Media 5-004-B). The cells are pelleted at low speed and washed 3 times with assay buffer [25 mM Hepes in HBSS-with Mg and Ca (GIBCO, 14025-092) with 0.1% Fatty Acid Free BSA (ICN)] then diluted to a final concentration of 250,000 cells per ml. Compounds are serially diluted into DMSO then diluted into assay buffer with a 3× concentration of glucagon and 3% DMSO. The EC80 of glucagon is pre-determined from a full glucagon dose response and represents the dose at which glucagons produces an 80% of the maximal glucagon response. A mixture of biotinylated cAMP (1 unit/well final) from the Alpha Screen Kit and 3× IBMX (1500 uM) is prepared in Assay Buffer.

The functional assay is performed in 96 well, low-volume, white, poylstyrene Costar Plates (3688). The biotinylated cAMP/IBMX mixture, 0.02 mls, is placed into each well, followed by addition of 0.02 mls of glucagon dose response, cAMP standard curve, or compound/glucagon mixtures. The reaction is started by addition of 0.02 mls of cells (5000/well final). After 60 minutes at room temperature, the reaction is stopped by the addition of 0.03 mls of Lysis Buffer [10 mM Hepes, pH 7.4, 1% NP40, and 0.01% fatty acid free BSA (ICN) containing 1 unit each/well of Acceptor and Donor beads from the Alpha Screen Kit]. Lysis Buffer addition is performed under a green light to prevent bleaching of the detection beads. The plates are wrapped in foil and left to equilibrate overnight at room temperature. The plates are read on a Packard Fusion™-Instrument.

Alpha screen units are converted to pmoles cAMP generated per well based upon the cAMP standard curve. The pmoles cAMP produced in the presence of compound are converted to % of a maximal response with the EC80 dose of glucagon alone. With each experiment, the dose of glucagon needed to produce a 50% response of pmoles cAMP is determined. This EC50 dose is used to normalize results to a Kb using a modified Cheng-Prusoff equation (Cheng Y., Prusoff W. H., Biochem. Pharmacol. 22, 3099-3108, 1973), where Kb=(EC50 compound)/[1+(pM glucagon used/EC50 in pM for glucagon dose response)].

In general the compounds according to the invention have a Ki value of less than 50 μM as determined by the Glucagon Receptor (hGlucR) Binding Assay disclosed herein. The examples provided have Ki values of less than 50 μM. Preferably the compounds according to the invention have a Ki value of less than 5 μM, and more preferably of less than 500 nM, and even more preferred of less than 100 nM, as determined by the Glucagon Receptor (hGlucR) Binding Assay disclosed herein. Generally, the compounds according to the invention show a higher affinity for the glucagon receptor compared to the GLP-1 receptor, and preferably have a 10 to 10000 fold higher binding affinity for the glucagon receptor than for the GLP-1 receptor.

The results are given below for the indicated compound.

TABLE 2

| Example | Ki (nM) |
|---|---|
| [structure with CF3-biphenyl-O-thiophene-amide-propanoic acid] | 390 |
| [structure with tert-butyl-phenyl-pyridine-O-thiophene-amide-propanoic acid] | 296 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound structurally represented by Formula I

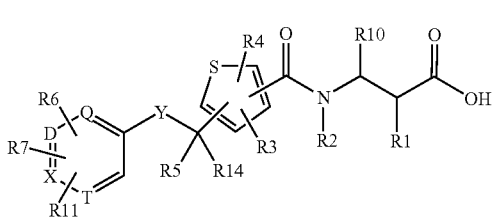

or a pharmaceutically acceptable salt thereof wherein:

Y is —O—, —S—, or —O—CH$_2$—;

Q, D, X and T represent carbon;

R1 is -hydrogen;

R2 is -hydrogen, or —(C$_1$-C$_3$)alkyl;

R3 and R4 are independently
-hydrogen, -halogen, —CN, —(C$_1$-C$_7$)alkoxy, —(C$_1$-C$_7$)alkyl, or —(C$_2$-C$_7$)alkenyl;

R5 and R14 are independently
-hydrogen, —(C$_1$-C$_{12}$)alkyl, —(C$_3$-C$_{12}$)cycloalkyl, —(C$_3$-C$_{12}$)cycloalkyl-(C$_1$-C$_{12}$)alkyl, -phenyl, -phenyl-phenyl-(C$_1$-C$_{12}$)alkyl, -phenyl-(C$_3$-C$_{12}$)cycloalkyl, -aryl, -aryl-(C$_1$-C$_{12}$)alkyl, -heteroaryl, -heteroaryl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, -aryl-(C$_2$-C$_{10}$)alkenyl, -heteroaryl-(C$_2$-C$_{10}$)alkenyl, —(C$_2$-C$_{12}$)alkynyl, —(C$_8$-C$_{12}$)cycloalkynyl, -aryl-(C$_2$-C$_{12}$)alkynyl, or -heteroaryl-(C$_2$-C$_{12}$)alkynyl, and wherein —(C$_1$-C$_{12}$)alkyl, —(C$_3$-C$_{12}$)cycloalkyl, -phenyl, -phenyl-phenyl-(C$_1$-C$_{12}$)alkyl, -phenyl-(C$_3$-C$_{12}$)cycloalkyl, -aryl, -aryl-(C$_1$-C$_{12}$)alkyl, -heteroaryl, -heteroaryl-(C$_1$-C$_{12}$)alkyl, -heterocycloalkyl, -heterocycloalkyl-(C$_1$-C$_{12}$)alkyl, —(C$_2$-C$_{12}$)alkenyl, —(C$_3$-C$_{12}$)cycloalkenyl, -aryl-(C$_2$-C$_{10}$)alkenyl, -heteroaryl-(C$_2$-C$_{10}$)alkenyl, —(C$_2$-C$_{12}$)alkynyl, —(C$_8$-C$_{12}$)cycloalkynyl, -aryl-(C$_2$-C$_{12}$)alkynyl, or -heteroaryl-(C$_2$-C$_{12}$)alkynyl are each optionally substituted with from one to three substituents each independently selected from the group consisting of
-hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxy, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12,
—OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$; wherein optionally R5 and R14 may form a four, five, or six membered ring with the atom to which they are attached, and the ring so formed may optionally include one or two double bonds, and optionally may be substituted with up to four halogens;

R6 and R7 are independently
-hydrogen, -halogen, -hydroxy, —CN, —(C$_1$-C$_7$)alkoxy, —(C$_2$-C$_7$)alkenyl, —(C$_1$-C$_7$)alkyl, -aryl, -heteroaryl, —(C$_3$-C$_7$)cycloalkyl, —(C$_3$-C$_7$)heterocycloalkyl, wherein —(C$_2$-C$_7$)alkenyl, —(C$_1$-C$_7$)alkyl, —(C$_1$-C$_7$)alkoxy, -aryl, -heteroaryl, —(C$_3$-C$_7$)cycloalkyl, or —(C$_3$-C$_7$)heterocycloalkyl, are each optionally substituted with from one to three substituents independently selected from the group consisting of -hydrogen,
-hydroxy, -cyano, -nitro, -halo, -oxo, —(C$_1$-C$_7$)alkyl, —(C$_1$-C$_7$)alkyl-COOR12, —(C$_1$-C$_7$)alkoxy, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12, —OS(O)$_2$R12, —N(R12)$_2$, —NR12C(O)R12, —C(O)NR12R12, —NR12SO$_2$R12, —SR12, —S(O)R12, —S(O)$_2$R12, and
—S(O)$_2$N(R12)$_2$;

and wherein R6 and R7 may optionally form a six membered ring with the atoms to which they are attached, and the ring so formed may optionally contain up to two oxygens, and further the ring so formed may optionally be substituted with up to four halogens;

R8 and R9 are independently
-hydrogen, -hydroxy, —CN, -nitro, -halo, —(C$_1$-C$_7$)alkyl, —CF$_3$, —(C$_1$-C$_7$)alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, —C(O)R12, —COOR12, —OC(O)R12, —OS(O)$_2$R12, —N(R12)$_2$, —NR12C(O) R12,
—N R12SO$_2$ R12, —SR12, —S(O)R12, —S(O)$_2$ R12, or —S(O)$_2$N(R12)$_2$;

and wherein —(C$_1$-C$_7$)alkyl, —(C$_1$-C$_7$)alkoxy, —(C$_3$-C$_7$)cycloalkyl, -aryl, -aryl-(C$_1$-C$_7$)alkyl, -heteroaryl, -heteroaryl-(C$_1$-C$_7$)alkyl, -aryloxy, are each optionally substituted with from one to three substituents independently selected from the group consisting of -hydrogen, -hydroxy, -cyano, -nitro, -halo, -oxo, —(C$_1$-C$_7$)alkyl, —(C$_1$-C$_7$)alkyl-COOR12, —(C$_1$-C$_7$)alkoxyl, —(C$_3$-C$_7$)cycloalkyl, -aryloxy, -aryl, -aryl-(C$_1$-C$_7$)alkyl, -heteroaryl, -heterocycloalkyl, —C(O)R12, —COOR12, —OC(O)R12, —OS(O)$_2$R12, —N(R12)$_2$, —NR12C(O)R12, —C(O)NR12R12, —NR12 SO$_2$ R12, —SR12, —S(O)R12, —S(O)$_2$R12, and —S(O)$_2$N(R12)$_2$;

R10 is -hydrogen;

R11 is independently

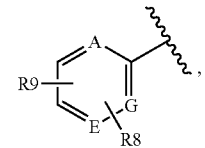

wherein the zig-zag mark represents the point of attachment to the R11 position in formula I, wherein A, G, and E represent carbon;

R12 is independently at each occurrence -hydrogen, —(C$_1$-C$_7$)alkyl.

2. A compound of claim 1 further represented by Formula Ia;

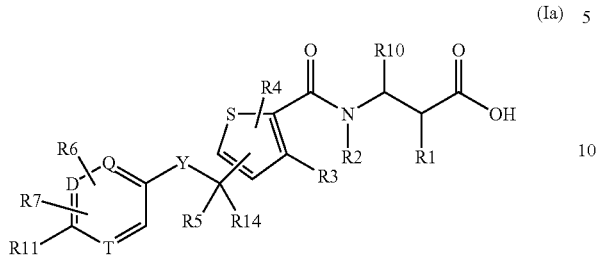

or a pharmaceutically acceptable salt thereof wherein:
Y is —O—, —S—, or —O—CH$_2$—;
Q, D, and T represent carbon;
R1 is -hydrogen;
R2 is -hydrogen;
R3 and R4 are independently -hydrogen, or -halogen;
R5 and R14 are independently
-hydrogen, —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl;
wherein —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl are each optionally substituted with one to three halogens;
wherein optionally R5 and R14 may form a four, five, or six membered ring with the atom to which they are attached, and the ring so formed may optionally include one or two double bonds, and optionally may be substituted with up to three halogens;
R6 and R7 are independently
-hydrogen, -halogen, -hydroxy, —CN, —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl,
wherein —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl, are each optionally substituted with one to three halogens;
and
wherein R6 and R7 may optionally form a six membered ring with the atoms to which they are attached, and the ring so formed may optionally contain up to two oxygens, and further the ring so formed may optionally be substituted with up to four halogens;
R8 and R9 are independently
-hydrogen, -hydroxy, —CN, -nitro, -halo, —(C$_1$-C$_7$)alkyl, —CF$_3$, —(C$_1$-C$_7$)alkoxy, —(C3-C$_7$)cycloalkyl, —C(O)R12, —COOR12, —OC(O)R12, —OS(O)$_2$R12, —N(R12)$_2$, —NR12C(O)R12, —N R12SO$_2$R12, —SR12, —S(O)R12, —S(O)$_2$R12, or —S(O)$_2$N(R12)$_2$;
wherein —(C$_1$-C$_7$)alkyl, —(C$_1$-C$_7$)alkoxy, —(C$_3$-C$_7$)cycloalkyl, are each optionally substituted with from one to three halogens;
R10 is -hydrogen;
R11 is independently

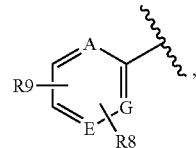

wherein the zig-zag mark represents the point of attachment to the R11 position in formula I;
wherein A, G, and E represent carbon;
and
R12 is independently -hydrogen or —(C$_1$-C$_7$)alkyl.

3. A compound of claim 1 further represented by Formula Ib;

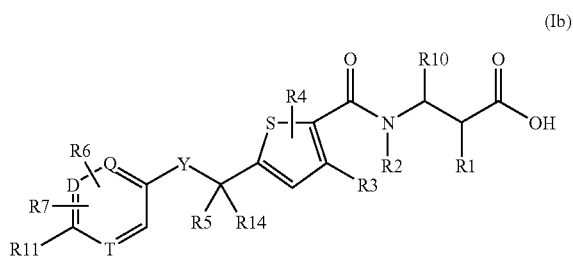

or a pharmaceutically acceptable salt thereof wherein:
Y is —O—, —S—, or —O—CH$_2$—;
Q, D, and T represent carbon;
R1 is -hydrogen;
R2 is -hydrogen;
R3 and R4 are -hydrogen;
R5 and R14 are independently
-hydrogen, —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl;
wherein —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl are each optionally substituted with one to three halogens;
wherein optionally R5 and R14 may form a four, five, or six membered ring with the atom to which they are attached, and the ring so formed may optionally include one or two double bonds, and optionally may be substituted with up to three halogens;
R6 and R7 are independently
-hydrogen, -halogen, -hydroxy, —CN, —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl,
wherein —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl, are each optionally substituted with one to three halogens;
and
wherein R6 and R7 may optionally form a six membered ring with the atoms to which they are attached, and the ring so formed may optionally contain up to two oxygens, and further the ring so formed may optionally be substituted with up to four halogens;

R8 and R9 are independently
-hydrogen, -hydroxy, —CN, -nitro, -halo, —(C$_1$-C$_7$)alkyl, —CF$_3$, —(C$_1$-C$_7$)alkoxy, —(C3-C$_7$)cycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, or —S(O)$_2$N(R12)$_2$;
wherein —(C$_1$-C$_7$)alkyl, —(C$_1$-C$_7$)alkoxy, —(C$_3$-C$_7$)cycloalkyl, are each optionally substituted with from one to three halogens;
R10 is -hydrogen;
R11 is independently

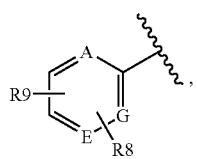

wherein the zig-zag mark represents the point of attachment to the R11 position in formula I;
wherein A, G, and E represent carbon; and
R12 is independently -hydrogen or —(C$_1$-C$_7$)alkyl.

4. A compound of Formula Ic;

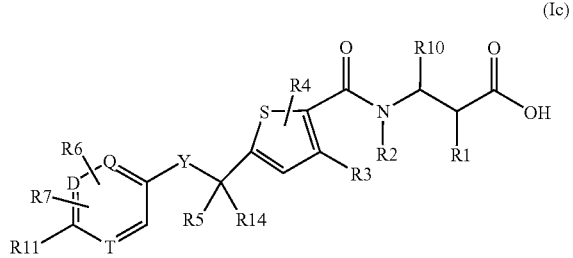

(Ic)

or a pharmaceutically acceptable salt thereof wherein:
Y is —O—, —S—, or —O—CH$_2$—;
Q, D, and T are carbon;
R1 is -hydrogen;
R2 is -hydrogen;
R3 and R4 are -hydrogen;
R5 is hydrogen;
R14 is
—(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C2-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl;
wherein —(C$_1$-C$_{12}$)alkyl, —(C$_3$-C$_{12}$)cycloalkyl, —(C$_3$-C$_{12}$)cycloalkyl-(C$_1$-C$_{12}$)alkyl, —(C$_2$-C$_{12}$)alkenyl, —(C$_3$-C$_{12}$)cycloalkenyl, -heterocycloalkyl, -heterocycloalkyl-(C$_1$-C$_{12}$)alkyl, —(C$_2$-C$_{12}$)alkynyl, or —(C$_8$-C$_{12}$)cycloalkynyl are each optionally substituted with one to three halogens;
R6 and R7 are independently
-hydrogen, -halogen, -hydroxy, —CN, —(C$_1$-C$_7$)alkoxy, —(C$_2$-C$_7$)alkenyl, —(C1-C$_7$)alkyl, —(C$_3$-C$_7$)cycloalkyl, or —(C$_3$-C$_7$)heterocycloalkyl,
wherein —(C$_1$-C$_7$)alkoxy, —(C$_2$-C$_7$)alkenyl, —(C$_1$-C$_7$)alkyl, —(C$_3$-C$_7$)cycloalkyl, or —(C$_3$-C$_7$)heterocycloalkyl, are each optionally substituted with one to three halogens;
and wherein R6 and R7 may optionally form a six membered ring with the atoms to which they are attached, and the ring so formed may optionally contain up to two oxygens, and further the ring so formed may optionally be substituted with up to four halogens;
R8 and R9 are independently
-hydrogen, -hydroxy, —CN, -nitro, -halo, —(C$_1$-C$_7$)alkyl, —CF$_3$, —(C$_1$-C$_7$)alkoxy, —(C$_3$-C$_7$)cycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, or —S(O)$_2$N(R12)$_2$;
wherein —(C$_1$-C$_7$)alkyl, —(C$_1$-C$_7$)alkoxy, —(C$_3$-C$_7$)cycloalkyl, are each optionally substituted with from one to three halogens;
R10 is -hydrogen;
R11 is independently

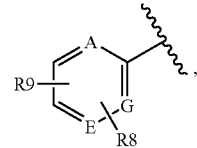

wherein the zig-zag mark represents the point of attachment to the R11 position in formula I;
wherein A, G, and E independently represent carbon; and
R12 is independently -hydrogen or —(C$_1$-C$_7$)alkyl.

5. A compound of claim 1, selected from the group consisting of:

TABLE 1

| Formula | Structure |
|---|---|
| X1 | ![structure] |

TABLE 1-continued
| Formula | Structure |
|---|---|
| X2 | 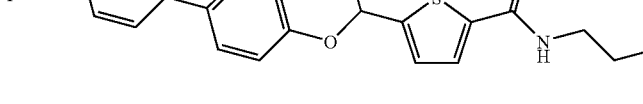 |
| X3 | 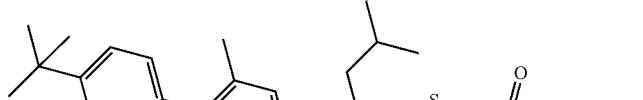 |
| X4 | 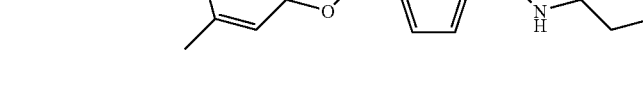 |
| X5 | 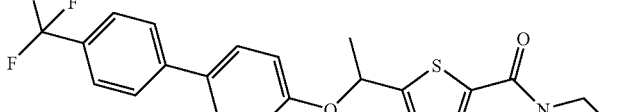 |
| X6 | 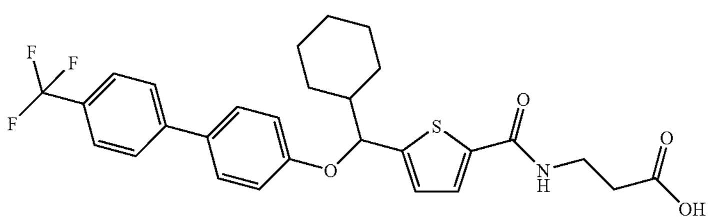 |
| X7 | 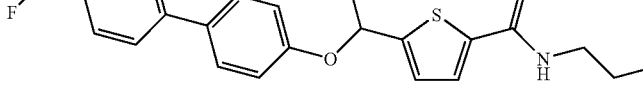 |
| X8 | 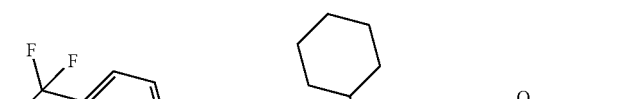 |

TABLE 1-continued
| Formula | Structure |
|---|---|
| X9 | 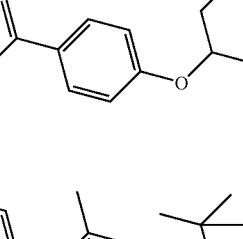 |
| X10 | 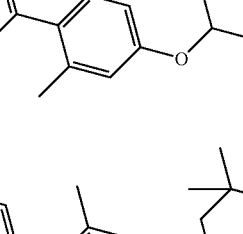 |
| X11 | 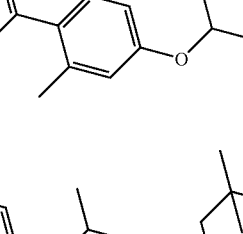 |
| X12 | 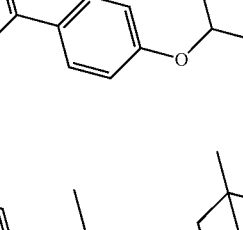 |
| X13 | 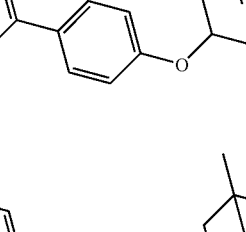 |
| X14 | 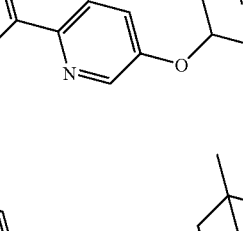 |
| X15 | 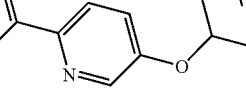 |

TABLE 1-continued

| Formula | Structure |
|---------|-----------|
| X16 | 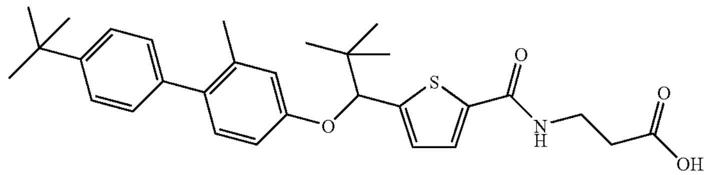 |
| X17 | 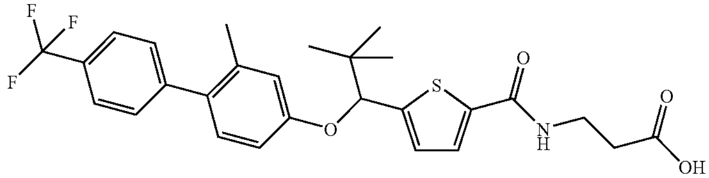 |
| X18 | 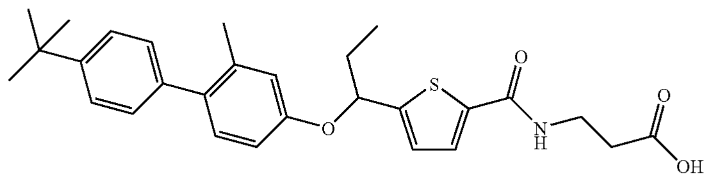 |
| X19 | 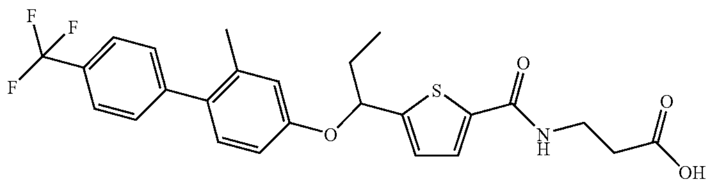 |
| X20 | 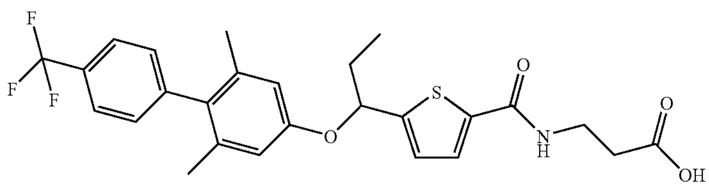 |
| X21 | 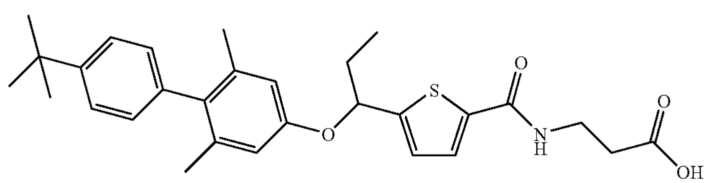 |
| X22 | 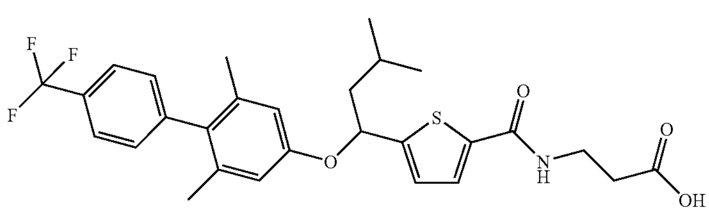 |
| X23 | 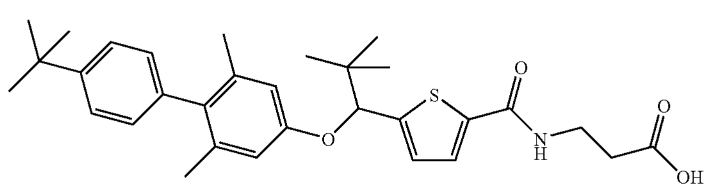 |

TABLE 1-continued

| Formula | Structure |
|---|---|
| X24 | 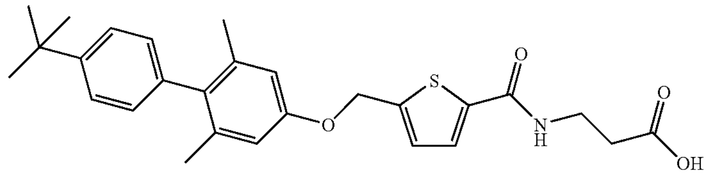 |
| X25 | 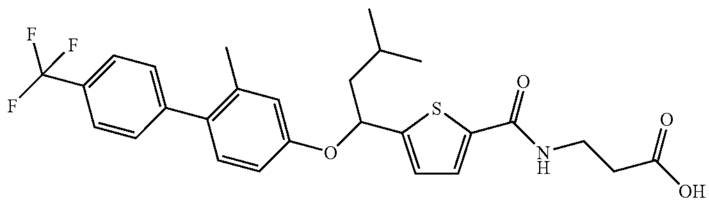 |
| X26 | 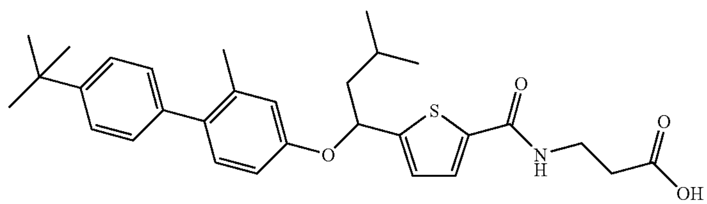 |
| X27 | 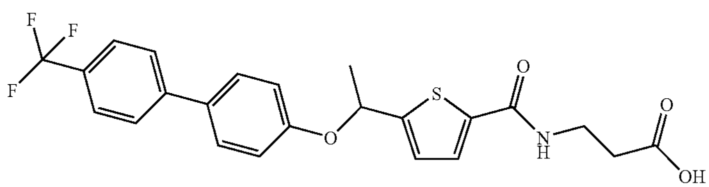 |
| X28 | 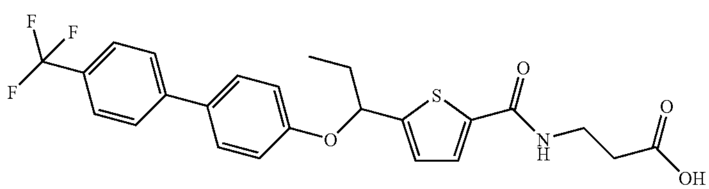 |
| X29 | 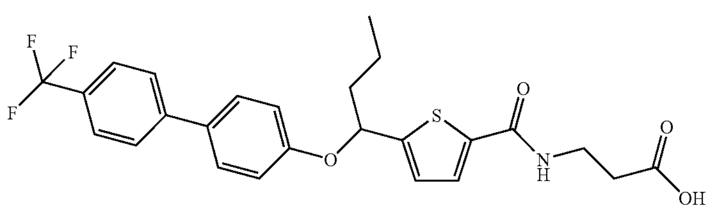 |
| X30 | 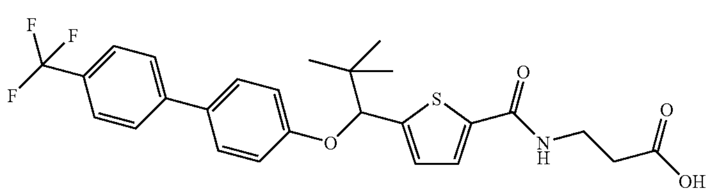 |
| X31 | 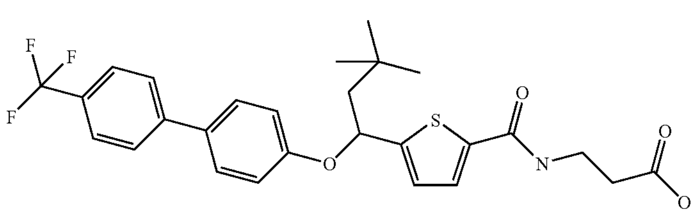 |

TABLE 1-continued

| Formula | Structure |
|---|---|
| X32 | 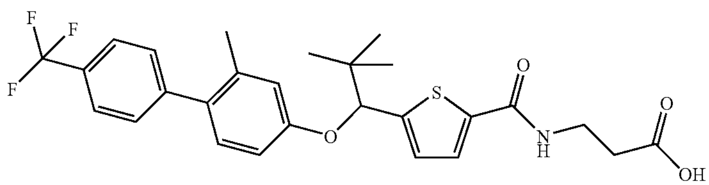 |
| X33 | 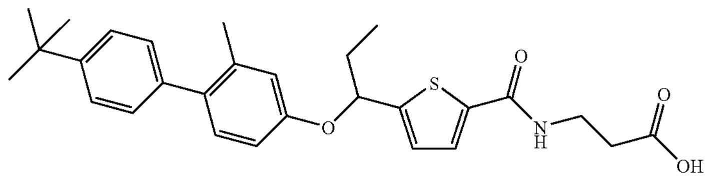 |
| X34 | 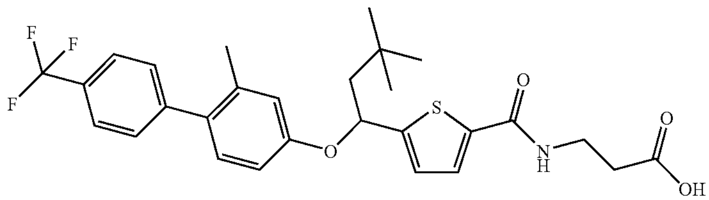 |
| X35 | 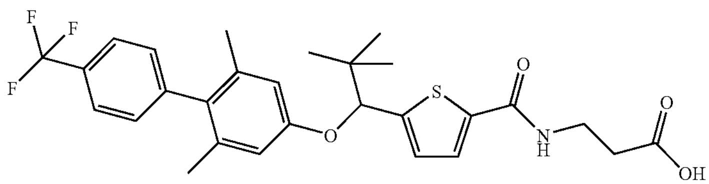 |
| X36 | 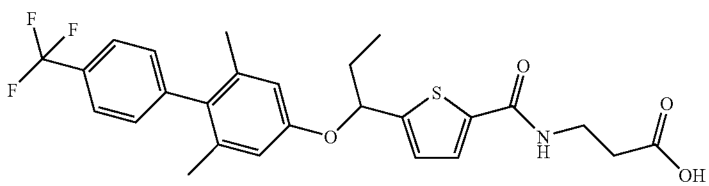 |
| X37 | 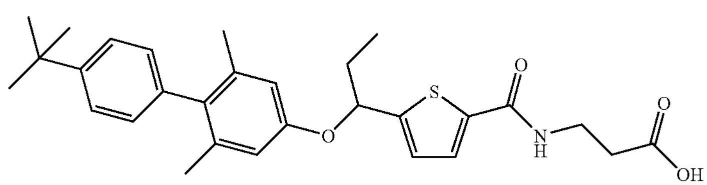 |
| X38 | 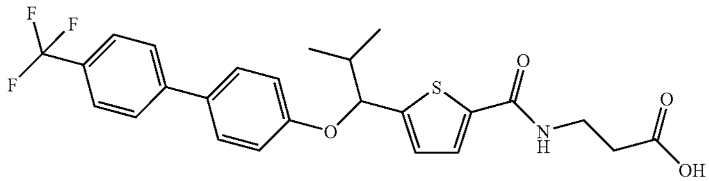 |
| X39 | 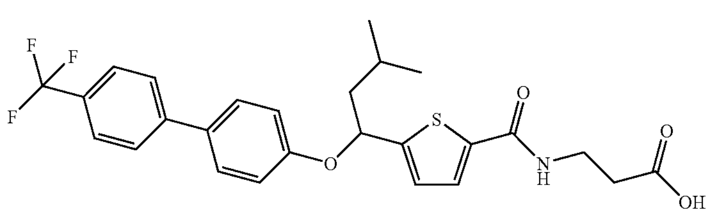 |

TABLE 1-continued
| Formula | Structure |
|---|---|
| X40 | 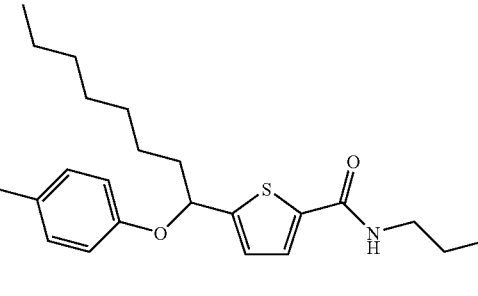 |
| X41 | 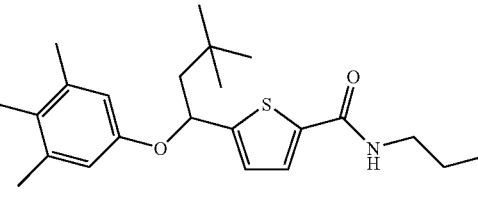 |
| X42 | 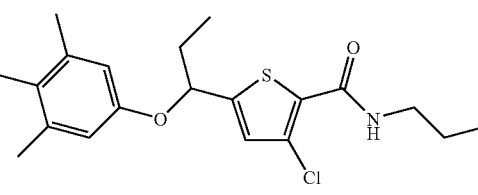 |
| X43 | 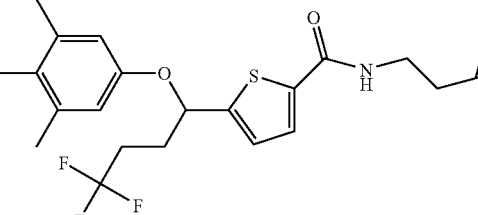 |
| X44 | 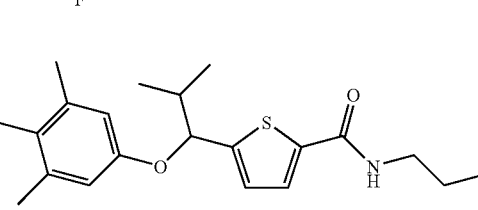 |
| X45 | 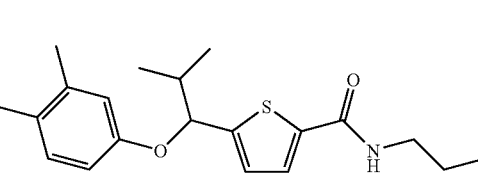 |
| X46 | 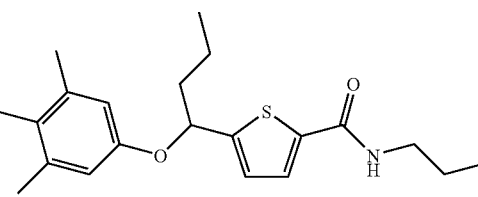 |

TABLE 1-continued
| Formula | Structure |
|---|---|
| X47 | 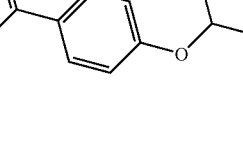 |
| X48 | 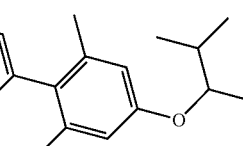 |
| X49 | 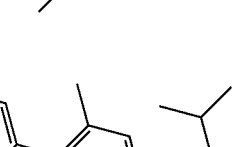 |
| X50 | 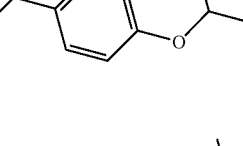 |
| X51 | 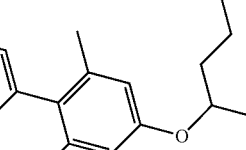 |
| X52 | 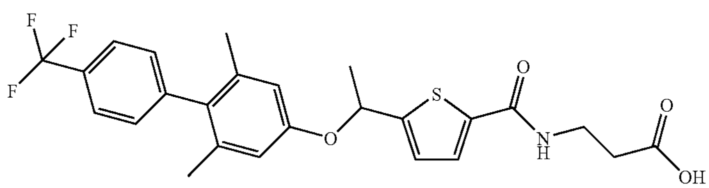 |
| X53 | 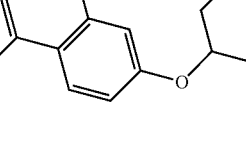 |

TABLE 1-continued
| Formula | Structure |
|---|---|
| X54 | 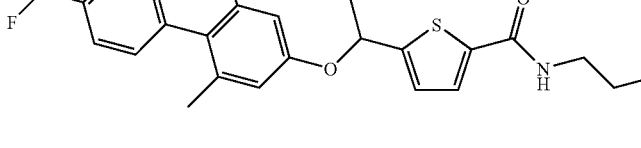 |
| X55 | 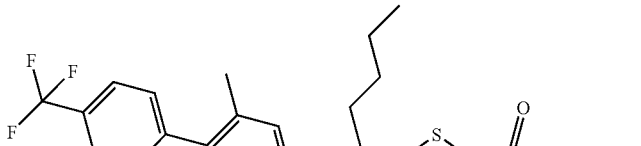 |
| X56 | 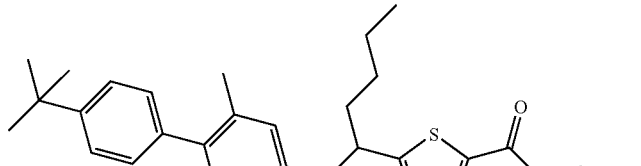 |
| X57 | 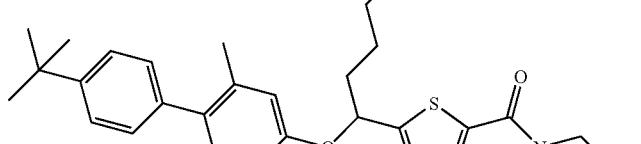 |
| X58 | 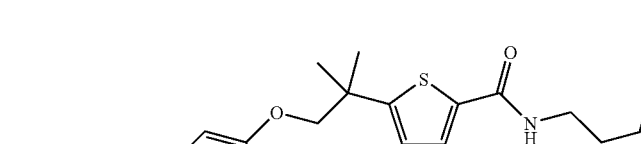 |

TABLE 1-continued

| Formula | Structure |
|---|---|
| X59 | 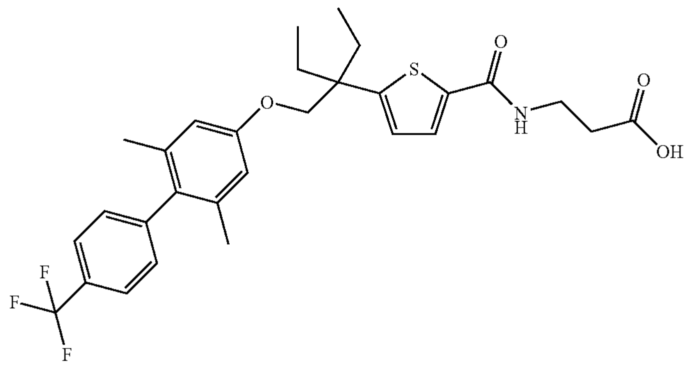 |
| X60 | 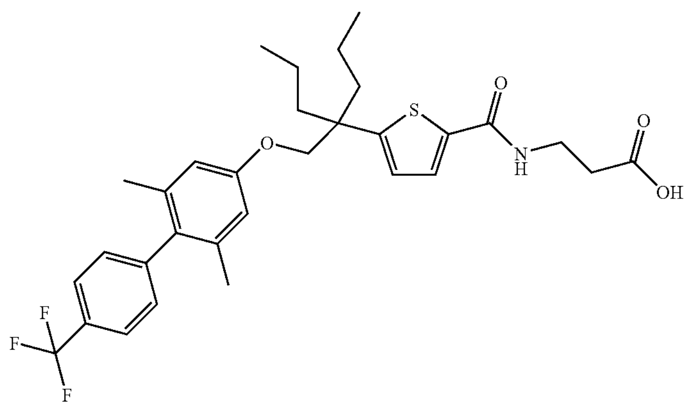 |
| X61 | 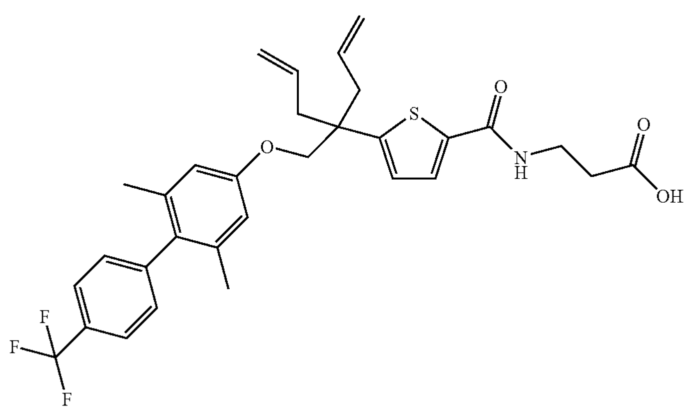 |
| X62 | 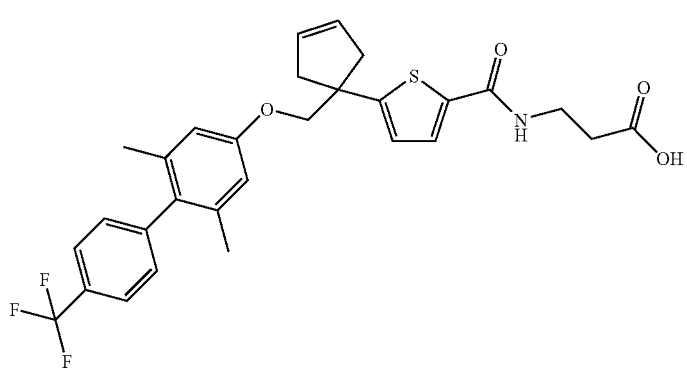 |

TABLE 1-continued
| Formula | Structure |
|---|---|
| X63 | 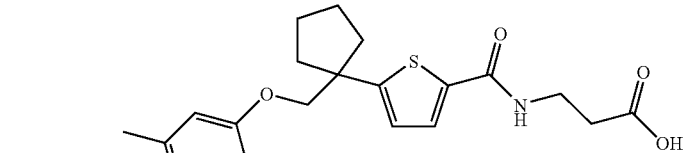 |
| X64 | 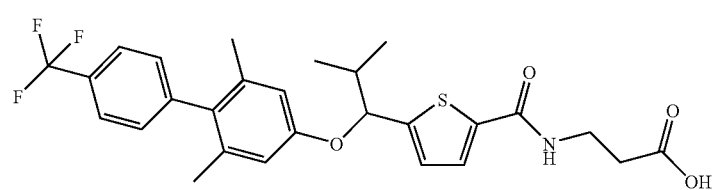 |
| X65 | 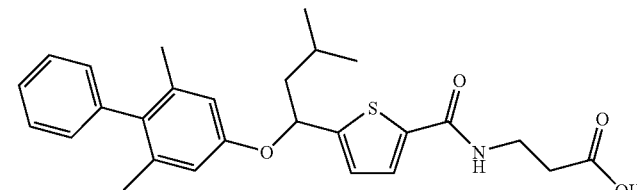 |
| X66 | 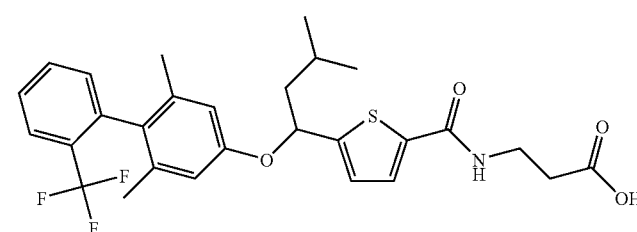 |
| X67 | 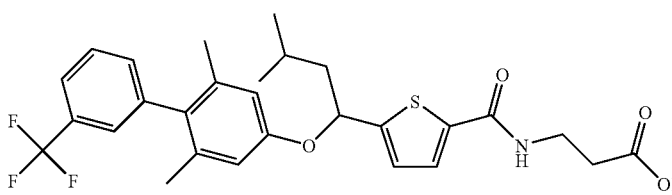 |
| X68 | 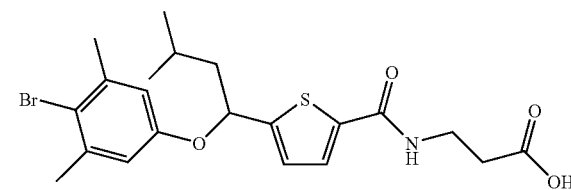 |
| X69 | 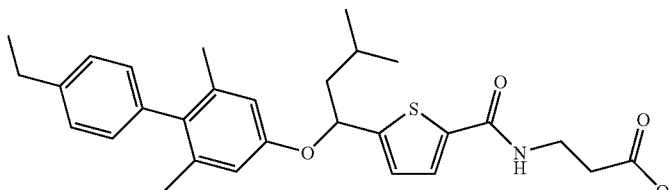 |

TABLE 1-continued

| Formula | Structure |
|---|---|
| X70 | 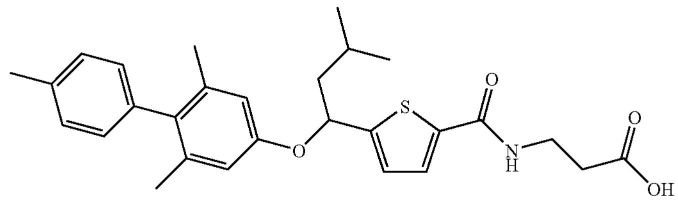 |
| X71 | 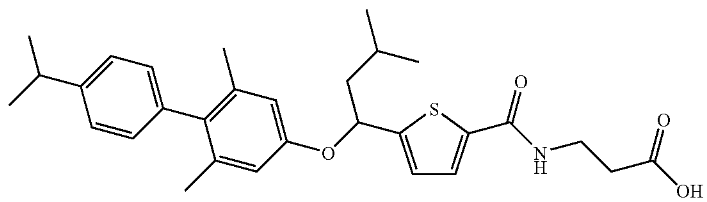 |
| X72 | 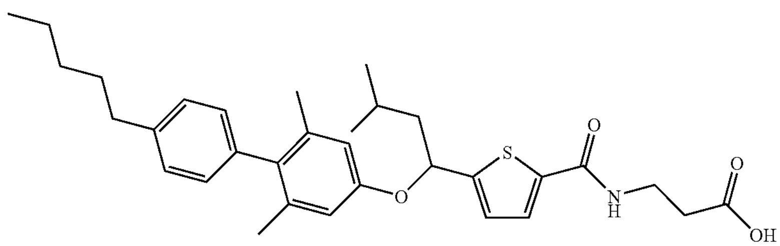 |
| X73 | 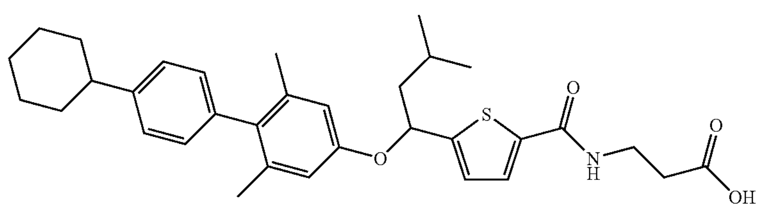 |
| X74 | 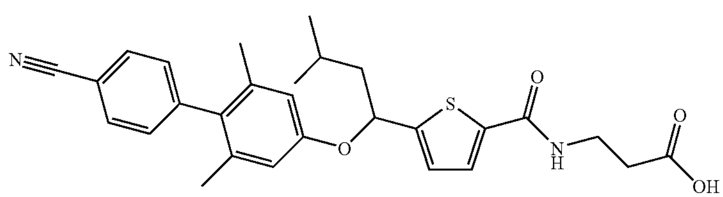 |
| X75 | 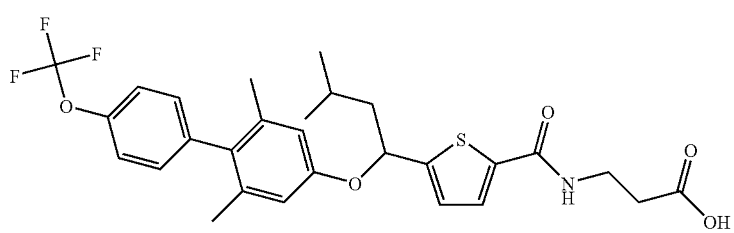 |
| X76 | 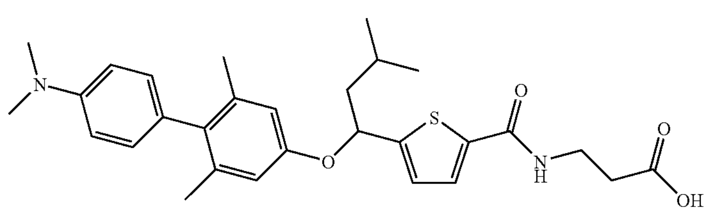 |

TABLE 1-continued

| Formula | Structure |
|---|---|
| X77 | 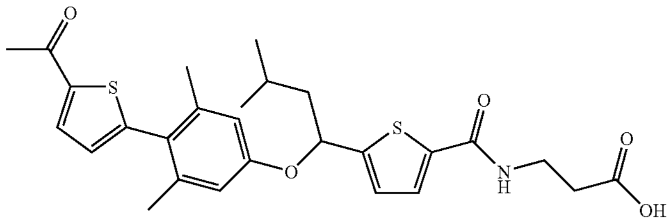 |
| X78 | 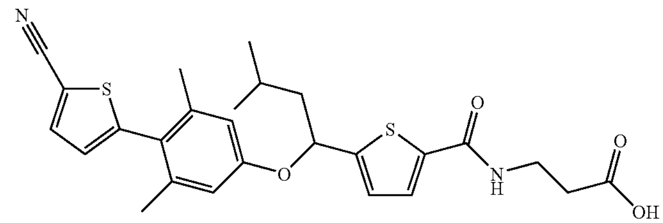 |
| X79 | 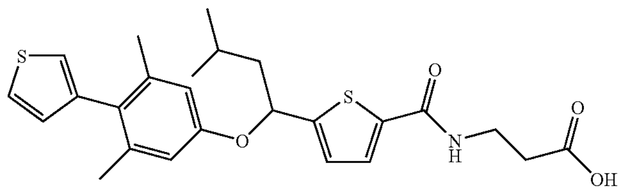 |
| X80 | 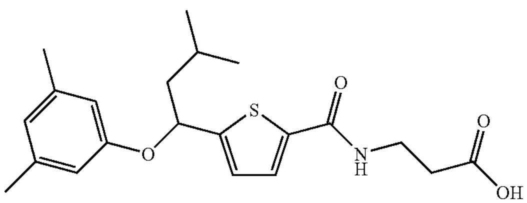 |
| X81 | 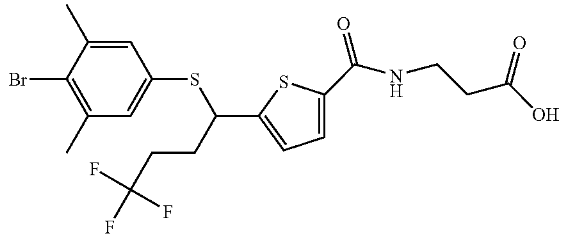 |
| X82 | 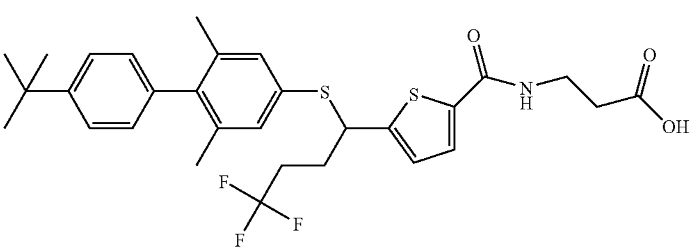 |
| X83 | 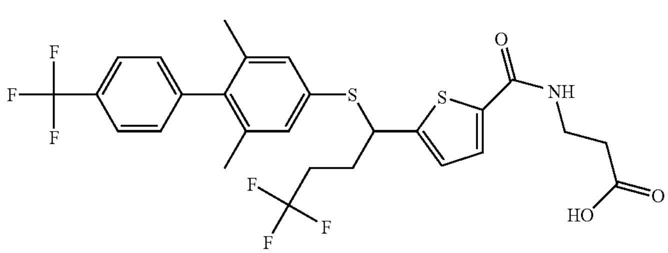 |

TABLE 1-continued
| Formula | Structure |
|---|---|
| X84 | 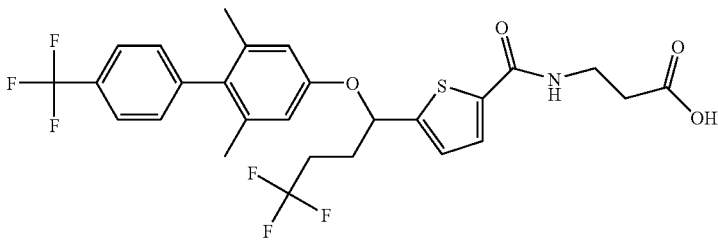 |
| X85 | 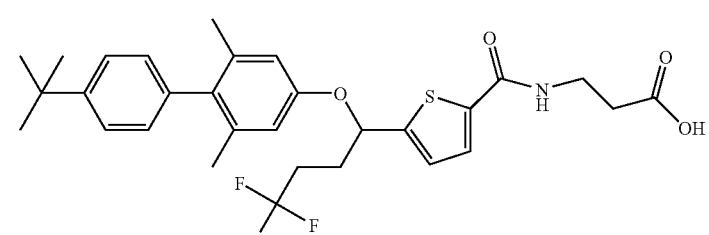 |
| X86 | 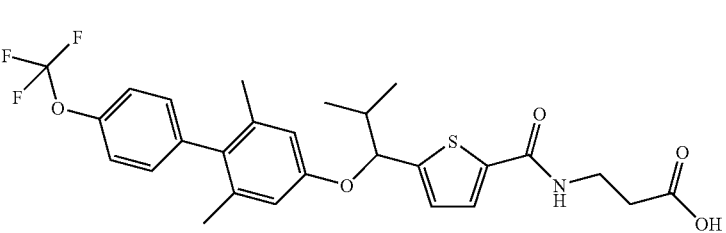 |
| X87 | 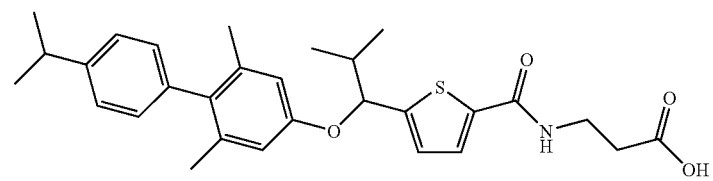 |
| X88 | 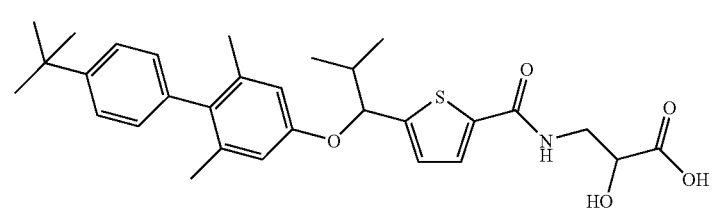 |
| X89 | 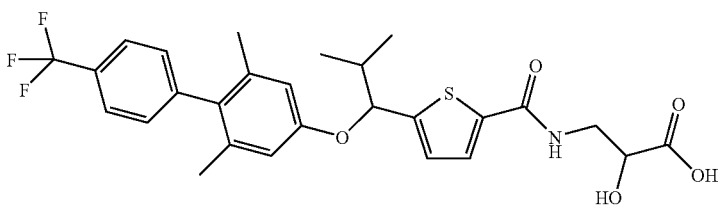 |
| X90 | 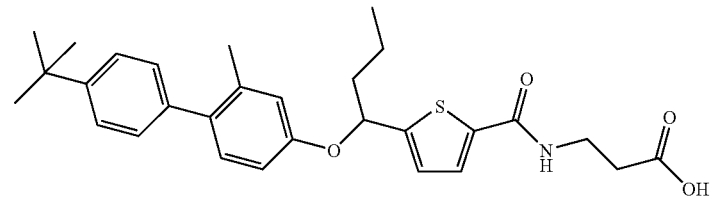 |

TABLE 1-continued

| Formula | Structure |
|---|---|
| X91 | 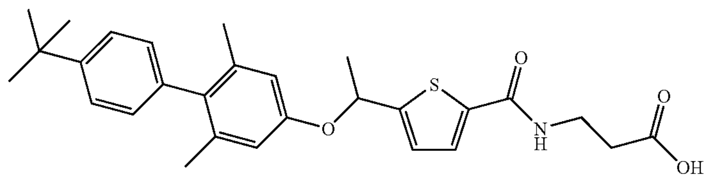 |
| X92 | 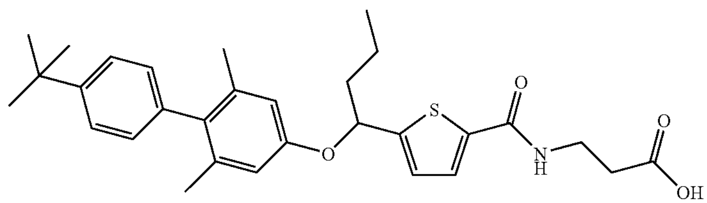 |
| X93 | 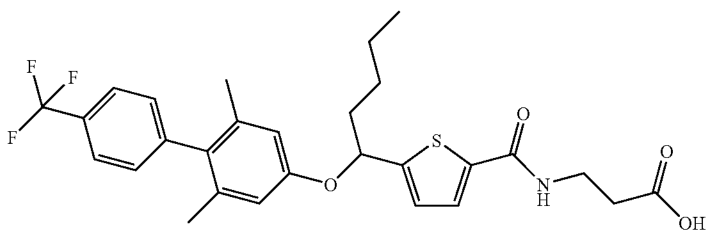 |
| X94 | 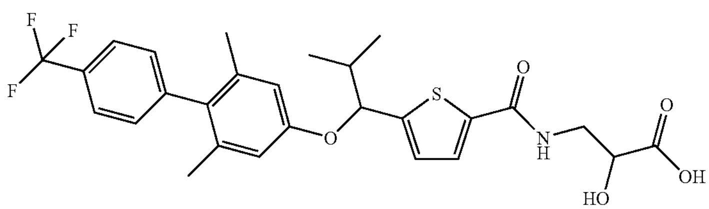 |
| X95 | 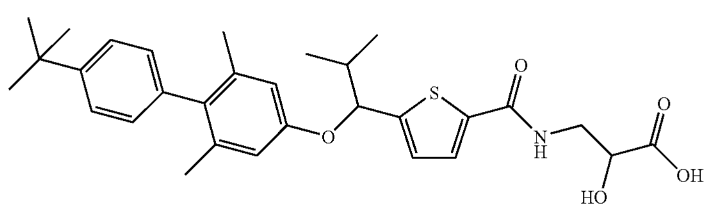 |
| X96 | 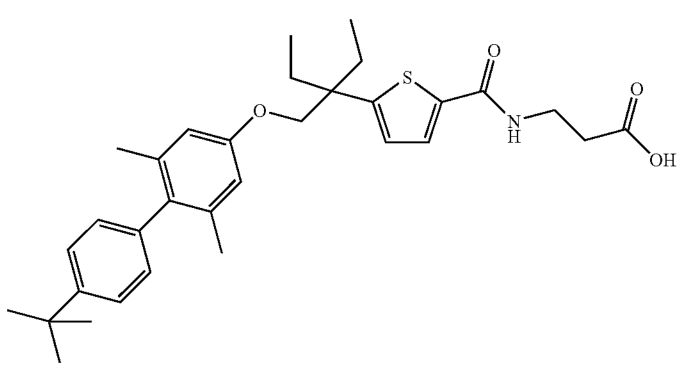 |

TABLE 1-continued
| Formula | Structure |
|---|---|
| X97 | 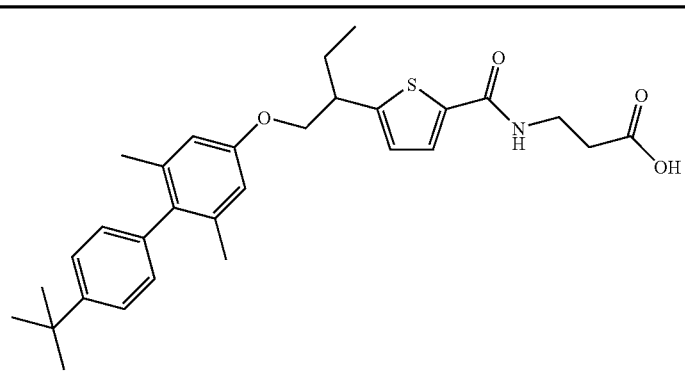 |
| X98 | 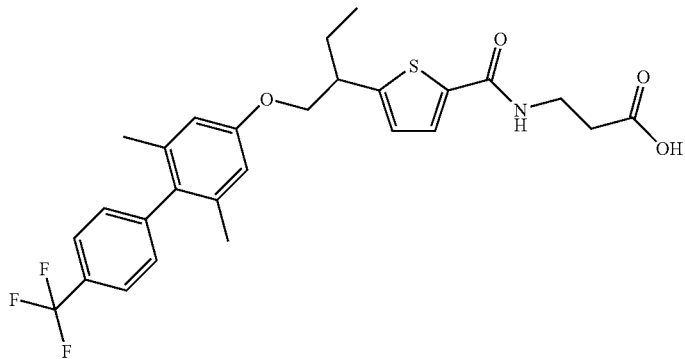 |
| X99 | 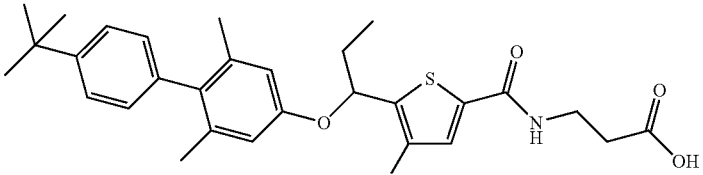 |
| X100 | 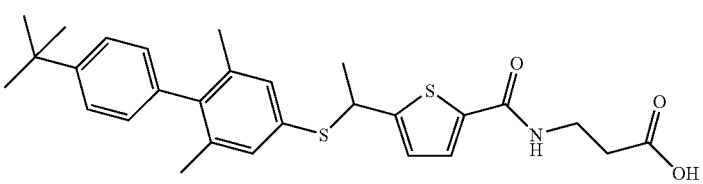 |
| X101 | 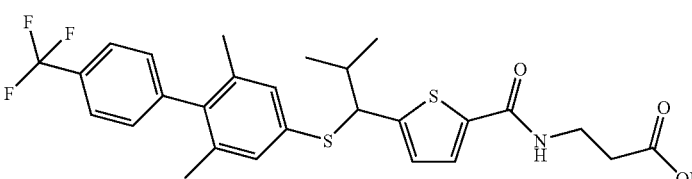 |
| X102 | 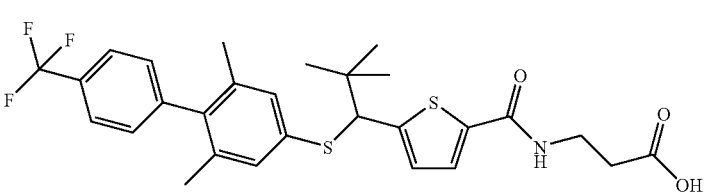 |

TABLE 1-continued
| Formula | Structure |
|---|---|
| X103 | 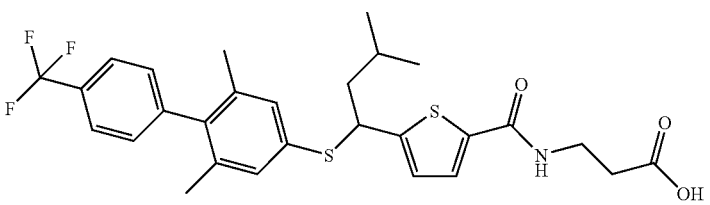 |
| X104 | 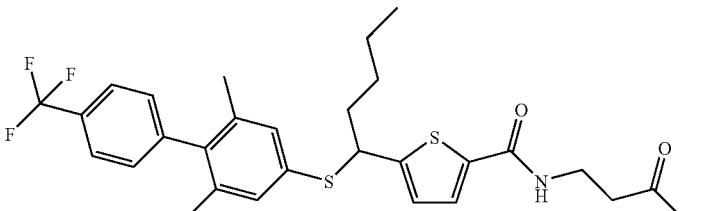 |
| X105 | 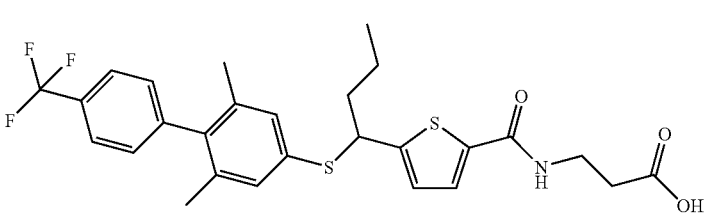 |
| X106 | 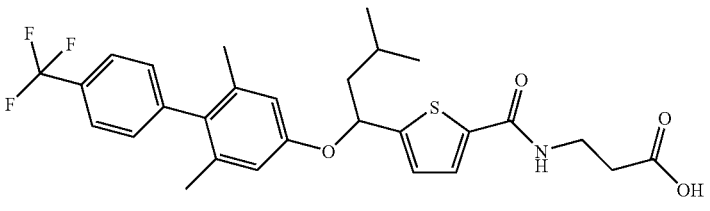 |
| X107 | 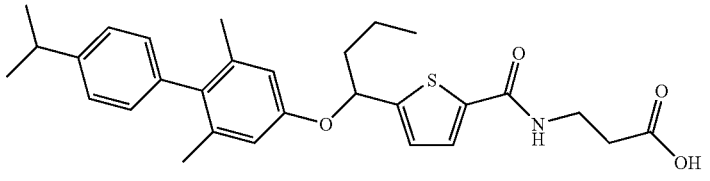 |
| X108 | 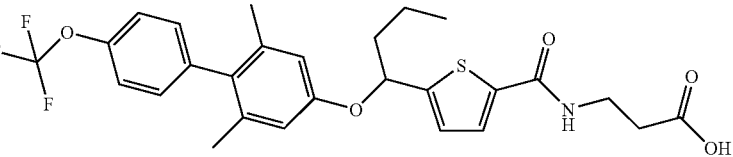 |
| X109 | 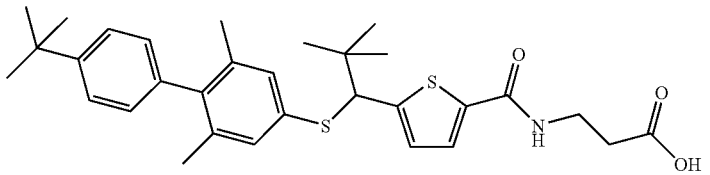 |
| X110 | 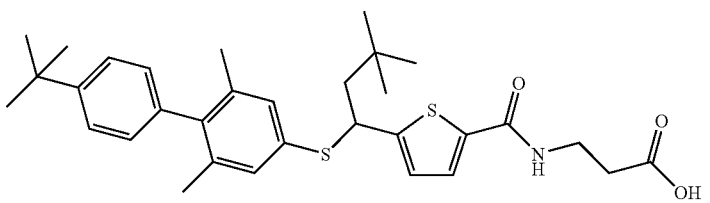 |

TABLE 1-continued
| Formula | Structure |
|---|---|
| X111 | 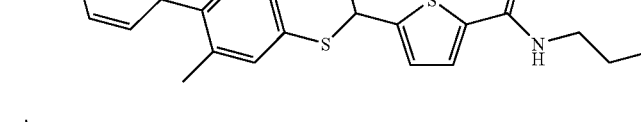 |
| X112 | 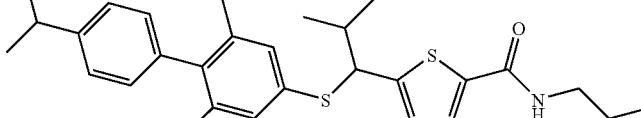 |
| X113 | 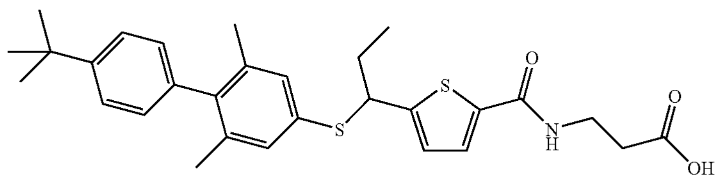 |
| X114 | 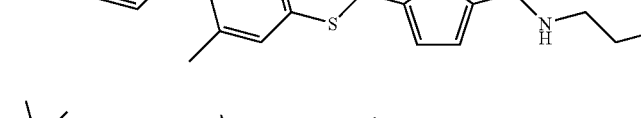 |
| X115 | 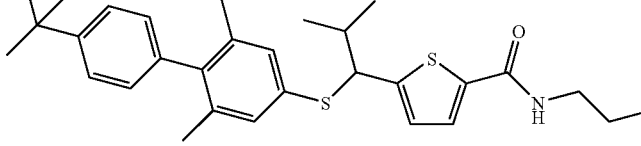 |
| X116 | 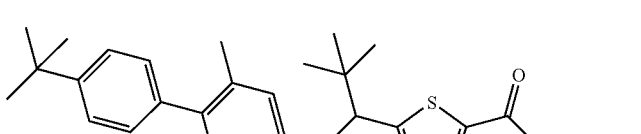 |
| X117 | 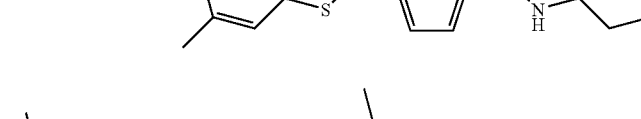 |
| X118 | 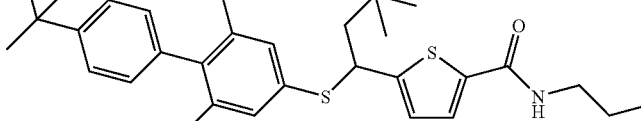 |

TABLE 1-continued

| Formula | Structure |
|---|---|
| X119 | 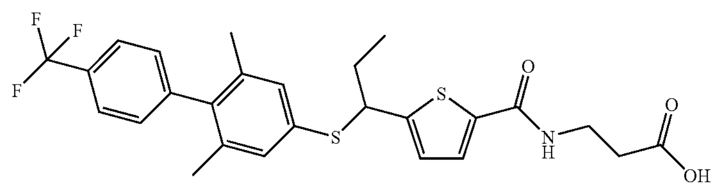 |
| X120 | 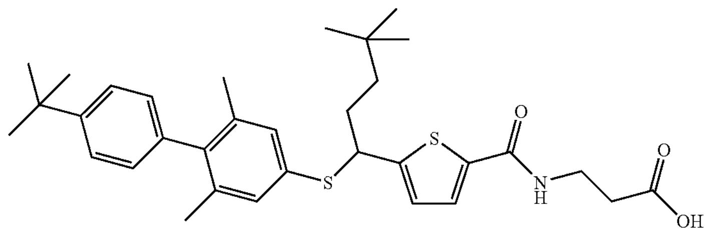 |
| X121 | 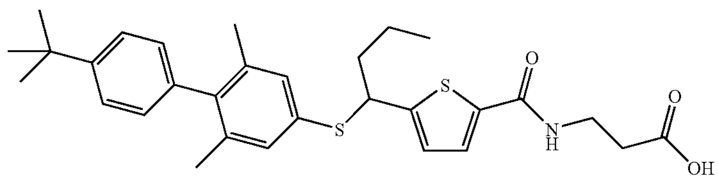 |
| X122 | 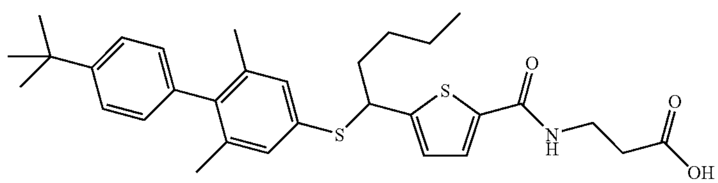 |
| X123 | 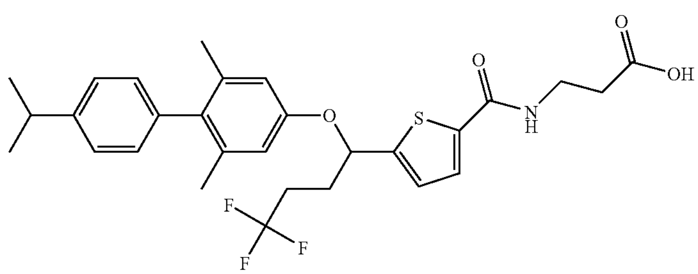 |
| X124 | 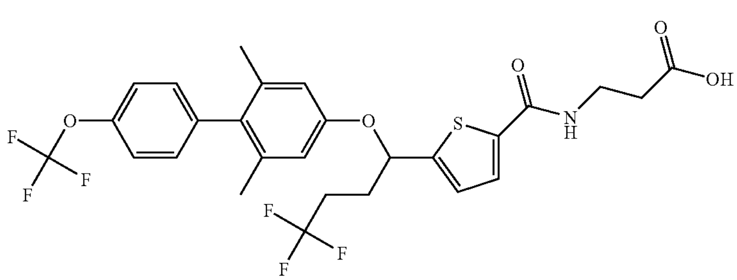 |

TABLE 1-continued
| Formula | Structure |
|---|---|
| X125 | 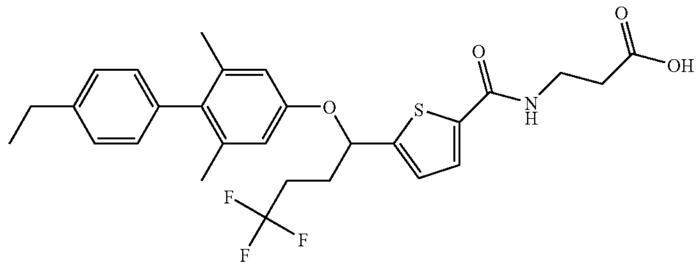 |
| X126 | 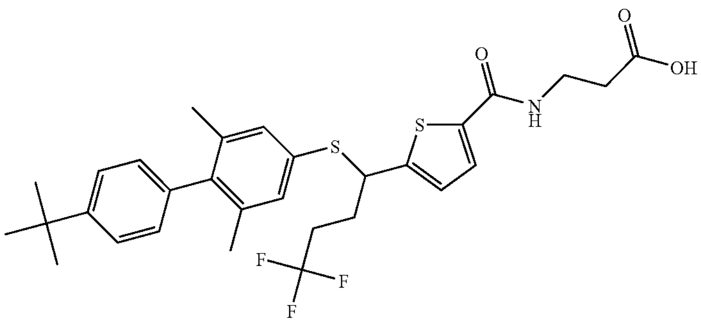 |
and a pharmaceutically acceptable salt thereof.
6. A pharmaceutical composition which comprises a compound or salt of claim 5 and a pharmaceutically acceptable carrier.
7. A compound of the formula
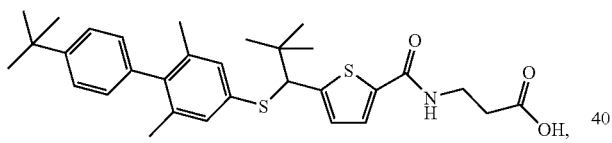
or a pharmaceutically acceptable salt thereof.
* * * * *